(12) United States Patent
Krupnick et al.

(10) Patent No.: US 11,713,342 B2
(45) Date of Patent: *Aug. 1, 2023

(54) COMPOSITIONS AND METHODS FOR TARGETED CYTOKINE DELIVERY

(71) Applicant: Washington University, St. Louis, MO (US)

(72) Inventors: Alexander Sasha Krupnick, St. Louis, MO (US); Eric Reed Lazear, St. Louis, MO (US); Daved Henry Fremont, St. Louis, MO (US)

(73) Assignee: Washington University, St. Louis, MO (US)

( * ) Notice: Subject to any disclaimer, the term of this patent is extended or adjusted under 35 U.S.C. 154(b) by 126 days.

This patent is subject to a terminal disclaimer.

(21) Appl. No.: 16/996,265

(22) Filed: Aug. 18, 2020

(65) Prior Publication Data

US 2021/0032306 A1 Feb. 4, 2021

Related U.S. Application Data

(63) Continuation of application No. 15/536,580, filed as application No. PCT/US2015/065872 on Dec. 15, 2015, now Pat. No. 10,793,613.

(60) Provisional application No. 62/243,829, filed on Oct. 20, 2015, provisional application No. 62/091,898, filed on Dec. 15, 2014.

(51) Int. Cl.
| | |
|---|---|
| *C07K 14/55* | (2006.01) |
| *C07K 14/005* | (2006.01) |
| *A61K 47/65* | (2017.01) |
| *A61K 47/64* | (2017.01) |
| *A61K 38/00* | (2006.01) |

(52) U.S. Cl.
CPC ............ *C07K 14/55* (2013.01); *A61K 47/642* (2017.08); *A61K 47/65* (2017.08); *C07K 14/005* (2013.01); *A61K 38/00* (2013.01); *C07K 2299/00* (2013.01); *C07K 2319/20* (2013.01); *C07K 2319/33* (2013.01); *C12N 2710/24122* (2013.01); *Y02A 50/30* (2018.01)

(58) Field of Classification Search
CPC ...... C07K 14/55; C07K 14/005; A61K 47/65; A61K 47/642; A61K 38/00; C12N 2710/24122; A61P 31/12; A61P 35/00
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 7,371,371 B2 | 5/2008 | Epstein et al. |
| 9,273,136 B2 | 3/2016 | Rader et al. |
| 10,184,009 B2 | 1/2019 | Ast et al. |
| 10,793,613 B2 | 10/2020 | Krupnick et al. |
| 11,053,293 B2 | 7/2021 | Krupnick et al. |
| 2003/0124678 A1 | 7/2003 | Epstein et al. |
| 2005/0249706 A1 | 11/2005 | Bermudes et al. |
| 2008/0274047 A1 | 11/2008 | Romagne et al. |
| 2009/0098609 A1 | 4/2009 | Gillies et al. |
| 2011/0150870 A1 | 6/2011 | Rader et al. |
| 2011/0311517 A1 | 12/2011 | Li et al. |
| 2012/0244112 A1 | 9/2012 | Ast et al. |
| 2014/0286898 A1 | 9/2014 | Gavin et al. |
| 2015/0216937 A1 | 8/2015 | Wen et al. |
| 2019/0092831 A1 | 3/2019 | Krupnick et al. |
| 2019/0119345 A1 | 4/2019 | Krupnick et al. |
| 2021/0284706 A1 | 9/2021 | Krupnick et al. |

FOREIGN PATENT DOCUMENTS

| | | |
|---|---|---|
| JP | 2009511550 A | 3/2009 |
| JP | 2011506406 A | 3/2011 |
| WO | 2003015697 A2 | 2/2003 |
| WO | 2003048334 A2 | 6/2003 |
| WO | 2010017103 A2 | 2/2010 |
| WO | 2012107417 A1 | 8/2012 |
| WO | 2012178137 A1 | 12/2012 |
| WO | 2016100375 A2 | 6/2016 |
| WO | 2016164937 A2 | 10/2016 |
| WO | 2017136818 A2 | 8/2017 |

OTHER PUBLICATIONS

Schubert, D. et al., "Self-reactive human CD4 T cell clones form unusual immunological synapses," J. Exp. Med., Feb. 6, 2012, pp. 335-352, vol. 209, No. 2, The Rockefeller University Press.

Sethi, D. et al., "A highly tilted binding mode by a self-reactive T cell receptor results in altered engagement of peptide and MHC," J Exp. Med , 2011, pp. 91-102, vol. 208, No. 1, The Rockefeller University Press.

Shane, H. et al., "Every breath you take: the impact of environment on resident memory CD8 T cells in the lung," Frontiers Immunol., Jul. 2014, pp. 1-10, vol. 5, No. 320.

(Continued)

*Primary Examiner* — Ruixiang Li
(74) *Attorney, Agent, or Firm* — Polsinelli PC

(57) ABSTRACT

The present disclosure encompasses compositions and methods for targeted cytokine delivery. The compositions disclosed herein comprise a cytokine linked to a ligand and may improve immunotherapy by limiting side effects associated with immunotherapy.

7 Claims, 80 Drawing Sheets
(79 of 80 Drawing Sheet(s) Filed in Color)
Specification includes a Sequence Listing.

(56) References Cited

OTHER PUBLICATIONS

Suman, O. et al., "Cell Surface Receptor-Antibody Association Constants and Enumeration of Receptor Sites for Monoclonal Antibodies," Cytometry, 2000, pp. 316-326, vol. 40, Wiley-Liss, Inc.
Sim, G. et al., "IL-2 therapy promotes suppressive ICOS+ Treg expansion in melanoma patients," J. Clin. Invest., Jan. 2014, pp. 99-110, vol. 124, No. 1.
Smyth, M. et al., "CD4+CD25+ T Regulatory Cells Suppress NK Cell-Mediated Immunotherapy of Cancer," J. Immunol., 2006, pp. 1582-1587, vol. 176.
Song H, et al., "Monkeypox Virus Infection of Rhesus Macaques Induces Massive Expansion of Natural Killer Cells but Suppresses Natural Killer Cell Functions," PLoS One, Oct. 2013, pp. 1-15, vol. 8, No. 10, e77804.
Spangler, J. et al., "Antibodies to Interleukin-2 Elicit Selective T Cell Subset Potentiation through Distinct Conformational Mechanisms," Immunity, May 19, 2015, pp. 815-825, vol. 42, Elsevier Inc.
Stemberger, C. et al., "A Single Naive CD8+ T Cell Precursor Can Develop into Diverse Effector and Memory Subsets," Immunity, Dec. 2007, pp. 985-997, vol. 27, Elsevier Inc.
Stern-Ginossar, N. et al., "Host Immune System Gene Targeting by a Viral miRNA," Science, Jul. 20, 2007, pp. 376-381, vol. 317, No. 5836.
Stewart, D. et al., "Occurrence and Role of Cis Peptide Bonds in Protein Structures," J. Mol. Biol., Jul. 5, 1990, pp. 253-260, vol. 214, No. 1, Academic Press Limited.
Strausberg, R., "Generation and initial analysis of more than 15,000 full-length human and mouse cDNA sequenes," PNAS, Dec. 24, 2002, p. 16899-16903, vol. 99, No. 26, with GenBank AAH66254.1 supplement, Mar. 6, 2007, 2 pgs.
Strong, R. et al., "NKG2D and Related Immunoreceptors," Adv. Protein Chem., 2004, pp. 281-312, vol. 68.
Strong, R., "Asymmetric ligand recognition by the activating natural killer cell receptor NKG2D, a symmetric homodimer," Mol. Immunol., 2001, pp. 1029-1037, vol. 38, Elsevier Science Ltd.
Tam, S. et al., "Abciximab (ReoPro, Chimeric 7E3 Fab) Demonstrates Equivalent Affinity and Functional Blockade of Glycoprotein IIb/IIIa and alpha(v)beta(3) Integrins," Circulation, 1998, pp. 1085-1091, vol. 98.
Thomas, M. et al., "Down-regulation of NKG2D and NKp80 ligands by Kaposi's sarcoma-associated herpesvirus K5 protects against NK cell cytotoxicity," PNAS, Feb. 5, 2008, pp. 1656-1661, vol. 105, No. 5.
Tietje, A. et al., "MULT1E/mIL-12: a novel bifunctional protein for natural killer cell activation," Gene Therapy, 2014, p. 468-475, vol. 21, Macmillan Publishers Limited.
Tomala, J. et al., "Chimera of IL-2 Linked to Light Chain of anti-IL-2 mAb Mimics IL-2/anti-IL-2 mAb Complexes Both Structurally and Functionally," ACS Chem. Biol., May 17, 2013, pp. 871-876, vol. 8, No. 5.
Trikha, M. et al., "CNTO 95, a fully human monoclonal antibody that inhibits alphav integrins, has antitumor and antiangiogenic activity in vivo," Int. J. Cancer, 2004, pp. 326-335, vol. 110, Wiley-Liss, Inc.
Tsao, P. et al., "Type-specific Sorting of G Protein-coupled Receptors after Endocytosis," J. Biol. Chem., Apr. 14, 2000, pp. 11130-11140, vol. 275, No. 15.
Tzeng, A. et al., "Antigen specificity can be irrelevant to immunocytokine efficacy and biodistribution," PNAS, Mar. 17, 2015, pp. 3320-3325, vol. 112, No. 11.
Ullrich, E. et al., "New prospects on the NKG2D/NKG2DL system for oncology," OncoImmunology, Oct. 2013, pp. e26097-1-e26097-9, vol. 2, No. 10, Taylor & Francis Group.
UniProtKB/Swiss-Prot Accession Q15116.3, Jan. 16, 2019; 7 pgs.
Wang, Y. et al., "Foxp3+ T Cells Inhibit Antitumor Immune Memory Modulated by mTOR Inhibition," Cancer Res., Feb. 26, 2014, pp. 2217-2228, vol. 74, No. 8.
Ward, J. et al., "HIV modulates the expression of ligands important in triggering natural killer cell cytotoxic responses an infected primary T-cell blasts," Blood, Aug. 15, 2007, pp. 1207-1214, vol. 110, No. 4.
Welte, S. et al., "Selective intracellular retention of virally induced NKG2D ligands by the human cytomegalovirus UL16 glycoprotein," Eur. J. Immunol., 2003, pp. 194-203, vol. 33, Wiley-VCH Verlag GmbH & Co. KGaA, Weinheim.
Wen, C. et al., "Hepatitis C Virus Infection Downregulates the Ligands of the Activating Receptor NKG2D," Cell. Mol. Immunol., Dec. 2008, pp. 475-478, vol. 5, No. 6.
Wu, X. et al., "Myosin-Reactive Autoantibodies in Rheumatic Carditis and Normal Fetus," Clinical Immunology and Immunopathology, May 1998, pp. 184-192, vol. 87, No. 2, with GenBank AAD56260.1 supplement, Jul. 26, 2016, 2 pgs.
Wucherpfennig, K. et al., "Structural Alterations in peptide-MHC Recognition by Self-reactive T cell Receptors," NIH Public Access Author Manuscript, available in PMC Dec. 1, 2010, pp. 1-12, published in final edited form as: Curr. Opin. Immunol., Dec. 2009, pp. 590-595, vol. 21, No. 6.
Yamane, B. et al., "The development of antibody-based immunotherapy with (EMD-273063) Hu14.18-IL2 in melanoma and neuroblastoma," NIH Public Access Author Manuscript, available in PMC Oct. 10, 2010, pp. 1-15, published in final edited form as: Expert Opin. Investig. Drugs, Jul. 2009, pp. 991-1000, vol. 18, No. 7.
Ye, L. et al., "Tumor necrosis therapy antibody interleukin-2 fusion protein elicits prolonged and targeted antitumor effects in vivo," Appl. Microbiol. Biotechnol., May 2014, pp. 4053-4061, vol. 98, No. 9, Springer-Verlag Berlin, Heidelberg.
Yin, Y. et al., "Structural basis for self-recognition by autoimmune T-cell receptors," Immunol. Rev., Nov. 2012, pp. 32-48, vol. 250, No. 1, John Wiley & Sons A/S, Singapore.
Zafirova, B. et al., "Regulation of immune cell function and differentiation by the NKG2D receptor," Cell. Mol. Life Sci., 2011, pp. 3519-3529, vol. 68, Springer.
Zhao, L., et al., "5-Fluorouracil and Interleukin-2 Immunochemotherapy Enhances Immunogenicity of Non-Small Cell Lung Cancer A549 Cells through Upregulation of NKG2D Ligands," Asian Pac. J. Cancer Prev., 2014, pp. 4039-4044, vol. 15, No. 9.
Zhou, Y-J., et al., "Distinct tyrosine phosphorylation sites in JAK3 kinase domain positively and negatively regulate its enzymatic activity," PNAS, Dec. 1997, pp. 13850-13855, vol. 94.
Zhu, Z., et al., "High-Avidity T Cells Are Preferentially Tolerized in the Tumor Microenvironment," Cancer Res., Jan. 5, 2013, pp. 595-604, vol. 73, No. 2.
Zou, W. et al., "DAP12 Couples c-Fms Activation to the Osteoclast Cytoskeleton by Recruitment of Syk," Mol. Cell, Aug. 8, 2008, pp. 422-431, vol. 31, Elsevier Inc.
Champsaur, M. et al., "Effect of NKG2D ligand expression on host immune responses," Immunol. Rev., 2010, pp. 267-285, vol. 235.
Office Action dated Mar. 23, 2021 from related Japanese Patent Application No. 2018-540749; 16 pgs.
GenBank accession No. 4FFE_X, dated Jan. 9, 2013, 2 pgs.
GenBank accession No. 4FFE_Y, dated Jan. 9, 2013, 2 pgs.
GenBank accession No. 4FFE_Z, dated Jan. 9, 2013, 2 pgs.
GenBank accession No. AAA59140.1, dated Jan. 6, 1995, 2 pgs.
GenBank accession No. AAA68969.1, dated Jun. 29, 1995, 2 pgs.
GenBank accession No. AAC23838.1, dated Jun. 8, 2000, 2 pgs.
GenBank accession No. AAH70338.1, dated Mar. 6, 2007, 2 pgs.
GenBank accession No. AAI00962.1, dated Oct. 4, 2006, 2 pgs.
GenBank accession No. AAI00963.1, dated Oct. 4, 2006, 2 pgs.
GenBank accession No. AAI16874.1, dated Jun. 29, 2006, 2 pgs.
GenBank accession No. AAP13470.1, dated Apr. 23, 2003; 1 pg.
GenBank accession No. AAQ10670.1, dated Jul. 7, 2005, 2 pgs.
GenBank accession No. AAQ10671.1, dated Jul. 7, 2005, 2 pgs.
GenBank accession No. AAV35056.1, dated Oct. 30, 2004, 2 pgs.
GenBank accession No. AAY97396, dated Sep. 28, 2005, 2 pgs.
GenBank accession No. ABK41601.1, dated Nov. 12, 2006, 2 pgs.
GenBank accession No. BC070338.1, dated Mar. 6, 2007, 3 pgs.
GenBank accession No. CAG46771.1, dated Oct. 16, 2008, 2 pgs.
GenBank accession No. CAG46777.1, dated Oct. 16, 2008, 2 pgs.
GenBank accession No. CR541973.1, dated Oct. 16, 2008, 2 pgs.
GenBank accession No. CR541980.1, dated Oct. 16, 2008, 2 pgs.

(56) References Cited

OTHER PUBLICATIONS

GenBank accession No. CR542001.1, dated Jul. 26, 2016, 2 pgs.
GenBank accession No. CR542007.1, dated Jul. 26, 2016, 2 pgs.
GenBank accession No. EDM01295.1, dated Jul. 26, 2016, 2 pgs.
GenBank accession No. ERE88380.1, dated Mar. 22, 2015, 2 pgs.
GenBank accession No. KJ891469.1, dated Mar. 19, 2015, 2 pgs.
GenBank accession No. KJ897054.1, dated Mar. 19, 2015, 2 pgs.
GenBank accession No. KR710147.1, dated Jun. 1, 2015, 2 pgs.
GenBank accession No. M22005.1, dated Jan. 6, 1995, 2 pgs.
GenBank accession No. NM_000585.4, dated Oct. 3, 2017, 2 pgs.
GenBank accession No. NM_001297562.1, dated Jan. 6, 2019; 5 pgs.
GenBank accession No. NM_003326.4, dated Oct. 21, 2018; 5 pgs.
GenBank accession No. NM_003811.3, dated Jun. 11, 2018; 4 pgs.
GenBank accession No. NM_172175.2, dated Oct. 3, 2017, 2 pgs.
GenBank accession No. NP_001020388.1, dated Mar. 4, 2017; 1 pg.
GenBank accession No. NP_001075454.1, dated Sep. 16, 2018; 2 pgs.
GenBank accession No. NP_001192644.1, dated May 30, 2018; 2 pgs.
GenBank accession No. NP_001284491.1, dated Jan. 6, 2019; 3 pgs.
GenBank accession No. NP_001306831.1, May 14, 2018; 2 pgs.
GenBank accession No. NP_003317.1, Jan. 6, 2019; 3 pgs.
GenBank accession No. NP_003802.1, Nov. 22, 2018; 3 pgs.
GenBank accession No. NP_033430.1, Jan. 20, 2019; 3 pgs.
GenBank accession No. NP_033478.1, Oct. 28, 2018; 3 pgs.
GenBank accession No. NP_446004.1, Jan. 19, 2019; 3 pgs.
GenBank accession No. NP_619807.1, dated Jan. 28, 2016, 2 pgs.
GenBank accession No. NP_852049.1, May 27, 2018; 3 pgs.
GenBank accession No. NP_999026.1, dated Oct. 1, 2017, 2 pgs.
GenBank accession No. XM_011509964.2, Mar. 26, 2018; 3 pgs.
GenBank accession No. XM_017002228.1, Mar. 26, 2018; 3 pgs.
GenBank accession No. XM_017002229.1, Mar. 26, 2018; 4 pgs.
Marcus, A. et al., "Evidence for Natural Killer Cell Memory," Curr. Biol., Sep. 9, 2013, pp. R817-R820, vol. 23.
McCoy, W. et al., "Cowpox virus employs a two-pronged strategy to outflank MHCI antigen presentation," NIH Public Access Author Manuscript, available in PMC Sep. 1, 2014, pp. 1-7, published in final edited form as: Mol. Immunol., Sep. 2013, pp. 156-158, vol. 55, No. 2.
McCoy, W. et al., "Structural Mechanism of ER Retrieval of MHC Class I by Cowpox," PLoS Biol., Nov. 2012, pp. 1-13, vol. 10, No. 11, e1001432.
McFarland, B. et al., "Symmetry Recognizing Asymmetry: Analysis of the Interactions between the C-Type Lectin-ike Immunoreceptor NKG2D and MHC Class I-like Ligands," Structure, Apr. 2003, pp. 411-422, vol. 11, Elsevier Science Ltd.
Meiraz, A. et al., "Switch from perforin-expressing to perforin-deficient CD8(+) T cells accounts for two distinct types of effector cytotoxic T lymphocytes in vivo," Immunol., 2009, pp. 69-82, vol. 128, Blackwell Publishing Ltd.
Meresse, B. et al., "Coordinated Induction by IL15 of a TCR-Independent NKG2D Signaling Pathway Converts CTL into Lymphokine-Activated Killer Cells in Celiac Disease," Immunity, Sep. 2004, pp. 357-366, vol. 21, Cell Press.
Mistry, A. et al., "Regulation of ligands for the activating receptor NKG2D," Immunol., 2007, pp. 439-447, vol. 121, Blackwell Publishing Ltd.
Mitra, S. et al., "Interleukin-2 Activity Can Be Fine Tuned with Engineered Receptor Signaling Clamps," Immunity, May 19, 2015, pp. 826-838, vol. 42, Elsevier Inc.
Morin, A. et al., "Collaboration gets the most out of software," eLIFE, 2013, pp. 1-6, vol. 2, No. e01456.
Nachmani, D. et al., "Diverse Herpesvirus MicroRNAs Target the Stress-Induced Immune Ligand MICB to Escape Recognition by Natural Killer Cells," Cell Host Microbe, Apr. 23, 2009, pp. 376-385, vol. 5, Elsevier Inc.
Nash, W. et al., "Know thyself: NK-cell inhibitory receptors prompt self-tolerance, education, and viral control," Front. Immunol., Apr. 2014, pp. 1-12, vol. 5, No. 175.
NCBI accession No. NM_001267706, Dec. 23, 2018; 5 pgs.
NCBI accession No. NM_001314029, Dec. 23, 2018; 4 pgs.
NCBI accession No. NM_014143, Dec. 23, 2018; 4 pgs.
NCBI accession No. NM_025239, Jan. 27, 2019; 5 pgs.
NCBI accession No. NP_001254635, Dec. 23, 2018; 3 pgs.
NCBI accession No. NP_001300958, Dec. 23, 2018; 3 pgs.
NCBI accession No. NP_054862, Dec. 24, 2018; 3 pgs.
NCBI accession No. NP_079515, Jan. 27, 2019; 3 pgs.
NCBI accession No. NR_052005, Feb. 6, 2019; 5 pgs.
NCBI accession No. XM_005251600, Mar. 26, 2018; 2 pgs.
NCBI accession No. XP_005251657, Mar. 26, 2018; 2 pgs.
Notice of Allowance dated May 19, 2020 from related U.S. Appl. No. 15/536,580; 5 pgs.
Notice of Allowance dated Jun. 12, 2020 from related European Patent Application No. 15870897.4; 7 pgs.
Obeidy, P. et al., "NKG2D and its ligands," Int. J. Biochem. Cell Biol., 2009, pp. 2364-2367, vol. 41, Elsevier Ltd.
O'Callaghan, C. et al., "Molecular Competition for NKG2D: H60 and RAE1 Compete Unequally for NKG2D with Dominance of H60," Immunity, Aug. 2001, pp. 201-211, vol. 15, Cell Press.
Office Action dated Dec. 20, 2018 from related European Patent Application No. 15870897.4; 4 pgs.
Office Action dated Oct. 2, 2019 from related European Patent Application No. 15870897.4; 4 pgs.
Office Action dated Sep. 19, 2019 from related U.S. Appl. No. 15/536,580; 9 pgs.
Office Action dated Jan. 16, 2020 from related U.S. Appl. No. 15/536,580; 8 pgs.
Office Action dated Aug. 7, 2020 from related U.S. Appl. No. 16/075,069; 15 pgs.
Office Action dated Oct. 21, 2020 from related European Patent Application No. 17748340.1; 8 pgs.
Ogasawara, K. et al., "Impairment of NK cell function by NKG2D modulation in NOD mice," Immunity, Jan. 2003, pp. 41-51, vol. 18, Cell Press.
Orange, J. et al., "Viral evasion of natural killer cells." Nat. Immunol., Nov. 2002, pp. 1006-1012, vol. 3, No. 11.
Otwinowski, Z. et al., "Processing of X-Ray Diffraction Data Collected in Oscillation Mode," Methods Enzymol., Part of Special Issue Macromolecular Crystallography Part A, 1997, pp. 307-326, vol. 276, Academic Press, Inc.
Pappworth, I. et al., "The Switch from Latent to Productive Infection in Epstein-Barr Virus-Infected B Cells Is Associated with Sensitization to NK Cell Killing," J. Virol., Jan. 2007, pp. 474-482, vol. 81, No. 2.
Park, J. et al., "Modulation of CD4+ T Lymphocyte Lineage Outcomes with Targeted, Nanoparticle-Mediated Cytokine Delivery," NIH Public Access, Author Manuscript, available in PMC Feb. 7, 2012, pp. 1-16, published in final edited form as: Mol. Pharm., Feb. 7, 2011, pp. 143-152, vol. 8, No. 1.
Plonquet, A. et al., "Peripheral blood natural killer cell count is associated with clinical outcome in patients with aaIPI 2-3 diffuse large B-cell lymphoma," Annals of Oncology, 2007, pp. 1209-1215, vol. 18.
Poschke, I., et al., "A phase I clinical trial combining dendritic cell vaccination with adoptive T cell transfer in patients with stage IV melanoma," Cancer Immunol. Immunother., 2014, pp. 1061-1071, vol. 63.
Radaev, S. et al., "Conformational Plasticity Revealed by the Cocrystal Structure of NKG2D and Its Class I MHC-like Ligand ULBP3," Immunity, Dec. 2001, pp. 1039-1049, vol. 15, Cell Press.
Radaev, S. et al., "Structure and Function of Natural Killer Cell Surface Receptors," Annu. Rev. Biophys. Biomol. Struct., Jun. 2003, pp. 93-114, vol. 32.
Rathanaswami, P. et al., "High-affinity binding measurements of antibodies to cell-surface-expressed antigens," Anal. Biochem., Feb. 1, 2008, pp. 52-60, vol. 373, No. 1, Elsevier.

(56) References Cited

OTHER PUBLICATIONS

Raulei, D. et al., "Regulation of ligands for the NKG2D activating receptor," NIH Public Access Author Manuscript, available in PMC Nov. 25, 2014, pp. 1-34, published in final edited form as: Annu. Rev. Immunol., 2013, pp. 413-441, vol. 31.
Raulet, D., "Roles of the NKG2D Immunoreceptor and its Ligands," Nat. Rev. Immunol., Oct. 2003, pp. 781-790, vol. 3.
Rosenberg, S. et al., "Experience with the Use of High-Dose Interleukin-2 in the Treatment of 652 Cancer Patients," Ann. Surg., Oct. 1989, pp. 474-484, vol. 210, No. 4.
Rosenberg, S., "IL-2: The First Effective Immunotherapy for Human Cancer," J. Immunol., 2014, pp. 5451-5458, vol. 192.
Rossi, A. et al., "Analysis of protein-ligand interactions by fluorescence polarization," Europe PMC Funders Group, Author Manuscript, available in PMC Sep. 3, 2011, published in final form as: Nat. Protoc., Mar. 2011, pp. 365-387, vol. 6, No. 3.
Ryu, M., et al., "Accumulation of cytolytic CD8+ T cells in B16-melanoma and proliferation of mature T cells in TIS21-knockout mice after T cell receptor stimulation," Exp. Cell Res., Oct. 1, 2014, pp. 209-221, vol. 327, No. 2, Elsevier, Inc.
Sallusto, F. et al., "Two subsets of memory T lymphocytes with distinct homing potentials and effector functions," Nature, Oct. 14, 1999, pp. 708-712, vol. 401, Macmillan Magazines Ltd.
Sauve, K. et al., "Localization in human interleukin 2 of the binding site to the alpha chain (p55) of the interleukin 2 receptor," PNAS, Jun. 1991, pp. 4636-4640, vol. 88.
Adams, E. et al., "The Adaptable Major Histocompatibility Complex (MHC) Fold: Structure and Function of Nonclassical and MHC Class I-Like Molecules," Annu. Rev. Immunol., 2013, p. 529-561, vol. 31.
Adams, J. et al., "T cell receptor signaling is limited by docking geometry to peptide-Major Histocompatibility Complex," NIH Public Access, Author Manuscript, available in PMC May 23, 2013, pp. 1-22, published in final edited form as: Immunity, Nov. 23, 2011, pp. 681-693, vol. 35, No. 5.
Adams, P. et al., "PHENIX: building new software for automated crystallographic structure determination," Acta Crystallographica Section D Biological Crystallography, 2002, pp. 1948-1954, vol. D58, International Union of Crystallography, Denmark.
Altschul, S. et al., "Basic Local Alignment Search Tool," J. Mol. Biol., 1990, pp. 403-410, vol. 215, Academic Press Limited.
Altschul, S. et al., "Gapped BLAST and PSI-BLAST: a new generation of protein database search programs," Nucleic Acids Res., 1997, pp. 3389-3402, vol. 25, No. 17, Oxford University Press.
Alzhanova, D. et al., "Cowpox Virus Inhibits the Transporter Associated with Antigen Processing to Evade T Cell Recognition," Cell Host Microbe, Nov. 19, 2009, pp. 433-445, vol. 6, with Supplemental Data, 12 pgs., Elsevier Inc.
Anichini, A., et al., "Tumor-Reactive CD8+ Early Effector T Cells Identified at Tumor Site in Primary and Metastatic Melanoma," Cancer Res , Nov. 1, 2010, pp. 8378-8387, vol. 70, No. 21.
Araki, K., et al., "mTOR regulates memory CD8 T cell differentiation," NIH Public Access, Author Manuscript, available in PMC Jan. 2, 2010, pp. 1-13, published in final edited form as Nature, Jul. 2, 2009, pp. 108-112, vol. 460, No. 7251.
Ashkenazy, H. et al., "ConSurf 2010: calculating evolutionary conservation in sequence and structure of proteins and nucleic acids," Nucl. Acids Res., 2010, pp. W529-W533, vol. 38, Oxford University Press.
Atkins, M. et al., "High-Dose Recombinant Interleukin 2 Therapy for Patients With Metastatic Melanoma: Analysis of 270 Patients Treated Between 1985 and 1993," J. Clin. Oncol., Jul. 1999, pp. 2105-2116, vol. 17, No. 7.
Atomic Coordinates accession code 4PDC Protein Data Bank, Research Collaboratory for Structural Bioinformatics, Apr. 17, 2014, 10 pgs.
Bauman, Y. et al., "An Identical miRNA of the Human JC and BK Polyoma Viruses Targets the Stress-Induced Ligand UULBP3 to Escape Immune Elimination," Cell Host Microbe, Feb. 17, 2011, pp. 93-102, vol. 9, Elsevier Inc.
Becker, J. et al., "T Cell-mediated Eradication of Murine Metastatic Melanoma Induced by Targeted Interleukin 2 Therapy," J Exp. Med., May 1996, pp. 2361-2366, vol. 183, The Rockefeller University Press.
Boyman, O. et al., "Selective Stimulation of T Cell Subsets With Antibody-Cytokine Immune Complexes," Science, Mar. 31, 2006, pp. 1924-1927, vol. 311, No. 5769.
Boyman, O. et al., "Selectively Expanding Subsets of T Cells in Mice by Injection of Interleukin-2/Antibody Complexes: Implications for Transplantation Tolerance," Transplantation Proceedings, May 2012, pp. 1032-1034, vol. 44, No. 4, Elsevier Inc.
Bui, J. et al., "Comparative Analysis of Regulatory and Effector T Cells in Progressively Growing versus Rejecting Tumors of Similar Origins," Cancer Res., Jul. 15, 2006, pp. 7301-7309, vol. 66, No. 14.
Byun, M. et al., "Cowpox Virus Exploits the Endoplasmic Reticulum Retention Pathway to Inhibit MHC Class I Transport to the Cell Surface," Cell Host Microbe, Nov. 2007, pp. 306-315, vol. 2, Elsevier Inc.
Byun, M. et al., "Two mechanistically distinct immune evasion proteins of cowpox virus combine to avoid antiviral CD8 T cells," NIH Public Access, Author Manuscript, available in PMC May 19, 2010, pp. 1-20, published in final form as: Cell Host Microbe, Nov. 19, 2009, pp. 422-432, vol. 6, No. 5.
Campbell, J. et al., "Cutting Edge: FcR-Like 5 on Innate B Cells Is Targeted by a Poxvirus MHC Class I-Like Immunoevasin," J. Immunol., 2010, pp. 28-32, vol. 185, The American Association of Immunologists, Inc.
Campbell, J. et al., "Zoonotic orthopoxviruses encode a high-affinity antagonist of NKG2D," JEM, Jun. 11, 2007, pp. 1311-1317, vol. 204, No. 6, The Rockefeller University Press.
Carayannopoulos, L. et al., "Ligands for murine NKG2D display heterogeneous binding behavior," Eur. J. Immunol., 2002, pp. 597-605, vol. 32, Wiley-VCH Verlag, Germany.
Carmenate, T. et al., "Human IL-2 Mutein with Higher Antitumor Efficacy Than Wild Type IL-2," J. Immunol., 2013, pp. 6230-6238, vol. 190, The American Association of Immunologists, Inc.
Celniker, G. et al., "ConSurf: Using Evolutionary Data to Raise Testable Hypotheses about Protein Function," Isr. J. Chem., 2013, pp. 199-206, vol. 53, Wiley-VCH Verlag GmbH & Co. KGaA, Germany.
Cerboni, C. et al., "Human immunodeficiency virus 1 Nef protein downmodulates the ligands of the activating receptor NKG2D and inhibits natural killer cell-mediated cytotoxicity," J. Gen. Virol., 2007, pp. 242-250, vol. 88, SGM, Great Britain.
Chalupny, N. et al., "Down-regulation of the NKG2D ligand MICA by the human cytomegalovirus glycoprotein UL142," Biochem. Biophys. Res. Commun., Jul. 21, 2006, pp. 175-181, vol. 346, No. 1, Elsevier Inc.
Chang, S. et al., "Unique pulmonary antigen presentation may call for an alternative approach toward lung cancer immunotherapy," Oncoimmunology, Mar. 2013, pp. pp e23563-1 to e23563-5, vol. 2, No. 3, Landes Bioscience.
Chen, V. et al., "MolProbity: all-atom structure validation for macromolecular crystallography," Acta Crystallogr. D Biol. Crystallogr., 2010, p. 12-21, vol. D66.
Copeland, R. et al., "Drug-target residence time and its implications for lead optimization," Nat. Rev. Drug Discov., Sep. 2006, pp. 730-739, vol. 5, with Corrigendum, 1 pg., Nature Publishing Group.
Cosman, D. et al., "ULBPs, Novel MHC Class I-Related Molecules, Bind to CMV Glycoprotein UL16 and Stimulate NK Cytotoxicity through the NKG2D Receptor," Immunity, Feb. 2001, pp. 123-133, vol. 14, Cell Press.
Coudert, J. et al., "The role of the NKG2D receptor for tumor immunity," Seminars in Cancer Biol., 2006, pp. 333-343, vol. 16.
Craveur, P. et al., "Cis-trans isomerization of omega dihedrals in proteins," Amino Acids, 2013, pp. 279-289, vol. 45, Springer.

(56) References Cited

OTHER PUBLICATIONS

Dandamudi, U. et al., "A Phase II Study of Bevacizumab and High-dose Interleukin-2 in Patients With Metastatic Renal Cell Carcinoma: A Cytokine Working Group (CWG) Study," J. Immunother., Nov./Dec. 2013, pp. 490-495, vol. 36, No. 9.

Dasgupta, A. et al., "Cowpox Virus Evades CTL Recognition and Inhibits the Intracellular Transport of MHC Class I Molecules," J. Immunol., 2007, 1654-1661, vol. 178, The American Association of Immunologists, Inc.

De Goer De Herve, M. et al., "FoxP3(+) regulatory CD4 T cells control the generation of functional CD8 memory," Mature Commun., 2012, pp. 1-10, vol. 3, No. 986, Macmillan Publishers Limited.

Debbia, M. et al., "Measurement of anti-D intrinsic affinity with unlabeled antibodies," Transfusion, Mar. 2004, pp. 399-406, vol. 44, Wiley-Blackwell.

Deng, L. et al., "Structural basis for recognition of MHC and MHC-like ligands by natural killer cell receptors," NIH Public Access Author Manuscript, available in PMC Aug. 25, 2008, pp. 1-15, published in final edited form as: Semin. Immunol., Jun. 2006, pp. 159-166, vol. 18, No. 3.

Deng, W. et al., "A shed NKG2D ligand that promotes natural killer cell activation and tumor rejection," Science, Apr. 3, 2015, pp. 136-139, vol. 348, No. 6230.

Dokun, A. et al., "Specific and nonspecific NK cell activation during virus infection," Nat. Immunol., Oct. 2001, pp. 951-956, vol. 2, No. 10, Nature Publishing Group.

Draghi, M. et al., "NKp46 and NKG2D Recognition of Infected Dendritic Cells Is Necessary for NK Cell Activation in the Human Response to Influenza Infection," J. Immunol., 2007, pp. 2688-2698, vol. 178.

Drake, A. et al., "Characterizing high-affinity antigen/antibody complexes by kinetic- and equilibrium-based methods," Anal. Biochem., 2004, pp. 35-43, vol. 328, Elsevier Inc.

Eagle, R. et al., "Promiscuity and the single receptor: NKG2D," Nat. Rev. Immunol., Sep. 2007, pp. 737-744, vol. 7, Mature Publishing Group.

Emsley, P. et al., "Coot: model-building tools for molecular graphics," Acta Crystallogr. D Biol. Crystallogr., 2004, pp. 2126-2132, vol. D60, International Union of Crystallography, Denmark.

Extended European Search Report dated Mar. 2, 2018 from related European Patent Application No. 15870897.4; 7 pgs.

Extended European Search Report dated Sep. 23, 2019 from related European Patent Application No. 17748340.1; 9 pgs.

Fang M. et al., "A role for NKG2D in NK Cell-Mediated Resistance to Poxvirus Disease," PLoS Pathog.,Feb. 2008, pp. 0001-0011, vol. 4, No. 2, e30.

Finton ,K. et al., "Structural insights into activation of antiviral NK cell responses," NIH Public Access Author Manuscript, available in PMC Nov. 1, 2013, pp. 1-29, published in final edited form as: Immunol. Rev., Nov. 2012, pp. 239-257, vol. 250, No. 1.

French, A. et al., "DAP12 Signaling Directly Augments Proproliferative Cytokine Stimulation of NK Cells during Viral Infections," J. Immunol., 2006, pp. 4981-4990, vol. 177, American Association of Immunologists, Inc.

Frese-Schaper, M. et al., "Influence of natural killer cells and perforin-mediated cytolysis on the development of chemically induced lung cancer in A/J mice," Cancer Immunol. Immunother., 2014, pp. 571-580, vol. 63, Springer.

Gainey, M. et al., "Viral MHC class I inhibition evades CD8+ T-cell effector responses in vivo but not CD8+ T-cell priming," PNAS, Oct. 29, 2012, pp. E3260-3267, vol. 109.

Gately, M. et al., "Role of asialo-GM1-positive lymphoid cells in mediating the toxic effects of recombinant IL-2 in mice," J Immunol., Jul. 1, 1988, pp. 189-200, vol. 141, No. 1.

GenBank accession No. XM_017002230.1, Mar. 26, 2018; 3 pgs.
GenBank accession No. XP_003480863.1, May 13, 2017; 2 pgs.
GenBank accession No. XP_003639215.1, Sep. 5, 2017; 2 pgs.
GenBank accession No. XP_005633029.1, Sep. 17, 2015; 1 pg.
GenBank accession No. XP_007610839.1, May 27, 2016; 2 pgs.
GenBank accession No. XP_007627369.1, May 27, 2016; 2 pgs.
GenBank accession No. XP_008251123.1, Jun. 13, 2014; 2 pgs.
GenBank accession No. XP_011508266.2, Mar. 26, 2018; 1 pg.
GenBank accession No. XP_012042680.1, Feb. 6, 2019; 2 pgs.
GenBank accession No. XP_013820683.1, Sep. 10, 2015; 2 pgs.
GenBank accession No. XP_013825644.1, Sep. 10, 2015; 2 pgs.
GenBank accession No. XP_014951136.1, Dec. 17, 2015; 2 pgs.
GenBank accession No. XP_016857717.1, Mar. 26, 2018; 1 pg.
GenBank accession No. XP_016857718.1, Mar. 26, 2018; 1 pg.
GenBank accession No. XP_016857719.1, Mar. 26, 2018; 1 pg.
GenBank accession No. XP_430147.2, May 17, 2018; 1 pg.
GenBank accession No. XR_001737393.1, Jun. 6, 2016; 4 pgs.
GenBank accession No. XR_001737394.1, Jun. 6, 2016; 4 pgs.
GenBank accession No. XR_001737395.1, Jun. 6, 2016; 4 pgs.
GenBank accession No. XR_001737396.1, Jun. 6, 2016; 2 pgs.
GenBank No. 148667521 (EDK99937.1), dated Jul. 26, 2016, 3 pgs.
GenBank No. 149049263 (EDM01717.1), dated Jul. 26, 2016, 2 pgs.
GenBank No. 21902299, dated Jul. 18, 2002, 2 pgs.
GenBank No. 30749494, dated Dec. 27, 2012, 3 pgs.
GenBank No. 332232684 (XP_003265533.1), dated May 13, 2015, 2 pgs.
GenBank No. 348569092 (XP_003470332.2), dated Jul. 14, 2015, 2 pgs.
GenBank No. 355785888 (EHH66071.1), dated Mar. 17, 2015, 2 pgs.
GenBank No. 380848799 (NP 001244177.1), dated Sep. 7, 2014, 2 pgs.
GenBank No. 410963826 (XP_003988460.2), dated Dec. 29, 2016, 2 pgs.
GenBank No. 505834608 (XP_004611478.1), dated May 20, 201, 2 pgs.
GenBank No. 507978716 (XP_004693215.1), dated Jun. 10, 2015, 2 pgs.
GenBank No. 512868733 (XP_004891778.1), dated Jun. 18, 2013, 2 pgs.
GenBank No. 532053033 (XP_005369262.1), dated Aug. 7, 2015, 2 pgs.
GenBank No. 532114387 (XP_005341860.1), dated Aug. 21, 2013, 2 pgs.
GenBank No. 537136230 (ERE66429.1), dated Mar. 22, 2015, 2 pgs.
GenBank No. 57113989 (NP_001009059.1), dated Oct. 1, 2017, 2 pgs.
GenBank No. 589967905 (XP_006996451.1), dated Mar. 21, 2016, 2 pgs.
GenBank No. 635063485 (XP_007965810.1), dated May 14, 2014, 2 pgs.

Germain, C. et al., "Redirecting NK cells mediated tumor cell lysis by a new recombinant bifunctional protein," Protein Eng. Des. Sel., 2008, pp. 665-672, vol. 21, No. 11, Oxford University Press.

Ghasemi, R. et al., "Selective targeting of IL-2 to NKG2D bearing cells for improved immunotherapy," Nat. Commun., 2016, pp. 1-15, vol. 7, No. 12878.

Ghiringhelli, F. et al., "The role of regulatory T cells in the control of natural killer cells: relevance during tumor progression," Immunol Rev., 2006, pp. 229-238, vol. 214, Blackwell Munksgaard, Singapore.

Gilfillan, S. et al., "NKG2D recruits two distinct adapters to trigger NK cell activation and costimulation," Nature Immunol., Dec. 2002, pp. 1150-1155, vol. 3, No. 12, Nature Publishing Group.

Giuliani, E. et al., "Release of Soluble Ligands for the Activating NKG2D Receptor: One More Immune Evasion Strategy Evolved by HIV-1?," Current Drug Targets, Jan. 2016, p. 54-64, vol. 17, No. 1, Bentham Science Publishers.

Glaser, F. et al., "ConSurf: Identification of Functional Regions in Proteins by Surface-Mapping of Phylogenetic Information," Bioinformatics, 2003, pp. 163-164, vol. 19, No. 1, Oxford University Press.

Glasner, A. et al., "Recognition and Prevention of Tumor Metastasis by the NK Receptor NKp46/NCR1," J. Immunol., 2012, pp. 2509-2515, vol. 188, The American Association of Immunologists, Inc.

(56) References Cited

OTHER PUBLICATIONS

Gorelik, E. et al., "Susceptibility of Various Strains of Mice to Urethan-lnduced Lung Tumors and Depressed Natural Killer Cell Activity," J. Natl. Cancer Inst., Dec. 1981, pp. 1317-1322, vol. 67, No. 6.
Graham, D. et al., "Vav1 Controls DAP 10-Mediated Natural Cytotoxicity by Regulating Actin and Microtubule Dynamics," J. Immunol, 2006, pp. 2349-2355, vol. 177, The American Association of Immunologists, Inc.
Graham, J. et al., "Regulatory T Cells Shape the Resident Memory T Cell Response to Virus Infection in the Tissues," J. Immunol., 2014, pp. 683-690, vol. 192,, The American Association of Immunologists, Inc.
Griffin, B. et al., "Herpesviruses and immunity: The art of evasion," Vet Microbiol., Jun. 16, 2010, pp. 89-100, vol. 143, No. 1.
Groh, V. et al., "Stimulation of T cell autoreactivity by anomalous expression of NKG2D and its MIC ligands in rheumatoid arthritis," PNAS, Aug. 5, 2003, pp. 9452-9457, vol. 100, No. 16.
Office Action dated Dec. 7, 2021 from related Japanese Patent Application No. 2018-540749; 12 pgs., with English translation.
Office Action dated Dec. 17, 2021 from related Chinese Patent Application No. 201780022070.9; 17 pgs., with English translation.
Biolegend, "APC anti-human CD314 (NKG2D) Antibody," Nov. 30, 2012, 6 pgs., Version 1.
Correia, D. et al., "Differentiation of human peripheral blood Vdelta1+ T cells expressing the natural cytotoxicity receptor NKp30 for recognition of lymphoid leukemia cells," Blood, 2011, pp. 992-1001, vol. 118, No. 4.
Kjellev, S. et al., "Inhibition of NKG2D receptor function by antibody therapy attenuates transfer-induced colitis in SCID mice," Eur. J. Immunol., 2007, pp. 1397-1406, vol. 37, Wiley-VCH Verlag GmbH & Co.
Vadstrup, K. et al., "Anti-NKG2D mAb: A New Treatment for Crohn's Disease," Int. J. Mol. Sci., 2017, pp. 1-18, vol. 18, No. 1997.
Notice of Allowance dated Feb. 22, 2021 from related U.S. Appl. No. 16/075,069 ; 7 pgs.
Extended European Search Report dated Jul. 9, 2021 from related European Patent Application No. 21155548.7; 7 pgs.
Office Action dated Aug. 24, 2021 from related Japanese Patent Application No. 2018-540749; 5 pgs.
Gutbrodt, K. et al., "Antibody-Based Delivery of IL2 and Cytotoxics Eradicates Tumors in Immunocompetent Mice," Mol. Cancer Ther., 2014, pp. 1772-1776, vol. 13, No. 7, American Association for Cancer Research.
Hahn, M. et al., "Unconventional topology of self peptide-major histocompatibility complex binding by a human autoimmune T cell receptor," Nat. Immunol., May 2005, pp. 490-496, vol. 6, No. 5, Nature Publishing Group.
Hank, J. et al., "Distinct Clinical and Laboratory Activity of Two Recombinant Interleukin-2 Preparations," Clin. Cancer Res., Feb. 1999, pp. 281-289, vol. 5.
Hansen, T. et al., "MHC class I antigen presentation: learning from viral evasion strategies," Nat. Rev. Immunol., Jul. 2009, pp. 503-513, vol. 9.
Heaton, K. et al., "Characterization of Lymphokine-Activated Killing by Human Peripheral Blood Mononuclear Cells Stimulated with Interleukin 2 (IL-2) Analogs Specific for the Intermediate Affinity IL-2 Receptor," Cellular Immunol., Mar. 1993, pp. 167-179, vol. 147, No. 1.
Heaton, K. et al., "Human Interleukin 2 Analogues That Preferentially Bind the Intermediate-Affinity Interleukin 2 Receptor Lead to Reduced Secondary Cytokine Secretion: Implications for the Use of These Interleukin 2 Analogues in Cancer Immunotherapy," Cancer Res., Jun. 1, 1993, pp. 2597-2602, vol. 53.
Hersey, P. et al., "Low natural-killer-cell activity in familial melanoma patients and their relatives," Br. J. Cancer, 1979, pp. 113-122, vol. 40.

Ho, E. et al., "Costimulation of Multiple NK Cell Activation Receptors by NKG2D," J. Immunol., 2002, pp. 3667-3675, vol. 169, The American Association of Immunologists, Inc.
Horng, T. et al., "NKG2D signaling is coupled to the interleukin 15 receptor signaling pathway," Nat. Immunol., Dec. 2007, pp. 1345-1352, vol. 8, No. 12, Nature Publishing Group.
Hue, S. et al., "A Direct Role for NKG2D/MICA Interaction in Villous Atrophy During Celiac Disease," Immunity, Sep. 2004, pp. 367-377, vol. 21, Cell Press.
Imai, K. et al., "Natural cytotoxic activity of peripheral-blood lymphocytes and cancer incidence: an 11-year follow-up study of a general population," Lancet, Nov. 25, 2000, pp. 1795-1799, vol. 356, No. 9244.
International Search Report and Written Opinion dated Apr. 26, 2018 from related International Patent Application No. PCT/US2017/016688; 17 pgs.
International Search Report and Written Opinion dated May 2, 2016 from related International Patent Application No. PCT/US2015/065872; 19 pgs.
Ji, Q. et al., "Provision of Granulocyte-Macrophage Colony-Stimulating Factor Converts an Autoimmune Response to a Self-Antigen into an Antitumor Response," J. Immunol., 2005, pp. 1456-1463, vol. 175.
Kang, T. et al., "Tumor-Targeted Delivery of IL-2 by NKG2D Leads to Accumulation of Antigen-Specific CD8+ T Cells in the Tumor Loci and Enhanced Anti-Tumor Effects," PLoS One, Apr. 2012, pp. 1-9, vol. 7, No. 4, e35141.
Karlin, S. et al., "Applications and statistics for multiple high-scoring segments in molecular sequences," PNAS, Jun. 1993, pp. 5873-5877, vol. 90.
Karlin, S. et al., "Methods for assessing the statistical significance of molecular sequence features by using general scoring schemes," PNAS, Mar. 1990, pp. 2264-2268, vol. 87.
Karre, K. et al., "Selective rejection of H-2-deficient lymphoma variants suggests alternative immune defence strategy," Nature, Feb. 1986, pp. 675-678, vol. 319, Nature Publishing Group.
Kim, H., "Antibody-based depletion of Foxp3+ T cells potentiates antitumor immune memory stimulated by mTOR inhibition," Oncoimmunology, Jun. 2014, pp. e29081-1 to e29081-3, vol. 3, Landes Bioscience.
Klein, O., et al,. "Melan-A-specific Cytotoxic T Cells are Associated with Tumor Regression and Autoimmunity Following Treatment with Anti-CTLA-4," Clinical Cancer Res., Apr. 1, 2009, pp. 2507-2513, vol. 15, No. 7.
Kolate, A. et al., "PEG—A versatile conjugating ligand for drugs and drug delivery systems," J. Controlled Release, Oct. 28, 2014, pp. 67-81, vol. 192, Elsevier, B.V.
Kolitz, J et al., "Recombinant Interleukin-2 in Patients Aged Younger Than 60 Years With Acute Myeloid Leukemia in First Complete Remission," Cancer, Apr. 1, 2014, pp. 1010-1017, vol. 120.
Konjevic, G. et al., "In-vitro IL-2 or IFN-alpha-induced NKG2D and CD161 NK cell receptor expression indicates novel aspects of NK cell activation in metastatic melanoma patients," Melanoma Res., 2010, pp. 459-467, vol. 20.
Kreisel, D. et al,. "Strain-Specific Variation in Murine Natural Killer Gene Complex Contributes to Differences in Immunosurveillance for Urethane-Induced Lung Cancer," Cancer Res., Jun. 29, 2012, Author Manuscript, 20 pgs.
Krieg, C. et al., "Improved IL-2 immunotherapy by selective stimulation of IL-2 receptors on lymphocytes and endothelial cells," PNAS, Jun. 29, 2010, pp. 11906-11911, vol. 107, No. 26, with Correction, 1 pg.
Krissinel, E. et al., "Inference of Macromolecular Assemblies from Crystalline State," J. Mol. Biol., Sep. 21, 2007, pp. 774-797, vol. 372, No. 3.
Krmpotic, A. et al., "NK cell activation through the NKG2D ligand MULT-1 is selectively prevented by the glycoprotein encoded by mouse cytomegalovirus gene m145," J. Exp. Med., Jan. 17, 2005, pp. 211-220, vol. 201, No. 2, The Rockefeller University Press.
Kwong, K. et al., "Generation, affinity maturation, and characterization of a human anti-human NKG2D monoclonal antibody with dual antagonistic and agonistic activity," NIH Public Access Author Manuscript, Dec. 31, 2009, pp. 1-25, published in final edited form as: J. Mol. Biol., Dec. 31, 2008, pp. 1143-1156, vol. 384, No. 5.
Landau, M. et al., "ConSurf 2005: the projection of evolutionary conservation scores of residues on protein structures," Nucl Acids Res., 2005, pp W299-W302, vol. 33, Oxford University Press.

(56) References Cited

OTHER PUBLICATIONS

Lanier, L., "NKG2D receptor and its ligands in host defense," HHS Public Access Author Manuscript, Jun. 1, 2016, pp. 1-14, published in final edited form as: Cancer Immunol. Res., Jun. 2015, pp. 575-582, vol. 3, No. 6.

Laskowski, R. et al., "LigPlot+: Multiple Ligand-Protein Interaction Diagrams for Drug Discovery," J. Chem. Inf. Model., 2011, pp. 2778-2786, vol. 51, American Chemical Society.

Lawrence, M. et al., "Shape Complementarity at Protein/Protein Interfaces," J. Mol. Biol., Dec. 20, 1993, pp. 946-950, vol. 234, No. 4.

Lazear, E. et al., "Cowpox virus OMCP antagonizes NKG2D via an unexpected binding orientation," PLoS Pathogens, unpublished, under review 2014, pp. 1-28 with Figs. 1-5 and Supplementary Fig. 1.

Lazear, E. et al., "Crystal Structure of the Cowpox Virus-Encoded NKG2D Ligand OMCP," J. Virol., Jan. 2013, pp. 840-850, vol. 87, No. 2.

Lefkowiiz, E. et al., "Poxvirus Bioinformatics Resource Center: a comprehensive Poxviridae informational and analytical resource," Nucl. Acids Res., 2005, pp. D311-D316, vol. 33, Oxford University Press.

Lenac, T. et al., "The herpesviral Fc receptor fcr-1 down-regulates the NKG2D ligands MULT-1 and H60," J. Exp. Med., Aug. 7, 2006, pp. 1843-1850, vol. 203, No. 8, The Rockefeller University Press.

Letourneau, S. et al., "IL-2/anti-IL-2 antibody complexes show strong biological activity by avoiding interaction with L-2 receptor alpha subunit CD25," PNAS, Feb. 2, 2010, pp. 2171-2176, vol. 107, No. 5.

Levin, A. et al., "Exploiting a natural conformational switch to engineer an Interleukin-2 superkine," HHS Public Access Author Manuscript, available in PMC Oct. 26, 2012, pp. 1-12, published in final form as: Nature, 2012, pp. 529-533, vol. 484, No. 7395.

Li, P. et al., "Crystal Structure of the MHC class I homolog MIC-A, a gammadelta T Cell Ligand," Immunity, May 1999, pp. 577-584, vol. 10, Cell Press.

Li, P. et al., "Crystal Structures of RAE-1 beta and Its Complex with the Activating Immunoreceptor NKG2D," Immunity, Jan. 2002, pp. 77-86, vol. 16, Cell Press.

Li, Y. et al., "Structural and biophysical insights into the role of CD4 and CD8 in T cell activation," Front. Immunol., Jul. 2013, pp. 1-11, vol. 4, No. 206.

Li, Y. et al., "Structural basis for recognition of cellular and viral ligands by NK cell receptors," Front. Immunol., Mar. 2014, pp. 1-20, vol. 5, No. 123.

Li. P. et al., "Complex structure of the activating immunoreceptor NKG2D and its MHC class I-like ligand MICA," Nat. Immunol., May 2001, pp. 443-451, vol. 2, No. 5, Nature Publishing Group.

Lisnic, V. et al., "Modulation of natural killer cell activity by viruses," Curr. Opin. Microbiol., 2010, pp. 530-539, vol. 13.

Liu, K. et al., "Janus kinases in interleukin-2-mediated signaling: JAK1 and JAK3 are differentially regulated by tyrosine phosphorylation," Curr. Biol., 1997, pp. 817-826, vol. 7.

Lodoen, M. et al., "NKG2D-mediated Natural Killer Cell Protection Against Cytomegalovirus Is Impaired by Viral gp40 Modulation of Retinoic Acid Early Inducible 1 Gene Molecules," J. Exp. Med., May 19, 2003, pp. 1245-1253, vol. 197, No. 10, The Rockefeller University Press.

Lodoen, M. et al., "The Cytomegalovirus m155 Gene Product Subverts Natural Killer Cell Antiviral Protection by Disruption of H60-NKG2D Interactions," J. Exp. Med., Oct. 18, 2004, pp. 1075-1081, vol. 200, No. 8, The Rockefeller University Press.

Lundholm, M. et al., "Prostate Tumor-Derived Exosomes Down-Regulate NKG2D Expression on Natural Killer Cells and CD8+ T Cells: Mechanism of Immune Evasion," PLoS One, Sep. 2014, pp. 1-9, vol. 9, No. 9, e108925.

Luteijn, R. et al., "Cowpox Virus Protein CPXV012 Eludes CTLs by Blocking ATP Binding to TAP," J. Immunol., 2014, pp. 1578-1589, vol. 193.

Mancia, F. et al., "Optimization of Protein Production in Mammalian Cells with a Coexpressed Fluorescent Marker," Structure, Aug. 2004, pp. 1355-1360, vol. 12, Elsevier Ltd.

Chinese Application No. 201780022070.9, filed Feb. 6, 2017, Fourth Office Action dated Sep. 2, 2022; 12 pages.

OMCP-mutIL-2, wild-type IL-2, mutIL-2, Saline

OMCP-mutIL-2, wild-type IL-2, mutIL-2, Saline

Lung    Liver
750,000IUe wtIL-2
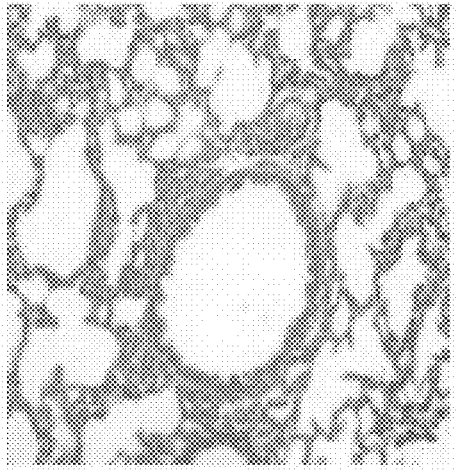 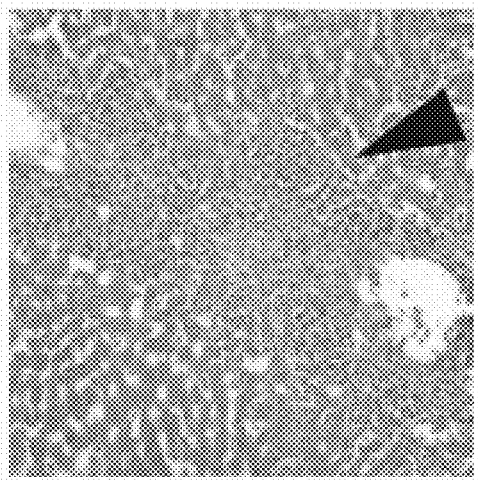
1,500,000IUe wtIL-2
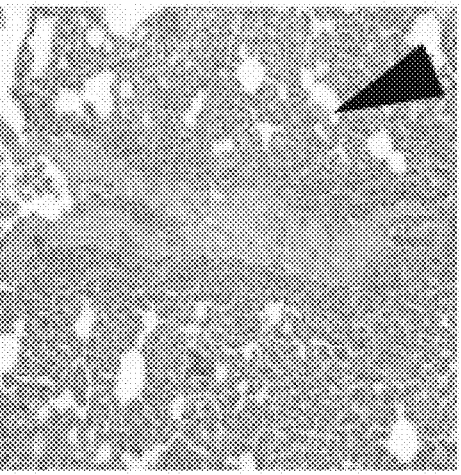 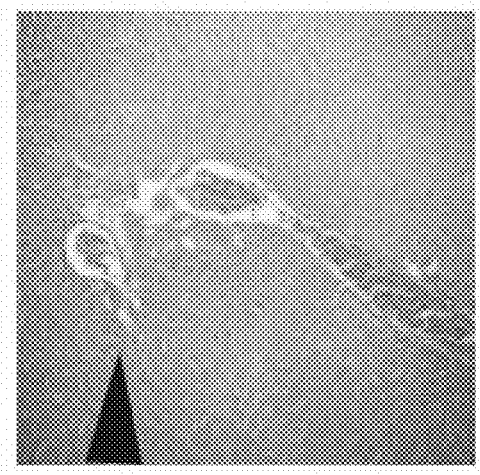
3,500,000IUe wtIL-2
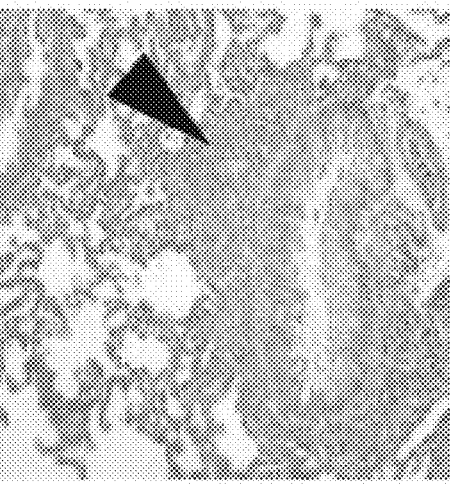 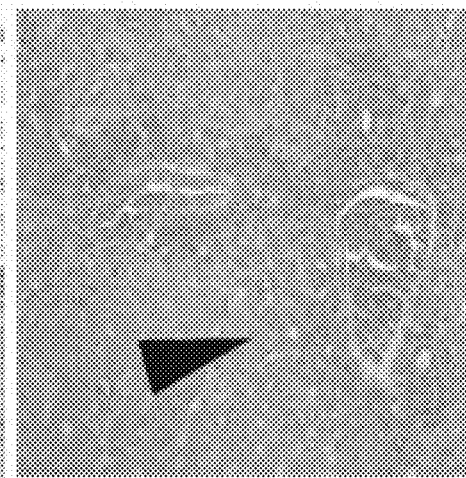
FIG. 2E

FIG. 4C

OMCP-mutIL-2, wtIL-2, mutIL-2

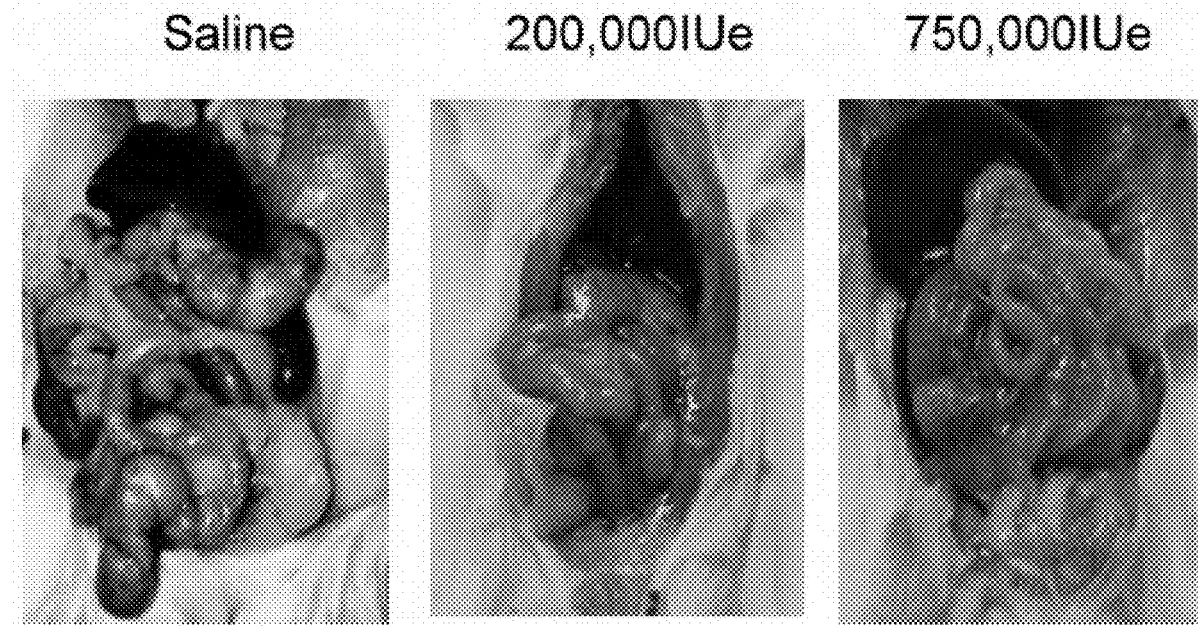
FIG. 7A    FIG. 7B    FIG. 7C
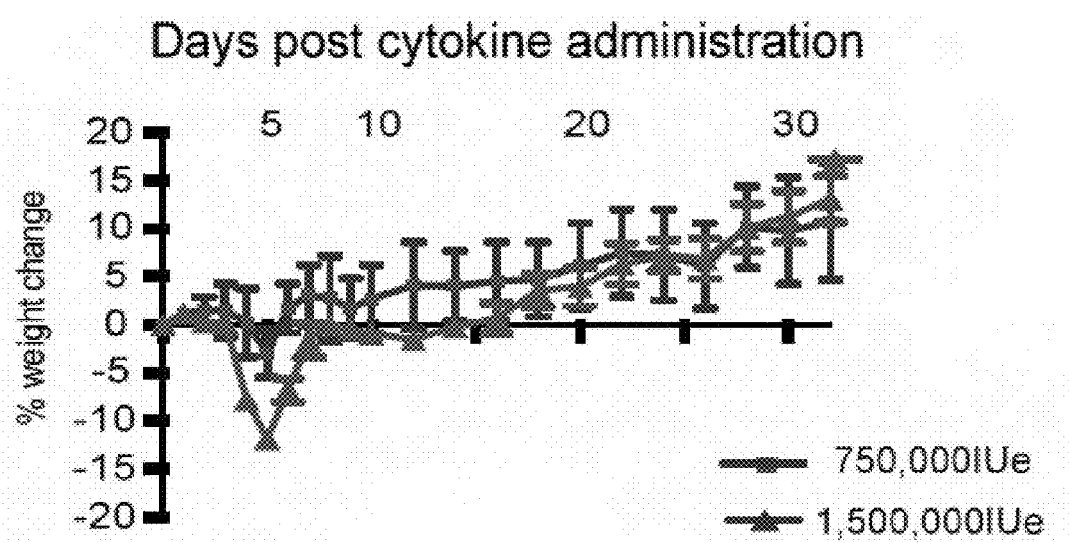
FIG. 7D

Saline, wtIL-2, mutIL-2, OMCP-mutIL-2,

Saline, wtIL-2, mutIL-2, OMCP-mutIL-2, saline, wtIL-2, mutIL-2, OMCP-mutIL-2

1. OMCP Peptide

OMCP helix 2 — Cytokine

2. Pegylation

PEG — OMCP — Cytokine (with PEG chains)

and/or

OMCP — Cytokine (with bi-functional PEG linker +/- PEG)

3. Engineered glycans

OMCP — Cytokine (with N-glycan)

4. Linker length/compositions

OMCP — $((G_4S)_3)$ — Cytokine

OMCP — $((G_2S)_3)$ — Cytokine

OMCP — $((G_2S)_{10})$ — Cytokine

.-etc.

5. Ab - cytokine

Fab specific for NKG2D, etc.

Fab — Cytokine

6. NKG2DL - cytokine

MIC or ULBP — Cytokine

7. Alternate OMCP

OMCP mpx — Cytokine or

Mutant OMCP — Cytokine

Via structure or selection mutagenesis

8. Re-targeting of OMCP

Re-directed OMCP — Cytokine i.e. selection for new immune receptors (NKB2A,C,E...)

9. Viral protein - cytokine

Viral Protein — Cytokine

10. Mutant cytokines

OMCP — Mutated Cytokine

FIG. 23

```
                              SEQUENCE LISTING

<160> NUMBER OF SEQ ID NOS: 34

<210> SEQ ID NO 1
<211> LENGTH: 944
<212> TYPE: DNA
<213> ORGANISM: Artificial Sequence
<220> FEATURE:
<223> OTHER INFORMATION: SYNTHESIZED

<400> SEQUENCE: 1
cacaaactcg cattcaactt caatctagaa ataaatggca gtgatacaca ttctacagta      60
gatgtatatc ttgatgattc tcaaattata acgtttgatg gaaagatat  ccgtccaacc     120 atcccgttca tgataggtga tgaaattttc ttaccgtttt ataaaaatgt gtttagtgag    180
tttttctctc tgtttagaag agttcctaca agtactccat atgaagactt gacatatttt    240
tatgaatgcg actatacaga caataaatct acatttgatc agtttatct  ttataatggc    300 gaagaatata ctgtcaaaac acaggaggcc actaataaaa atatgtggct aactacttcc    360
gagtttagac taaaaaaatg gttcgatggc gaagattgta taatgcatct tagatcgtta    420
gttagaaaaa tggaggacag taaacgaaac actggtggta ccggaagtag cggtagtagt    480
```

```
gattacaagg acgatgacga caagcaccac catcatcatc atcaccacgg tagcagcggc    540
agcagtgccc ccacctctag cagcacaaag aagacccagc tgcaactgga acacctcctg    600
ctggacctgc agatgatcct gaacggcatc aacaactaca agaaccccaa gctgaccgcc    660
atgctgacca aaagttttta catgcccaag aaggccaccg agcttaaaca cctgcaatgc    720
cttgaggagg agctgaagcc ctggaggagg tactgaacct ggcccagagc aagaactttc    780
atctgaggcc cagggacctg attagcaaca tcaacgtgat cgtgttggag ttgaagggca    840
gcgagaccac gttcatgtgc gagtacgccg acgagacggc caccatagtg gagtttctta    900
acaggtggat caccttctca cagtctatca tcagcaccct gacc                     944
```

<210> SEQ ID NO 2
<211> LENGTH: 315
<212> TYPE: PRT
<213> ORGANISM: Artificial Sequence
<220> FEATURE:
<223> OTHER INFORMATION: SYNTHESIZED

<400> SEQUENCE: 2

```
His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
            20                  25                  30

Asp Gly Lys Asp Ile Arg Pro Thr Ile Pro Phe Met Ile Gly Asp Glu
        35                  40                  45

Ile Phe Leu Pro Phe Tyr Lys Asn Val Phe Ser Glu Phe Phe Ser Leu
    50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
        115                 120                 125

Asp Gly Glu Asp Cys Ile Met His Leu Arg Ser Leu Val Arg Lys Met
    130                 135                 140

Glu Asp Ser Lys Arg Asn Thr Gly Gly Thr Gly Ser Ser Gly Ser Ser
145                 150                 155                 160

Asp Tyr Lys Asp Asp Asp Lys His His His His His His
                165                 170                 175

Gly Ser Ser Gly Ser Ser Ala Pro Thr Ser Ser Ser Thr Lys Lys Thr
            180                 185                 190

Gln Leu Gln Leu Glu His Leu Leu Leu Asp Leu Gln Met Ile Leu Asn
        195                 200                 205

Gly Ile Asn Asn Tyr Lys Asn Pro Lys Leu Thr Ala Met Leu Thr Lys
    210                 215                 220

Lys Phe Tyr Met Pro Lys Lys Ala Thr Glu Leu Lys His Leu Gln Cys
225                 230                 235                 240

Leu Glu Glu Glu Leu Lys Pro Leu Glu Glu Val Leu Asn Leu Ala Gln
                245                 250                 255

Ser Lys Asn Phe His Leu Arg Pro Arg Asp Leu Ile Ser Asn Ile Asn
            260                 265                 270

Val Ile Val Leu Glu Leu Lys Gly Ser Glu Thr Thr Phe Met Cys Glu
        275                 280                 285
```

```
Tyr Ala Asp Glu Thr Ala Thr Ile Val Glu Phe Leu Asn Arg Trp Ile
            290                 295                 300

Thr Phe Ser Gln Ser Ile Ile Ser Thr Leu Thr
305                 310                 315

<210> SEQ ID NO 3
<211> LENGTH: 9
<212> TYPE: PRT
<213> ORGANISM: Homo sapiens

<400> SEQUENCE: 3

Ser Val Tyr Asp Phe Phe Val Trp Leu
1               5

<210> SEQ ID NO 4
<211> LENGTH: 8
<212> TYPE: PRT
<213> ORGANISM: Homo sapiens

<400> SEQUENCE: 4

Ser Ile Ile Asn Phe Glu Lys Leu
1               5

<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 6
<211> LENGTH: 133
<212> TYPE: PRT
<213> ORGANISM: Artificial Sequence
<220> FEATURE:
<223> OTHER INFORMATION: SYNTHESIZED

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30
```

Asn Pro Lys Leu Thr Ala Met Leu Thr Lys Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 7
<211> LENGTH: 151
<212> TYPE: PRT
<213> ORGANISM: Artificial Sequence
<220> FEATURE:
<223> OTHER INFORMATION: SYNTHESIZED

<400> SEQUENCE: 7

His Lys Leu Ala Phe Asn Phe Asn Leu Glu Ile Asn Gly Ser Asp Thr
  1               5                  10                  15

His Ser Thr Val Asp Val Tyr Leu Asp Asp Ser Gln Ile Ile Thr Phe
                20                  25                  30

Asp Gly Lys Asp Ile Arg Pro Thr Ile Pro Phe Met Ile Gly Asp Glu
            35                  40                  45

Ile Phe Leu Pro Phe Tyr Lys Asn Val Phe Ser Glu Phe Phe Ser Leu
 50                  55                  60

Phe Arg Arg Val Pro Thr Ser Thr Pro Tyr Glu Asp Leu Thr Tyr Phe
 65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
            115                 120                 125

Asp Gly Glu Asp Cys Ile Met His Leu Arg Ser Leu Val Arg Lys Met
130                 135                 140

Glu Asp Ser Lys Arg Asn Thr
145                 150

<210> SEQ ID NO 8
<211> LENGTH: 28
<212> TYPE: PRT
<213> ORGANISM: Artificial Sequence
<220> FEATURE:
<223> OTHER INFORMATION: SYNTHESIZED

<400> SEQUENCE: 8

Gly Ser Ser Gly Ser Ser Asp Tyr Lys Asp Asp Asp Lys His His
  1               5                  10                  15

His His His His His Gly Ser Ser Gly Ser Ser
                20                  25

-continued

```
<210> SEQ ID NO 9
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 9

Asp Tyr Lys Asp Asp Asp Lys
1               5

<210> SEQ ID NO 10
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 10

Tyr Pro Tyr Asp Val Pro Asp Tyr Ala
1               5

<210> SEQ ID NO 11
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 11

Glu Gln Lys Leu Ile Ser Glu Glu Asp Leu
1               5                   10

<210> SEQ ID NO 12
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 12

Gly Lys Pro Ile Pro Asn Pro Leu Leu Gly Leu Asp Ser Thr
1               5                   10

<210> SEQ ID NO 13
<211> LENGTH: 150
<212> TYPE: PRT
<213> ORGANISM: Cowpox virus

<400> SEQUENCE: 13

Gly His Lys Leu Ala Phe Asn Phe Asn Leu Glu Ile Asn Gly Ser Asp
1               5                   10                  15

Thr His Ser Thr Val Asp Val Tyr Leu Asp Asp Ser Gln Ile Ile Thr
                20                  25                  30

Phe Asp Gly Lys Asp Ile Arg Pro Thr Ile Pro Phe Met Ile Gly Asp
            35                  40                  45

Glu Ile Phe Leu Pro Phe Tyr Lys Asn Val Phe Ser Glu Phe Phe Ser
        50                  55                  60

Leu Phe Arg Arg Val Pro Thr Ser Thr Pro Tyr Glu Asp Leu Thr Tyr
65                  70                  75                  80

Phe Tyr Glu Cys Asp Tyr Thr Asp Asn Lys Ser Thr Phe Asp Gln Phe
                85                  90                  95

Tyr Leu Tyr Asn Gly Glu Glu Tyr Thr Val Lys Thr Gln Glu Ala Thr
            100                 105                 110
```

Asn Lys Asn Met Trp Leu Thr Thr Ser Glu Phe Arg Leu Lys Lys Trp
            115                 120                 125

Phe Asp Gly Glu Asp Cys Ile Met His Leu Arg Ser Leu Val Arg Lys
130                 135                 140

Met Glu Asp Ser Lys Arg
145                 150

<210> SEQ ID NO 14
<211> LENGTH: 150
<212> TYPE: PRT
<213> ORGANISM: Monkeypox virus

<400> SEQUENCE: 14

His Lys Leu Val His Tyr Phe Asn Leu Lys Ile Asn Gly Ser Asp Ile
1               5                   10                  15

Thr Asn Thr Ala Asp Ile Leu Leu Asp Asn Tyr Pro Ile Met Thr Phe
            20                  25                  30

Asp Gly Lys Asp Ile Tyr Pro Ser Ile Ala Phe Met Val Gly Asn Lys
        35                  40                  45

Leu Phe Leu Asp Leu Tyr Lys Asn Ile Phe Val Glu Phe Arg Leu
50                  55                  60

Phe Arg Val Ser Val Ser Ser Gln Tyr Glu Glu Leu Glu Tyr Tyr Tyr
65                  70                  75                  80

Ser Cys Asp Tyr Thr Asn Asn Arg Pro Thr Ile Lys Gln His Tyr Phe
                85                  90                  95

Tyr Asn Gly Glu Glu Tyr Thr Glu Ile Asp Arg Ser Lys Lys Ala Thr
            100                 105                 110

Asn Lys Asn Ser Trp Leu Ile Thr Ser Gly Phe Arg Leu Gln Lys Trp
            115                 120                 125

Phe Asp Ser Glu Asp Cys Ile Ile Tyr Leu Arg Ser Leu Val Arg Arg
130                 135                 140

Met Glu Asp Ser Asn Lys
145                 150

<210> SEQ ID NO 15
<211> LENGTH: 181
<212> TYPE: PRT
<213> ORGANISM: Homo sapiens

<400> SEQUENCE: 15

Met Glu Pro His Ser Leu Arg Tyr Asn Leu Thr Val Leu Ser Trp Asp
1               5                   10                  15

Gly Ser Val Gln Ser Gly Phe Leu Thr Glu Val His Leu Asp Gly Gln
            20                  25                  30

Pro Phe Leu Arg Cys Arg Asp Arg Gln Lys Cys Arg Ala Lys Pro Gln
        35                  40                  45

Gly Gln Trp Ala Glu Asp Val Leu Gly Asn Lys Thr Trp Asp Arg Glu
    50                  55                  60

Thr Arg Asp Leu Thr Gly Asn Gly Lys Asp Leu Arg Met Thr Leu Ala
65                  70                  75                  80

His Ile Lys Asp Gln Lys Glu Gly Leu His Ser Leu Gln Glu Ile Arg
                85                  90                  95

Val Cys Glu Ile His Glu Asp Asn Ser Thr Arg Ser Ser Gln His Phe
            100                 105                 110

Tyr Tyr Asp Gly Glu Leu Phe Leu Ser Gln Asn Leu Glu Thr Lys Glu
            115                 120                 125

Trp Thr Met Pro Gln Ser Ser Arg Ala Gln Thr Leu Ala Met Asn Val
130                 135                 140

Arg Asn Phe Leu Lys Glu Asp Ala Met Lys Thr Lys Thr His Tyr His
145                 150                 155                 160

Ala Met His Ala Asp Cys Leu Gln Glu Leu Arg Arg Tyr Leu Lys Ser
                165                 170                 175

Gly Val Val Leu Arg
            180

<210> SEQ ID NO 16
<211> LENGTH: 180
<212> TYPE: PRT
<213> ORGANISM: Homo sapiens

<400> SEQUENCE: 16

Met Glu Pro His Ser Leu Arg Tyr Asn Leu Met Val Leu Ser Gln Asp
1               5                   10                  15

Gly Ser Val Gln Ser Gly Phe Leu Ala Glu Gly His Leu Asp Gly Gln
                20                  25                  30

Pro Phe Leu Arg Tyr Asp Arg Gln Lys Arg Arg Ala Lys Pro Gln Gly
            35                  40                  45

Gln Trp Ala Glu Asp Val Leu Gly Ala Glu Thr Trp Asp Thr Glu Thr
50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asn Gly Glu Leu Phe Leu Ser Gln Asn Leu Glu Thr Gln Glu Ser
            115                 120                 125

Thr Val Pro Gln Ser Ser Arg Ala Gln Thr Leu Ala Met Asn Val Thr
130                 135                 140

Asn Phe Trp Lys Glu Asp Ala Met Lys Thr Lys Thr His Tyr Arg Ala
145                 150                 155                 160

Met Gln Ala Asp Cys Leu Gln Lys Leu Gln Arg Tyr Leu Lys Ser Gly
                165                 170                 175

Val Ala Ile Arg
            180

<210> SEQ ID NO 17
<211> LENGTH: 178
<212> TYPE: PRT
<213> ORGANISM: Homo sapiens

<400> SEQUENCE: 17

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
                20                  25                  30

Phe Leu Ser Tyr Asp Cys Gly Ser Asp Lys Val Leu Ser Met Gly His
            35                  40                  45

Leu Glu Glu Gln Leu Tyr Ala Thr Asp Ala Trp Gly Lys Gln Leu Glu
50                  55                  60

Met Leu Arg Glu Val Gly Gln Arg Leu Arg Leu Glu Leu Ala Asp Thr
65                  70                  75                  80

```
Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Phe Asp Ser Asn Asn Arg
        115                 120                 125

Lys Trp Thr Val Val His Ala Gly Ala Arg Arg Met Lys Glu Lys Trp
        130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu
```

```
<210> SEQ ID NO 18
<211> LENGTH: 174
<212> TYPE: PRT
<213> ORGANISM: Homo sapiens

<400> SEQUENCE: 18
```

```
Asp Ala His Ser Leu Arg Cys Asn Leu Thr Ile Lys Asp Pro Thr Pro
1               5                   10                  15

Ala Asp Pro Leu Trp Tyr Glu Ala Lys Cys Phe Val Gly Glu Ile Leu
            20                  25                  30

Ile Leu His Leu Ser Asn Ile Asn Lys Thr Met Thr Ser Gly Asp Pro
        35                  40                  45

Gly Glu Thr Ala Asn Ala Thr Glu Val Lys Lys Cys Leu Thr Gln Pro
    50                  55                  60

Leu Lys Asn Leu Cys Gln Lys Leu Arg Asn Lys Val Ser Asn Thr Lys
65                  70                  75                  80

Val Asp Thr His Lys Thr Asn Gly Tyr Pro His Leu Gln Val Thr Met
                85                  90                  95

Ile Tyr Pro Gln Ser Gln Gly Arg Thr Pro Ser Ala Thr Trp Glu Phe
            100                 105                 110

Asn Ile Ser Asp Ser Tyr Phe Phe Thr Phe Tyr Thr Glu Asn Met Ser
        115                 120                 125

Trp Arg Ser Ala Asn Asp Glu Ser Gly Val Ile Met Asn Lys Trp Lys
    130                 135                 140

Asp Asp Gly Glu Phe Val Lys Gln Leu Lys Phe Leu Ile His Glu Cys
145                 150                 155                 160

Ser Gln Lys Met Asp Glu Phe Leu Lys Gln Ser Lys Glu Lys
                165                 170
```

```
<210> SEQ ID NO 19
<211> LENGTH: 16
<212> TYPE: PRT
<213> ORGANISM: Homo sapiens

<400> SEQUENCE: 19
```

```
Leu Thr Ile Ile Glu Met Gln Lys Gly Asp Cys Ala Leu Tyr Ala Ser
1               5                   10                  15
```

```
<210> SEQ ID NO 20
<211> LENGTH: 16
<212> TYPE: PRT
<213> ORGANISM: Chlorocebus sabaeus
```

```
<400> SEQUENCE: 20

Leu Thr Ile Ile Glu Met Gln Lys Gly Glu Cys Ala Leu Tyr Ala Ser
1               5                   10                  15

<210> SEQ ID NO 21
<211> LENGTH: 16
<212> TYPE: PRT
<213> ORGANISM: Callithrix jacchus

<400> SEQUENCE: 21

Leu Thr Ile Ile Glu Met Gln Lys Gly Asp Cys Ala Val Tyr Ala Ser
1               5                   10                  15

<210> SEQ ID NO 22
<211> LENGTH: 16
<212> TYPE: PRT
<213> ORGANISM: Mus musculus

<400> SEQUENCE: 22

Leu Thr Leu Val Glu Ile Pro Lys Gly Ser Cys Ala Val Tyr Gly Ser
1               5                   10                  15

<210> SEQ ID NO 23
<211> LENGTH: 16
<212> TYPE: PRT
<213> ORGANISM: Rattus norvegicus

<400> SEQUENCE: 23

Leu Thr Leu Val Lys Thr Pro Ser Gly Thr Cys Ala Val Tyr Gly Ser
1               5                   10                  15

<210> SEQ ID NO 24
<211> LENGTH: 16
<212> TYPE: PRT
<213> ORGANISM: Cavia porcellus

<400> SEQUENCE: 24

Leu Thr Leu Met Asp Thr Gln Asn Gly Lys Cys Ala Leu Tyr Gly Ser
1               5                   10                  15

<210> SEQ ID NO 25
<211> LENGTH: 16
<212> TYPE: PRT
<213> ORGANISM: Spermophilus sensu stricto

<400> SEQUENCE: 25

Leu Thr Leu Val Glu Met Gln Asn Gly Thr Cys Ile Val Tyr Gly Ser
1               5                   10                  15

<210> SEQ ID NO 26
<211> LENGTH: 16
<212> TYPE: PRT
<213> ORGANISM: Peromyscus maniculatus

<400> SEQUENCE: 26

Leu Thr Val Val Glu Met Gln Ser Gly Ser Cys Ala Val Tyr Gly Ser
1               5                   10                  15

<210> SEQ ID NO 27
<211> LENGTH: 16
<212> TYPE: PRT
<213> ORGANISM: Heterocephalus glaber
```

```
<400> SEQUENCE: 27

Leu Ser Met Val Glu Met Gln Asn Gly Thr Cys Ala Val Tyr Ala Ser
1               5                   10                  15

<210> SEQ ID NO 28
<211> LENGTH: 16
<212> TYPE: PRT
<213> ORGANISM: Microtus ochrogaster

<400> SEQUENCE: 28

Leu Thr Leu Val Glu Met Gln Arg Gly Ser Cys Ala Val Tyr Gly Ser
1               5                   10                  15

<210> SEQ ID NO 29
<211> LENGTH: 16
<212> TYPE: PRT
<213> ORGANISM: Sorex araneus

<400> SEQUENCE: 29

Val Ser Ile Val Glu Met Gln Gly Gly Asn Cys Ala Val Tyr Gly Ser
1               5                   10                  15

<210> SEQ ID NO 30
<211> LENGTH: 16
<212> TYPE: PRT
<213> ORGANISM: Condylura cristata

<400> SEQUENCE: 30

Val Thr Val Tyr Glu Met Gln Asn Gly Ser Cys Ala Val Tyr Gly Ser
1               5                   10                  15

<210> SEQ ID NO 31
<211> LENGTH: 16
<212> TYPE: PRT
<213> ORGANISM: Cricetulus griseus

<400> SEQUENCE: 31

Leu Thr Leu Val Glu Met Gln Asn Gly Ser Cys Ala Val Tyr Gly Ser
1               5                   10                  15

<210> SEQ ID NO 32
<211> LENGTH: 16
<212> TYPE: PRT
<213> ORGANISM: Felis catus

<400> SEQUENCE: 32

Leu Thr Met Val Asp Met Gln Asn Gly Thr Cys Ala Val Tyr Gly Ser
1               5                   10                  15

<210> SEQ ID NO 33
<211> LENGTH: 5
<212> TYPE: PRT
<213> ORGANISM: Cowpox virus

<400> SEQUENCE: 33

Ala Ser Ser Phe Lys
1               5

<210> SEQ ID NO 34
<211> LENGTH: 4
<212> TYPE: PRT
<213> ORGANISM: Artificial Sequence
```

```
<220> FEATURE:
<223> OTHER INFORMATION: SYNTHESIZED

<400> SEQUENCE: 34

Tyr Ile Asn Met
1
```

COMPOSITIONS AND METHODS FOR TARGETED CYTOKINE DELIVERY

CROSS REFERENCE TO RELATED APPLICATIONS

This application claims the benefit of U.S. application Ser. No. 15/536,580, filed Jun. 15, 2017 which claims the benefit of PCT Application PCT/US2015/065872, filed Dec. 15, 2015, which claims the benefit of U.S. Provisional Application No. 62/243,829, filed Oct. 20, 2015 and U.S. Provisional Application No. 62/091,898, filed Dec. 15, 2014, each of the disclosures of which is hereby incorporated by reference in its entirety.

GOVERNMENTAL RIGHTS

This invention was made with government support under A1073552, HHSN27220070058C, and HL113931 awarded by the National Institutes of Health. The government has certain rights in the invention.

FIELD OF THE INVENTION

The present disclosure encompasses compositions and methods for targeted cytokine delivery. Through specific delivery of cytokines, the compositions disclosed herein may improve immunotherapy by limiting side effects associated with immunotherapy.

BACKGROUND OF THE INVENTION

Systemic administration of high dose interleukin 2 (IL2) is one of the most potent forms of immunotherapy and is currently approved by the FDA for treatment of several malignancies. Efficacy of this treatment depends on activating cytotoxic lymphocytes (CTLs) such as natural killer cells (NK) and CD8+ T lymphocytes (CD8+ CTLs). Clinical trials have demonstrated approximately 15% partial or complete tumor responses, with up to 5% of patients having a durable long-lasting response resembling a cure. Despite these encouraging results in a minority of patients, most do not achieve a benefit or stop IL2 therapy prematurely due to complications such as blood pressure changes and pulmonary or systemic capillary leak. It is thought that the direct action of IL2 on vascular endothelium contributes to the majority of these side effects. The efficacy of IL2 is also limited by preferential activation of CD4+Foxp3+ regulatory T cells ($T_{regs}$), which decrease the tumor immune response. For these reasons treatment with high-dose IL2 has fallen out of favor clinically.

Side effects and deceased efficacy of IL2 therapy occur due to the high affinity trimeric αβγ IL2 receptor (IL2R), which is expressed by vascular endothelial cells and $T_{regs}$ at baseline. Thus CD4+Foxp3+ $T_{regs}$ and vascular endothelium are activated at much lower doses of IL2 than NK cells, which express the lower affinity βγ chains of the IL2R at rest. NK cells do express the high affinity α chain of IL2R after activation and depend on this trimeric receptor for peak cytolytic capacity. Mutant forms of IL2 with decreased affinity for IL2Rα have been described and offer a more favorable side effect profile. However, they also result in lower efficacy and decreased therapeutic potential due to decreased CTL activation. Therefore, there is a need in the art for a form of IL2 that could preferentially bind to and activate CTLs without activating $T_{regs}$ and endothelial cells. Such an IL2 derivative might overcome such clinical barriers and result in more efficacious immunotherapy with fewer side effects.

SUMMARY OF THE INVENTION

In an aspect the disclosure provides, a composition comprising a cytokine linked to a ligand, wherein the ligand is not a corresponding binding partner to the cytokine.

In another aspect, the disclosure provides a method to deliver a cytokine to a target cell comprising contacting a target cell with a composition comprising a cytokine linked to a ligand. The ligand specifically binds to a receptor on the target cell and the ligand is not a corresponding binding partner to the cytokine.

In still another aspect, the disclosure provides a method to activate immune cells comprising contacting an immune cell with a composition comprising a proinflammatory cytokine linked to a ligand. The ligand specifically binds to a receptor on the immune cell thereby activating the cell and the ligand is not a corresponding binding partner to the cytokine.

In still yet another aspect, the disclosure provides a method to treat a tumor comprising identifying a subject with a tumor and administering to the subject a therapeutically effective amount of a composition comprising a proinflammatory cytokine linked to a ligand. The ligand specifically binds to a receptor on a target cell and the ligand is not a corresponding binding partner to the cytokine.

In a different aspect, the disclosure provides a method to treat a viral infection comprising administering to the subject a therapeutically effective amount of a composition comprising a proinflammatory cytokine linked to a ligand. The ligand specifically binds to a receptor on a target cell and the ligand is not a corresponding binding partner to the cytokine.

In other aspects, the disclosure provides a chimeric peptide comprising a cytokine peptide and a ligand peptide. The cytokine peptide is not a binding partner of the ligand peptide.

In certain aspects, the disclosure provides a chimeric peptide comprising a cytokine peptide and a ligand peptide. The ligand peptide binds to an NKG2D receptor.

In another different aspect, the disclosure provides a nucleic acid molecule comprising a sequence encoding a chimeric peptide of the disclosure.

In yet another different aspect, the disclosure provides a pharmaceutical composition comprising a chimeric peptide of the disclosure.

In still yet another different aspect, the disclosure provides a method of treating a subject diagnosed with cancer comprising administering to the subject a pharmaceutical composition of the disclosure.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Schematic structure of OMCP-mutIL-2. (FIG. 1B) Molecular weight of OMCP-mutIL-2 compared to mutIL-2 and wild-type IL-2. IL-2, mutIL-2, and OMCP-mutIL-2 were produced in mammalian cells and have higher molecular weights due to glycosylation. The lower migrating band for mutIL-2 corresponds to unglycosylated protein, likely due to lysis of the producing cells. Based on differences in molecular weight all cytokines and construct were administered on a molar basis with 1 µl of 4.4 µM solution defined as 1000 IU equivalents (IUe) herein. This effectively allows for equimolar comparison between IL-2, mutIL-2 and OMCP-mutIL-2 despite different molecular weights. (FIG. 1C, FIG. 1D) In vitro activation of A/J lymphocyte subsets after 36 hours of culture in 100 IUe of cytokines or OMCP-mutIL-2 construct. (FIG. 1E, FIG. 1F) Proliferation of B6 lymphocyte subsets after 5-day culture in 1000 IUe/ml of cytokines or OMCP-mutIL-2 construct. Graphs representative of 3-6 replicates per condition. black=saline; blue=wtIL-2, red=OMCP-mutIL-2, green=mutIL-2.

FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N and FIG. 2O depict graphs and images showing in vivo dosing of IL-2 and IL-2 constructs. Animal mortality (FIG. 2A) and morbidity assessed by weight loss (FIG. 2B) accumulation of ascites and pleural fluid (representative syringe-FIG. 2C; average from all mice in the group-FIG. 2D) and (FIG. 2E) organ inflammation after administration of wtIL-2. Animal mortality (FIG. 2F, FIG. 2H, FIG. 2J) and morbidity as assessed by weight loss (FIG. 2G, FIG. 2I, FIG. 2K) after administration of high dose wtIL-2 (FIG. 2F, FIG. 2G), OMCP-mutIL-2 (FIG. 2H, FIG. 2I) and mutIL-2 (FIG. 2J, FIG. 2K) in anti-AsialoGM1 (solid line) or rabbit IgG-treated (dotted line) in A/J mice. Weight loss (FIG. 2L), ascites (representative syringe-FIG. 2M; average from all mice in the group-FIG. 2N) and organ inflammation (FIG. 2O) in mice treated with 200,000 IUe of either wt IL-2, OMCP-mutIL-2 or mutIL-2. All graphs represent 46 animals per treatment condition. ns p>0.05; * p<0.05;  p<0.01; * p<0.001; black=saline; blue=wtIL-2, red=OMCP-mutIL-2, green=mutIL-2.

(FIG. 3A, FIG. 3B) Total splenocyte counts after a five-day course of 200,000 IUe of IL-2 (blue), mutIL-2 (green) and OMCP-mutIL-2 (red). (FIG. 3C) NK cell expansion and activation after IL-2, mutIL-2, OMCP-mutIL-2, high dose IL-2, high dose mutIL-2 and IL-2/anti-IL-2 complexes measured by cell counts in the spleen (top) and KLRG1 upregulation (bottom). (FIG. 3D) CD4$^+$Foxp3$^+$T$_{reg}$ expansion and activation as measured by cell counts in the spleen (top) and ICOS upregulation (bottom) as well as (FIG. 3E) NK/T$_{reg}$ ratio in the spleen. Expansion of splenocytes (FIG. 3F, FIG. 3G) and NK cells (FIG. 3H) in B6 mice treated with 750,000 IUe of cytokine or construct. T$_{reg}$ expansion and activation (FIG. 3I) as well as NK:T$_{reg}$ ratio (FIG. 3J) in the spleen of B6 mice. All graphs represent an average cell count±SEM from 5-10 mice per group. ns p>0.05; * p<0.05;  p<0.01; *p<0.001; black=saline; blue=wtIL-2, red=OMCP-mutIL-2, green=mutIL-2.

FIG. 4A, FIG. 4B, FIG. 4C, FIG. 4D and FIG. 4E depict graphs and images showing cytokine-mediated tumor immunotherapy. (FIG. 4A) In vivo cytotoxicity for YAC-1 lymphoma after intravenous injection. (FIG. 4B, FIG. 4C) LLC tumor growth after a five-day course of 750,000 IUe of cytokine treatment given as ten doses on days 5-10 post tumor injection. LLC tumor growth in mice depleted on NK cells (FIG. 4D) or mutant mice deficient in NKG2D (FIG. 4E). Data represents 5-6 mice per group. ns p>0.05; * p<0.05;  p<0.01; * p<0.001; black=saline; blue=wtIL-2, red=OMCP-mutIL-2, green=mutIL-2.

(FIG. 5A, FIG. 5B) Serum levels after injection of 1×10$^6$ IUe of fluorochrome-labeled cytokine or construct i.v. (FIG. 5C) Degranulation of NK cells in the presence of cytokines and pentameric OMCP-mediated crosslinking of NKG2D as measured by surface CD107a expression at 1000 IUe/ml. STAT5 phosphorylation in isolated NK cells from A/J (FIG. 5D) or B6 mice (FIG. 5E) by increasing doses of cytokine. Decay in STAT5 phosphorylation after a 15 minute stimulation by 1000 IUe/ml (FIG. 5F) or 100 IUe/ml (FIG. 5G) of IL-2 or OMCP-mutIL-2. (FIG. 5H) Proposed model of competition between NK cells and stromal cells for IL-2. (FIG. 5I) STAT5 phosphorylation of B6 NK cells in the presence of other splenocytes by wtIL-2 and OMCP-mutIL-2. (FIG. 5J) STAT5 phosphorylation of wild-type or NKG2D$^{-/-}$ NK cells by wtIL-2 and OMCP-mutIL-2 in the presence of competing splenocytes. (FIG. 5K) STAT5 phosphorylation, as measured by fold change over saline-treated controls, of wild-type NK cells in the presence of competing splenocytes treated with saturating concentrations of rat anti-mouse CD25 (clone 3C7) or rat IgG isotype control.

FIG. 7A, FIG. 7B and FIG. 7C depict imaging showing that inspection of the viscera demonstrates limited food consumption after a 5-day course of 200,000 or 750,000 IUe of wtIL-2. FIG. 7D depicts a graph showing that unlike the A/J strain, B6 mice are able to tolerate higher doses of wtIL-2 with only moderate weight loss after 750,000 IUe. Higher doses of 1,500,000 IUe IL-2 resulted in increased weight loss. Doses above this regimen led to animal death.

(FIG. 11A) Regular wild-type IL2 preferentially binds to cells such as CD4$^+$Foxp3$^+$T$_{regs}$ and vascular endothelium, both of which express the high affinity α chain along with the signaling 13 and γ chains of the IL2 receptor. (FIG. 11B) The R38A and F42K mutations in IL2 decrease affinity for the α chain of the IL2 receptor. (FIG. 11C) By linking R38A/F42K IL2 to the high affinity NKG2D ligand OMCP delivery and binding of this cytokine to NKG2D-expressing CTLs such as NK cells and activated CD8$^+$ T cells is increased. Width of arrows indicates proposed strength of IL2 binding and/or signaling.

(FIG. 14A) AJ and 129 mouse strains are susceptible to lung cancer as evidenced by tumor burden whereas B6 and C3H mouse strains are resistant to lung cancer as evidenced by tumor burden. (FIG. 14B) Upon incubation with freshly isolated NK cells from the various mouse strains, B6 and C3H NK cells result in significantly more LM2 lung carcinoma cell lysis than AJ and 129 NK cells.

(FIG. 17A) DX5+CD3− NK cell; (FIG. 17B) CD4+CD3+ T cells; (FIG. 17C) CD8+ CD3+ T cells; (FIG. 17D) CD11C+ CD11b− DCs; (FIG. 17E) CD11c−CD11 b+ Macs; (FIG. 17F) CD19+CD3− B cells.

(FIG. 20A) Ribbon diagram of CPXV OMCP. Secondary structure elements are noted, S for beta strands and H for helix. The α1/α2 portions of the platform domain are indicated in cyan and magenta, respectively. (FIG. 20B) Ribbon diagram of the α1/α2 domain of MICA (PDB identifier 1HYR), with the α3 domain removed for clarity. Residues that contact NKG2D are colored yellow. (FIG. 20C) Structure alignment of OMCP with NKG2DLs. The mature sequences of OMCP$_{BR}$ (CPXV-BR-018; GenBank accession number NP_619807; PDB identifier 4FFE) and OMCP$_{MPX}$ (MPXV-ZAR_1979_005-198; N3R; GenBank accession number AAY97396) are aligned with the ectodomain sequences of MICA (1HYR), MICB (1JE6), ULBP3 (1KCG), and RAE-1β (1JFM). Known NKG2D contact residues for NKG2DLs are indicated in yellow. Asn residues likely to be glycosylated are noted by black boxes in panel C and as black side chains in panels A and B. OMCPbr=SEQ ID NO:13; OMCPmpx=SEQ ID NO:14; MICA=SEQ ID NO:15; MICB=SEQ ID NO:16; ULBP3=SEQ ID NO:17; and RAE-1B=SEQ ID NO:18

FIG. 23 depicts various embodiments of the invention. 1. depicts OMCP helix 2 linked to cytokine. 2. depicts pegylation of the composition. 3. depicts a composition comprising engineered glycans. 4. depicts various linker lengths and compositions. 5. depicts an antibody linked to a cytokine. For example a Fab specific NKG2D antibody. 6. depicts a NKG2DL linked to a cytokine. For example, MIC or ULBP. 7 depicts an alternative OMCP linked to a cytokine. For example, OMCP$_{mpx}$ could represent a preferred variant of OMCP, and mutant OMCP could represent either a gain or loss of function for NKG2D binding. 8. depicts re-targeting of the OMCP in a composition. For example, a mutant OMCP may be directed to NKG2A, NKG2C, NKG2E, etc. 9. depicts other viral protein liked to a cytokine. For example, the other viral protein may also bind to receptors on immune cells. 10. depicts OMCP linked to mutant cytokines. It is understood that the OMCP sequence could be from various sources such as cowpox or monkeypox. Also, Fc-chimeras of OMCP and IL2, and variants thereof may be used.

(FIG. 24A) OMCP bound to NKG2D. OMCP is colored magenta and the protomers of NKG2D are colored cyan ("A") and yellow ("B"). NKG2D$^A$ makes contacts primarily with the H2a helix and NKG2D$^B$ with H2b. Mutations introduced to facilitate alternate crystal packing are shown in red. The S193-S194 bond is shown as a ball on each NKG2D protomer. The asparagines of putative hNKG2D glycosylation sites are shown in orange. The asparagine of the confirmed N-glycan site of OMCP is shown green (data not shown) (FIG. 24B) View of the interface between OMCP-NKG2D. The α2 domain of OMCP is shown in the front with the α1 domain behind. OMCP and NKG2D are shown with cartoon representations for the main chain, with the side chains of contact residues shown as sticks. Hydrogen bonds and salt bridges are indicated with green dotted lines.

(FIG. 25A) The local environment of the OMCP-NKG2D binding interface surrounding the D132R residue. The D132R mutation ablates OMCP-NKG2D binding. (FIG. 25B) A representative experiment for binding of WT and (D132R) OMCP to NKG2D by SPR. 100 nM of OMCP or (D132R) OMCP were injected at 50 μl/min over flowcells containing immobilized biotinylated murine NKG2D. (FIG. 25C) Ba/F3 cells transduced with NKG2D, FCRL5, or empty vector were stained with OMCP tetramers (solid line), D132R tetramers (dashed line), or WNV DIII tetramer control (gray histogram). Representative results from three independent experiments.

(FIG. 26A, FIG. 26B) Superimposition of mNKG2D (grey) (PDB ID: 1HQ8) with the structure of OMCP-hNKG2D (yellow and cyan). Core binding residues Y152 (Y168) and Y199 (Y215) are positionally conserved, while core binding residue M184 (I200) is not. (FIG. 26C) Surface representation of OMCP (magenta) interacting with the β5'-β5 loop. (FIG. 26D) Conservation of M184 and Q185. Only the NKG2D of mice, rats, guinea pigs, and flying foxes (not shown) differ. Conservation score is as computed by the ConSurf server. Human, organgutan, chimpanzee, gibbon, macaque-SEQ ID NO:19; Green monkey-SEQ ID NO:20; Marmoset-SEQ ID NO:21; Mouse-SEQ ID NO:22; Rat-SEQ ID NO:23; Guinea pig-SEQ ID NO:24; Ground squirrel-SEQ ID NO:25; Deer mouse-SEQ ID NO:26; Naked mole rat-SEQ ID NO:27; Prairie vole-SEQ ID NO:28; European shrew-SEQ ID NO:29; Star-nosed mole-SEQ ID NO:30; Chinese hamster-SEQ ID NO:31; Cat-SEQ ID NO:32.

(FIG. 28E) IL-2-activated splenocytes were used as cytotoxic effectors against stably transduced Ba/F3 cell lines. Splenocytes were activated with 200 U/ml of IL-2 for 24 hours. Labeled target cells were co-incubated with activated splenocytes for 4 hours at effector:target ratios of 10:1, 20:1, and 40:1. Killing was measured by incorporation of 7AAD by CFSE-labeled target cells using flow cytometry. Representative data from five independent experiments is shown FIG. 29A and FIG. 29B depict the electron density supporting a cis peptide conformation. Stereo view of the β5-β6 loop of hNKG2D. Residues 193-Ala-Ser-Ser-Phe-Lys-197 (SEQ ID NO:33) is displayed for the OMCP-hNKG2D structure (yellow) and the structure of hNKG2D alone (grey). The 2Fo-Fc map for OMCP-hNKG2D is displayed at 2a.

FIG. 31A shows that a relatively higher proportion of NK cells was evident in the OMCP-mutant IL2 group. FIG. 31B shows that perforin levels were higher in OMCP-mutant IL2 treated NK cells (red) compared to saline (black), IL2 (blue) or mutant IL2 (green) treated ones. FIG. 31C shows that similar to NK cells, higher intracellular levels of perforin were evident in CD8+ T cells treated with OMCP-mutant IL2 compared to other conditions. FIG. 31D shows that when gating on CD4+Foxp3+ CD45RA− T cells a relatively higher proportion of activated CD25+CD127− regulatory T cells was evident in IL2 treated peripheral blood lymphocyte cultures compared to other conditions.

DETAILED DESCRIPTION OF THE INVENTION

Figure 1A:
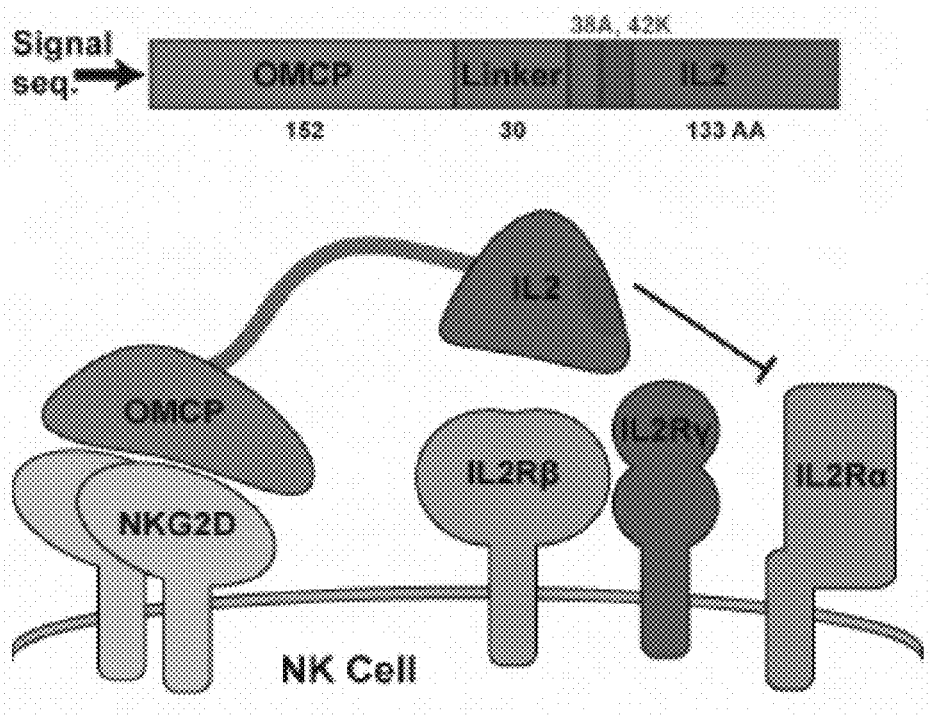
FIG. 1A, FIG. 1B, FIG. 1C, FIG. 1D, FIG. 1E and FIG. 1F depict a diagram, immunoblot and graphs showing the generation and in vitro evaluation of OMCP-mutIL-2.
Figure 1B:
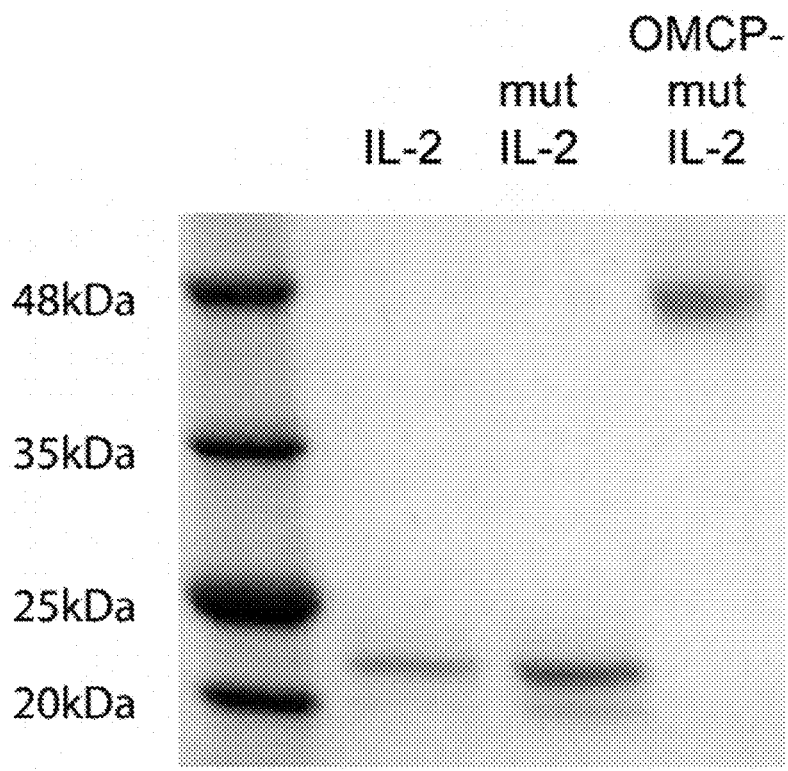

The compositions and methods described herein provide for delivery of cytokines to a defined cell via a ligand. The fusion of a cytokine to a ligand which specifically binds to a protein on the target cell creates an "address" for delivery of the cytokine. Specifically, using the invention disclosed herein, IL2 is directly targeted to lymphocytes, such as natural killer (NK) cells and CD8+ cytotoxic T lymphocytes (CTLs), via the orthopoxvirus major histocompatibility complex class I-like protein (OMCP) ligand. However other NKG2D ligands, including but not limited to ULBP1, ULBP2, ULBP3, H60, Rae-1α, Rae-1β, Rae-1δ, Rae-1γ, MICA, MICB, h-HLA-A, could also be used instead of OMCP. Specific delivery of IL2 to lymphocytes will enhance the efficacy of IL2, which could lead to reduced dosages and a significant decrease in associated toxicity. This methodology may be used for other cytokines, including, but not limited to, IL15, IL18 and interferons.

Specific aspects of the invention are described in detail below.

I. Composition

In an aspect, the invention encompasses a composition comprising a cytokine linked to a ligand. The composition may further comprise a linker to connect the cytokine to the ligand. The cytokine, ligand and linker are described in greater detail below. It should be understood that any of the cytokines described in detail below can be linked to any of the ligands described in detail below in the absence or presence of any of the linkers described below. In another aspect, the invention provides a nucleic acid molecule encoding a cytokine, a ligand, and optionally a linker.

(a) Cytokine

As used herein, a "cytokine" is a small protein (~5-20 kDa) that is important in cell signaling. Cytokines are released by cells and affect the behavior of other cells and/or the cells that release the cytokine. Non-limiting examples of cytokines include chemokines, interferons, interleukins, lymphokines, tumor necrosis factor, monokines, and colony stimulating factors. Cytokines may be produced by a broad range of cells including, but not limited to, immune cells such as macrophages, B lymphocytes, T lymphocytes, mast cells and monocytes, endothelial cells, fibroblasts and stromal cells. A cytokine may be produced by more than one type of cell. Cytokines act through receptors and are especially important in the immune system, modulate the balance between humoral and cell-based immune responses, and regulate maturation, growth and responsiveness of cell populations. Cytokines are important in host responses to infection, immune responses, inflammation, trauma, sepsis, cancer and reproduction. A cytokine of the invention may be a naturally occurring cytokine or may be a mutated version of a naturally occurring cytokine. As used herein, "naturally occurring", which may also be referred to as wild-type, includes allelic variances. A mutated version or "mutant" of a naturally occurring cytokine refers to specific mutations that have been made to the naturally occurring sequence to alter the function, activity and/or specificity of the cytokine. In one embodiment, the mutations may enhance the function, activity and/or specificity of the cytokine. In another embodiment, the mutations may decrease the function, activity and/or specificity of the cytokine. The mutation may include deletions or additions of one or more amino acid residues of the cytokine.

Cytokines may be classified based on structure. For example, cytokines may be classified into four types: the four-α-helix bundle family, the IL1 family, the IL17 family and the cysteine-knot cytokines. Members of the four-α-helix bundle family have three-dimensional structures with four bundles of α-helices. This family is further divided into three sub-families: the IL2 subfamily, the interferon (IFN) subfamily and the IL10 subfamily. The IL2 subfamily is the largest and comprises several non-immunological cytokines including, but not limited to, erythropoietin (EPO) and thrombopoietin (TPO). In certain embodiments, a cytokine of the composition is a cytokine from the four-α-helix bundle family or a mutant thereof. A skilled artisan would be able to determine cytokines within the four-α-helix bundle family. In other embodiments, a cytokine of the composition is an IL2 subfamily cytokine or a mutant thereof. Non-limiting examples of members of the IL2 subfamily include IL2, IL4, IL7, IL9, IL15 and IL21. In a specific embodiment, a cytokine of the composition is IL2 or a mutant thereof. In certain embodiments, a cytokine of the composition is IL15 or a mutant thereof. The sequence information for the full length human IL15 amino acid sequence can be found using, for example, the GenBank accession number CAG46777.1, AAI00962.1 or AAI00963.1. The sequence information for the full length human 11_15 mRNA sequence can be found using, for example, the GenBank accession number CR542007.1, KJ891469.1, NM_172175.2, NM_000585.4 or CR541980.1. A skilled artisan will appreciate that IL15 may be found in a variety of species and methods of identifying analogs or homologs of IL15 are known in the art as described in detail below.

In another embodiment, a cytokine of the invention is an IL1 family cytokine or a mutant thereof. The IL1 family is a group of 11 cytokines, which plays a central role in the regulation of immune and inflammatory responses. Generally, the IL1 family of cytokines are proinflammatory cytokines that regulate and initiate inflammatory responses. Non-limiting examples of IL1 family cytokines include IL1α, IL1β, IL1Ra, IL18, IL36Ra, IL36α, IL37, IL36β, IL36γ, IL38, and IL33. IL1 family members have a similar gene structure. A skilled artisan would be able to determine cytokines within the IL1 family. In certain embodiments, a cytokine of the composition is IL18 or a mutant thereof. The sequence information for the full length human IL18 amino acid sequence can be found using, for example, the GenBank accession number CAG46771.1. The sequence information for the full length human IL18 mRNA sequence can be found using, for example, the GenBank accession number KR710147.1, CR542001.1, CR541973.1 or KJ1897054.1. A skilled artisan will appreciate that IL18 may be found in a variety of species and methods of identifying analogs or homologs of IL18 are known in the art as described in detail below.

In other embodiments, a cytokine of the composition is an interferon subfamily cytokine or a mutant thereof. Interferons are named for their ability to "interfere" with viral replication by protecting cells from virus infection. IFNs also have other functions: they activate immune cells, such as natural killer cells and macrophages; they increase host defenses by up-regulating antigen presentation by virtue of increasing the expression of major histocompatibility complex (MHC) antigens. Based on the type of receptor through which they signal, human interferons have been classified into three major types: Type I IFN, Type II IFN, and Type III IFN. Type I IFNs bind to a specific cell surface receptor complex known as the IFN-α/β receptor (IFNAR) that consists of IFNAR1 and IFNAR2 chains. Non-limiting examples of type I interferons present in humans are IFN-α, IFN-β, IFN-ε, IFN-κ and IFN-ω. Thus, in certain embodiments, a cytokine of the composition is a Type 1 IFN cytokine or a mutant thereof, including, but not limited to wild-type and mutant forms of IFN-α, IFN-β, IFN-ε, IFN-κ and IFN-ω. Type II IFNs bind to IFNGR that consists of IFNGR1 and IFNGR2 chains. Non-limiting examples of type II interferons present in humans is IFN-γ. Thus, in certain embodiments, a cytokine of the composition is a Type II IFN cytokine or a mutant thereof, including, but not limited to wild-type and mutant forms of IFN-γ. Type III IFNs signal through a receptor complex consisting of IL10R2 (also called CRF2-4) and IFNLR1 (also called CRF2-12). Non-limiting examples of type III interferons include IFN-λ1, IFN-λ2 and IFN-λ3 (also called IL29, IL28A and IL28B respectively). Thus, in certain embodiments, a cytokine of the composition is a Type III IFN cytokine or a mutant thereof, including, but not limited to wild-type and mutant forms of IFN-A1, IFN-A2 and IFN-A3.

In certain embodiments, a cytokine of the invention is an interleukin or mutant thereof. The majority of interleukins are synthesized by helper CD4 T lymphocytes, as well as through monocytes, macrophages, and endothelial cells. Interleukins may promote the development and differentiation of T and B lymphocytes and hematopoietic cells. Non-limiting examples of interleukins include IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. Thus, in certain embodiments, a cytokine of the composition is an interleukin or a mutant thereof, including, but not limited to wild-type and mutant forms of IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. In a specific embodiment, a cytokine of the composition is IL2 or a mutant thereof. IL2 is a lymphokine that induces the proliferation of responsive T cells. In addition, it acts on some B cells, via receptor-specific binding, as a growth factor and antibody production stimulant. The IL2 protein is secreted as a single glycosylated polypeptide, and cleavage of a signal sequence is required for its activity. The structure of IL2 comprises a bundle of 4 helices (termed A-D), flanked by 2 shorter helices and several poorly defined loops. Residues in helix A, and in the loop region between helices A and B, are important for receptor binding. Secondary structure analysis suggests similarity to IL4 and granulocyte-macrophage colony stimulating factor (GMCSF). In a specific embodiment, a cytokine of the composition is IL2 or a variant thereof. A variant may be a truncated or mutated IL2. The sequence information for the full length human IL2 amino acid sequence can be found using, for example, the GenBank accession number AAA59140.1 or AAH70338.1. The sequence information for the full length human IL2 mRNA sequence can be found using, for example, the GenBank accession number BC070338.1 or M22005.1.

A skilled artisan will appreciate that IL2 may be found in a variety of species. Non-limiting examples include mouse (AAI16874.1), pig (NP_999026.1), cattle (AAQ10670.1), rat (EDM01295.1), rabbit (AAC23838.1), goat (AAQ10671.1), sheep (ABK41601.1), chicken (AAV35056.1), hamster (ERE88380.1), and dog (AAA68969.1). It is appreciated that the present invention is directed to analogs of IL2 in other organisms and is not limited to the human analog. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215: 403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to IL2.

In a specific embodiment, a cytokine of the composition is a wildtype sequence of IL2 such as the sequence set forth in SEQ ID NO:5 (APTSSSTKKTQLQLEHLLLD-LQMILNGINNYKNPKLTRMLTFKFYMPK-KATELKHLQCL EEELKPLEEVLNLAQSKNFHLR-PRDLISNINVIVLELKGSETTFMCEYADETATIVEFLNR WITFCQSIISTLT). In an alternative embodiment, a cytokine is a mutated version of IL2. In an embodiment, a mutation is a mutation that causes IL2 to preferentially bind the receptor IL2βγ. In another embodiment, a mutation is a mutation that alters the function of IL2 such that IL2 has a decreased affinity for the IL2 receptor alpha (IL2Rα). For example, a mutation may be one or more mutations selected from the group consisting of R38A, F42K and/or C125S relative to SEQ ID NO:5. The C125S mutation may be included to reduce protein aggregation. In a specific embodiment, a mutated version of IL2 comprises at least one mutation selected from the group consisting of R38A, F42K and C125S relative to SEQ ID NO:5. In another specific embodiment, a mutated version of IL2 comprises the mutations R38A, F42K and C125S relative to SEQ ID NO:5. In a specific embodiment, a cytokine of the composition is a mutated sequence of IL2 such as the sequence set forth in SEQ ID NO:6 (APTSSSTKKTQLQLEHLLLD-LQMILNGINNYKNPKLTAMLTKKFYMPK-KATELKHLQCL EEELKPLEEVLNLAQSKNFHLR-PRDLISNINVIVLELKGSETTFMCEYADETATIVEFLNR WITFSQSIISTLT).

In an alternative aspect, a toxin is substituted for a cytokine. The term "toxin" means the toxic material or product of plants, animals, microorganisms (including, but not limited to, bacteria, viruses, fungi, rickettsiae or protozoa), or infectious substances, or a recombinant or synthesized molecule, whatever their origin and method of production. A toxin may be a small molecule, peptide, or protein that is capable of causing disease on contact with or absorption by body tissues interacting with biological macromolecules such as enzymes or cellular receptors. A toxin may be a "biotoxin" which is used to explicitly identify the toxin as from biological origin. Biotoxins may be further classified into fungal biotoxins, or short mycotoxins, microbial biotoxins, plant biotoxins, short phytotoxins and animal biotoxins. Non-limiting examples of biotoxins include: cyanotoxins, produced by cyanobacteria, such as microcystins, nodularins, anatoxin-a, cylindrospermopsins, lyngbyatoxin-a, saxitoxin, lipopolysaccharides, aplysiatoxins, BMAA; dinotoxins, produced by dinoflagellates, such as saxitoxins and gonyautoxins; necrotoxins produced by, for example, the brown recluse or "fiddle back" spider, most rattlesnakes and vipers, the puff adder, Streptococcus pyogenes; neurotoxins, produced by, for example, the black widow spider, most scorpions, the box jellyfish, elapid snakes, the cone snail, the Blue-ringed octopus, venomous fish, frogs, palythoa coral, various different types of algae, cyanobacteria and dinoflagellates, such as botulinum toxin (e.g. Botox), tetanus toxin, tetrodotoxin, chlorotoxin, conotoxin, anatoxin-a, bungarotoxin, caramboxin, curare; myotoxins, found in, for example, snake and lizard venoms; and cytotoxins such as ricin, from castor beans, apitoxin, from honey bees, and T-2 mycotoxin, from certain toxic mushrooms. In certain embodiments, a toxin is a cytotoxin. In an embodiment, a cytotoxin is selected from the group consisting of ricin, apitoxin, and T-2 mycotoxin. In a specific embodiment, a toxin is ricin.

In certain embodiments, a cytokine or toxin of the invention may be PEGylated for improved systemic half-life and reduced dosage frequency. In an embodiment, PEG may be added to a cytokine or toxin. As such, a composition of the invention may comprise a cytokine or toxin comprising PEG. In an embodiment, PEG may be selected from the group consisting of PEG-10K, PEG-20K and PEG-40K. Methods of conjugating PEG to a protein are standard in the art. For example, see Kolate et al, *Journal of Controlled*

*Release* 2014; 192(28): 67-81, which is hereby incorporated by reference in its entirety. Still further, a cytokine or toxin of the invention may be modified to remove T cell epitopes. T cell epitopes can be the cause of an immunogenicity issue upon administration of a composition to a subject. Through their presentation to T cells, they activate the process of anti-drug antibody development. Preclinical screening for T cell epitopes may be performed in silico, followed by in vitro and in vivo validation. T cell epitope-mapping tools such as EpiMatrix can be highly accurate predictors of immune response. Deliberate removal of T cell epitopes may reduce immunogenicity. Other means of improving the safety and efficacy of a composition of the invention by reducing their immunogenicity include humanization and PEGylation.

(b) Ligand

As used herein, a "ligand" is a protein that specifically binds to a receptor on a target cell and is not the corresponding binding partner to the cytokine linked to the ligand. A ligand may be from a eukaryote, a prokaryote or a virus. In certain embodiments, a ligand may be from a virus. The phrase "specifically binds" herein means ligands bind to the target protein with an affinity ($K_d$) in the range of at least 0.1 mM to 1 µM, or in the range of at least 0.1 µM to 200 nM, or in the range of at least 0.1 µM to 10 nM. A dissociation constant ($K_d$) measures the propensity of a larger object to separate (dissociate) reversibly into smaller components. The dissociation constant is the inverse of the association constant. The dissociation constant may be used to describe the affinity between a ligand (L) and a target protein (P). As such, $K_d=([P]\times[L])/[C]$, wherein C is a ligand-target protein complex and wherein [P], [L] and [C] represent molar concentrations of the protein, ligand and complex, respectively. Methods of determining whether a ligand binds to a target protein are known in the art. For instance, see the Rossi and Taylor, Nature Protocols 2011; 6: 365-387.

A ligand may trigger a signal through its binding to a receptor on a target cell. A receptor is a protein molecule that may be embedded within the plasma membrane surface of a cell that receives chemical signals from outside the cell. When such chemical signals bind to a receptor, they cause some form of cellular/tissue response. In preferred embodiments, a target cell is an immune cell. Accordingly, a ligand of the composition binds to a receptor expressed on immune cells. Non-limiting example of immune cells include macrophages, B lymphocytes, T lymphocytes, mast cells, monocytes, dendritic cells, eosinophils, natural killer cells, basophils, neutrophils. Thus, in certain embodiments, immune cells include, but are not limited to, macrophages, B lymphocytes, T lymphocytes, mast cells, monocytes, dendritic cells, eosinophils, natural killer cells, basophils, neutrophils. In a specific embodiment, an immune cell is a natural killer cell or a T lymphocyte. Non-limiting examples of receptors expressed on immune cells include major histocompatibility complex (MHC; e.g. MHCI, MHCII, and MHCIII), toll-like receptors (TLRs; e.g. TLR1, TLR2, TLR3, TLR4, TLR5, TLR6, TLR7, TLR8, TLR9, TLR10, TLR11, TLR12, and TLR13), CD94/NKG2 family receptor, endothelin receptors, signaling lymphocytic activation molecule (SLAM) family of receptors. Thus, in certain embodiments, a receptor on a target cell includes, but is not limited to, major histocompatibility complex (MHC; e.g. MHCI, MHCII, and MHCIII), toll-like receptors (TLRs; e.g. TLR1, TLR2, TLR3, TLR4, TLR5, TLR6, TLR7, TLR8, TLR9, TLR10, TLR11, TLR12, and TLR13), CD94/NKG2 family receptor, endothelin receptors, signaling lymphocytic activation molecule (SLAM) family of receptors. In a specific embodiment, the receptor on a target cell is a CD94/NKG2 family receptor. In another specific embodiment, a ligand of the composition specifically binds to a receptor expressed on natural killer (NK) cells and CD8+ cytotoxic T lymphocytes (CTLs). In preferred embodiments, a ligand of the composition does not specifically bind to a receptor on vascular endothelial cells or regulatory T cells ($T_{regs}$).

A receptor expressed on NK cells and CTLs may be a CD94/NKG2 family receptor or KLRG1. KLRG1 (Killer cell lectin-like receptor subfamily G member 1) is a protein that in humans is encoded by the KLRG1 gene. CD94/NKG2 family receptors are a family of C-type lectin receptors which are expressed predominantly on the surface of NK cells and a subset of CD8+T-lymphocyte. These receptors stimulate or inhibit cytotoxic activity of NK cells, therefore they are divided into activating and inhibitory receptors according to their function. CD94/NKG2 recognize MHC class I-related glycoproteins. CD94/NKG2 family includes seven members: NKG2A, NKG2B, NKG2C, NKG2D, NKG2E, NKG2F and NKG2H. Thus, in certain embodiments, a ligand of the invention specifically binds to a receptor selected from the group consisting of NKG2A, NKG2B, NKG2C, NKG2D, NKG2E, NKG2F and NKG2H. NKG2 receptors are transmembrane proteins type II which dimerize with CD94 molecule. CD94 contains a short cytoplasmic domain and it is responsible for signal transduction. Therefore NKG2 receptors form disulfide bonded heterodimers. NKG2D represents an exception, it is a homodimer. NKG2A and NKG2B receptors transmit inhibitory signal. NKG2C, NKG2E and NKG2H are activating receptors. NKG2D is activating receptor as well but it couples with adaptor protein DAP10 which carries signaling motif YINM (SEQ ID NO:34). Src or Jak kinases phosphorylate DAP10, which can then associate with p85 subunit of PI(3)K or adaptor molecule Grb2. This signaling triggers actin reorganization (cell polarization) and degranulation. NKG2F receptor function has not been clarified yet.

In a specific embodiment, a ligand of the composition specifically binds to the NKG2D receptor. NKG2D is an activating receptor found on NK cells and CD8+ T cells (both αβ and γδ). The structure of NKG2D consists of two disulphide-linked type H transmembrane proteins with short intracellular domains incapable of transducing signals. The function of NKG2D on CD8+ T cells is to send co-stimulatory signals to activate them. In an embodiment, a ligand that binds to NKG2D may be an anti-NKG2D antibody. An "anti-NKG2D" includes all antibodies that specifically bind an epitope within NKG2D. The term "antibody' includes the term "monoclonal antibody". "Monoclonal antibody" refers to an antibody that is derived from a single copy or clone, including e.g., any eukaryotic, prokaryotic, or phage clone. Monoclonal antibodies can be produced using e.g., hybridoma techniques well known in the art, as well as recombinant technologies, phage display technologies, synthetic technologies or combinations of such technologies and other technologies readily known in the art. Further by "antibody" is meant a functional monoclonal antibody, or an immunologically effective fragment thereof; such as an Fab, Fab', or F(ab')2 fragment thereof. As long as the protein retains the ability specifically to bind its intended target, it is included within the term "antibody." Also included within the definition "antibody" for example are single chain forms, generally designated Fv, regions, of antibodies with this specificity. These scFvs are comprised of the heavy and light chain variable regions connected by a linker. Methods of making and using scFvs are known in the art. Additionally, included within the definition "antibody" are single-domain antibodies, generally designated sdAb, which is an antibody fragment consisting of a single monomeric variable antibody domain. A sdAb antibody may be derived from camelids ($V_HH$ fragments) or cartilaginous fishes ($V_{NAR}$ fragments). As used herein "humanized antibody" includes an anti-NKG2D antibody that is composed partially or fully of amino acid sequence sequences derived from a human antibody germ line by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for NKG2D is maintained or enhanced in the context of fully human germline framework regions or framework regions that are substantially human. In certain embodiments, an anti-NKG2D antibody is a Fab, Fab', or F(ab')$_2$ fragment.

In another embodiment, ligands that bind to NKG2D share an MHC class I-related α1α2 superdomain that constitutes the common site for interaction with NKG2D. Non-limiting examples of ligands that bind to NKG2D include MHC class I-related glycoproteins such as MIC family proteins (i.e., MICA, MICB), UL16-binding family proteins (i.e., ULBP1, ULBP2, ULPB3, ULBP4, ULBP5, ULBP6), retinoid acid early induce gene 1 (Rae1)-like proteins (i.e., Rae1α, Rae1β, Rae1γ, Rae1δ, Rae1ε), members of the H60 protein family (i.e., H60a, H60b, H60c), h-HLA-A, as well as Mult1 in mice and orthopoxvirus major histocompatibility complex class I-like protein (OMCP). In certain embodiments, a ligand is a MHC class-I-related glycoprotein. In other embodiments, a ligand of the invention is selected from the group consisting of MICA, MICB, ULBP1, ULBP2, ULBP3, ULBP4, ULBP5, ULBP6, Rae1α, Rae1β, Rae1γ, Rae1δ, Rae1ε, H60a, H60b, H60c, h-HLA-A, Mult1 and OMCP. In an embodiment, a ligand is a UL16-binding family protein or a MIC family protein. In a specific embodiment, a ligand is selected from the group consisting of ULBP1, ULBP2, ULBP3, ULBP4, ULBP5, and ULBP6. In another specific embodiment, a ligand is ULBP3. In a specific embodiment, a ligand is orthopoxvirus major histocompatibility complex class I-like protein (OMCP) or a variant thereof. A variant may be a truncated or mutated OMCP that has about the same binding affinity of the full length OMCP. In an embodiment, a variant may be a truncated or mutated OMCP that has a slightly lower binding affinity relative to the binding affinity of the full length OMCP. In another embodiment, a variant is a truncated or mutated OMCP that has a slightly higher binding affinity relative to the binding affinity of the full length OMCP. Methods to determine binding affinity of a ligand to target protein are known in the art and described above. OMCP specifically binds to NKG2D with a binding affinity of about 0.1 to about 5 nM. For example, OMCP specially binds to human NKG2D with a binding affinity of about 0.2 nM and mouse NKG2D with a binding affinity of about 3 nM. In a preferred embodiment, OMCP or a variant thereof binds to human NKG2D with a binding affinity of about 1000 nM to about 0.1 nM. In certain embodiments, OMCP or a variant thereof binds to human NKG2D with a binding affinity of about 100 nM to about 0.1 nM, about 10 nM to about 0.1 nM, or about 1 nM to about 0.1 nM. In other embodiments, OMCP or a variant thereof binds to human NKG2D with a binding affinity of about 1000 nM to about 1 nM, or about 1000 nM to about 10 nM, or about 1000 nM to about 100 nM. In still other embodiments, OMCP or a variant thereof binds to human NKG2D with a binding affinity of about 100 nM to about 1 nM, or about 100 nM to 10 nM. For example, OMCP or a variant thereof binds to human NKG2D with a binding affinity of about 1000 nM, about 500 nM, about 100 nM, about 50 nM, about 10 nM, about 9 nM, about 8 nM, about 7 nM, about 6 nM about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM or about 0.1 nM. In another embodiment, a variant is a truncated or mutated OMCP that has binding affinity for one or more NKG2 family receptors other than NKG2D. For example, a variant is a truncated or mutated OMCP that has binding affinity for one or more NKG2 family receptors selected from the group consisting of NKG2A, NKG2B, NKG2C, NKG2E, NKG2F and NKG2H. Mutations to OMCP may be rationally selected via structure-based knowledge or mutations to OMCP may be identified via selection-based mutagenesis. In certain embodiments, mutations may be rationally selected to occur in the OMCP-NKG2D interface to either enhance or reduce binding affinity. Amino acids involved in binding at the OMCP-NKG2D interface are described in the Examples.

Figure 20A:
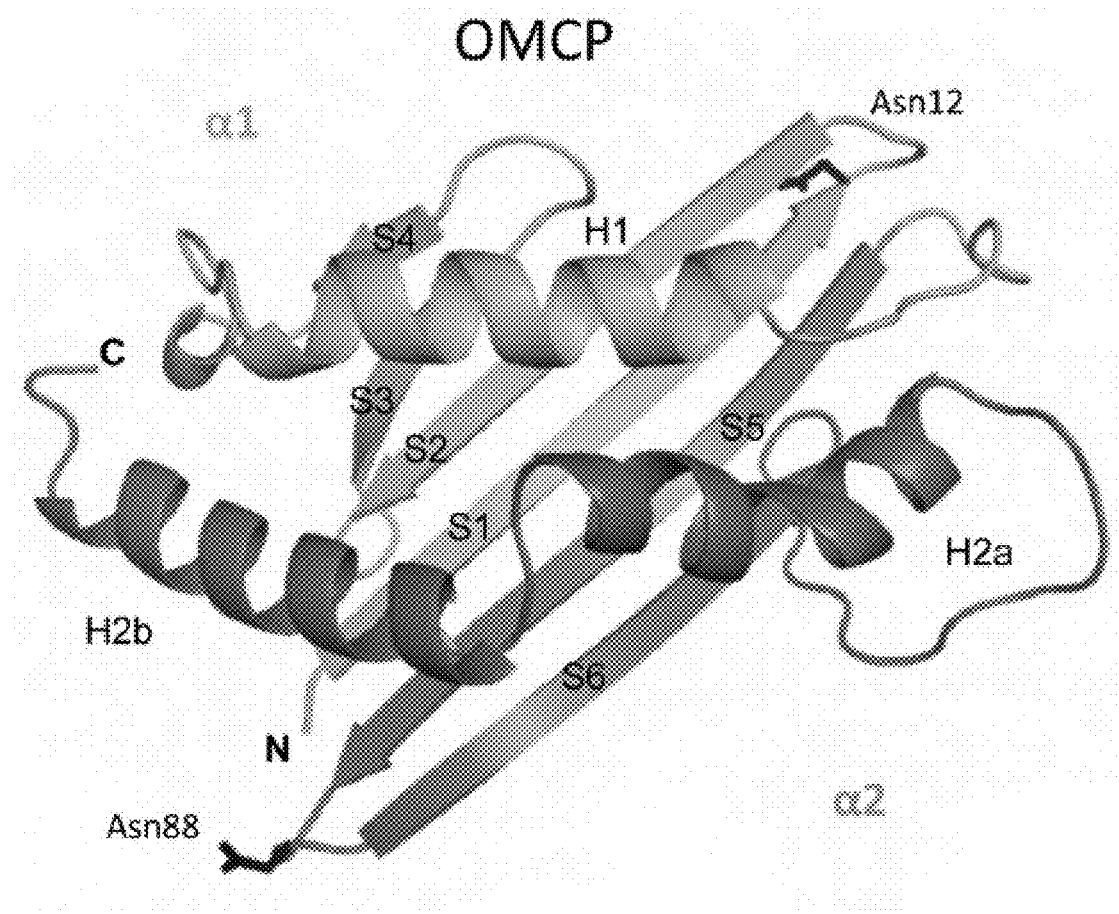
FIG. 20A, FIG. 20B and FIG. 20C depict images and alignments of the OMCP structure.
Figure 20B:
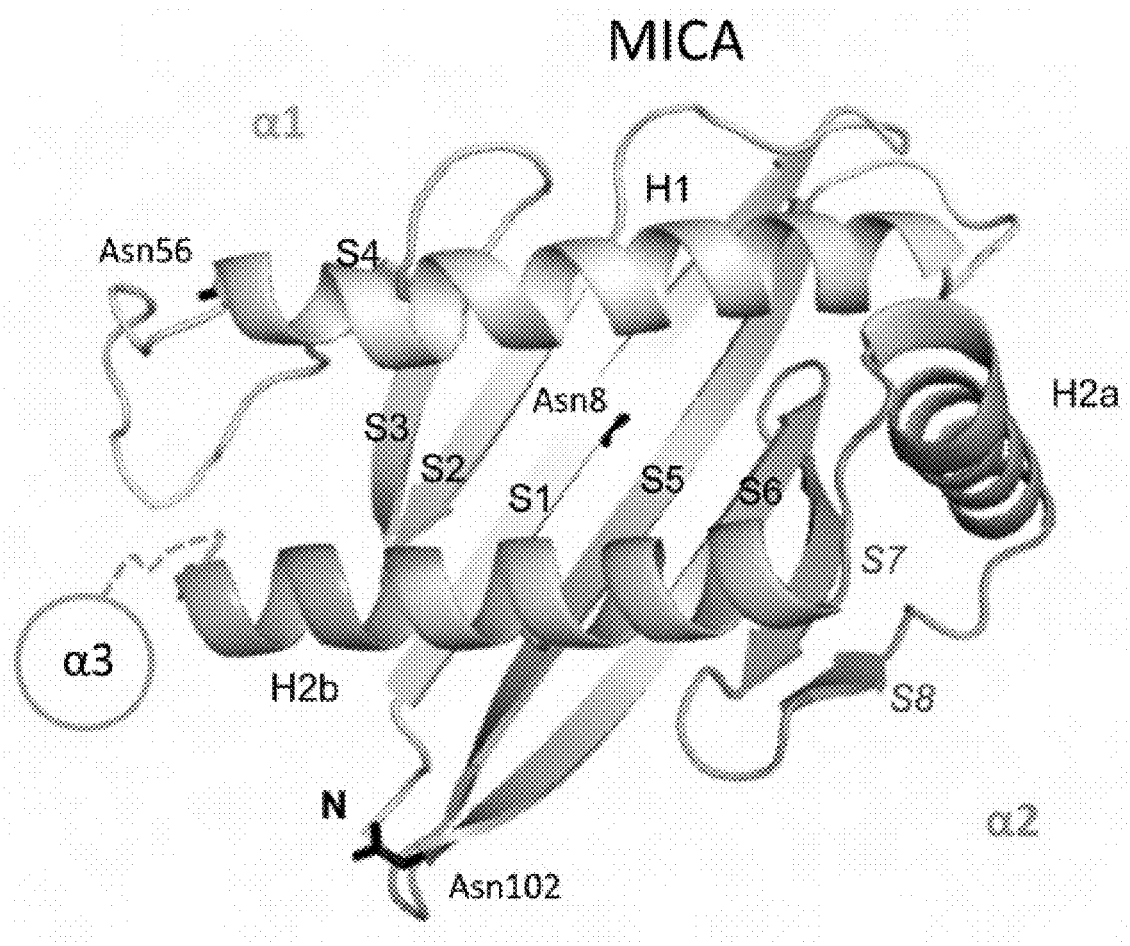
Figure 20C:
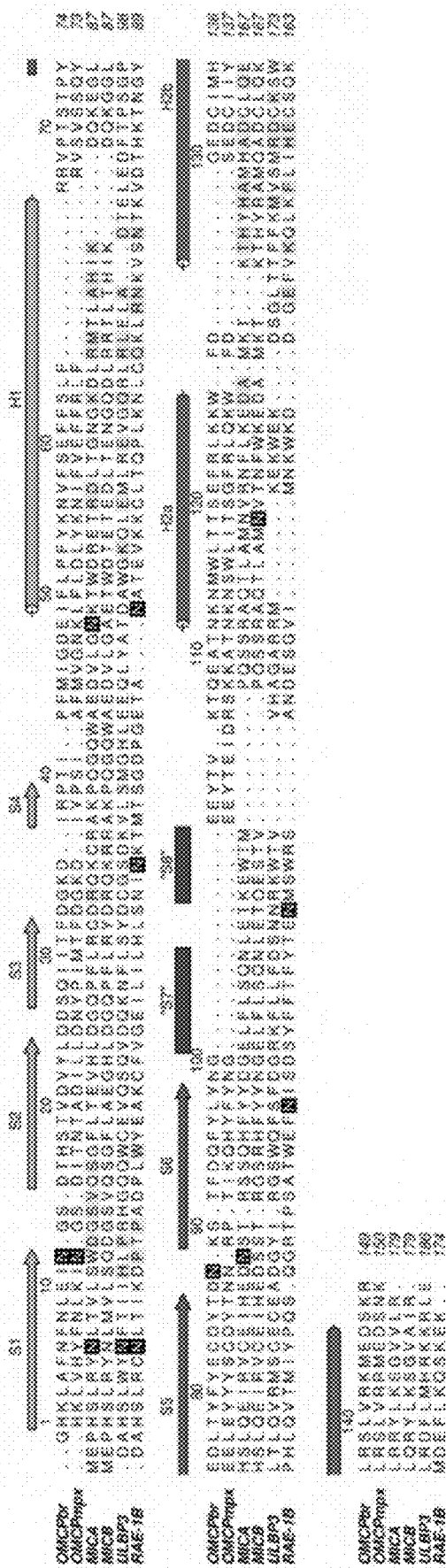

The structure of OMCP consists of an MHCI-like α1/α2 platform domain (FIG. 20A). The platform domain of OMCP has been trimmed to have only a six-stranded beta sheet with shorter flanking helices. The helix of the OMCP α1 domain (H1) is continuous, while the helix of the α2 domain is broken into two regions (H2a and H2b). The helices flank a six-stranded beta sheet and together form the characteristic platform that defines MHC proteins. Like other NKG2DLs (FIG. 20B), the alpha helices of OMCP are close together and thus have no groove for binding peptides or other ligands like antigen-presenting MHC platform domains. OMCP contains one disulfide bond between S5 and H2b, and this disulfide bond is conserved in most NKG2DLs (FIG. 20C). In certain embodiments, a ligand of the invention comprises one or more of the α helices of a MHC class I-related glycoprotein. In other embodiments, a ligand of the invention consists of one or more of the α helices of a MHC class I-related glycoprotein. More specifically, a ligand of the invention comprises the α1 domain (H1), α2 domain (H2), H2a, H2b, or combinations thereof of a MHC class I-related glycoprotein. Or, a ligand of the invention consists of the α1 domain (H1), α2 domain (H2), H2a, H2b, or combinations thereof of a MHC class I-related glycoprotein. In a specific embodiment, a ligand of the invention comprises the α2 domain (H2) of a MHC class I-related glycoprotein. In another specific embodiment, a ligand of the invention consists of the α2 domain (H2) of a MHC class I-related glycoprotein. A skilled artisan would be able to determine the location of the α helices in other MHC class I-related glycoproteins, for example, using sequence alignment (see FIG. 20C, which is reproduced from Lazear et al. *J Virol* 2013; 87(2): 840-850, which is hereby incorporated by reference in its entirety). In an embodiment, a ligand of the invention comprises one or more of the α helices of OMCP. In another embodiment, a ligand of the invention comprises the α1 domain (H1), α2 domain (H2), H2a, H2b, or combinations thereof of OMCP. In still another embodiment, a ligand of the invention comprises the α2 domain (H2) of OMCP. In a specific embodiment, a ligand of the invention consists of one or more of the α helices of OMCP. In another specific embodiment, a ligand of the invention consists of the α1 domain (H1), α2 domain (H2), H2a, H2b, or combinations thereof of OMCP. In still another specific embodiment, a ligand of the invention consists of the α2 domain (H2) of OMCP.

The sequence information for the full length OMCP amino acid sequence can be found using, for example, the GenBank accession number 4FFE_Z, 4FFE_Y or 4FFE_X. A skilled artisan will appreciate that homologs of OMCP may be found in other species or viruses. For example, see Lefkowitz et al, Nucleic Acids Res 2005; 33: D311-316, which is herein incorporated by reference in its entirety, which describes eighteen OMCP variants between cowpox and monkeypox virus strains. In an embodiment, OMCP is from an orthopoxvirus. In a specific embodiment, OMCP is from a cowpox virus or a monkeypox virus. In another specific embodiment, OMCP is from the Brighton Red strain of cowpoxvirus. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to OMCP.

A skilled artisan will appreciate that structural homologs of OMCP may be found in other species or viruses. A structural homolog may be a protein that is structurally related but the sequence is a distal homolog. For example, OMCP has low sequence identity for endogenous NKG2D ligands however it was discovered that OMCP would bind to NKG2D based on structural homology. Structural homologs can be found in other species by methods known in the art. For example, protein structure prediction may be determined by various databases, such as Phyre and Phyre2. Such databases generate reliable protein models that may be used to determine structural homologs. The main results table in Phyre2 provides confidence estimates, images and links to the three-dimensional predicted models and information derived from either Structural Classification of Proteins database (SCOP) or the Protein Data Bank (PDB) depending on the source of the detected template. For each match a link takes the user to a detailed view of the alignment between the user sequence and the sequence of known three-dimensional structure. See www.sbg.bio.ic.ac.uk/phyre2/ for more details. Generally, a structural homolog will have a least 50, 51, 52, 53, 54, 55, 56, 57, 58, or 59% confidence with OMCP. In an embodiment, a structural homolog will have a least 60, 61, 62, 63, 64, 65, 66, 67, 68, or 69% confidence with OMCP. In another embodiment, a structural homolog will have a least 70, 71, 72, 73, 74, 75, 76, 77, 78, or 79% confidence with OMCP. In still another embodiment, a structural homolog will have a least 80, 81, 82, 83, 64, 85, 86, 87, 88, or 89% confidence with OMCP. In still yet another embodiment, a structural homolog may have at least 90, 91, 92, 93, 94, 95, 96, 97, 98, 99, or 100% confidence with OMCP. The structural information for OMCP-human NKG2D may be found using the PDB ID: 4PDC.

In a specific embodiment, a ligand of the composition is a sequence of OMCP such as the sequence set forth in SEQ ID NO:7 (HKLAFNFNLEINGSDTHSTVDVYLDDSQII TFDGKDIRPTIPFMIGDEIFLPFYKNVFSEFFSLFRRVP TSTPYEDLTYFYECDYTDNKSTFDQFYLYNGEEYTV KTQEATNKNMWLTTSEFRLKKWFDGEDCIMHLRSL VRKMEDSKRNT). In an embodiment, a ligand of the composition is a sequence of OMCP comprising at least 80% identity to SEQ ID NO:7.

For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:7.

In another specific embodiment, a ligand of the composition is a sequence of OMCP such as the sequence set forth in SEQ ID NO:13 (GHKLAFNFNLEINGSDTH-STVDVYLDDSQIITFDGKDIRPTIPFMIGDEIFLPFYKN VFSEFFSLFRRVPTSTPYEDLTYFYECDYTDNKSTFD QFYLYNGEEYTVKTQEATNKNMWLTTSEFRLKKWF DGEDCIMHLRSLVRKMEDSKR). In an embodiment, a ligand of the composition is a sequence of OMCP comprising at least 80% identity to SEQ ID NO:13. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:13.

In still another specific embodiment, a ligand of the composition is a sequence of OMCP such as the sequence set forth in SEQ ID NO:14 (HKLVHYFNLKINGSDITN-TADILLDNYPIMTFDGKDIYPSIAFMVGNKLFLDLYK NIFVEFFRLFRVSVSSQYEELEYYYSCDYTNNRPTIK QHYFYNGEEYTEIDRSKKATNKNSWLITSGFRLQKW FDSEDCIIYLRSLVRRMEDSNK). In an embodiment, a ligand of the composition is a sequence of OMCP comprising at least 80% identity to SEQ ID NO:14.

For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:14.

In an alternative aspect, a receptor expressed on immune cells may be PD1. PD1, also known as programmed cell death protein 1 and CD279 (cluster of differentiation 279), is a protein that in humans is encoded by the PDCD1 gene. PD1 is a cell surface receptor that belongs to the immunoglobulin superfamily and is expressed on T cells and pro-B cells. PD1 binds two ligands, PDL1 and PDL2. PD1, functioning as an immune checkpoint, plays an important role in down regulating the immune system by preventing the activation of T-cells. In certain embodiments, a ligand of the composition specifically binds to PD1. In an embodiment, a ligand that specifically binds to PD1 may be an anti-PD1 antibody. An "anti-PD1" includes all antibodies that specifically bind an epitope within PD1. The term "antibody" is described above. In another embodiment, a ligand that specifically binds to PD1 may be PDL1. PDL1 (programmed death-ligand 1 also known as cluster of differentiation 274 (CD274) or B7 homolog 1 (B7-H1), is a protein that in humans is encoded by the CD274 gene. PDL1 binds to its receptor, PD1, found on activated T cells, B cells, and myeloid cells, to modulate activation or inhibition. The affinity between PDL1 and PD1, as defined by the dissociation constant $K_d$, is 770 nM.

In another aspect, a ligand of the composition may be Glucocorticoid-induced TNFR-related (GITR) ligand (GITRL). GITR activation by GITRL influences the activity of effector and regulatory T cells, thus participating in the development of immune response against tumors and infectious agents, as well as in autoimmune and inflammatory diseases. GITR triggering stimulates T effector activity and inhibits Treg activity. GITR inhibition may ameliorate autoimmune/inflammatory diseases whereas GITR activation may treat viral, bacterial and parasitic infections, as well as boost immune responses against tumors. GITRL is a type II transmembrane protein expressed at high levels on antigen presenting cells (APC) and endothelial cells.

In certain embodiments, a ligand of the invention is modified for improved systemic half-life and reduced dosage frequency. In an embodiment, N-glycans may be added to a ligand. While the biological function is typically determined by the protein component, carbohydrate can play a role in molecular stability, solubility, in vivo activity, serum half-life, and immunogenicity. The sialic acid component of carbohydrate in particular, can extend the serum half-life of protein therapeutics. Accordingly, new N-linked glycosylation consensus sequences may be introduced into desirable positions in the peptide backbone to generate proteins with increased sialic acid containing carbohydrate, thereby increasing in vivo activity due to a longer serum half-life. In another embodiment, PEG may be added to a ligand. Methods of conjugating PEG to a protein are standard in the art. For example, see Kolate et al, *Journal of Controlled Release* 2014; 192(28): 67-81, which is hereby incorporated by reference in its entirety. In an embodiment, a composition of the invention may comprise a ligand comprising PEG and/or one or more N-glycans. In an embodiment, PEG is selected from the group consisting of PEG-10K, PEG-20K and PEG-40K. Still further, a ligand of the invention may be modified to remove T cell epitopes. T cell epitopes can be the cause of an immunogenicity issue upon administration of a composition to a subject. Through their presentation to T cells, they activate the process of anti-drug antibody development. Preclinical screening for T cell epitopes may be performed in siico, followed by in vitro and in vivo validation. T cell epitope-mapping tools such as EpiMatrix can be highly accurate predictors of immune response. Deliberate removal of T cell epitopes may reduce immunogenicity. Other means of improving the safety and efficacy of a composition of the invention by reducing their immunogenicity include humanization and PEGylation.

(c) Linker

In an aspect, a composition of the invention further comprises a linker. The linker may be used to connect the cytokine to the ligand. It is to be understood that linking the cytokine to the ligand will not adversely affect the function of the cytokine or the ligand. Suitable linkers include amino acid chains and alkyl chains functionalized with reactive groups for coupling to both the cytokine and the ligand or combinations thereof.

In an embodiment, the linker may include amino acid side chains, referred to as a peptide linker. Amino acid residue linkers are usually at least one residue and can be 50 or more residues, but alone do not specifically bind to the target protein. In an embodiment, a linker may be about 1 to about 10 amino acids. In another embodiment, a linker may be about 10 to about 20 amino acids. In still another embodiment, a linker may be about 20 to about 30 amino acids. In still yet another embodiment, a linker may be about 30 to about 40 amino acids. In different embodiments, a linker may be about 40 to about 50 amino acids. In other embodiments, a linker may be more than 50 amino acids. For instance, a linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. In a specific embodiment, a linker is about 20 to about 30 amino acids. In another specific embodiment, a linker is about 26 amino acids.

Any amino acid residue may be used for the linker provided the linker does not specifically bind to the target protein. Typical amino acid residues used for linking are glycine, serine, alanine, leucine, tyrosine, cysteine, lysine, glutamic and aspartic acid, or the like. For example, a linker may be $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. Accordingly, n may be 1, 2, 3, 4, 5, 6, 7, 8, 9, 10, 11, 12, 13, 14, 15, 16, 17, 18, 19 or 20. Thus, in certain embodiments, a linker includes, but is not limited to, $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. A linker may comprise one or more epitope tags. For instance, a linker may comprise 1, 2, 3, 4, 5, 6, 7 or 8 epitope tags. In a specific embodiment, a linker comprises 2 epitope tags. Non-limiting examples of epitope tags include FLAG tag (DYKDDDK epitope (SEQ ID NO:9)), HA tag (YPYDVPDYA epitope (SEQ ID NO:10)), His tag (6x-His or 8x-His), Myc tag (EQKLISEEDL epitope (SEQ ID NO:11)) and V5 tag (GKPIPNPLLGLDST epitope (SEQ ID NO:12)). In an embodiment, a linker may comprise at least one tag selected from the group consisting of a FLAG tag and a His tag. In a specific embodiment, a linker comprises a FLAG tag and a His tag. In another specific embodiment, a linker comprises the sequence set forth in SEQ ID NO:8 (GSSGSSDYKDDDDKHHHHHHHGS SGSS).

In another embodiment, an alkyl chain linking group may be coupled to the cytokine by reacting the terminal amino group or the terminal carboxyl group with a functional group on the alkyl chain, such as a carboxyl group or an activated ester. Subsequently the ligand is attached to the alkyl chain to complete the formation of the complex by reacting a second functional group on the alkyl chain with an appropriate group on the ligand. The second functional group on the alkyl chain is selected from substituents that are reactive with a functional group on the ligand while not being reactive with the cytokine. For example, when the ligand incorporates a functional group, such as a carboxyl group or an activated ester, the second functional group of the alkyl chain linking group can be an amino group or vice versa. It will be appreciated that formation of the conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis may be used. It will be appreciated that linking groups may alternatively be coupled first to the ligand and then to the cytokine.

An alternative chemical linking group to an alkyl chain is polyethylene glycol (PEG), which is functionalized in the same manner as the alkyl chain described above. Such a linker may be referred to as a heterobifunctional PEG linker or a homobifunctional PEG linker. Non-limiting examples of heterobifunctional PEG linkers include: O-(2-Aminoethyl)-O'-[2-(biotinylamino)ethyl]octaethylene glycol; O-(2-Aminoethyl)-O'-(2-carboxyethyl)polyethylene glycol hydrochloride $M_p$ 3000; O-(2-Aminoethyl)-O'-(2-carboxyethyl)polyethylene glycol 5,000 hydrochloride $M_p$ 5,000; O-(2-Aminoethyl)polyethylene glycol 3,000 Mp 3,000; O-(2-Aminoethyl)-O'-(2-(succinylamino)ethyl)polyethylene glycol hydrochloride $M_p$ 10,000; O-(2-Azidoethyl)heptaethylene glycol; O-[2-(Biotinylamino)ethyl]-O'-(2-carboxyethyl)undecaethylene glycol; 21-[D(+)-Biotinylamino]-4,7,10,13,16,19-hexaoxaheneicosanoic acid; O-(2-Carboxyethyl)-O'-[2-(Fmoc-amino)-ethyl]heptacosaethylene glycol; O-(2-Carboxyethyl)-O'-(2-mercaptoethyl)heptaethylene glycol; O-(3-Carboxypropyl)-O'-[2-(3-mercaptopropionylamino)ethyl]-polyethylene glycol Mw 3000; O-(3-Carboxypropyl)-O'-[2-(3-mercaptopropionylamino)ethyl]-polyethylene glycol Mw 5000; O—[N-(3-Maleimidopropionyl)aminoethyl]-O'-[3-(N-succinimidyloxy)-3-oxopropyl]heptacosaethylene glycol; and O-[2-(3-Tritylthiopropionylamino)ethyl]polyethylene glycol $M_p$ 3,000. Non-limiting examples of homobifunctional PEG linkers include: MAL-PEG-MAL (Bifunctional Maleimide PEG Maleimide); OPSS-PEG-OPSS (OPSS: orthopyridyl disulfide; PDP-PEG-PDP); HS-PEG-SH (Bifunctional Thiol PEG Thiol); SG-PEG-SG (Bifunctional PEG Succinimidyl Glutarate NHS ester); SS-PEG-SS (Bifunctional PEG Succinimidyl Succinate NHS ester); GAS-PEG-GAS (Bifunctional PEG Succinimidyl ester NHS-PEG-NHS); SAS-PEG-SAS (Bifunctional PEG Succinimidyl ester NHS-PEG-NHS); Amine-PEG-Amine (Bifunctional PEG Amine NH2-PEG-NH2); AC-PEG-AC (Bifunctional Acrylate PEG Acrylate); ACA-PEG-ACA (Bifunctional Polymerizable PEG Acrylate Acrylamide); Epoxide-PEG-Epoxide (Bifunctional PEG Epoxide or EP); NPC-PEG-NPC (Bifunctional NPC PEG, Nitrophenyl Carbonate); Aldehyde-PEG-Aldehyde (ALD-PEG-ALD, bifunctional PEG propionaldehyde); AA-PEG-AA (Acid-PEG-Acid, AA-acetic acid or carboxyl methyl); GA-PEG-GA (Acid-PEG-Acid, GA: Glutaric acid); SA-PEG-SA (Bifunctional PEG carboxylic acid-Succinic Acid); GAA-PEG-GAA (Bifunctional PEG carboxylic acid, Glutaramide Acid); SAA-PEG-SAA (Bifunctional PEG carboxylic acid, Succinamide Acid); Azide-PEG-Azide (Bifunctional PEG azide, N3-PEG-N3); Alkyne-PEG-Alkyne (Bifunctional alkyne or acetylene PEG); Biotin-PEG-Biotin (Bifunctional biotin PEG linker); Silane-PEG-Silane (Bifunctional silane PEG); Hydrazide-PEG-Hydrazide (Bifunctional PEG Hydrazide); Tosylate-PEG-Tosylate (Bifunctional PEG Tosyl); and Chloride-PEG-Chloride (Bifunctional PEG Halide).

In certain embodiments, a linker of the invention may be modified for improved systemic half-life and reduced dosage frequency. In an embodiment, N-glycans are added to a linker. While the biological function is typically determined by the protein component, carbohydrates can play a role in molecular stability, solubility, in vivo activity, serum half-life, and immunogenicity. The sialic acid component of carbohydrate in particular, can extend the serum half-life of protein therapeutics. Accordingly, new N-linked glycosylation consensus sequences may be introduced into desirable positions in the peptide backbone to generate proteins with increased sialic acid containing carbohydrate, thereby increasing in vivo activity due to a longer serum half-life. In another embodiment, PEG is added to a linker. Methods of conjugating PEG to a protein are standard in the art. For example, see Kolate et al, *Journal of Controlled Release* 2014; 192(28): 67-81, which is hereby incorporated by reference in its entirety. In an embodiment, a composition of the invention comprises a ligand comprising PEG and/or one or more N-glycans. In an embodiment, PEG is selected from the group consisting of PEG-10K, PEG-20K and PEG-40K.

Another aspect of the invention involves cross-linking the peptides of the invention to improve their pharmacokinetic, immunogenic, diagnostic, and/or therapeutic attributes. Cross-linking involves joining two molecules by a covalent bond through a chemical reaction at suitable site(s) (e.g., primary amines, sulfhydryls) on the cytokine and ligand of the invention. In an embodiment, the cytokine and ligand may be cross-linked together. The cross-linking agents may form a cleavable or non-cleavable linker between the cytokine and the ligand. Cross-linking agents that form non-cleavable linkers between the cytokine and the ligand may comprise a maleimido- or haloacetyl-based moiety. According to the present invention, such non-cleavable linkers are said to be derived from maleimido- or haloacetyl-based moiety. Cross-linking agents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), K-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester [AMAS], succinimidyl-6-(3-maleimidopropionamido) hexanoate (SMPH), N-succinimidyl 4-(α-maleimidophenyl)-butyrate (SMPB), and N-(p-maleimidophenyl)isocyanate (PMPI). These cross-linking agents form non-cleavable linkers derived from maleimido-based moieties. Cross-linking agents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP). These cross-linking agents form non-cleavable linkers derived from haloacetyl-based moieties. Cross-linking agents that form non-cleavable linkers between the cytokine and the ligand may comprise N-succinimidyl 3-(2-pyridyldithio)propionate, 4-succinimidyl-oxycarbonyl-α-methyl-alpha-(2-pyridyldithio)-toluene (SMPT), N-succinimidyl-3-(2-pyridyldithio)-butyrate (SDPB), 2-iminothiolane, or acetylsuccinic anhydride.

(d) Chimeric Peptide

In another aspect, the invention encompasses a chimeric peptide comprising a cytokine peptide and a ligand peptide, wherein the cytokine peptide is not a binding partner of the ligand peptide. In still another aspect, the invention encompasses a chimeric peptide comprising a cytokine peptide and a ligand peptide, wherein the ligand peptide binds to an NKG2D receptor. It should be understood that "ligand peptideis" used interchangeably with "liganda" and "cytokine peptide" is used interchangeably with "cytokine" for purposes of descriptions herein of various cytokines and ligands that are suitable for use in the present compositions and methods.

In certain embodiments, the cytokine peptide is in the IL2 subfamily. More specifically, the cytokine peptide is selected from the group consisting of IL2, IL7, IL15 and IL21. In a specific embodiment, the cytokine peptide is IL15 or a mutant thereof. In another specific embodiment, the cytokine peptide is IL2 or a mutant thereof. In another embodiment, the cytokine peptide is mutant IL2 comprising at least one mutation selected from the group consisting of R38A, F42K and C125S. In a specific embodiment, the cytokine peptide comprises the amino acid sequence set forth in SEQ ID NO:5 or SEQ ID NO:6. In other embodiments, the cytokine peptide is in the IL1 family. More specifically, the cytokine peptide is selected from the group consisting of IL1α, IL1β, IL1Ra, IL18, IL36Ra, IL36α, IL37, IL36β, IL36γ, IL38, and IL33. In a specific embodiment, the cytokine peptide is IL18 or a mutant thereof.

In certain embodiments, the ligand peptide is a MHC class-I-related glycoprotein. In another embodiment, the ligand peptide is OMCP, a portion thereof, or a mutant thereof. In an embodiment, the ligand peptide binds to a receptor expressed on NK cells and CD8+ CTLs. In a specific embodiment, the ligand peptide binds to an NKG2D receptor. In certain embodiments, the ligand peptide comprises the amino acid sequence set forth in SEQ ID NO:7 or a portion thereof that is capable of binding to the NKG2D receptor.

In other embodiments, a chimeric peptide further comprises a linker peptide. In certain embodiments, a linker peptide comprises the amino acid sequence selected from the group consisting of $(AAS)_n$, $(AAAL)_n$, $(G_nS)_n$ or $(G_2S)_n$, wherein A is alanine, S is serine, L is leucine, and G is glycine and wherein n is an integer from 1-20, or 1-10, or 3-10. In a different embodiment, a linker peptide comprises at least one tag selected from the group consisting of a FLAG tag and a His tag. In an embodiment, a linker peptide is about 20 to about 30 amino acids. In a specific embodiment, a linker peptide comprises the amino acid sequence set forth in SEQ ID NO:8.

The invention also encompasses a nucleic acid molecule encoding a chimeric peptide as described herein. Additionally, the invention encompasses a pharmaceutical composition comprising a chimeric peptide as described herein. Pharmaceutical compositions are described in more detail in Section I(f).

(e) Preferred Embodiments

By way of non-limiting example, several preferred compositions of the invention are depicted in FIG. 23. 1. depicts a composition comprising α2 domain (H2) of OMCP linked to a cytokine. 2. depicts a composition comprising OMCP linked to a cytokine, wherein the composition is pegylated. 3. depicts a composition comprising OMCP linked to a cytokine, wherein the composition comprises N-glycan. 4. depicts a composition comprising, OMCP linked to a cytokine, wherein the linker comprises various sequences and various lengths. 5. depicts a composition comprising a Fab specific antibody for NKG2D linked to a cytokine. 6. depicts a composition comprising various NKG2D ligands linked to a cytokine. 7. depicts a composition comprising a mutated version of OMCP linked to a cytokine, wherein the OMCP may be mutated to have improved binding affinity or weaker binding affinity. 8. depicts a composition comprising a mutated version of OMCP linked to a cytokine, wherein the OMCP may be mutated to have binding affinity for other NKG2 receptors. 9. depicts a composition comprising a viral protein linked to a cytokine. For example, OMCP binds to NKG2D. Additionally, CPXV203 binds to MHCI. 10. depicts a composition comprising OMCP linked to a mutated cytokine. It is understood that the OMCP sequence could be from various sources such as cowpox or monkeypox. Also, Fc-chimeras of OMCP and IL2, and variants thereof may be used.

In a preferred embodiment, the composition comprises IL2, IL15 or IL18 linked to OMCP. In another preferred embodiment, the composition comprises IL2, IL15 or IL18 linked to OMCP via a peptide linker. In still another preferred embodiment, the composition comprises IL2, IL15 or IL18 linked to OMCP via a peptide linker comprising about 20 to about 30 amino acids. In still yet another preferred embodiment, the composition comprises IL2, IL15 or IL18 linked to OMCP via a peptide linker comprising a FLAG tag and a His tag. In each of the foregoing embodiments, the IL2 may be a mutated version of IL2 comprising the mutations R38A and F42K.

In a different preferred embodiment, the composition comprises IL2 linked to OMCP. In another preferred embodiment, the composition comprises IL2 linked to OMCP via a peptide linker. In still another preferred embodiment, the composition comprises IL2 linked to OMCP via a peptide linker comprising about 20 to about 30 amino acids. In still yet another preferred embodiment, the composition comprises IL2 linked to OMCP via a peptide linker comprising a FLAG tag and a His tag. In each of the foregoing embodiments, the IL2 may be a mutated version of IL2 comprising the mutations R38A and F42K.

```
In an exemplary embodiment, the composition
comprises the DNA sequence set forth in
SEQ ID NO: 1
(CACAAACTCGCATTCAACTTCAATCTAGAAATAAATGGCAGTGATACAC

ATTCTACAGTAGATGTATATCTTGATGATTCTCAAATTATAACGTTTGAT

GGAAAAGATATCCGTCCAACCATCCCGTTCATGATAGGTGATGAAATTTT

CTTACCGTTTTATAAAAATGTGTTTAGTGAGTTTTTCTCTCTGTTTAGAA

GAGTTCCTACAAGTACTCCATATGAAGACTTGACATATTTTTATGAATGC

GACTATACAGACAATAAATCTACATTTGATCAGTTTTATCTTTATAATGG

CGAAGAATATACTGTCAAAACACAGGAGGCCACTAATAAAAATATGTGGC

TAACTACTTCCGAGTTTAGACTAAAAAAATGGTTCGATGGCGAAGATTGT

ATAATGCATCTTAGATCGTTAGTTAGAAAAATGGAGGACAGTAAACGAAA

CACTGGTGGTACCGGAAGTAGCGGTAGTAGTGATTACAAGGACGATGACG

ACAAGCACCACCATCATCATCATCACCACGGTAGCAGCGGCAGCAGTGCC

CCCACCTCTAGCAGCACAAAGAAGACCCAGCTGCAACTGGAACACCTCCT

GCTGGACCTGCAGATGATCCTGAACGGCATCAACAACTACAAGAACCCCA

AGCTGACCGCCATGCTGACCAAAAAGTTTTACATGCCCAAGAAGGCCACC

GAGCTTAAACACCTGCAATGCCTTGAGGAGGAGCTGAAGCCCTGGAGGAG

GTACTGAACCTGGCCCAGAGCAAGAACTTTCATCTGAGGCCCAGGGACCT

GATTAGCAACATCAACGTGATCGTGTTGGAGTTGAAGGGCAGCGAGACCA
```

-continued

CGTTCATGTGCGAGTACGCCGACGAGACGGCCACCATAGTGGAGTTTCTT

AACAGGTGGATCACCTTCTCACAGTCTATCATCAGCACCCTGACC).

In another exemplary embodiment, the composition comprises the amino acid sequence set forth in SEQ ID NO: 2
(HKLAFNFNLEINGSDTHSTVDVYLDDSQIITFDGKDIRPTIPFMIGDEI

FLPFYKNVFSEFFSLFRRVPTSTPYEDLTYFYECDYTDNKSTFDQFYLYN

GEEYTVKTQEATNKNMWLTTSEFRLKKWFDGEDCIMHLRSLVRKMEDSKR

NTGGTGSSGSSDYKDDDDKHHHHHHHGSSGSSAPTSSSTKKTQLQLEHL

LLDLQMILNGINNYKNPKLTAMLTKKFYMPKKATELKHLQCLEEELKPLE

EVLNLAQSKNFHLRPRDLISNINVIVLELKGSETTFMCEYADETATIVEF

LNRWITFSQSIISTLT).

(f) Pharmaceutical Compositions

The present disclosure also provides pharmaceutical compositions. The pharmaceutical composition comprises a composition of the invention which is detailed above, as an active ingredient and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm

II. Methods

In an aspect, the invention encompasses a method to deliver a cytokine to a target cell. The method comprises contacting a target cell with a composition comprising a cytokine linked to a ligand, wherein the ligand specifically binds to a receptor on the target cell. Additionally, the method comprises contacting a target cell with a composition comprising a chimeric peptide as described in Section I. A target cell may be any cell comprising a target receptor for which the ligand specifically binds to. The ligand and specific binding are described in Section I. In certain embodiments, a target cell may be an immune cell. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, a target cell is a natural killer (NK) cell and/or a CD8+ T cell. In other embodiments, a target cell is a NKG2D-expressing cell. Non-limiting examples of NKG2D-expressing cell include natural killer (NK) cells and CD8+ T cells (both $\alpha\beta$ and $\gamma\delta$).

In another aspect, the invention encompasses a method to activate immune cells. The method comprises contacting an immune cell with a composition comprising a cytokine linked to a ligand, wherein the ligand specifically binds to a receptor on the immune cell thereby activating the cell. Additionally, the method comprises contacting an immune cell with a composition comprising a chimeric peptide as described in Section I. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, an immune cell is a natural killer (NK) cell and/or a CD8+ T cell. To facilitate activation of immune cells, a cytokine may be a proinflammatory cytokine. The term "proinflammatory cytokine" is a cytokine which promotes systemic inflammation. A skilled artisan would be able to determine those cytokines that are proinflammatory. In certain embodiments, a proinflammatory cytokine is IL1$\alpha$, IL1$\beta$, IL2, IL3, IL6, IL7, IL9, IL12, IL15, IL17, IL18, IL21, IFN$\alpha$, IFN$\gamma$, TNF$\alpha$, MIF, G-CSF, GM-CSF or mutants thereof. In an embodiment, a proinflammatory cytokine is an IL1 family cytokine. In certain embodiments, an IL1 family cytokine is selected from the group consisting of IL1$\alpha$, IL1$\beta$, IL1Ra, IL18, IL36Ra, IL36$\alpha$, IL37, IL36$\beta$, IL36$\gamma$, IL38, IL33 and mutants thereof. In a specific embodiment, a proinflammatory cytokine is selected from the group consisting of IL2, IL7, IL15, IL18, IL21 and mutants thereof. In another specific embodiment, a proinflammatory cytokine is selected from the group consisting of IL2, IL15, IL18, and mutants thereof. In an exemplary embodiment, a proinflammatory cytokine is IL2 or a mutant thereof. Activation of the immune cells may result in lysis of tumor cells. Accordingly, activation of immune cells may be measured by determining the amount of tumor cell lysis. In an embodiment, activation of the immune cells may result in about 10% to about 100% lysis of tumor cells. In another embodiment, activation of the immune cells may result in about 20% to about 80% lysis of tumor cells. In still another embodiment, activation of the immune cells may result in greater than 40% lysis of tumor cells. For example, activation of the immune cells may result in greater than 40%, greater than 45%, greater than 50%, greater than 55%, greater than 60%, greater than 65%, greater than 70%, greater than 75%, greater than 80%, greater than 85%, greater than 90%, greater than 95%, or greater than 99% lysis of tumor cells. The lysis of tumor cells may be measured using any standard assay (e.g., caspase assays, TUNEL and DNA fragmentation assays, cell permeability assays, and Annexin V assays).

In still another aspect, the invention encompasses a method to treat a tumor. The method comprises identifying a subject with a tumor and administering to the subject a composition comprising a cytokine linked to a ligand, wherein the ligand specifically binds to a receptor on a target cell. Additionally, the method comprises administering to the subject a composition comprising a chimeric peptide as described in Section I. Specifically, the inventors have shown that delivering a cytokine to a target cell activates the cells bound by the composition, wherein the activated cells specifically lyse tumor cells thereby reducing the amount of cancer cells. In a specific embodiment, a cytokine is a proinflammatory cytokine as described in the preceding paragraph. Accordingly, a composition of the present invention, may be used in treating, stabilizing and preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. The inventors have shown that a composition of the invention activates natural killer (NK) cells bound by the composition, wherein the activated NK cells specifically lyse tumor cells thereby reducing the amount of tumor cells. For example, as cancerous cells are "stressed", NKG2D ligands become upregulated, rendering the cell susceptible to NK cell-mediated lysis. In a desired embodiment, the percent of tumor or cancerous cells surviving the treatment is at least 20, 30, 40, 50, 60, 70, 80, 90 or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a composition of the invention is at least 2, 5, 10, 15, 20, 25, 30, 35, 40, 45 or 50-fold greater than the decrease in the number of non-tumor or non-cancerous cells. Desirably, the methods of the present invention result in a decrease of 20, 30, 40, 50, 60, 50, 80, 90 or 100% in the size of a tumor or in the number of cancerous cells, as determined using standard methods. Desirably, at least 20, 30, 40, 50, 60, 70, 80, 90, or 95% of the treated subjects have a complete remission in which all evidence of the tumor or cancer disappears. Desirably, the tumor or cancer does not reappear or reappears after at least 1, 2, 3, 4, 5, 10, 15, or 20 years.

In another aspect, the invention encompasses a method to suppress immune cells. The method comprises contacting an immune cell with a composition comprising a cytokine linked to a ligand, wherein the ligand specifically binds to a receptor on the immune cell thereby suppressing the cell. Additionally, the method comprises contacting an immune cells with a composition comprising a chimeric peptide as described in Section I. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, an immune cell is a natural killer (NK) cell and/or a CD8+ T cell. To facilitate suppression of immune cells, a cytokine may be an anti-inflammatory cytokine. The term "anti-inflammatory cytokine" is a cytokine that counteracts various aspects of inflammation, for example cell activation or the production of proinflammatory cytokines, and thus contributes to the control of the magnitude of the inflammatory response. A skilled artisan would be able to determine those cytokines that are anti-inflammatory. In certain embodiments, an anti-inflammatory cytokine is IL4, IL5, IL10, IL11, IL13, IL16, IL35, IFNα, TGFβ, G-CSF or a mutant thereof. In a specific embodiment, an anti-inflammatory cytokine is IL10 or a mutant thereof. In another embodiment, the invention encompasses a method to kill immune cells. The method comprises contacting an immune cell with a composition comprising a toxin linked to a ligand, wherein the ligand specifically binds to a receptor on the immune cell thereby killing the cell. Suppression or killing of the immune cells may result in treatment, stabilization and prevention of autoimmune diseases caused by overactive immune cells. NKG2D-expressing cells and/or aberrant expression of host NKG2DLs have been implicated in diabetes, celiac disease and rheumatoid arthritis. For example, NK cells can recognize pancreatic beta cells and destroy them. The destruction of pancreatic beta cells may lead to type 1 diabetes. By way of another example, overactive immune cells are involved in transplant/graft rejection. Accordingly, a composition of the present invention, may be used in treating, stabilizing and preventing an automimmune disease in a subject. In a specific embodiment, the autoimmune disease is type 1 diabetes. In another specific embodiment, the autoimmune disease is transplant or graft rejection. In still another specific embodiment, the autoimmune disease is rheumatoid arthritis.

In still yet another aspect, the invention encompasses a method to treat an infection comprising administering a composition comprising a cytokine linked to a ligand. For example, a composition comprising a cytokine linked to a ligand may specifically bind an immune cell that is then activated to target and lyse the infected host cell. Additionally, the method comprises administering to the subject a composition comprising a chimeric peptide as described in Section I. The term "infection" as used herein includes the presence of pathogens in or on a subject, which, if its growth were inhibited, would result in a benefit to the subject. As such, the term "infection" in addition to referring to the presence of pathogens also refers to normal flora which are not desirable. The term "pathogen" as used herein refers to an infectious agent that can produce disease. Non-limiting examples of an infectious agent include virus, bacterium, prion, fungus, viroid, or parasite that cause disease in a subject. In a specific embodiment, an infection is caused by pathogens such as bacteria or viruses. In certain embodiments, the infection is an intracellular infection. In an embodiment, the infection is a viral infection. In another embodiment, the viral infection is caused by a flavivirus. Flavivirus is a genus of viruses in the family Flaviviridae. Non-limiting examples of flaviviruses include Gadget's Gully virus, Kadam virus, Kyasanur Forrest disease virus, Langat virus, Omsk hemorrhagic fever virus, Tick-borne encephalitis virus, Louping ill virus, Aroa virus, Dengue viruses 1-4, Kedougou virus, Cacipacore virus, Koutango virus, Murray Valley encephalitis virus, St. Louis encephalitis virus, Usutu virus, West Nile virus, Yaounde virus, Kokobera virus group, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, hepatitis C virus, e.g., hepatitis C virus genotypes 1-6, and GB virus A and B. In a certain embodiment, the flavivirus may be selected from the group consisting of West Nile virus, dengue virus, Japanese encephalitis virus, and yellow fever virus. In a specific embodiment, the viral infection is caused by West Nile virus. In certain embodiments, a pathogen, more specifically a virus, can induce the expression of proteins for which NKG2D binds. Accordingly, a composition comprising a cytokine linked to a ligand may specifically bind a NK cell that is then activated to target and lyse the infected host cell expressing NKG2D. In another embodiment, a composition comprising a cytokine linked to a ligand may activate cytotoxic T lymphocytes that recognize infected cells via other mechanisms for targeted killing.

In a different aspect, the invention encompasses a method to alleviate immunosuppression related to radiation exposure or lympotoxic substances comprising administering a composition comprising a cytokine linked to a ligand. Additionally, the method comprises administering a composition comprising a chimeric peptide as described in Section I. Additionally, a composition of the invention may be used to raise CD4 counts in HIV positive subjects. For example, a composition of the invention may be used to activate immune cells which can help restore the immune system of the subject.

In an alternative aspect, the invention encompasses a method of use as an adjuvant in a vaccine composition. For example, a composition of the invention may be used to expand CD8+ memory cells.

(a) Administration

In certain aspects, a pharmacologically effective amount of a composition of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. Pheresis may be used to deliver a composition of the invention. In certain embodiments, a composition of the invention may be administered via an infusion (continuous or bolus).

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable response (e.g., an immunostimulatory, an anti-angiogenic response, a cytotoxic response, tumor regression, immunoinhibitory, immunosuppression, infection reduction). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, the autoimmune disease, infection, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 10 IU/kg to about 1,000,000 IU/kg of a cytokine described herein. In an embodiment, a typical dose contains from about 10 IU/kg to about 100 IU/kg. In another embodiment, a typical dose contains about 100 IU/kg to about 1,000 IU/kg. In still another embodiment, a typical dose contains about 1,000 IU/kg to about 10,000 IU/kg. In yet still another embodiment, a typical dose contains about 10,000 IU/kg to about 100,000 IU/kg. In a different embodiment, a typical dose contains about 100,000 IU/kg to about 1,000,000 IU/kg. In certain embodiments, a typical dose contains about 500,000 IU/kg to about 1,000,000 IU/kg. In other embodiments, a typical dose contains about 100,000 IU/kg to about 500,000 IU/kg. Alternatively, a typical dose contains about 50,000 IU/kg to about 100,000 IU/kg. In another embodiment, a typical dose contains about 10,000 IU/kg to about 50,000 IU/kg. In still another embodiment, a typical dose contains about 5,000 IU/kg to about 10,000 IU/kg. In a specific embodiment, a typical dose contains about 5,000 IU/kg to about 200,000 IU/kg. In another specific embodiment, a typical dose contains about 5,000 IU/kg to about 500,000 IU/kg. In still another specific embodiment, a typical dose contains about 50,000 IU/kg to about 500,000 IU/kg. In still yet another specific embodiment, a typical dose contains about 250,000 IU/kg to about 750,000 IU/kg.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In a specific embodiment, the frequency of dosing may be twice daily.

Duration of treatment could range from a single dose administered on a one-time basis to a life-long course of therapeutic treatments. The duration of treatment can and will vary depending on the subject and the cancer or autoimmune disease or infection to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The timing of administration of the treatment relative to the disease itself and duration of treatment will be determined by the circumstances surrounding the case. Treatment could begin immediately, such as at the time of diagnosis, or treatment could begin following surgery. Treatment could begin in a hospital or clinic itself, or at a later time after discharge from the hospital or after being seen in an outpatient clinic.

Although the foregoing methods appear the most convenient and most appropriate and effective for administration of a composition of the invention, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

(b) Tumor

A composition of the invention may be used to treat or recognize a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/ carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sézary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, the neoplasm or cancer may be selected from the group consisting of melanoma, renal cell carcinoma, lung cancer and blood cancer. As used herein, a "blood cancer" is a cancer that affects the blood, bone marrow and lymphatic system. There are three main groups of blood cancer: leukemia, lymphoma and myeloma. The four broad classification of leukemia are: acute lymphocytic leukemia (ALL), acute myelogenous leukemia (AML), chronic lymphocytic leukemia (CLL) and chronic myelogenous leukemia (CML).

Lymphomas are divided into two categories: Hodgkin lymphoma and non-Hodgkin lymphoma. Most non-Hodgkin lymphomas are B-cell lymphomas, and either grow quickly (high-grade) or slowly (low-grade). There are 14 types of B-cell non-Hodgkin lymphomas. The rest are T-cell lymphomas, named after a different cancerous white blood cell, or lymphocyte. Because myeloma frequently occurs at many sites in the bone marrow, it is often referred to as multiple myeloma.

(c) Subject

A suitable subject includes a human, a livestock animal, a companion animal, lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

TABLE A

Sequences

| SEQ ID NO | Name | Sequence | Source |
|---|---|---|---|
| 1 | R38A, F42K, C125S IL2-OMCP construct | CACAAACTCGCATTCAACTTCAATCTAGAAATAAATG GCAGTGATACACATTCTACAGTAGATGTATATCTTG ATGATTCTCAAATTATAACGTTTGATGGAAAAGAT ATCCGTCCAACCATCCCGTTCATGATAGGTGATGAA ATTTTCTTACCGTTTTATAAAAATGTGTTTAGTGAGTT TTTCTCTCTGTTTAGAAGAGTTCCTACAAGTACTCCAT ATGAAGACTTGACATATTTTTATGAATGCGACTATACA GACAATAAATCTACATTTGATCAGTTTTATCTTTATAA TGGCGAAGAATATACTGTCAAAACACAGGAGGCCAC TAATAAAAATATGTGGCTAACTACTTCCGAGTTTAGA CTAAAAAAATGGTTCGATGGCGAAGATTGTATAATGC ATCTTAGATCGTTAGTTAGAAAAATGGAGGACAGTAA ACGAAACACTGGTGGTACCGGAAGTAGCGGTAGTAG TGATTACAAGGACGATGACGACAAGCACCACCATCA TCATCATCACCACGGTAGCAGCGGCAGCAGTGCCCC CACCTCTAGCAGCACAAAGAAGACCCAGCTGCAACT GGAACACCTCCTGCTGGACCTGCAGATGATCCTGAA CGGCATCAACAACTACAAGAACCCCAAGCTGACCGC CATGCTGACCAAAAAGTTTTACATGCCCAAGAAGGC CACCGAGCTTAAACACCTGCAATGCCTTGAGGAGGA GCTGAAGCCCTGGAGGAGGTACTGAACCTGGCCCA GAGCAAGAACTTTCATCTGAGGCCCAGGGACCTGAT TAGCAACATCAACGTGATCGTGTTGGAGTTGAAGGG CAGCGAGACCACGTTCATGTGCGAGTACGCCGACGA GACGGCCACCATAGTGGAGTTTCTTAACAGGTGGAT CACCTTCTCACAGTCTATCATCAGCACCCTGACC | Synthesized |
| 2 | R38A, F42K, C125S IL2-OMCP construct | HKLAFNFNLEINGSDTHSTVDVYLDDSQIITFDGKDIRPT IPFMIGDEIFLPFYKNVFSEFFSLFRRVPTSTPYEDLTYF YECDYTDNKSTFDQFYLYNGEEYTVKTQEATNKNMWL TTSEFRLKKWFDGEDCIMHLRSLVRKMEDSKRNTGGT GSSGSSDYKDDDDKHHHHHHHGSSGSSAPTSSSTK KTQLQLEHLLLDLQMILNGINNYKNPKLTAMLTKKFYMP KKATELKHLQCLEEELKPLEEVLNLAQSKNFHLRPRDLI SNINVIVLELKGSETTFMCEYADETATIVEFLNRWITFSQ SIISTLT | Synthesized |
| 3 | Melanoma tumor associate antigen tyrosinase-related protein 2 peptide | SVYDFFVWL | *Homo sapiens* |

TABLE A-continued

Sequences

| SEQ ID NO | Name | Sequence | Source |
|---|---|---|---|
| 4 | Highly immunogenic peptide | SIINFEKL | Homo sapiens |
| 5 | WT IL2 (C125S) | APTSSSTKKTQLQLEHLLLDLQMILNGINNYKNPKLTRM LTFKFYMPKKATELKHLQCLEEELKPLEEVLNLAQSKNF HLRPRDLISNINVIVLELKGSETTFMCEYADETATIVEFL NRWITFCQSIISTLT | Homo sapiens |
| 6 | R38A, F42K, C125S IL2 | APTSSSTKKTQLQLEHLLLDLQMILNGINNYKNPKLTAM LTKKFYMPKKATELKHLQCLEEELKPLEEVLNLAQSKNF HLRPRDLISNINVIVLELKGSETTFMCEYADETATIVEFL NRWITFSQSIISTLT | Synthesized |
| 7 | OMCP | HKLAFNFNLEINGSDTHSTVDVYLDDSQIITFDGKDIRPT IPFMIGDEIFLPFYKNVFSEFFSLFRRVPTSTPYEDLTYF YECDYTDNKSTFDQFYLYNGEEYTVKTQEATNKNMWL TTSEFRLKKWFDGEDCIMHLRSLVRKMEDSKRNT | Synthesized |
| 8 | Linker | GSSGSSDYKDDDDKHHHHHHHGSSGSS | Synthesized |
| 9 | FLAG tag | DYKDDDDK | Synthesized |
| 10 | HA tag | YPYDVPDYA | Synthesized |
| 11 | Myc tag | EQKLISEEDL | Synthesized |
| 12 | V5 tag | GKPIPNPLLGLDST | Synthesized |
| 13 | OMCPbr | GHKLAFNFNLEINGSDTHSTVDVYLDDSQIITFDGKDIRP TIPFMIGDEIFLPFYKNVFSEFFSLFRRVPTSTPYEDLTY FYECDYTDNKSTFDQFYLYNGEEYTVKTQEATNKNMW LTTSEFRLKKWFDGEDCIMHLRSLVRKMEDSKR | Cowpox virus |
| 14 | OMCPmpx | HKLVHYFNLKINGSDITNTADILLDNYPIMTFDGKDIYPSI AFMVGNKLFLDLYKNIFVEFFRLFRVSVSSQYEELEYYY SCDYTNNRPTIKQHYFYNGEEYTEIDRSKKATNKNSWLI TSGFRLQKWFDSEDCIIYLRSLVRRMEDSNK | Monkeypox virus |
| 15 | MICA | MEPHSLRYNLTVLSWDGSVQSGFLTEVHLDGQPFLRC RDRQKCRAKPQGQWAEDVLGNKTWDRETRDLTGNG KDLRMTLAHIKDQKEGLHSLQEIRVCEIHEDNSTRSSQH FYYDGELFLSQNLETKEWTMPQSSRAQTLAMNVRNFL KEDAMKTKTHYHAMHADCLQELRRYLKSGVVLR | Homo sapiens |
| 16 | MICB | MEPHSLRYNLMVLSQDGSVQSGFLAEGHLDGQPFLRY DRQKRRAKPQGQWAEDVLGAETWDTETEDLTENGQD LRRTLTHIKDQKGGLHSLQEIRVCEIHEDSSTRGSRHFY YNGELFLSQNLETQESTVPQSSRAQTLAMNVTNFWKE DAMKTKTHYRAMQADCLQKLQRYLKSGVAIR | Homo sapiens |
| 17 | ULBP3 | DAHSLWYNFTIIHLPRHGQQWCEVQSQVDQKNFLSYD CGSDKVLSMGHLEEQLYATDAWGKQLEMLREVGQRL RLELADTELEDFTPSGPLTLQVRMSCECEADGYIRGSW QFSFDGRKFLLFDSNNRKWTVVHAGARRMKEKWEKD SGLTTFFKMVSMRDCKSWLRDFLMHRKKRLE | Homo sapiens |
| 18 | RAE-1B | DAHSLRCNLTIKDPTPADPLWYEAKCFVGEILILHLSNIN KTMTSGDPGETANATEVKKCLTQPLKNLCQKLRNKVS NTKVDTHKTNGYPHLQVTMIYPQSQGRTPSATWEFNIS DSYFFTFYTENMSWRSANDESGVIMNKWKDDGEFVK QLKFLIHECSQKMDEFLKQSKEK | Homo sapiens |
| 19 | NKG2D portion | LTIIEMQKGDCALYAS | Homo sapiens |
| 20 | NKG2D portion | LTIIEMQKGECALYAS | Green monkey |
| 21 | NKG2D portion | LTIIEMQKGDCAVYAS | Marmoset |
| 22 | NKG2D portion | LTLVEIPKGSCAVYGS | Mouse |

TABLE A-continued

Sequences

| SEQ ID NO | Name | Sequence | Source |
|---|---|---|---|
| 23 | NKG2D portion | LTLVKTPSGTCAVYGS | Rat |
| 24 | NKG2D portion | LTLMDTQNGKCALYGS | Guinea pig |
| 25 | NKG2D portion | LTLVEMQNGTCIVYGS | Ground squirrel |
| 26 | NKG2D portion | LTVVEMQSGSCAVYGS | Deer mouse |
| 27 | NKG2D portion | LSMVEMQNGTCAVYAS | Naked mole rat |
| 28 | NKG2D portion | LTLVEMQRGSCAVYGS | Prairie vole |
| 29 | NKG2D portion | VSIVEMQGGNCAVYGS | European shrew |
| 30 | NKG2D portion | VTVYEMQNGSCAVYGS | Star-nosed mole |
| 31 | NKG2D portion | LTLVEMQNGSCAVYGS | Chinese hamster |
| 32 | NKG2D portion | LTMVDMQNGTCAVYGS | Cat |
| 33 | OMCP portion | ASSFK | Cowpox virus |
| 34 | DAP10 signaling motif | YINM | Synthesized |

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-6

The IL-2Rα chain serves to capture IL-2 at the cell surface to facilitate subsequent binding to the signaling part of the receptor, namely the IL-2Rβγ chains. Resting cytotoxic lymphocytes, such as natural killer (NK) and CD8+ T cells, do not express appreciable IL-2Rα at the cell surface and are thus not activated by low levels of IL-2[1]. IL-2Rα is expressed on this population after initial activation, however, and is required for maximum cytotoxic lymphocyte expansion[2]. High dose IL-2 can induce the activation of all cytotoxic lymphocytes and is approved for treatment of several malignancies with an approximately 15% partial or complete tumor response[3-5]. Most patients do not benefit from such therapy due to activation of regulatory T cell ($T_{regs}$) and complications such as severe blood pressure alteration, generalized capillary leak, and end organ failure due to activation of vascular endothelium[6,3,7]. Both vascular endothelium and $T_{regs}$ express IL-2Rα and are thus preferentially activated by IL-2 over cytotoxic lymphocytes. Lowering the IL-2 dose can ameliorate side effects but also decreases efficacy. Mutant forms of IL-2, such as those with substitutions of alanine for arginine at the 38 position (R38A) and/or lysine for phenylalanine at the 42 position (F42K), decrease the affinity of IL-2 for IL-2Rα and thus eliminate many side effects[9]. Such IL-2α mutants may also decrease the efficacy of immunotherapy[2]. A form of IL-2 that could preferentially activate cytotoxic lymphocytes in the absence of IL-2Rα reactivity would be highly advantageous for clinical applications.

NKG2D recognizes MHC class-I-related stress ligands expressed by malignant or virally-transformed cells[10]. Of all the activating immunoreceptors NKG2D has the highest specificity for cytotoxic lymphocytes as it is constitutively expressed on both murine and human NK cells as well as activated $CD8^+$ T cells. Consequentially it has been argued that tumors and virally infected cells utilize shed NKG2D ligands as a mechanism of immune evasion[12,13]. Orthopox major histocompatibility complex class I-like protein, or OMCP, is an NKG2D ligand decoy shed by monkeypox and cowpox virus infected cells. It is not expressed by small pox or vaccinia virus and thus not recognized by those immunized with small pox vaccine. As OMCP binds to both human and murine NKG2D with the highest affinity of any known ligand we thought it might function as an ideal targeting vector to optimally deliver IL-2 to cytotoxic lymphocytes[14,15]. Here we describe the construction and function of a fusion protein designed to deliver an IL-2Rα mutant to NKG2D-expressing lymphocytes[15]. We demonstrate that this construct overcomes decreased efficacy associated with mutations in the IL-2Rα binding region while retaining a favorable safety profile. Systemic administration of this fusion protein improves immunotherapy against both solid and liquid tumors. Targeted delivery of IL-2 can thus be safely used to maximally activate NKG2D-expressing lymphocytes, such as NK cells, to optimize immunotherapy without systemic side effects.

Example 1. NKG2D-Targeted Delivery of an IL-2 Mutant Preferentially Activates Cytotoxic Lymphocytes In Vitro To overcome the preferential activation of IL-2Ra-expressing cells, we designed an IL-2 fusion protein that would target cytotoxic lymphocytes directly via the NKG2D receptor. This fusion protein combines the high affinity NKG2D ligand OMCP with an IL-2 mutated to reduce IL-2Ra reactivity. Our construct, termed OMCP-mutIL-2, consists of the 152 residue OMCP protein fused to the N-terminus of the 133 amino acid R38A/F42K mutant form of human IL-2 (mutIL-2) via a flexible 30 residue linker (FIG. 1A-B). The construct was first assessed for its in vitro binding ability. Binding of fluorescently labeled construct was tested in vitro at 37° C. in bulk splenocytes. FIG. 17 shows that the construct appears to only bind to NK cells which express NKG2D. The construct does not show binding to CD4+ CD3+ T cells, CD8+CD3+ T cells, CD11C+CD11b− DCs, CD11c−CD11b+ Macs or CD19+CD3− B cells.

We have previously demonstrated strain-specific differences in murine NK cell cytotoxicity and lung cancer immunosurveillance[18] (and Example 7). Therefore, we set out to examine the efficacy of OMCP-mut-IL2 in activation of NK cells from two different strains of mice, namely A/J and B6 with poor and robust NK function, respectively. Compared to wild-type IL-2 (wtIL-2) or mutIL-2, OMCP-mutIL-2 strongly upregulated CD69 on NK cells of both strains after 36-hour co-culture with 100 IUe/ml of cytokine (FIG. 1C, left; FIG. 6, left two graphs)[16,17]. At high concentrations a similar increase in CD69 expression was observed with OMCP-mut-IL-2, wtIL-2 or mutIL-2 (FIG. 6). Activation of $CD4^+Foxp3^+$ $T_{regs}$, as measured by upregulation of ICOS, was evident with wtIL-2 only, but not with mutIL-2 nor OMCP-mutIL-2 (FIG. 1C-D). $CD8^+$ and $CD4^+$ $Foxp3^-$ effector T cells, on the other hand, demonstrated no upregulation of CD69 after 36 hours, even at highest doses of cytokines (FIGS. 1C-D and data not shown). Longer exposure over a period of five days led to proliferation of both NK and $CD8^+$ T cells exposed to wtIL-2 and OMCP-mutIL-2 (FIGS. 1E-F). Importantly, OMCP-mutIL-2 activated $CD8^+$ T cells and NK cells equivalently to mutIL-2 in $NKG2D^{-/-}$ splenocytes, indicating that the increased activation was due to the effect of OMCP targeting upon NKG2D-bearing cells (FIG. 1F; FIG. 6, right two graphs). Only incubation with wtIL-2 led to $CD4^+Foxp3^+$ $T_{regs}$ and $CD4^+Foxp3^-$ effector cell proliferation (FIG. 1E-F). Thus exposure to OMCP-mutIL-2 results in preferential NK activation that is superior or equivalent to wtIL-2 in a dose-dependent manner. $CD8^+$ T cells can also be activated but require prolonged exposure to higher doses of OMCP-mutIL-2.

Example 2. Low-Dose Cytokine Therapy Offers a Favorable Safety Profile

Dose-dependent toxicity can limit cytokine administration in vivo. To model human immunotherapy protocols we next treated A/J mice with wtIL-2 given as ten doses over a five day cycle[18]. While A/J mice tolerated 750,000 IUe of wtIL-2, significant mortality was evident at higher doses (FIG. 2A-B). Even after a 750,000 IUe dose mice demonstrated extreme distress, weight loss, decreased food consumption, ascites and hepatic inflammation (FIG. 2A-E; FIG. 7A-C). These side-effects mirror the capillary leak and distress associated with high dose IL-2 therapy in humans[7]. Treatment with anti-Asialo-GM1 ameliorated mortality, but not weight loss, induced by high dose wtIL-2 (1,500,000 IUe) in A/J mice, confirming that side effects of such therapy can occur independent of NK cells (FIG. 2F-K). Unlike the case for wtIL-2 no animal death was evident after 1,500,000 IUe of OMCP-mutIL-2 or mutIL-2 in the presence or absence of NK cells. Animal weight loss after 1,500,000 IUe of OMCP-mutIL-2 occurred only in NK-sufficient mice suggesting that toxicity of our construct was solely due to immunoactivation (FIG. 2F-K). A regimen of 200,000 IUe was well tolerated in A/J mice with minimal weight loss, distress, or organ inflammation for all cytokines (FIG. 2L-O). Capillary leak, however, was still evident by accumulation of pleural effusion and ascites after wtIL-2, but not OMCP-mutIL-2 or mutIL-2, at this dose. B6 mice were able to tolerate higher doses of wtIL-2 but still suffered significant morbidity over 750,000 IUe (FIG. 7D).

Example 3. OMCP-mutIL-2 Preferentially Expands and Activates NK Cells In Vivo Compared to wtIL-2 or mutIL-2

To evaluate immunologic changes associated with cytokine treatment, A/J mice received 200,000 IUe of cytokine or construct given as ten equal doses over five days. Splenic lymphocytes were evaluated flow cytometrically on day six. Both wtIL-2 and OMCP-mutIL-2 increased lymphocyte content and splenic size over saline-treated controls (FIG. 3A-B). OMCP-mutIL-2 led to a substantial expansion and activation of NK cells measured by cellularity and surface KLRG1 levels (FIG. 3C). In OMCP-mutIL-2 treated mice NK cells comprised close to half of all splenic lymphocytes, paralleling or even surpassing the total lymphocyte counts of saline or mutIL-2-treated mice (FIG. 3A vs. FIG. 3C). NK expansion by 200,000 IUe of OMCP-mutIL-2 was superior to near toxic doses of wtIL-2 (750,000 IU), high dose mutIL-2 (3,500,000 IUe), or wtIL-2 complexed to anti-IL-2 antibody (clone MAB602)[19] (FIG. 3C). In fact, the majority of mice could not tolerate the full 200,000 IUe of wtIL-2/anti-IL-2 antibody and injections had to be terminated at 160,000 or 180,000 IUe with requisite animal sacrifice due to animal distress and rapid weight loss (FIG. 8A). WtIL-2 led to a significant expansion of $CD4^+Foxp3^+$ $T_{regs}$, specifically the $ICOS^+$ Subset® in A/J mice even when complexed to anti-IL-2 antibodies (FIG. 3D). Importantly the NK/$T_{reg}$ ratio, which has been described as a predictive factor for success of immunotherapy[20], was dramatically increased in OMCP-mutIL-2 treated mice compared to all other treatment conditions (FIG. 3E). Superior expansion of NK cells by OMCP-mutIL-2 was even possible at doses 2-fold lower than wtIL-2 (FIG. 8B). However, targeting NKG2D with a ~500-fold lower affinity NKG2D ligand, ULBP3, ameliorated efficacy of the fusion construct for expansion but still offered superior NK activation compared to mutIL-2 alone (FIG. 8B). No statistically significant increase in $CD4^+$ $Foxp3^-$ or $CD8^+$ T lymphocytes was evident after wtIL-2 or OMCP-mutIL-2 treatment, although a trend for $CD8^+$ T cell expansion was evident (FIG. 8C-D). Such data is consistent with the prevalence of naïve T lymphocytes, expressing low levels of IL-2 receptors and NKG2D in specific pathogen-free mice.

Figure 3A:
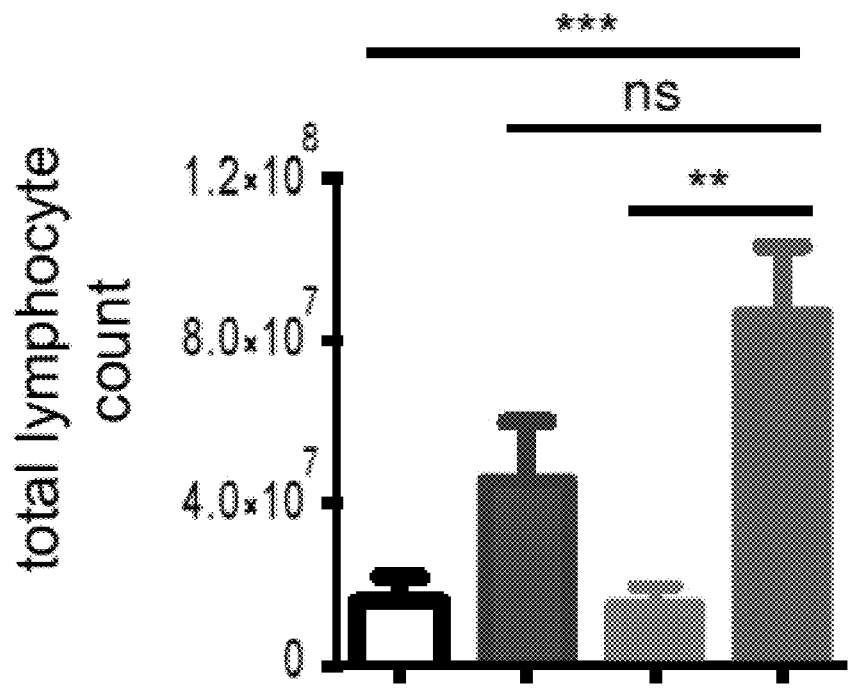
FIG. 3A, FIG. 3B, FIG. 3C, FIG. 3D, FIG. 3E, FIG. 3F, FIG. 3G, FIG. 3H, FIG. 3I and FIG. 3J depict graphs and images showing immunologic changes associated with IL-2 and IL-2 construct administration in vivo.
Figure 3B:
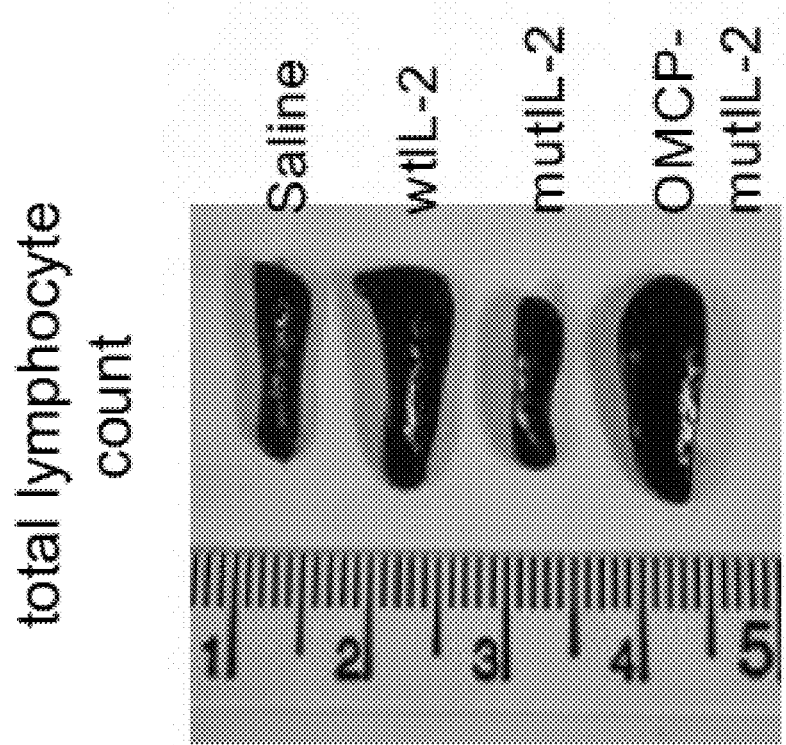
Figure 3C:
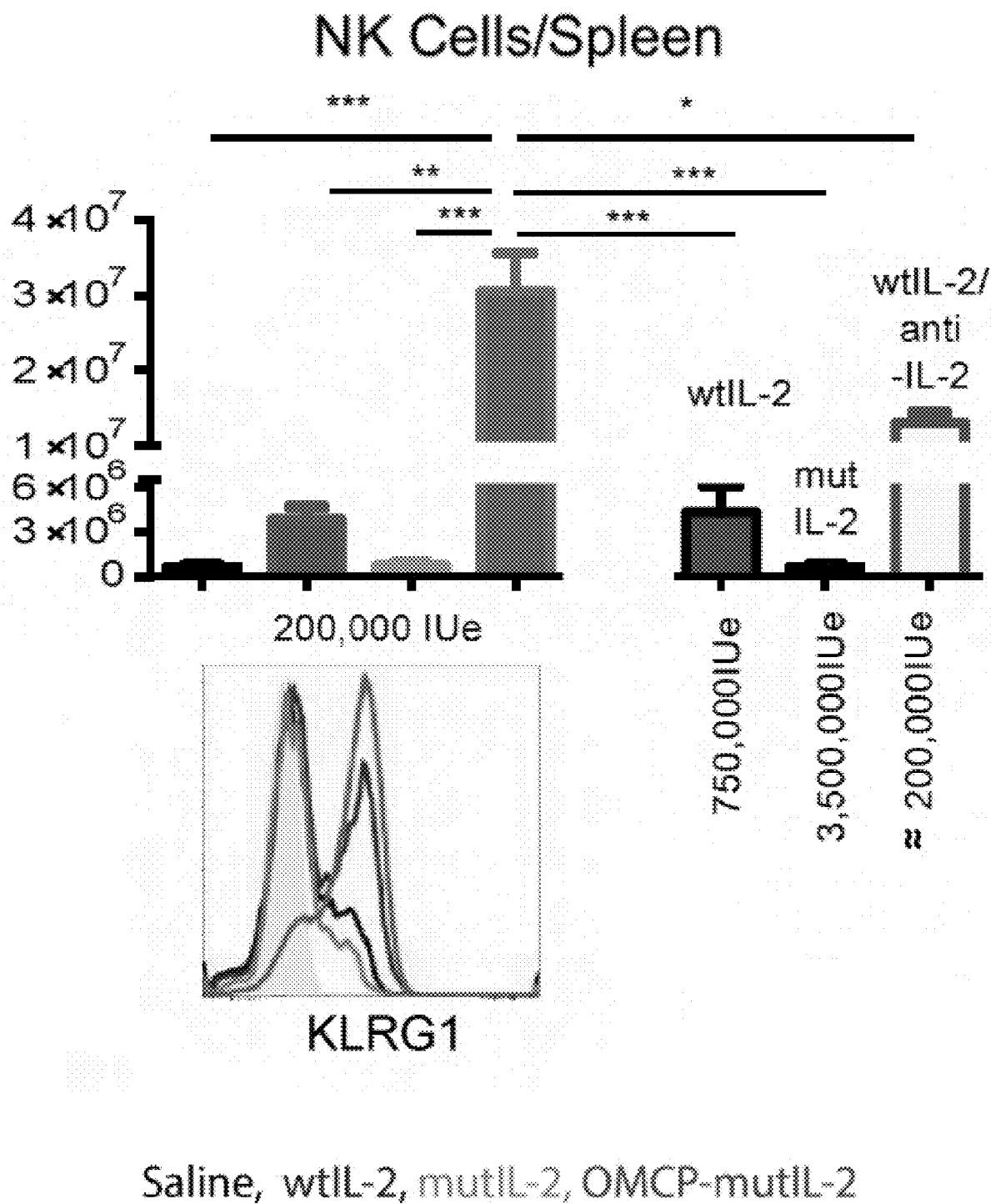
Figure 3D:
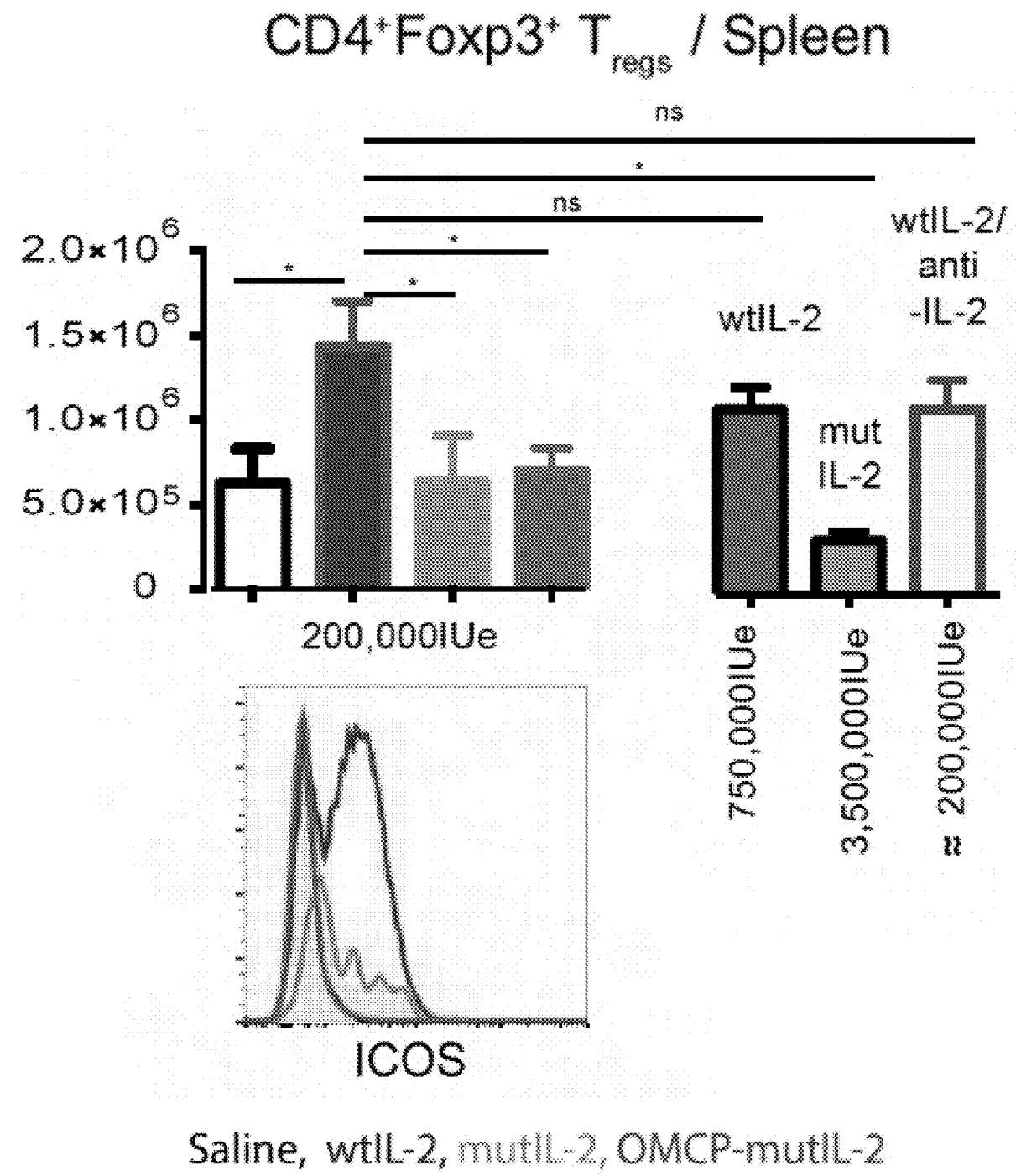
Figure 3E:
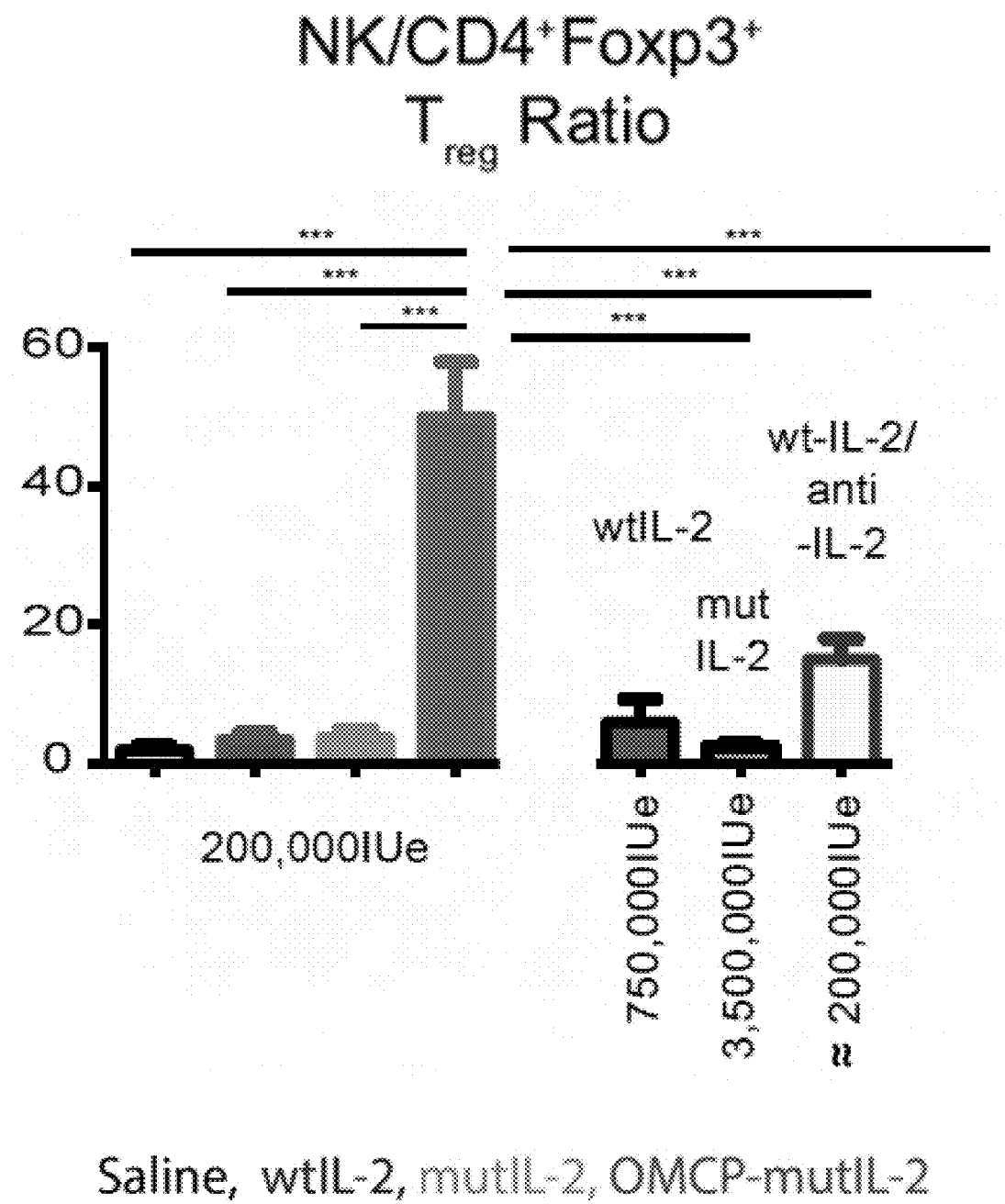
Figure 3F:
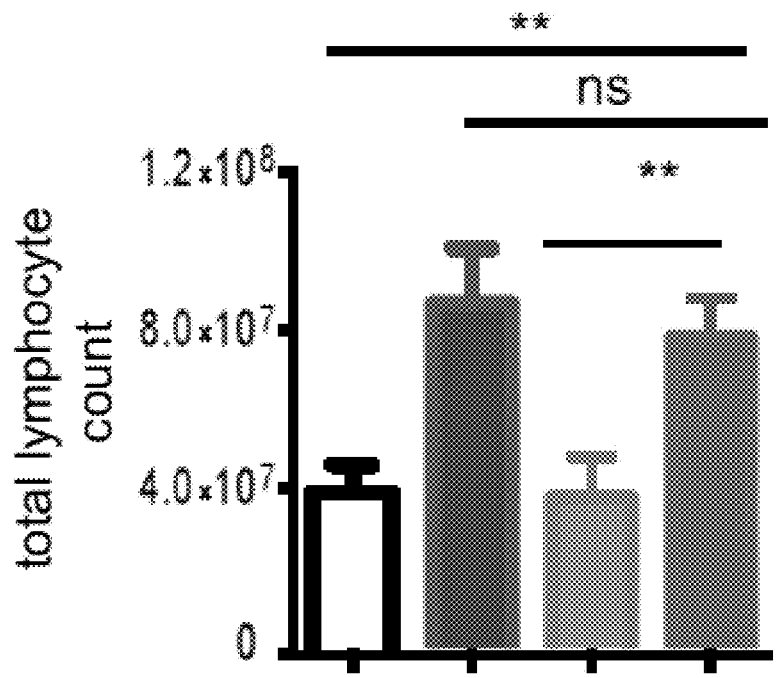
Figure 3G:
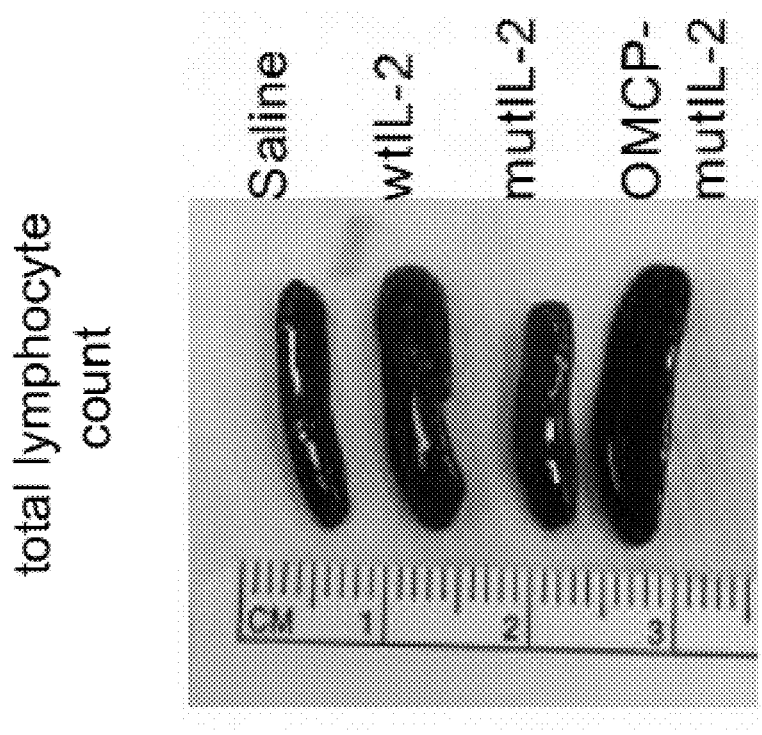
Figure 3H:
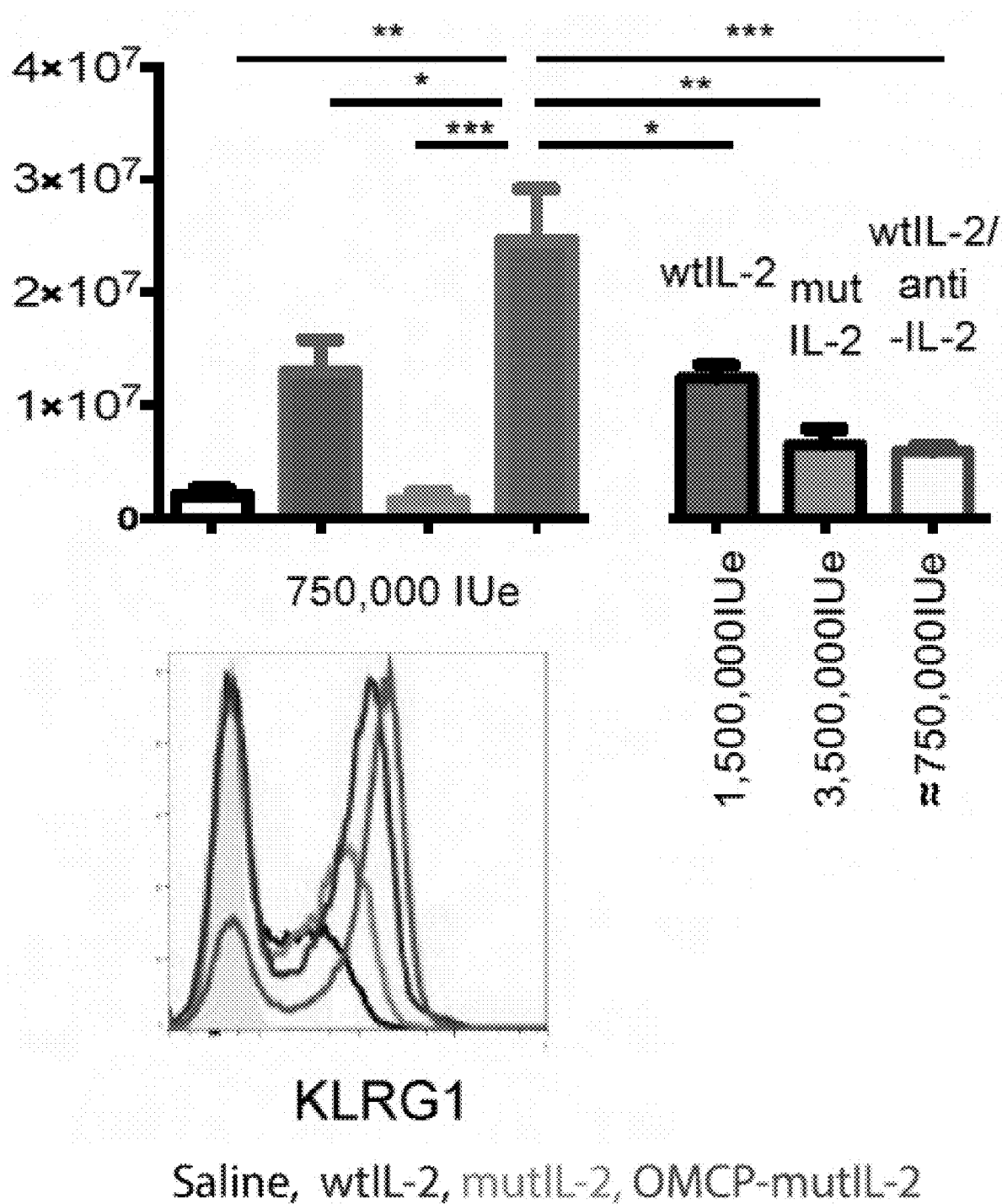
Figure 3I:
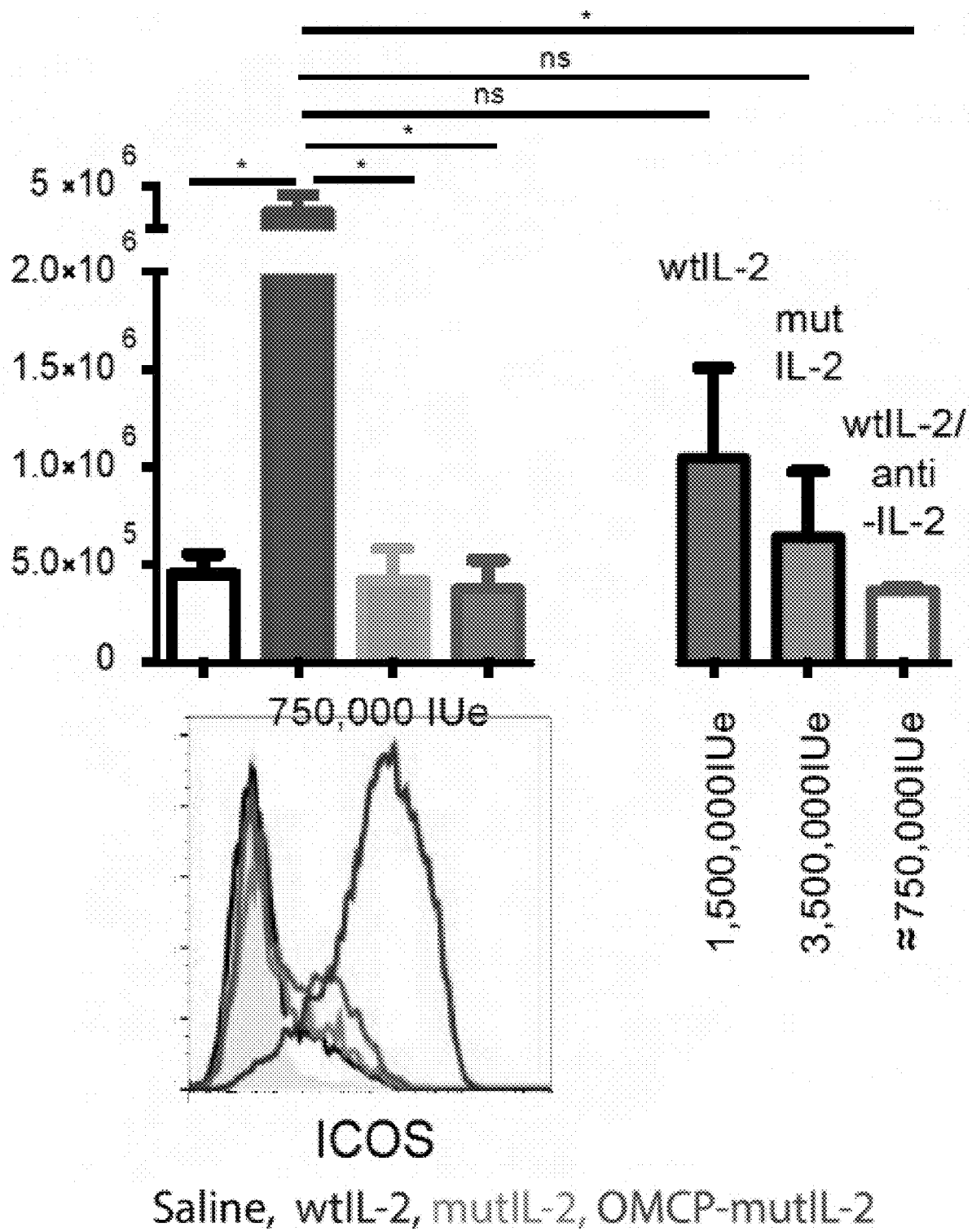
Figure 3J:
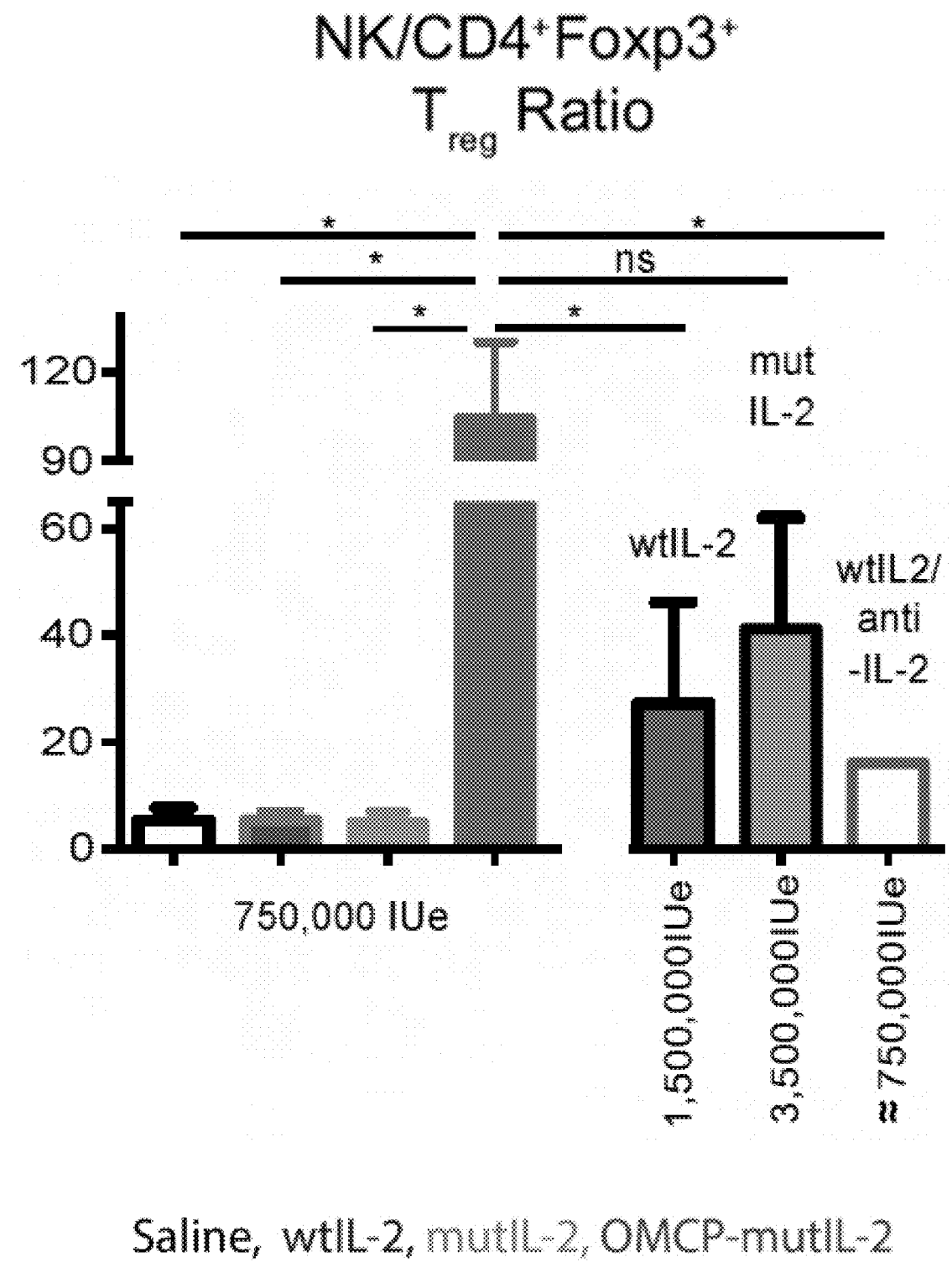
Figure 8A:
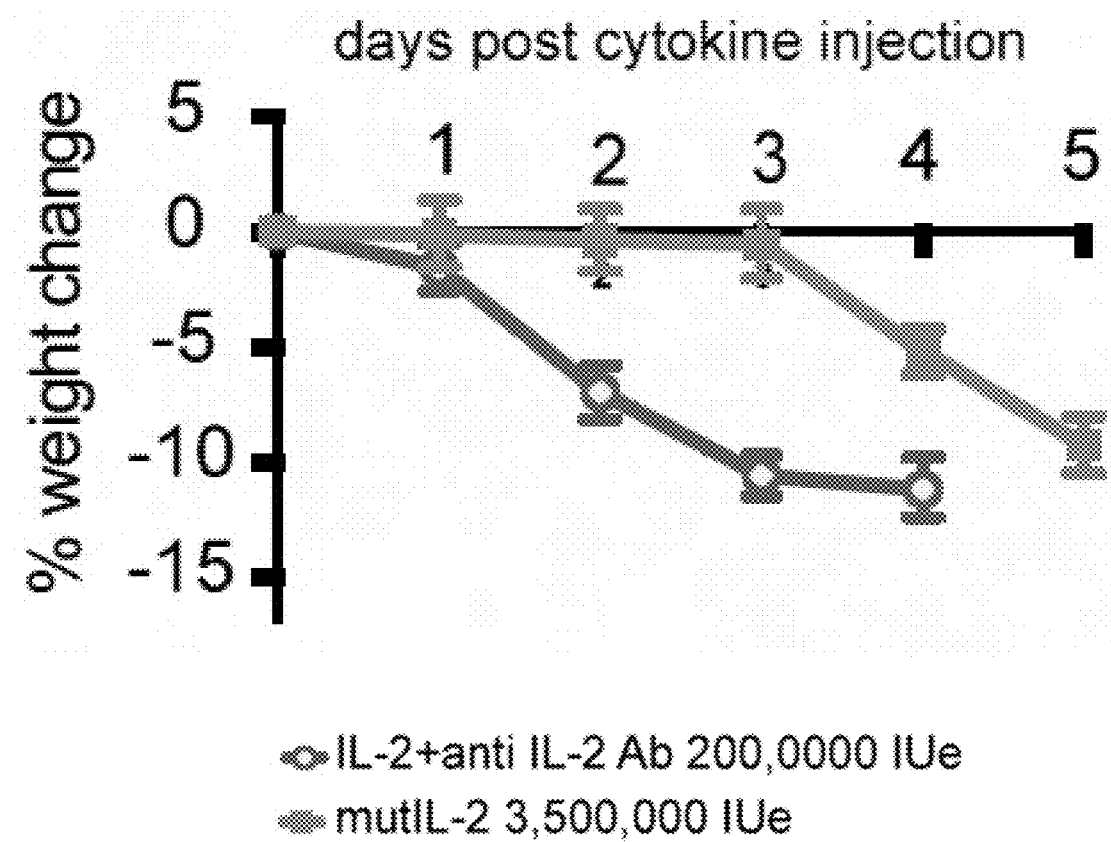
FIG. 8A depicts a graph showing that A/J mice treated with IL-2/anti-IL-2 antibodies or high dose mutIL-2 lost significant weight during treatment. The majority of IL-2/anti-IL-2 treated mice could not survive the full 200,000 IUe dosing and were sacrificed four days after starting treatment thus receiving 160,000-180,000 IUe.
Figure 8B:
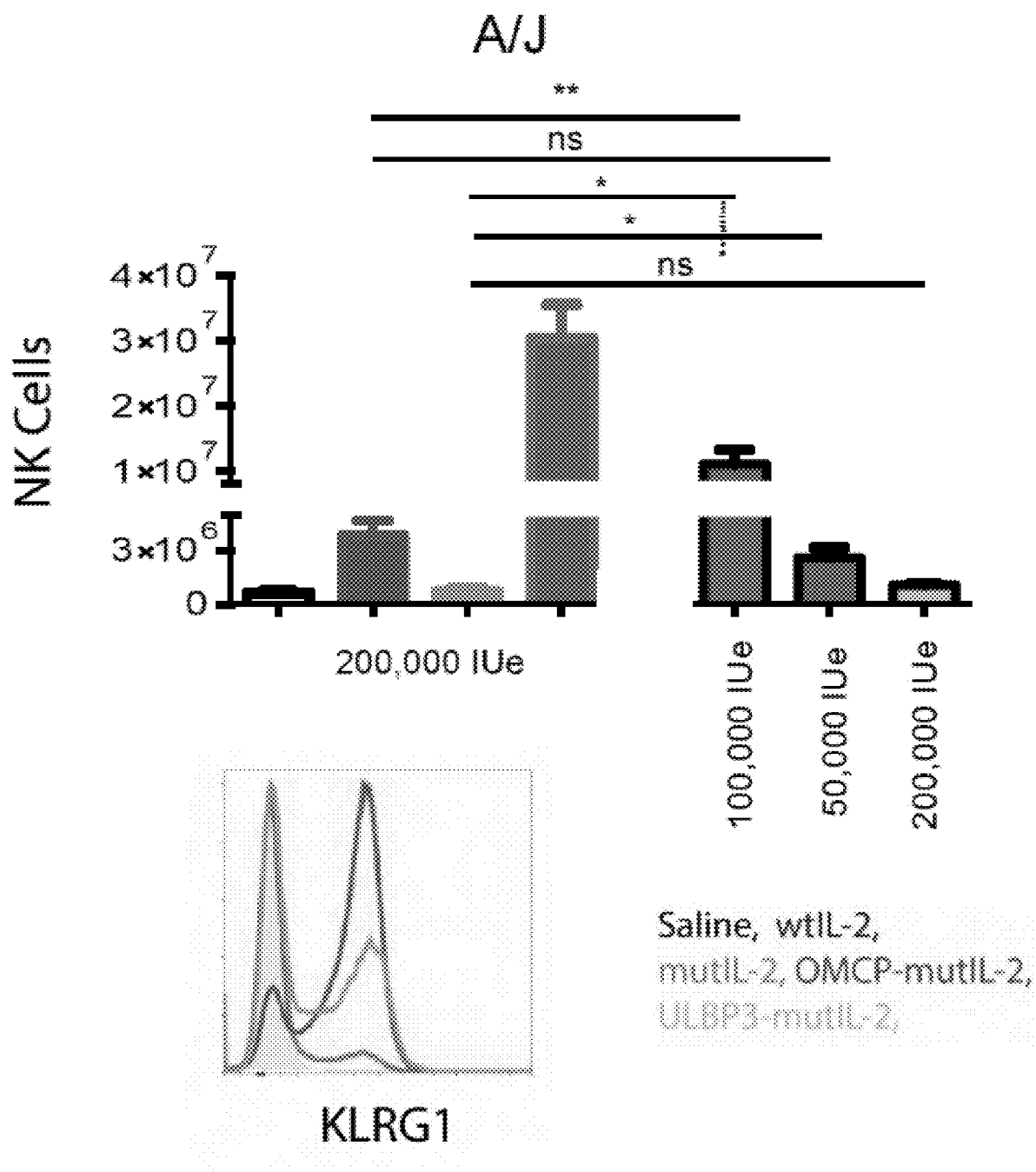
FIG. 8B depicts a graph and flow cytometric plot showing NK expansion with ULBP3-mutIL-2 and lower doses of OMCP-mutIL-2 in A/J spleen (top). NK activation, as measured by surface KLRG1 expression on NK cells treated with 200,000 IUe of mutIL-2 (green) or ULBP3-mutIL-2 (purple) in A/J spleen (bottom).
Figure 8C:
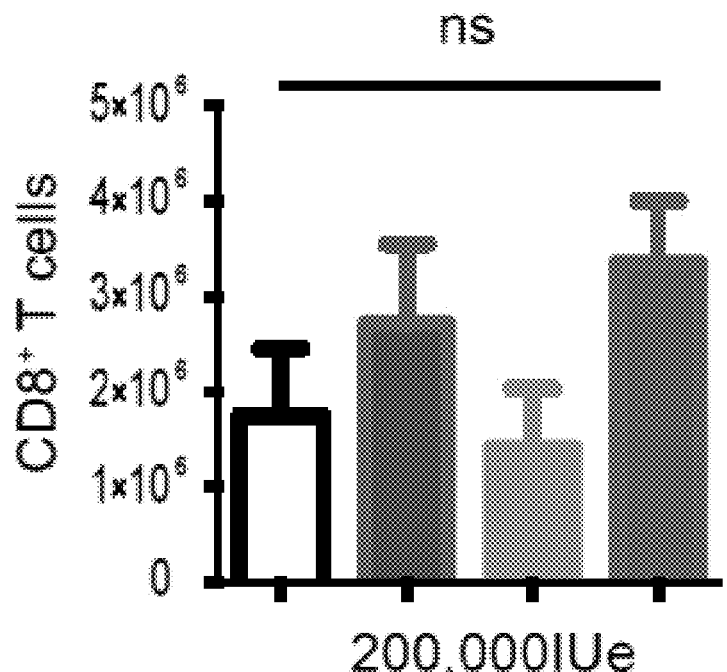
FIG. 8C and FIG. 8D depict graphs showing that unlike the case for NK cells, little expansion of CD8$^+$ or CD4$^+$ Foxp3$^-$ T cells was evident in either IL-2, OMCP-mut-IL-2, or mutIL-2 treated mice.
Figure 8D:
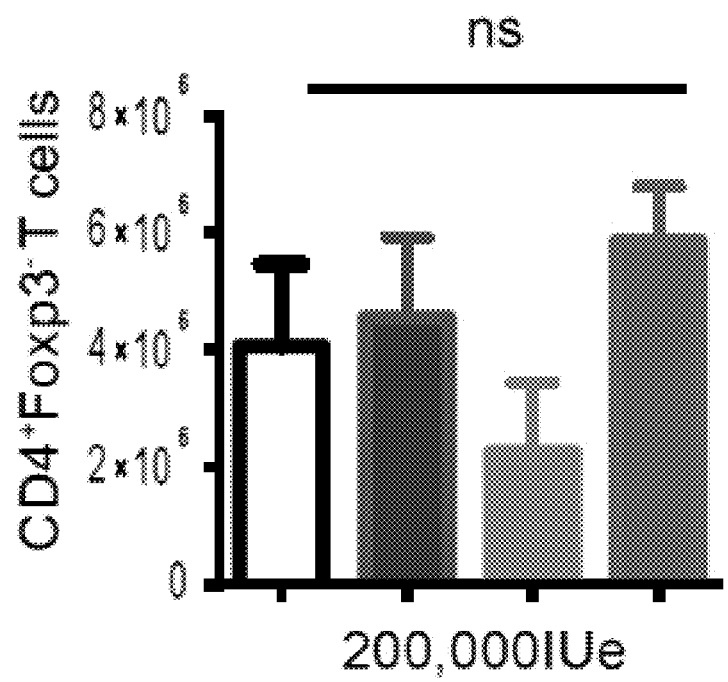
Figure 8E:
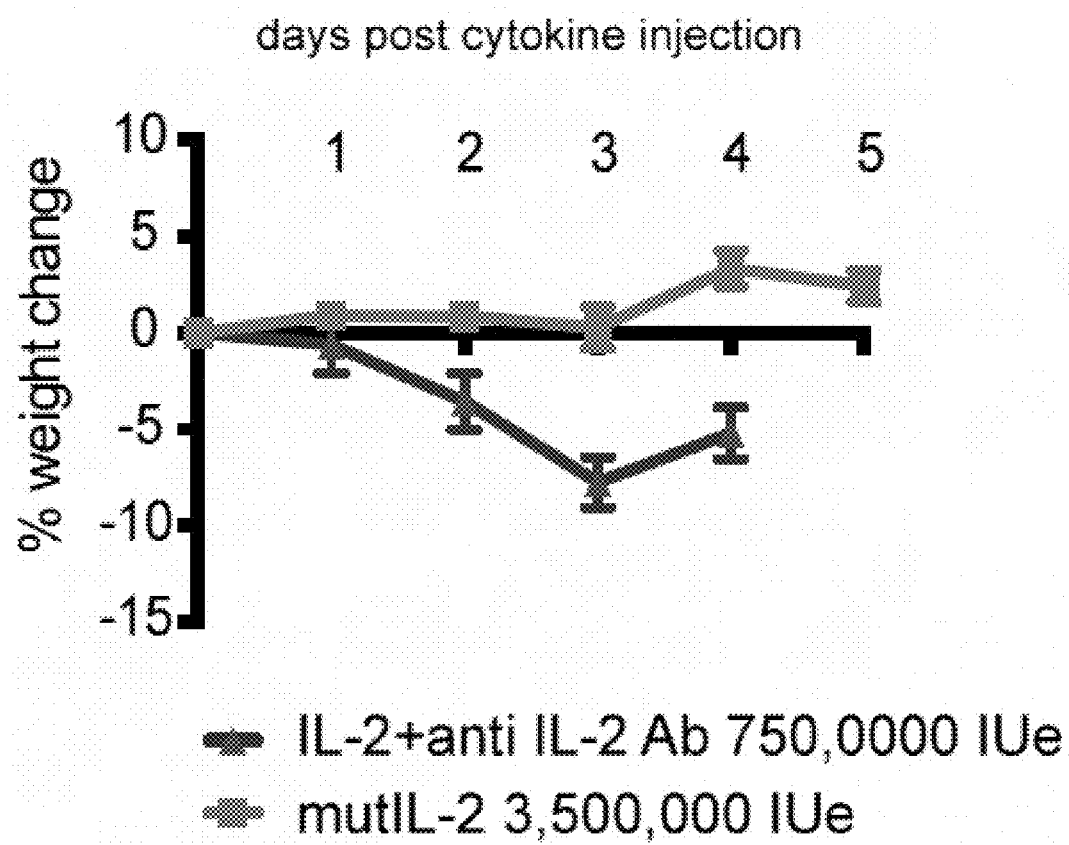
FIG. 8E depicts a graph showing weight loss in B6 mice treated with high dose mutIL-2 or IL2/anti-IL-2 antibody complex.
Figure 8F:
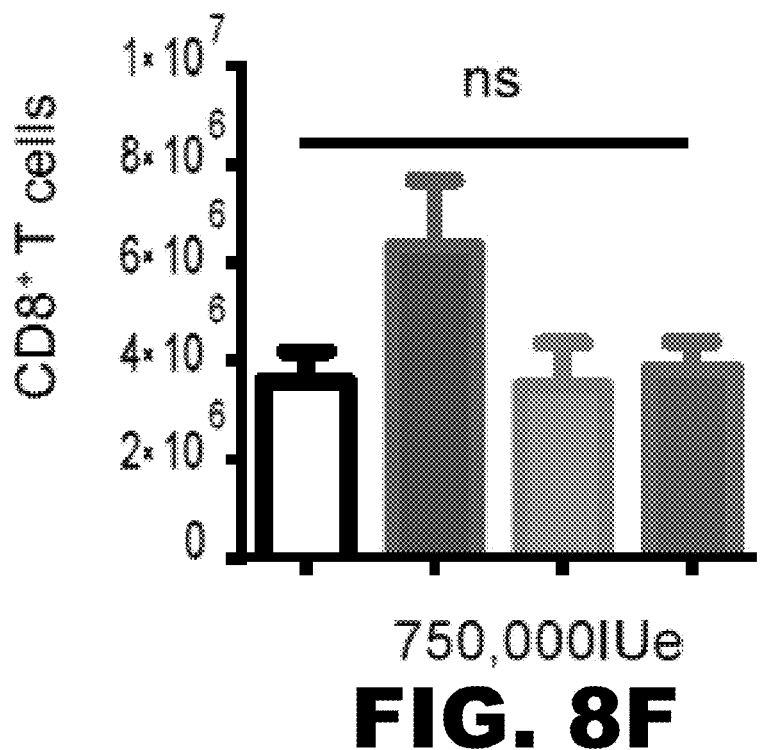
FIG. 8F and FIG. 8G depict graphs showing expansion of CD8$^+$ or CD4$^+$Foxp3$^-$ T cells in cytokine treated B6 mice. Graphs represent 5-10 mice per group.
Figure 8G:
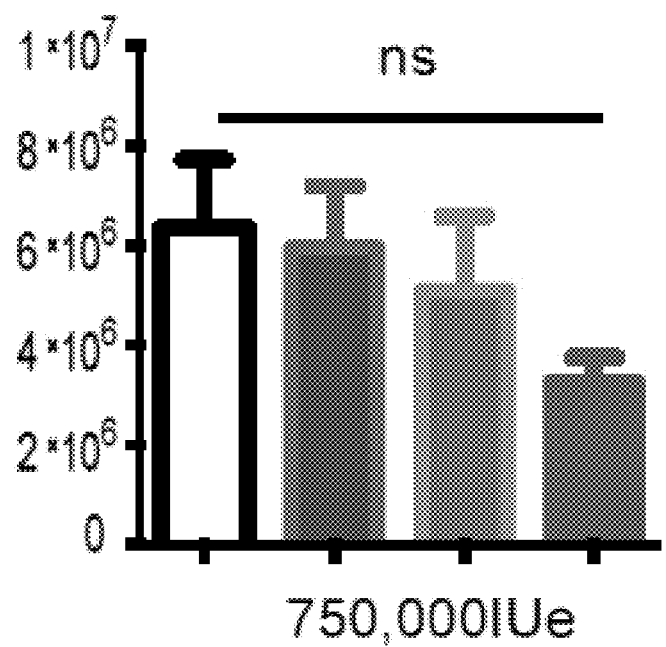

Unlike the A/J strain little immunoactivation of lymphocytes was evident in B6 mice treated with 200,000 IUe of wtIL-2 (data not shown). At higher doses of 750,000 IUe OMCP-mutIL-2 expanded NK cells more robustly than wtIL-2 in this strain (FIG. 3F-H). IL-2/anti-IL-2 antibody complexes prevented $T_{reg}$ expansion but, similar to the NJ strain, such treatment had toxicity and the majority of B6 mice could not tolerate the full 750,000 IUe dose (FIG. 3I). OMCP-mutIL-2, however, was well tolerated at this dose and led to a high NK/$T_{reg}$ ratio (FIG. 3J). No expansion of NK cells was evident in OMCP-mutIL-2 treated B6 NKG2D$^{-/-}$ mutants, confirming the requirement for NKG2D in the function of our construct (data not shown). No statistically significant expansion of B6 CD8$^+$ or CD4$^+$ Foxp3$^-$ T cells was evident in any treatment group although a trend for CD8$^+$ T cell expansion was evident after wtIL-2 administration (FIG. 8F-G). Identical data was obtained for lung resident lymphocytes in both the A/J and B6 strains (data not shown).

Example 4. OMCP-mutIL-2 Preferentially Expands and Activates NK Cells in Human Peripheral Blood Lymphocytes Compared to wtIL-2 or mutIL-2

To demonstrate the effectiveness of OMCP-mutIL-2 in human lymphocytes, human peripheral blood lymphocytes were co-cultured for 36 hours in 100 IUe of either wild-type IL2, R38A/F42K mutant form of IL-2 or OMCP-mutant IL-2.

Figure 31A:
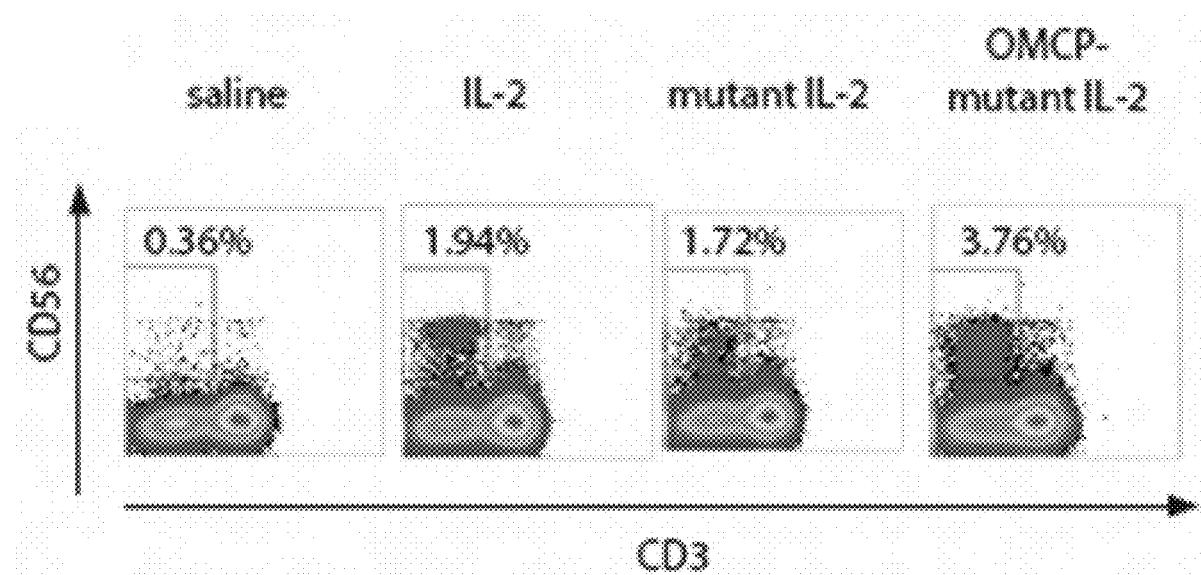
FIG. 31A, FIG. 31B, FIG. 31C and FIG. 31D depicts flow cytometry data showing that OMCP-Mutant IL2 activates NK and CD8+ T cells.
Figure 31B:
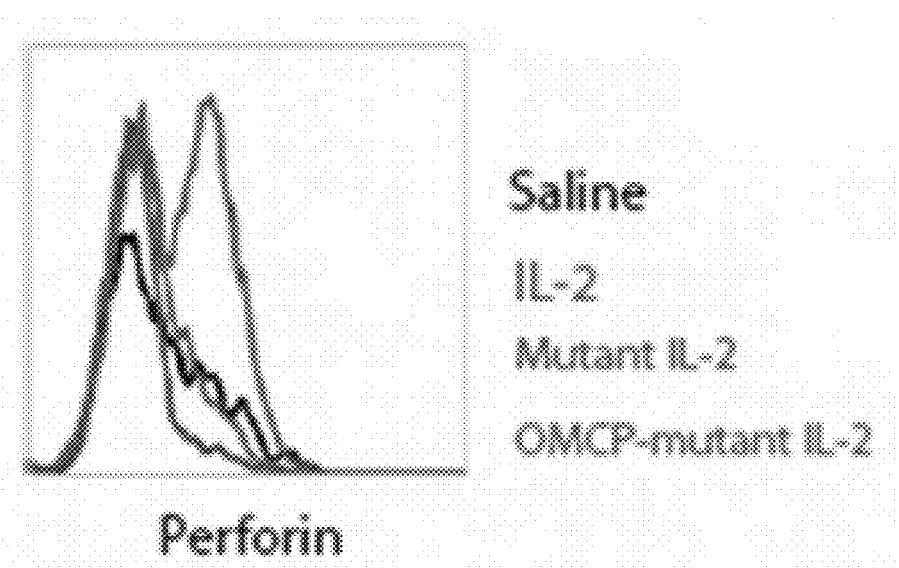

NK cells: The cells were flow cytometrically analyzed and relative prevalence of CD56+CD3− NK cells compared between conditions. A relatively higher proportion of NK cells was evident in the OMCP-mutant IL-2 group (FIG. 31A). Perforin levels were higher in OMCP-mutant IL-2 treated NK cells (red) compared to saline (black), IL-2 (blue) or mutant IL-2 (green) treated ones (FIG. 31B).

Figure 31C:
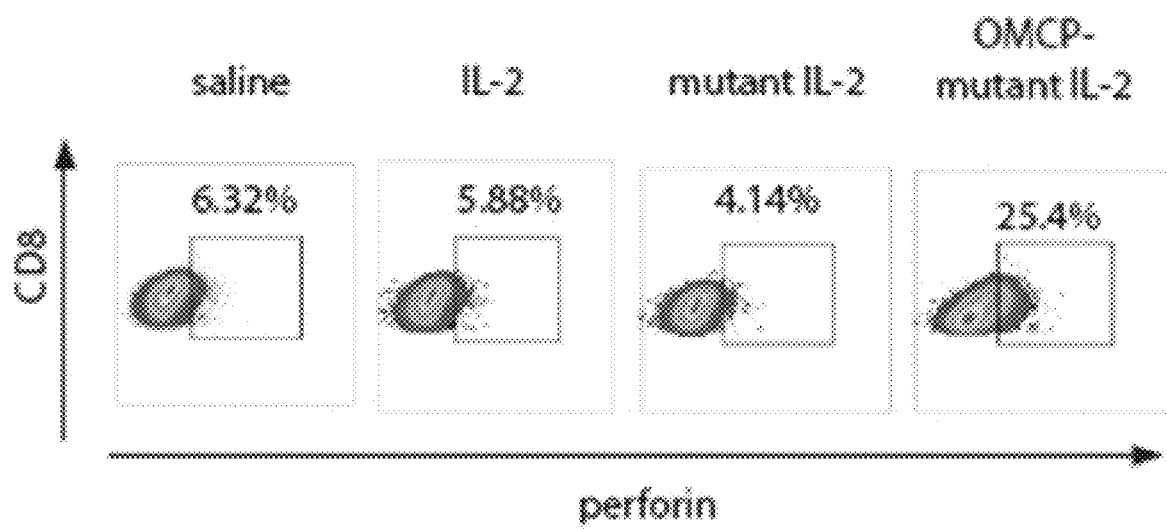

CD8+ T cells: Similar to NK cells, higher intracellular levels of perforin were evident in CD8+ T cells treated with OMCP-mutant IL-2 compared to other conditions (FIG. 31C).

Figure 31D:
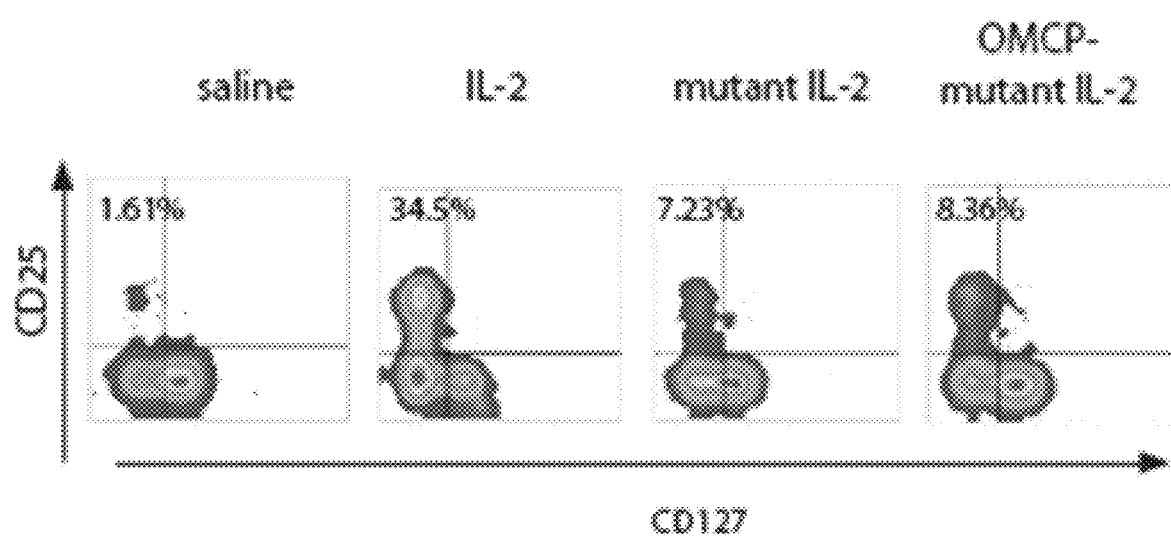

Tregs: When gating on CD4+Foxp3+CD45RA− T cells a relatively higher proportion of activated CD25+CD127− regulatory T cells was evident in IL-2 treated peripheral blood lymphocyte cultures compared to other conditions (FIG. 31D). Taken together this data suggests that OMCP-mutIL-2 preferentially expands and activates NK cells and CD8+ cells in human peripheral blood lymphocytes compared to wtIL-2 or mutIL-2. Importantly, OMCP-mutIL-2 does not activated regulatory T cells significantly relative to IL2.

Figure 4A:
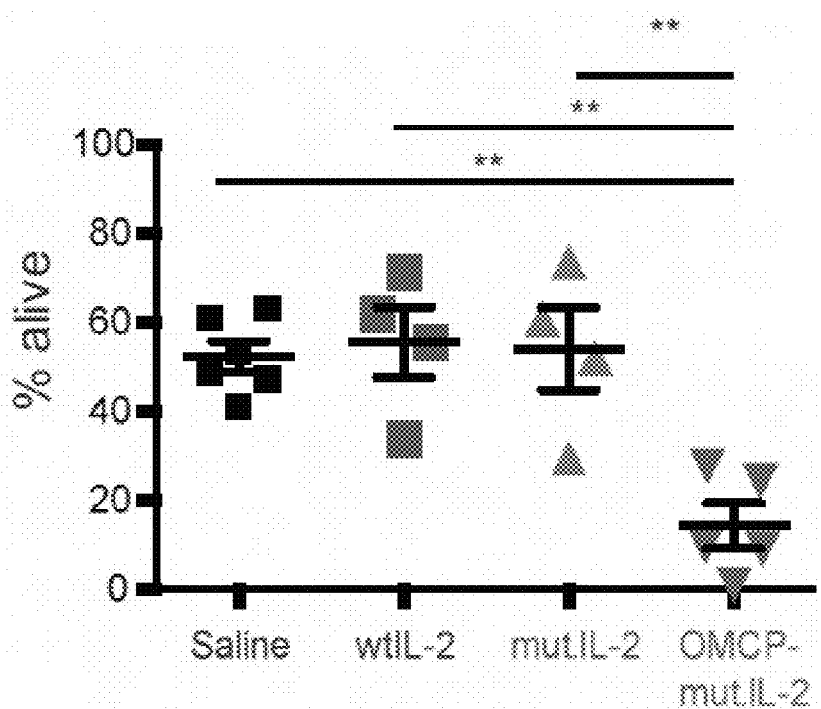
Figure 4B:
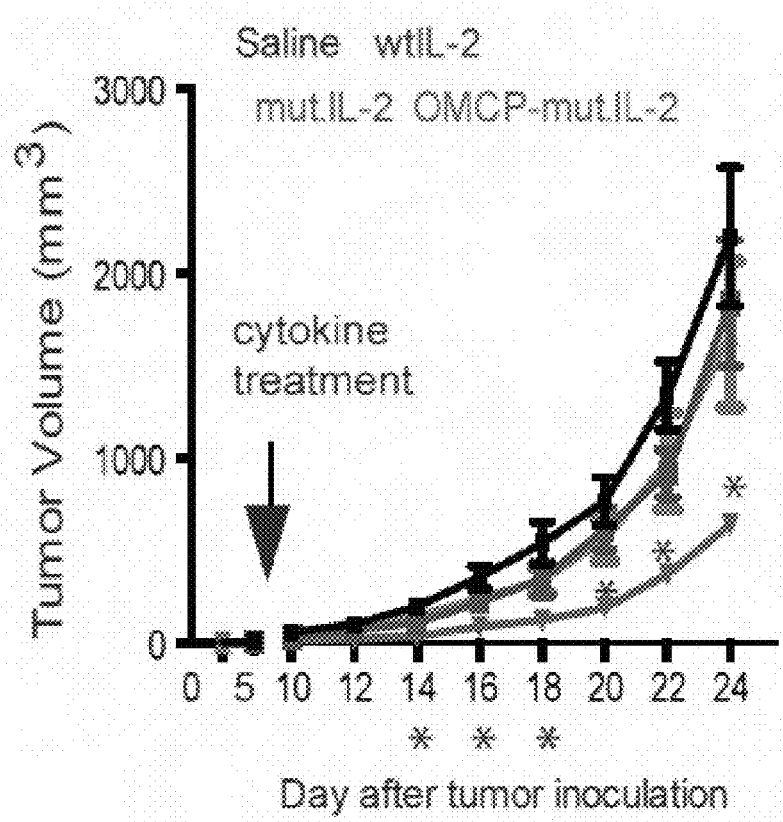
Figure 4C:
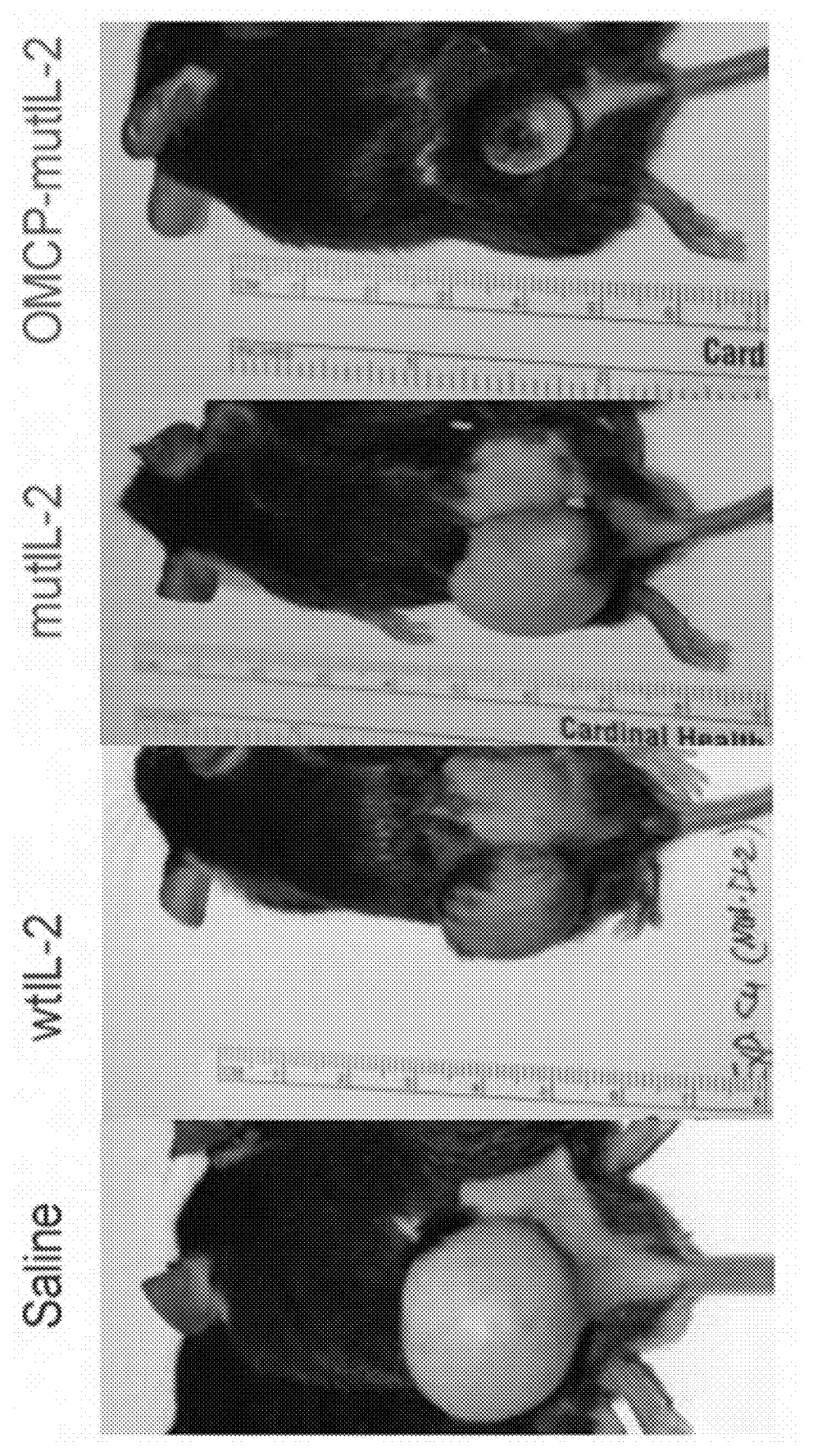
Figure 4D:
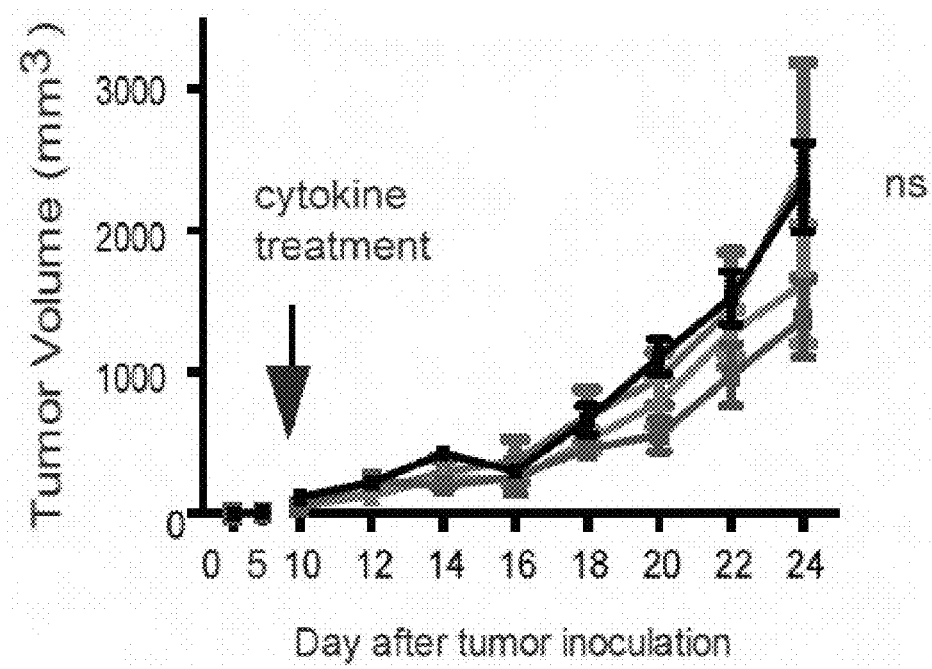
Figure 4E:
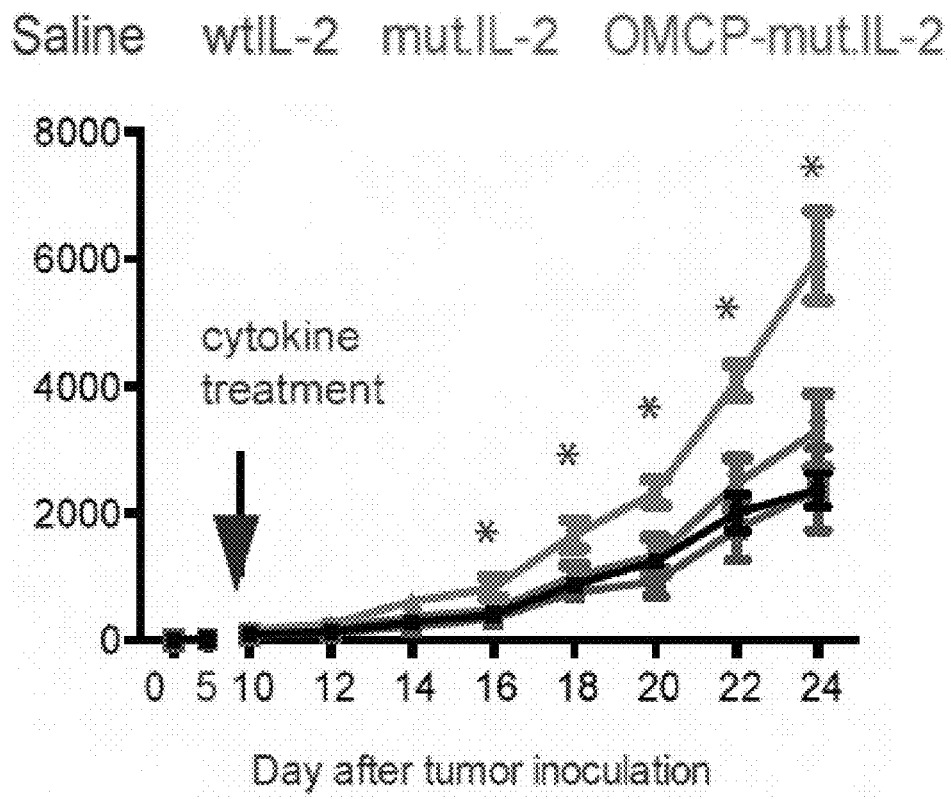
Figure 9A:
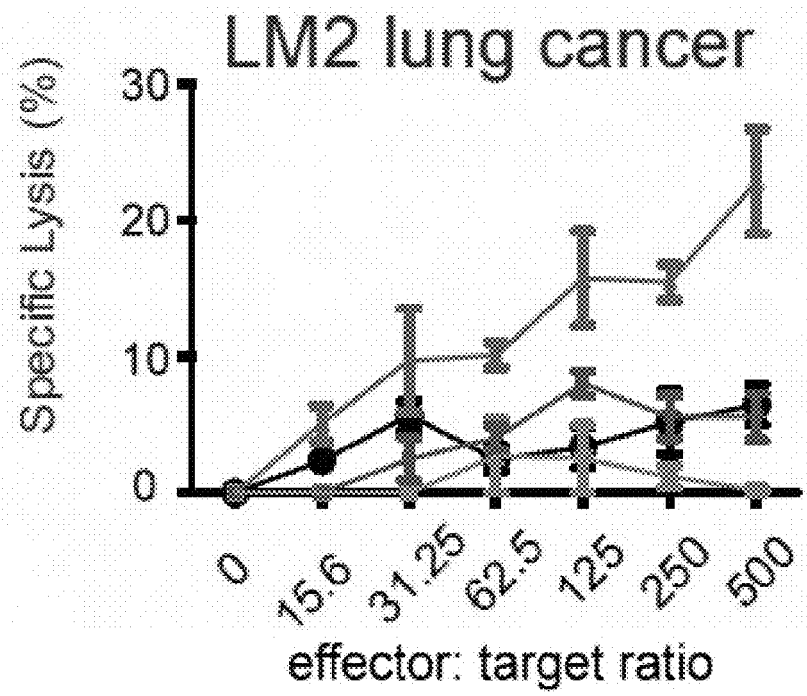
FIG. 9A and FIG. 9B depict graphs showing in vitro lysis of A/J tumors, such as LM2 lung adenocarcinoma (FIG. 9A) or YAC-1 lymphoma (FIG. 9B) by bulk splenocytes after a five day course of 200,000 IUe of cytokine given over ten doses.
Figure 9B:
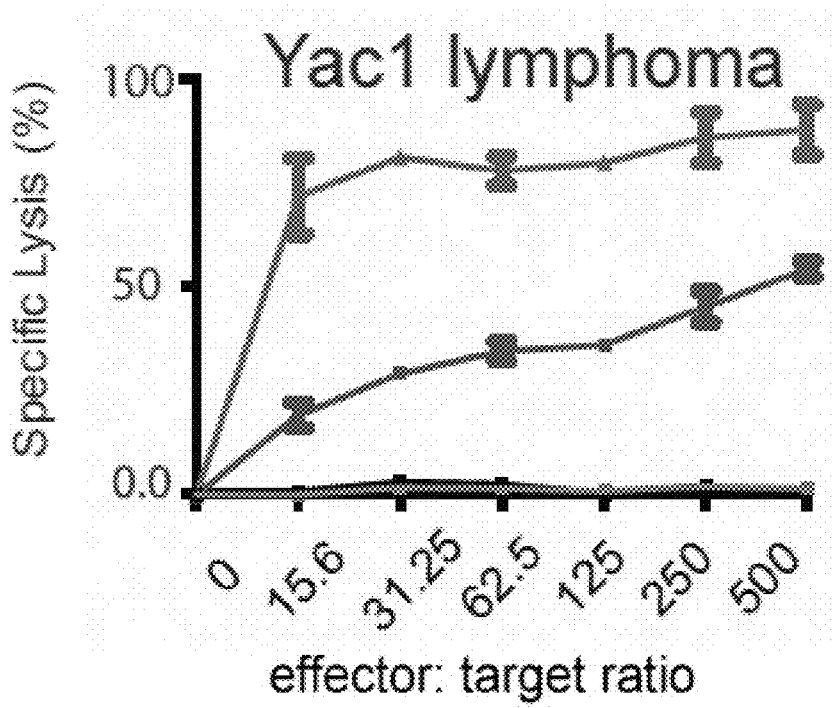
Figure 9C:
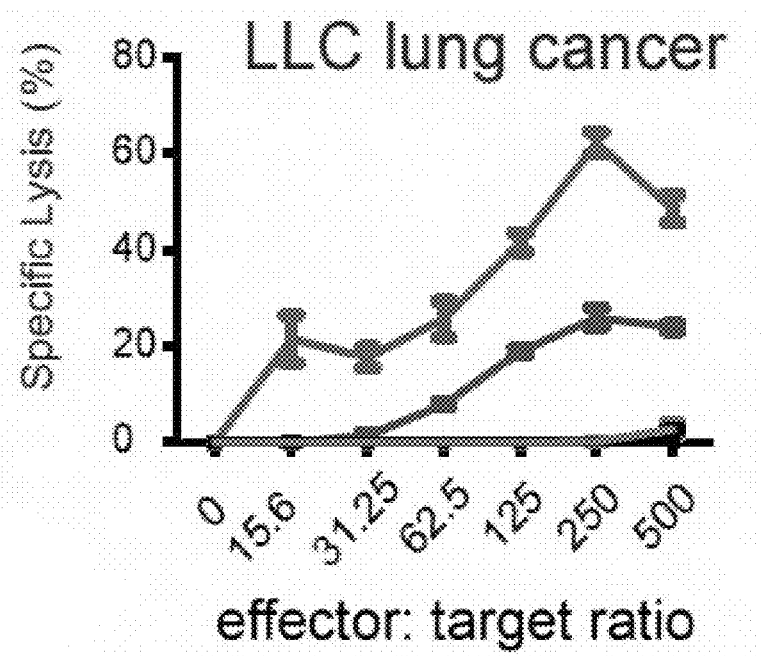
FIG. 9C shows in vitro lysis of LLC lung cancer by B6 splenocytes treated with 750,000 IUe of cytokines or constructs given over five days in ten doses.

Example 5. Treatment with OMCP-mutIL-2 Offers Superior Immunologic Control of Malignancies In Vivo Unlike T lymphocytes, which require prior antigen encounter for optimal antigen-specific tumor cytotoxicity, NK cells can mediate natural cytotoxicity without prior sensitization. NK cells also form the primary barrier for expansion of select malignancies, such as lymphoma and lung cancer[16,17,21,22]. Treatment of AJ mice with OMCP-mutIL-2, compared to wtIL-2 or mutIL-2, led to enhanced in vivo clearance and in vitro lysis of YAC-1 cells by bulk splenocytes (FIG. 4A, FIG. 9A-B). Decreased growth of the highly aggressive Lewis Lung Carcinoma (LLC) cell line was evident in B6 mice after 750,000 IUe of OMCP-mutIL-2 compared to wtIL-2 or mutIL-2. Increased cytotoxicity was evident in OMCP-mutIL-2 treated splenocytes for the LLC cell line as well (FIG. 4B-C; FIG. 9A-C). Enhanced immunotherapy was lost in NKG2D$^{-/-}$ mice or following NK depletion (FIG. 4D-E). In the absence of host NKG2D mutIL-2 actually increased the rate of LLC growth. Thus OMCP-mediated targeting of mutIL-2 offers a safer and more efficacious form of immunotherapy for both solid and liquid tumors in various strains of mice.

Example 6. Impact of NKG2D Targeting on IL-2 Signaling

Figure 5A:
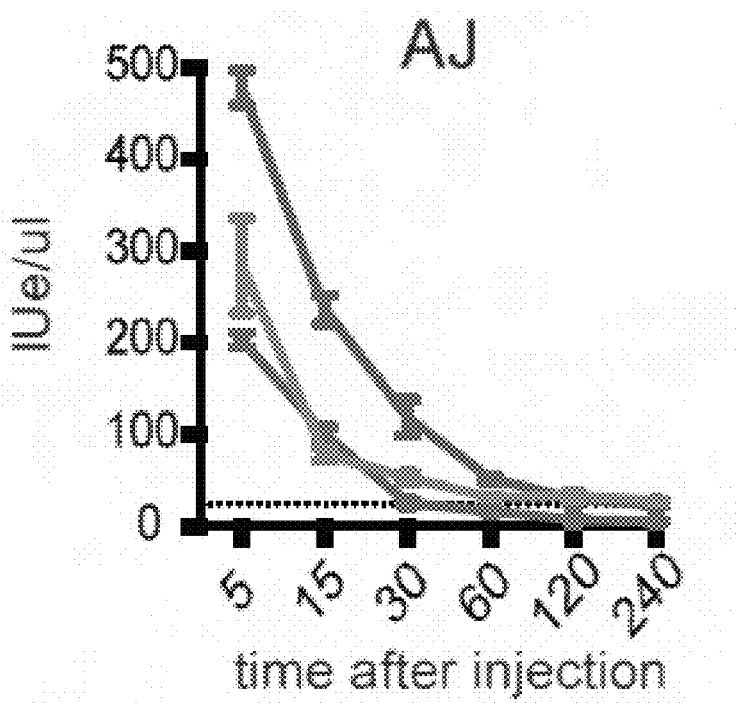
FIG. 5A, FIG. 5B, FIG. 5C, FIG. 5D, FIG. 5E, FIG. 5F, FIG. 5G, FIG. 5H, FIG. 5I, FIG. 5J and FIG. 5K depict graphs and a schematic showing IL-2 signaling in NK cells.
Figure 5B:
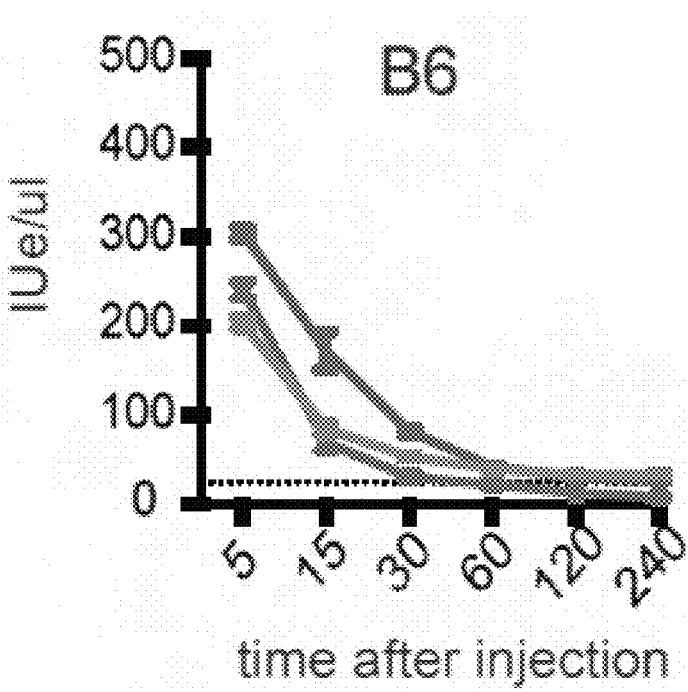

Antibody-IL-2 conjugates, or IL-2/anti-IL-2 antibody complexes demonstrate improved biologic activity over purified cytokine by extending the duration of serum half-life[23,24]. To investigate whether linking IL-2 to OMCP increased serum half-life, we injected 500,000 IUe of fluorescently-labeled wtIL-2, mutIL-2 or OMCP-mutIL-2 into A/J and B6 mice and monitored serum clearance by serial blood draws. While OMCP-mutIL-2 had a slightly higher serum concentration at early time points, all constructs were undetectable in the blood one hour post-injection (FIG. 5A-B). This is significantly shorter than the described 11-14 hour serum half-life of antibody-IL-2 conjugates[23]. Interestingly, despite the injection of identical amount of cytokine, lower cytokine levels were detected in B6 mice compared to A/J mice at all time points. Such data points to strain-specific differences in clearance of IL-2 and may explain why B6 mice are able to both tolerate and require higher doses of cytokine for NK expansion. Nevertheless, based on this data it is unlikely that prolonged circulation of construct was responsible for the increased activity of OMCP-mutIL-2 over wtIL-2.

Figure 5C:
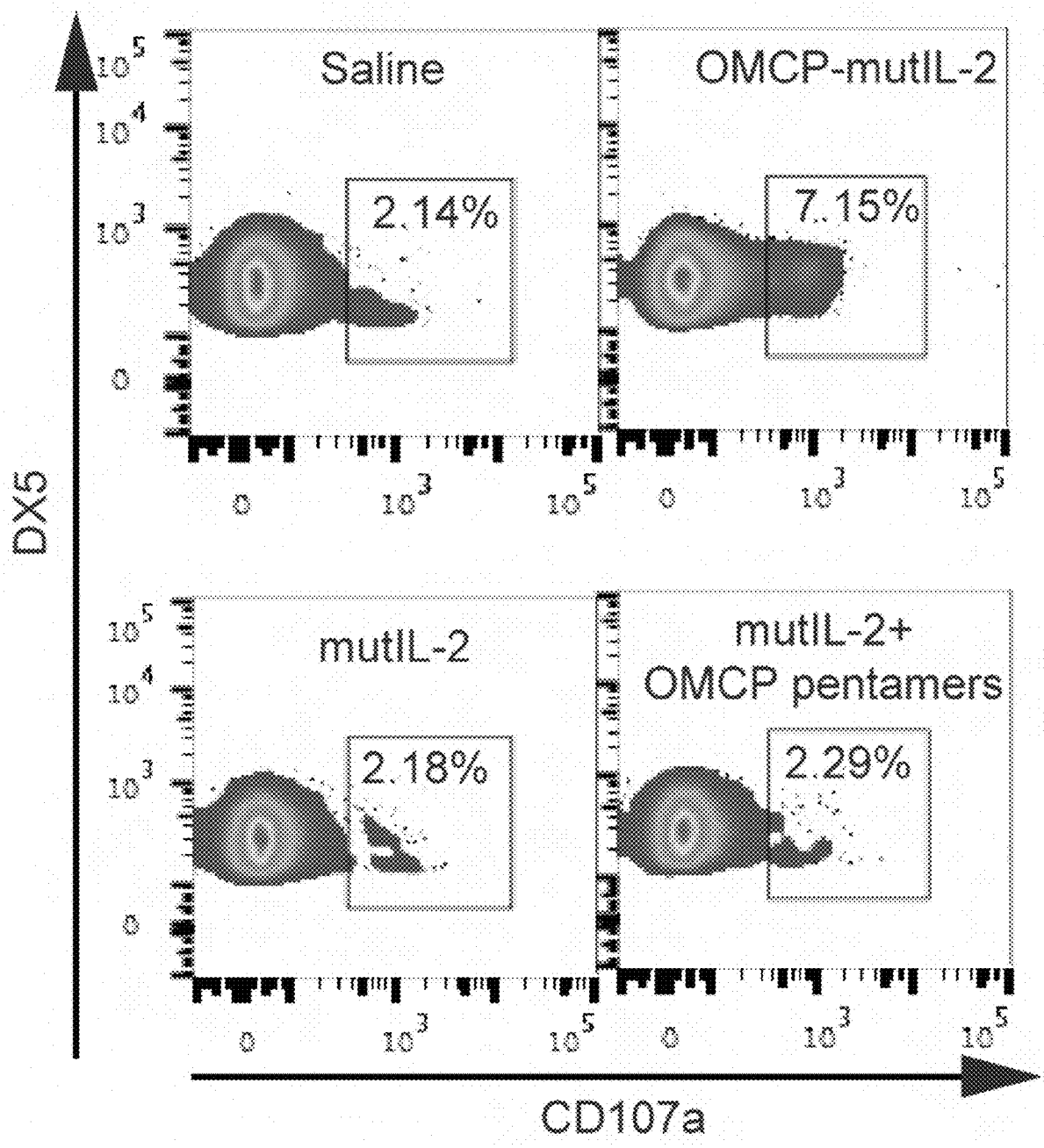
Figure 10A:
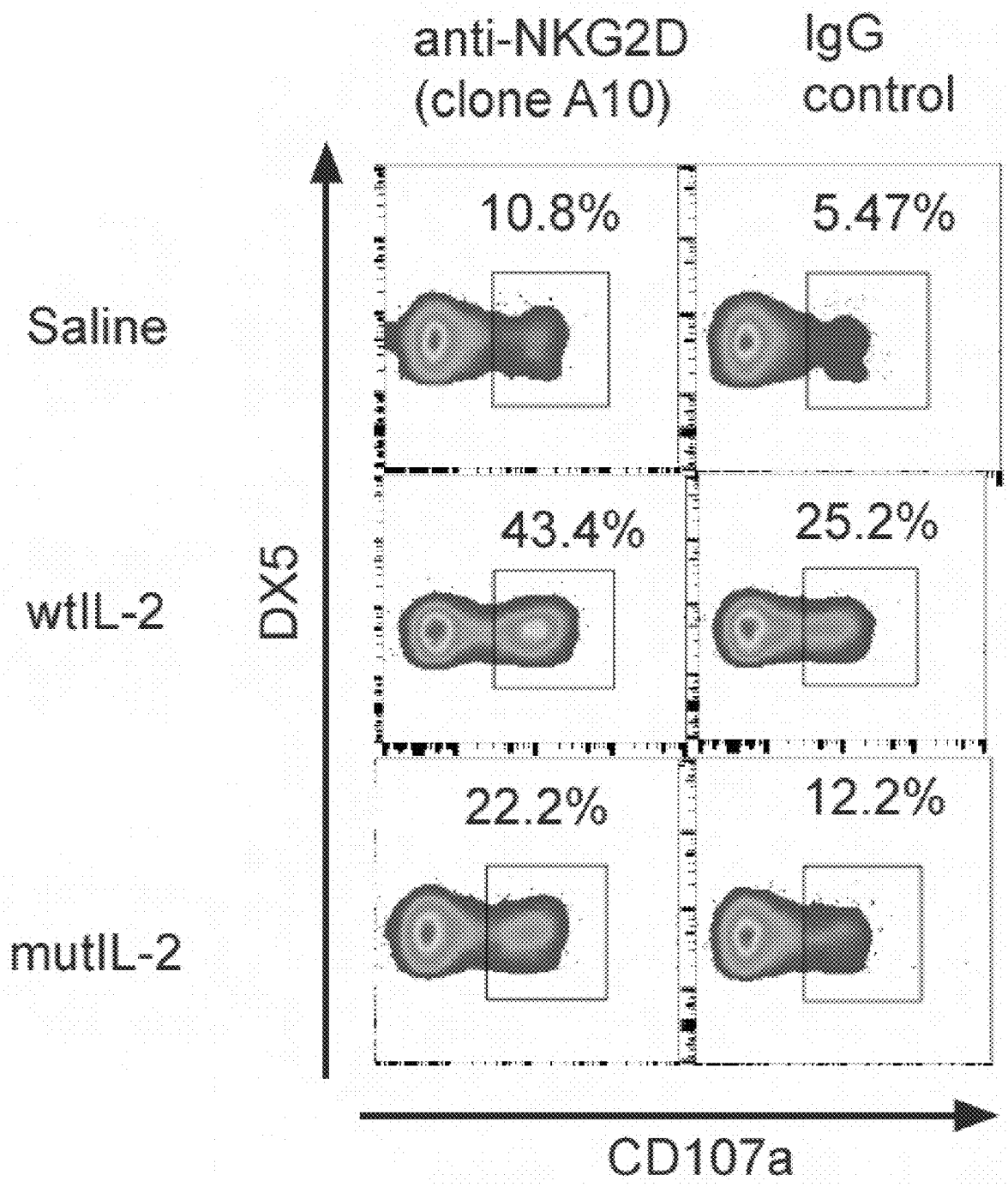
FIG. 10A depicts flow cytometric plots showing that plate bound anti-NKG2D antibody (clone A10)-mediated augmentation of NK degranulation with cytokines added at 1000 IUe/ml.
Figure 10B:
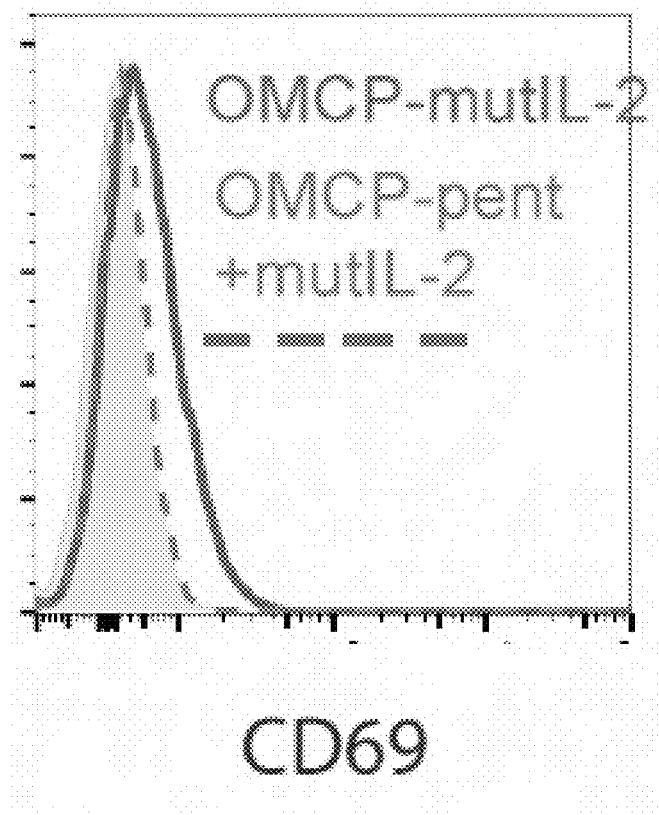
FIG. 10B depicts a flow cytometric plot showing CD69 levels on NK cells cultured at 100 IUe/ml of OMCP-mut-IL2 or mutIL-2 with pentameric OMCP.
Figure 11A:
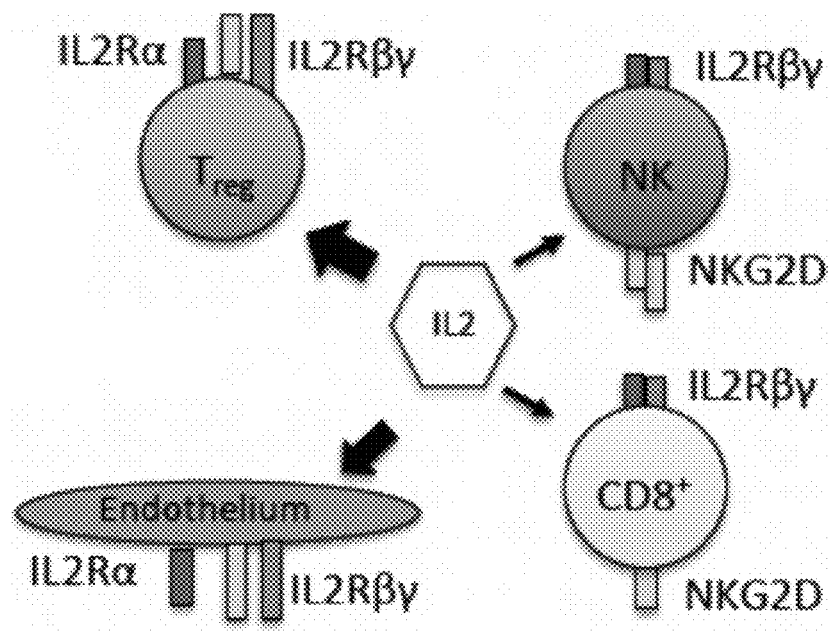
FIG. 11A, FIG. 11B and FIG. 11C depict a schematic of the differential IL2 binding and activation in vivo.
Figure 11B:
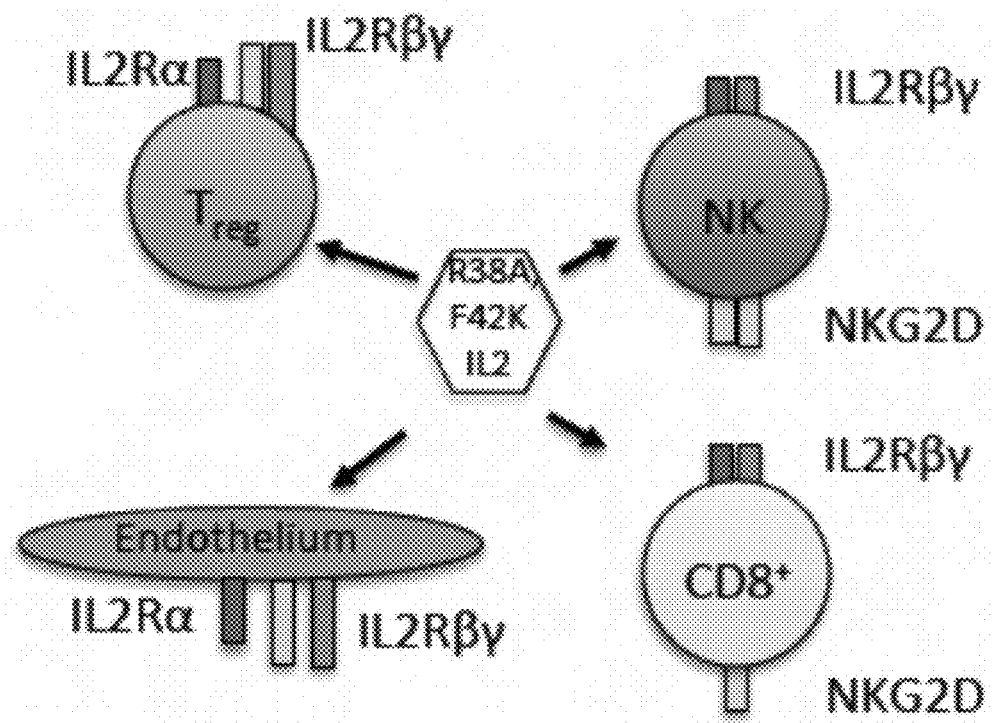
Figure 11C:
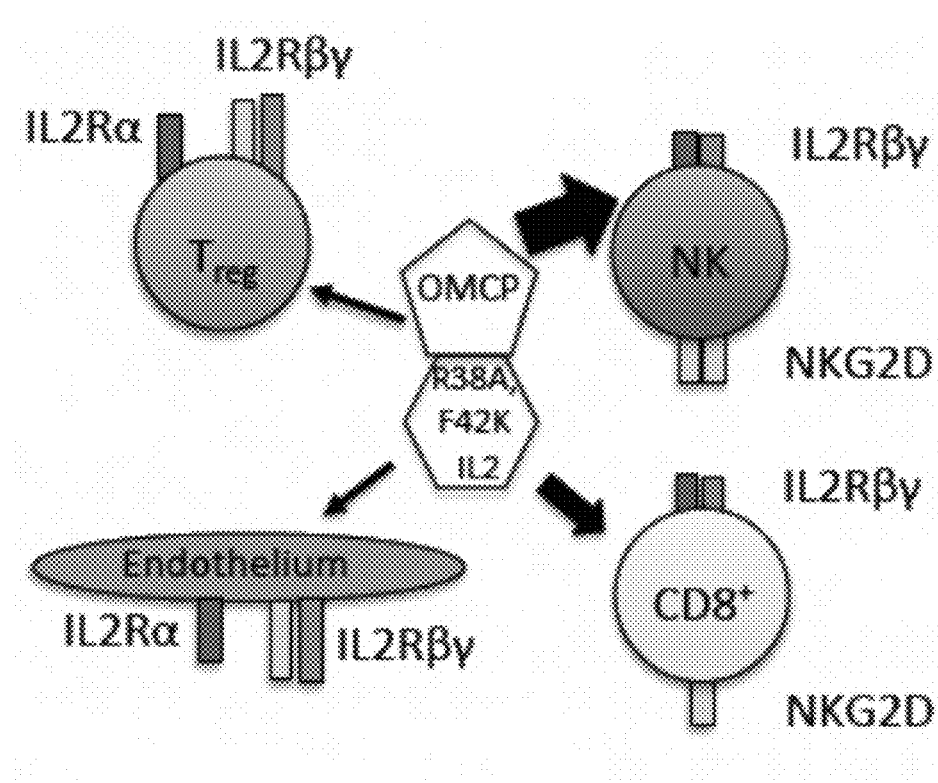

We next considered the possibility that the superiority of OMCP-mutIL-2 was the result of signaling through NKG2D as antibody-mediated crosslinking of this receptor can activate NK cells (FIG. 10A)[25]. While the addition of purified OMCP to mutIL-2 did not augment NK activation or expansion in vitro or in vivo (data not shown) we would not expect a monomeric ligand to crosslink NKG2D. We thus directly compared NK cell activation in the presence of 1000 IUe of OMCP-mutIL-2, mutIL-2 and mutIL-2 combined with equimolar concentration of pentamerized OMCP. No increase in NK activation, as measured by CD69 upregulation or degranulation, was evident in the presence of pentamerized OMCP (FIG. 5C, FIG. 10B). This suggests that NKG2D crosslinking is not responsible for augmented NK cell activation by OMCP-mutIL-2 at physiologic concentrations.

Figure 1C:
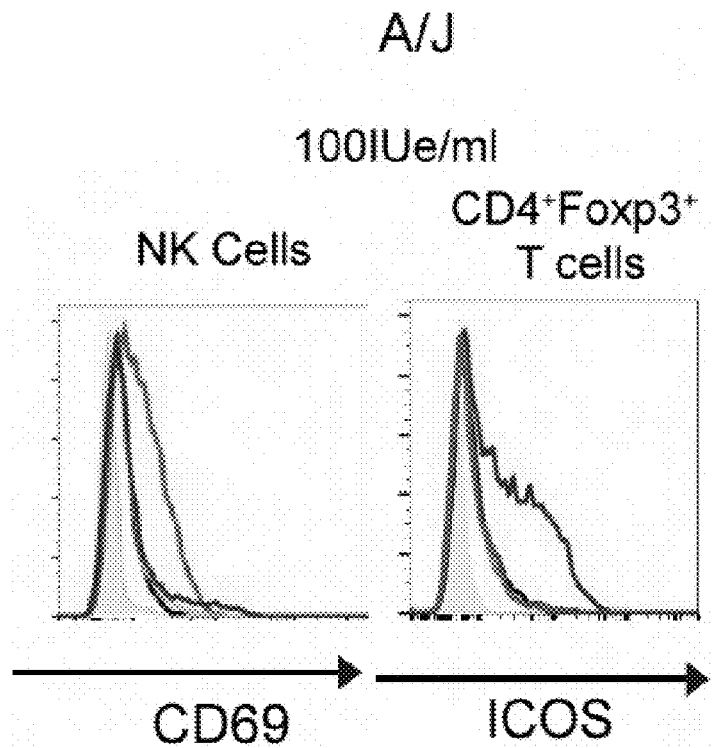
Figure 1D:
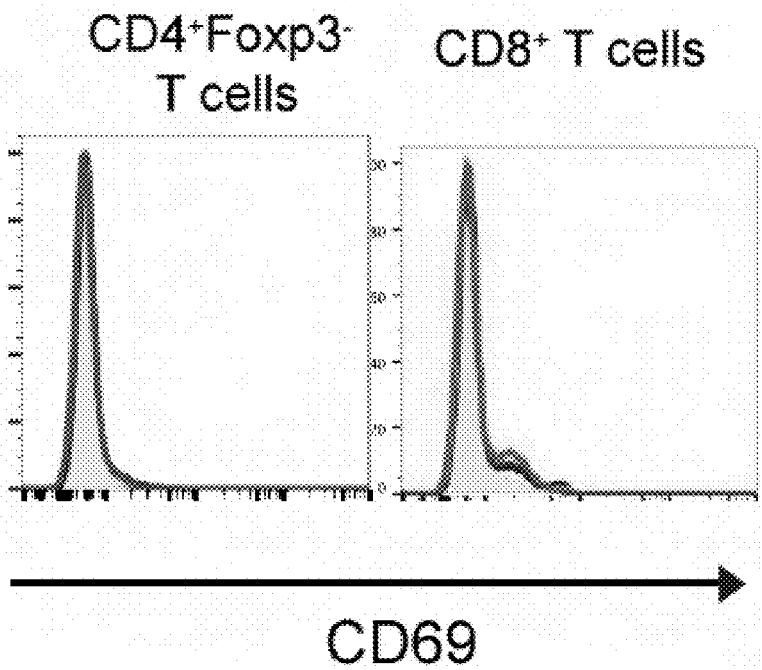
Figure 5D:
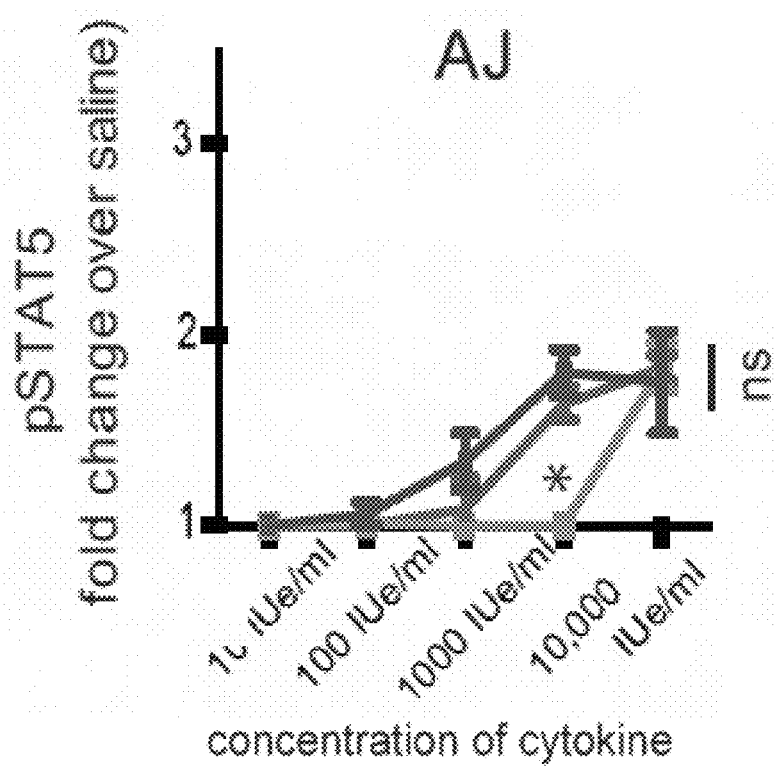
Figure 5E:
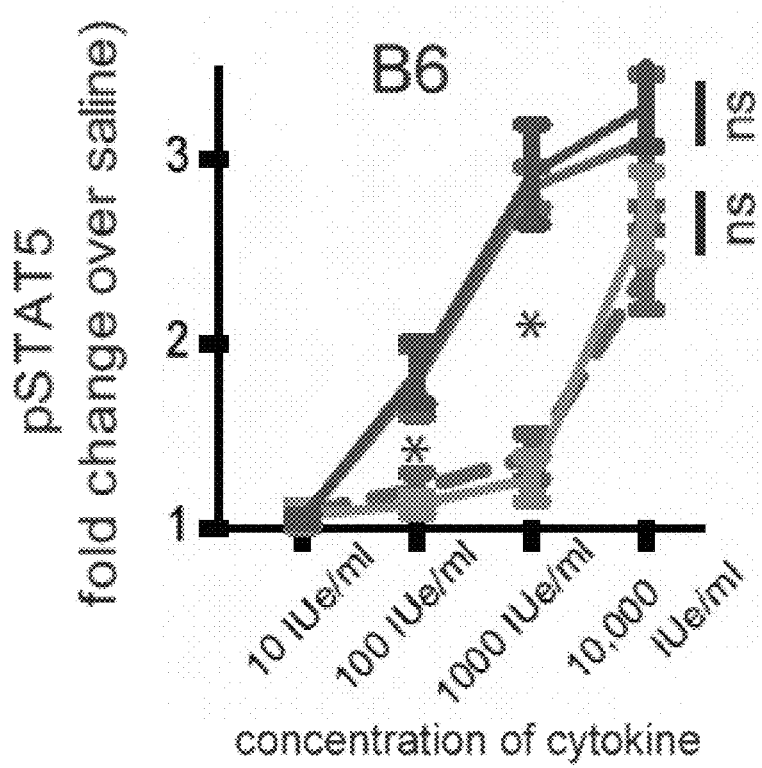
Figure 5F:
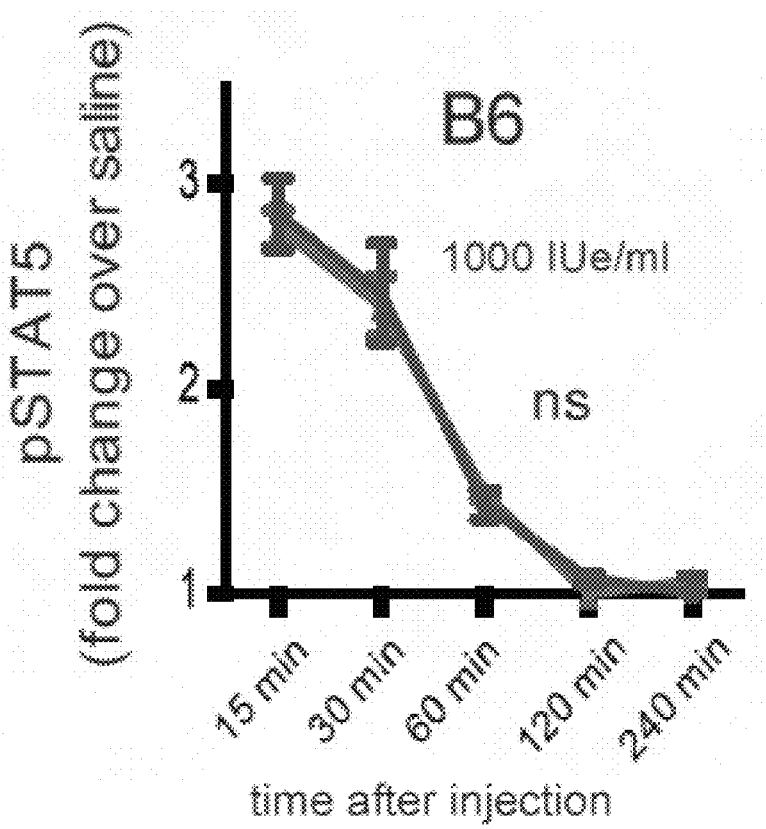
Figure 5G:
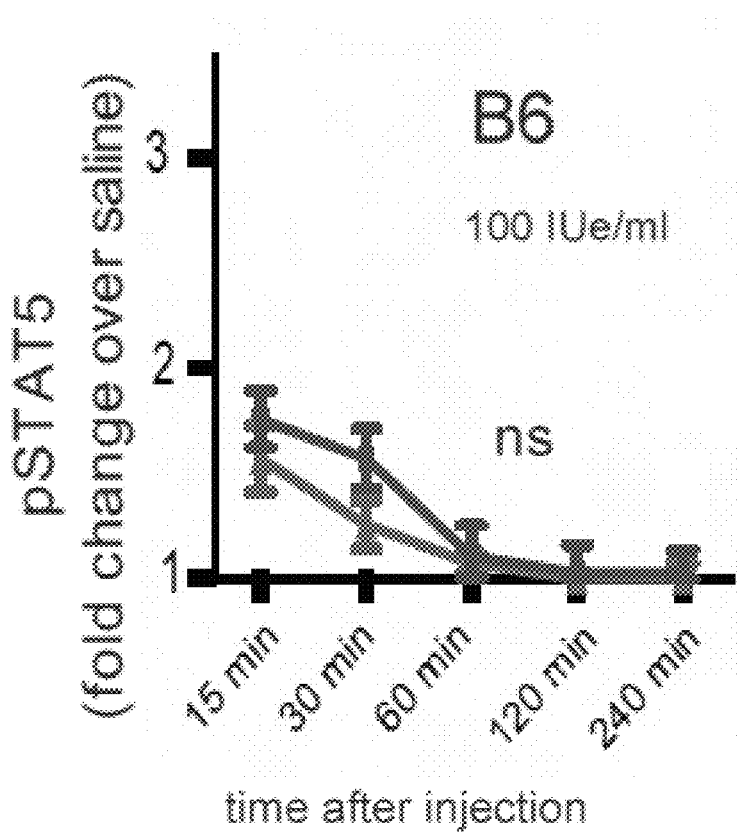
Figure 5H:
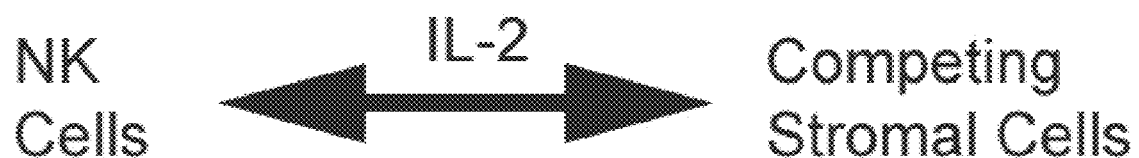
Figure 5I:
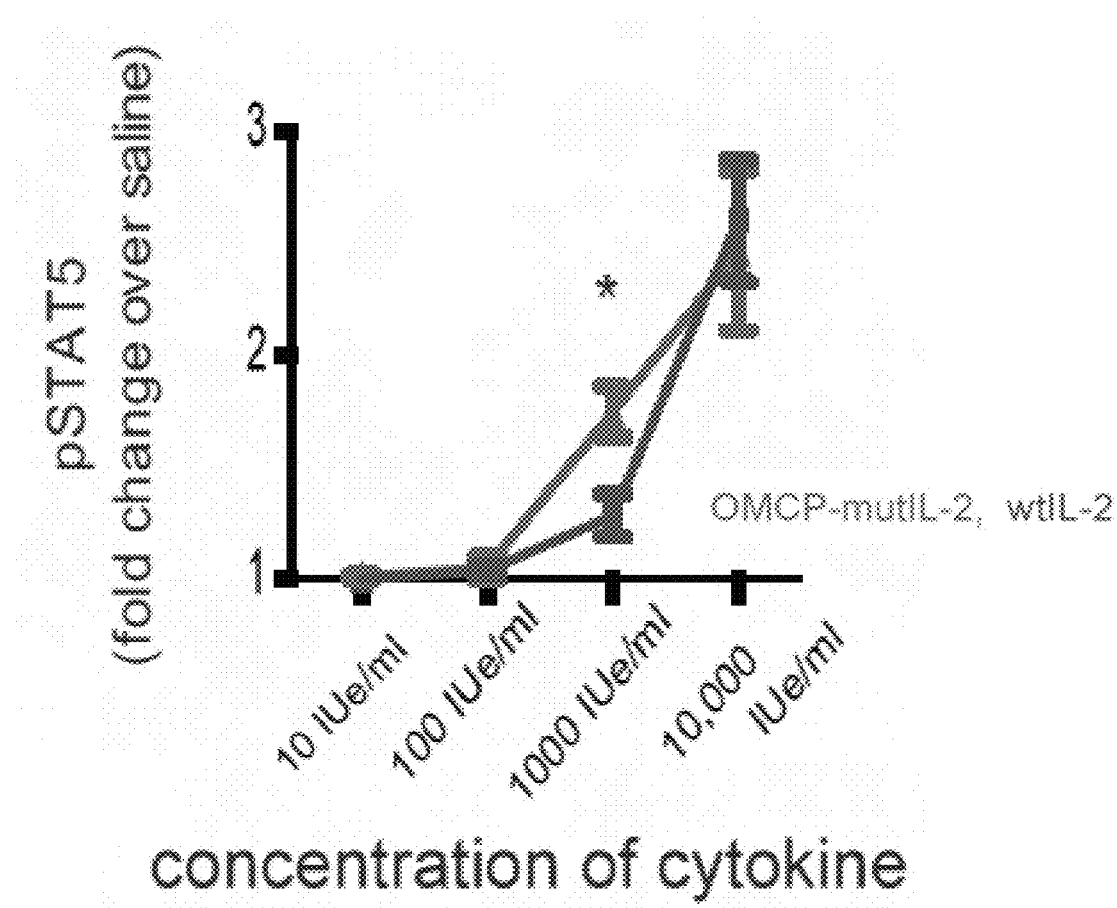
Figure 5J:
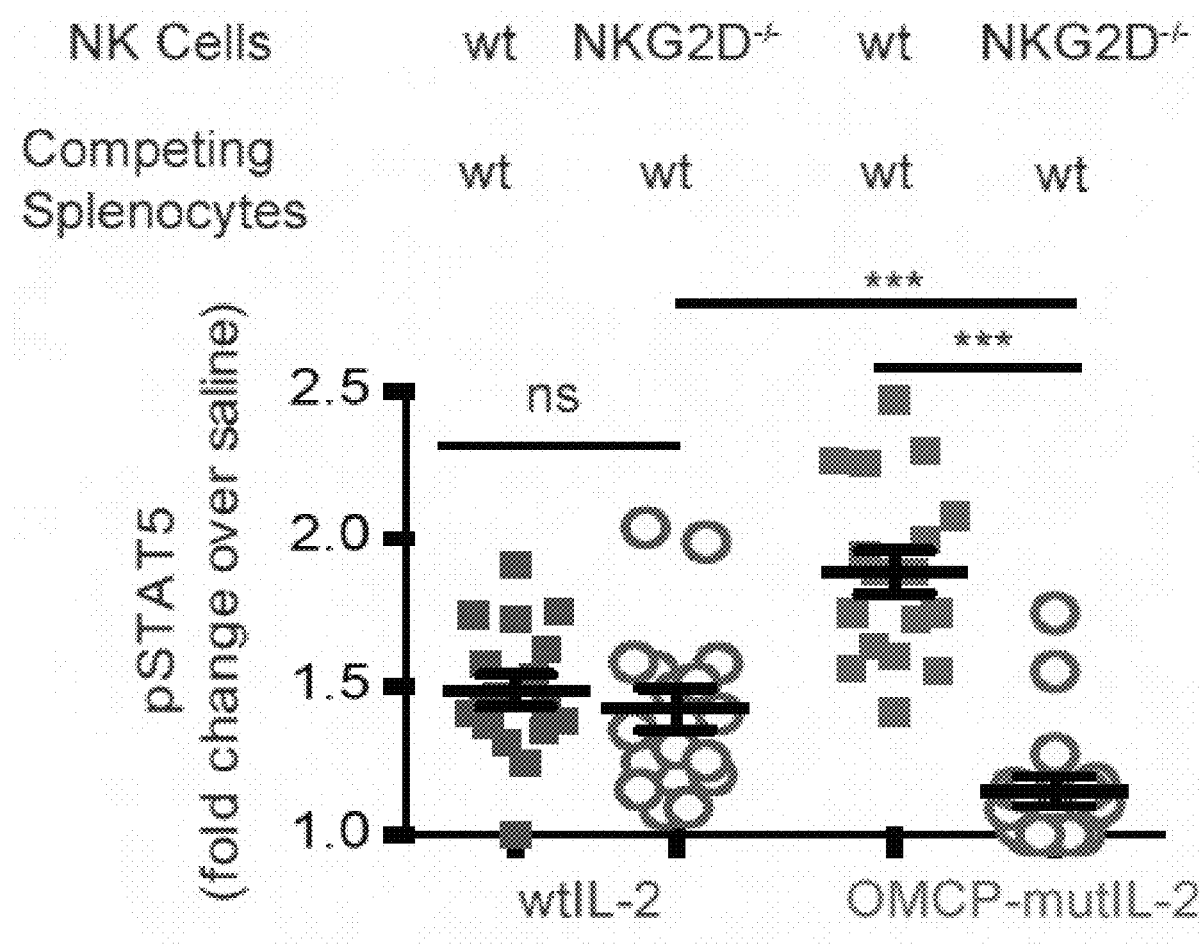
Figure 5K:
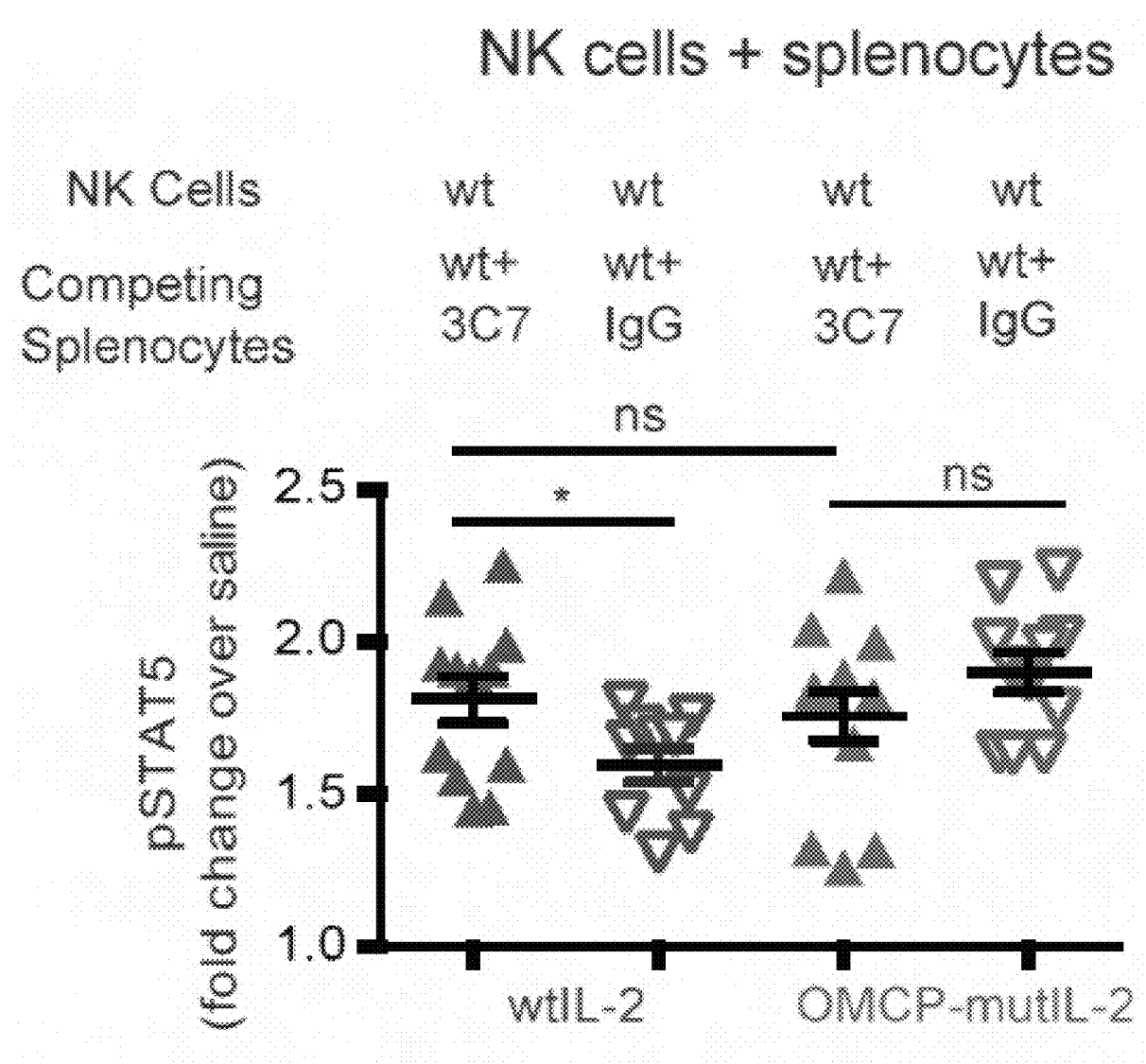
Figure 6:
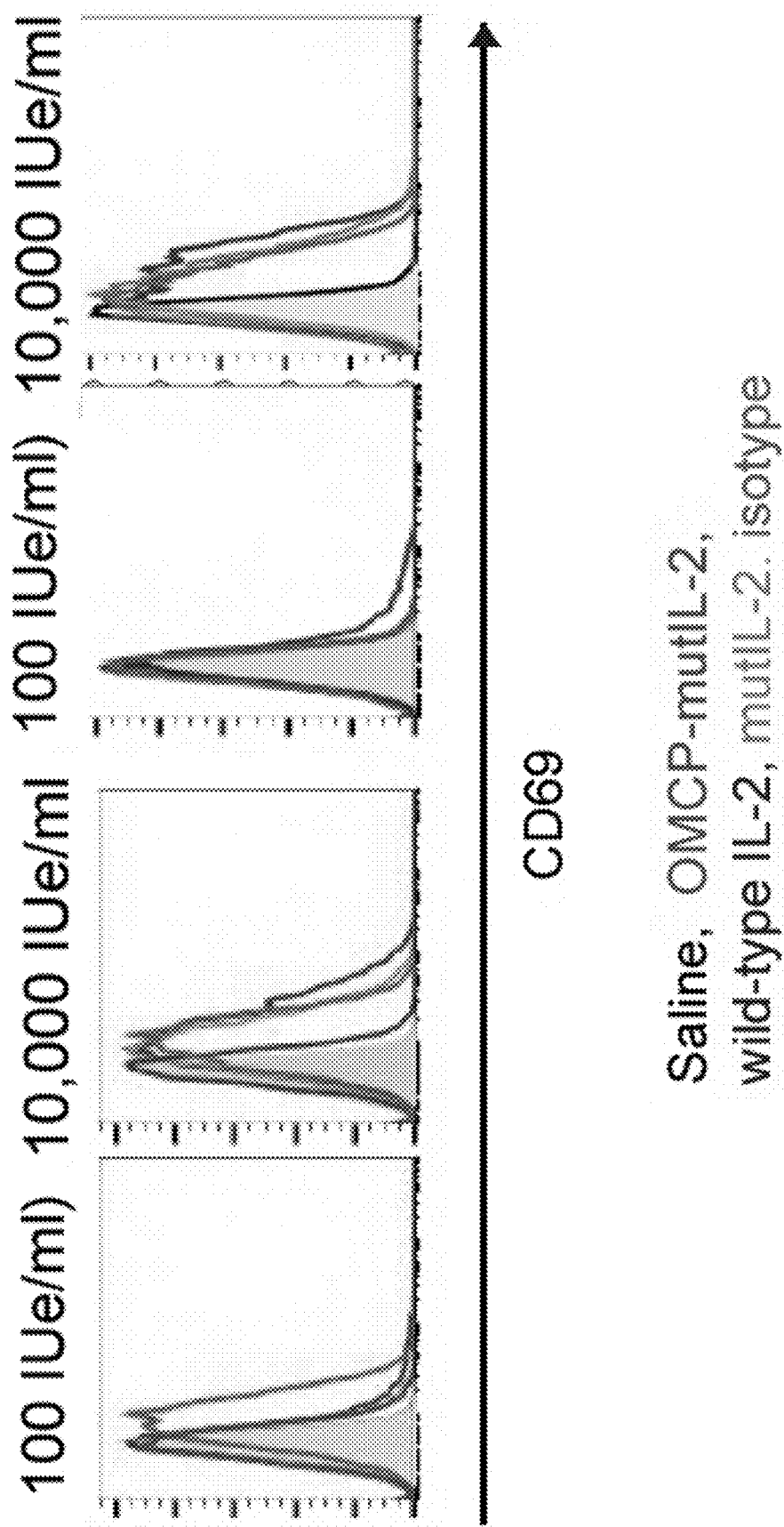
FIG. 6 depicts graphs showing B6 NK cells are preferentially activated by low dose OMCP-mutIL-2 but this selectivity disappears at the highest doses of cytokine or in the absence of NKG2D expression by NK cells. Left two graphs show B6 NK cells and right two graphs show BK NKG2D$^{-/-}$ NK cells.

To evaluate IL-2 signaling we next quantitated STAT5 phosphorylation after a 15 minute cytokine stimulation of freshly isolated NK cells in vitro. Lower levels of STAT5 phosphorylation were evident in A/J compared to B6 NK cells at all concentrations tested (FIG. 5D-E) suggesting that lymphocyte dysfunction of A/J mice may at least partially be the result of inefficient IL-2 signal transduction. Surprisingly, for both B6 and A/J NK cells wtIL-2 and OMCP-mutIL-2 demonstrated an identical dose-dependent pattern of STAT5 phosphorylation (FIG. 5D-E). In the absence of NKG2D reactivity OMCP-mutIL-2 failed to increase STAT5 phosphorylation over mutIL-2 alone. Taken together these data suggested that IL-2a reactivity is important for peak IL-2 signaling in resting NK cells, and that NKG2D-binding may effectively substitute for IL-2Ra-binding in IL-2-mediated signal transduction. Such data, however, failed to explain the superior NK activation by OMCP-mutIL-2 in vivo or in bulk splenocyte cultures (FIG. 1C-D, FIG. 3).

Figure 1E:
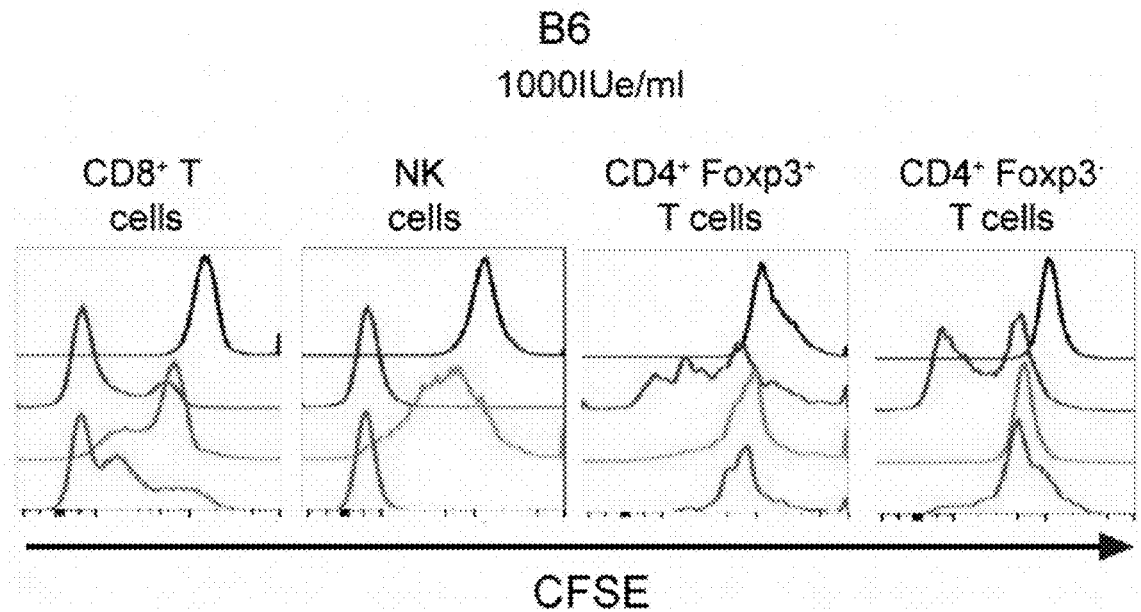
Figure 1F:
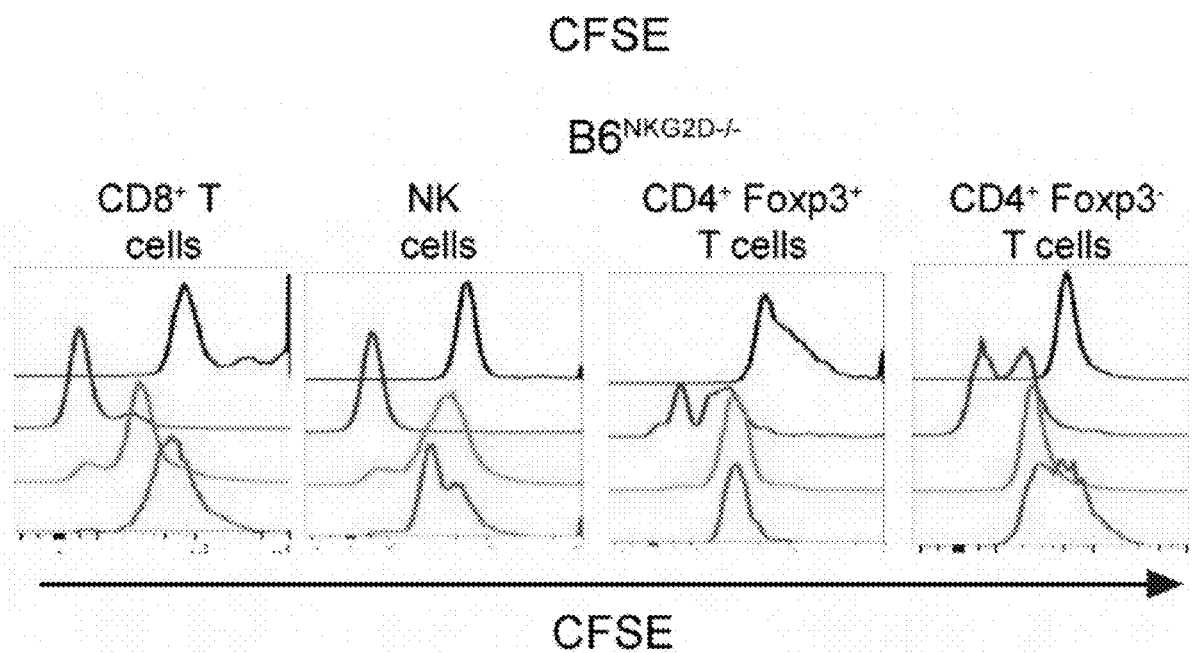
Figure 2A:
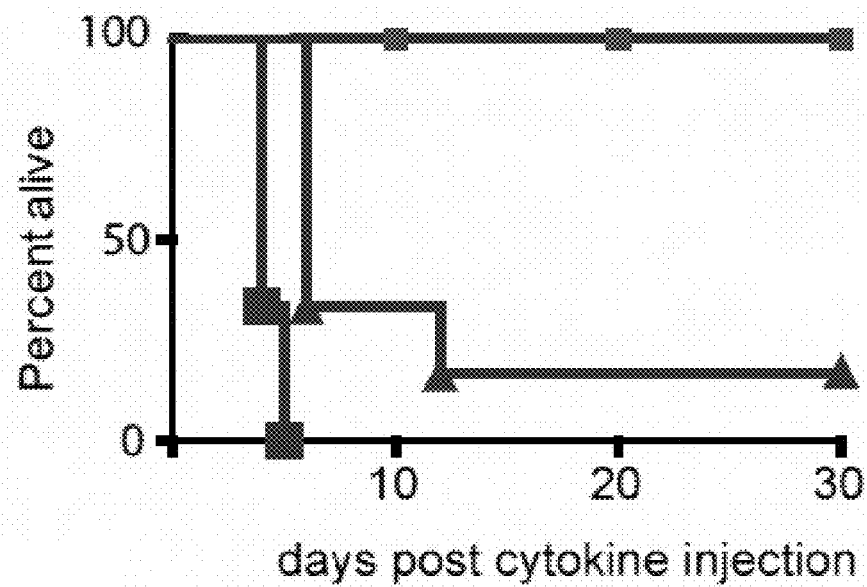
Figure 2B:
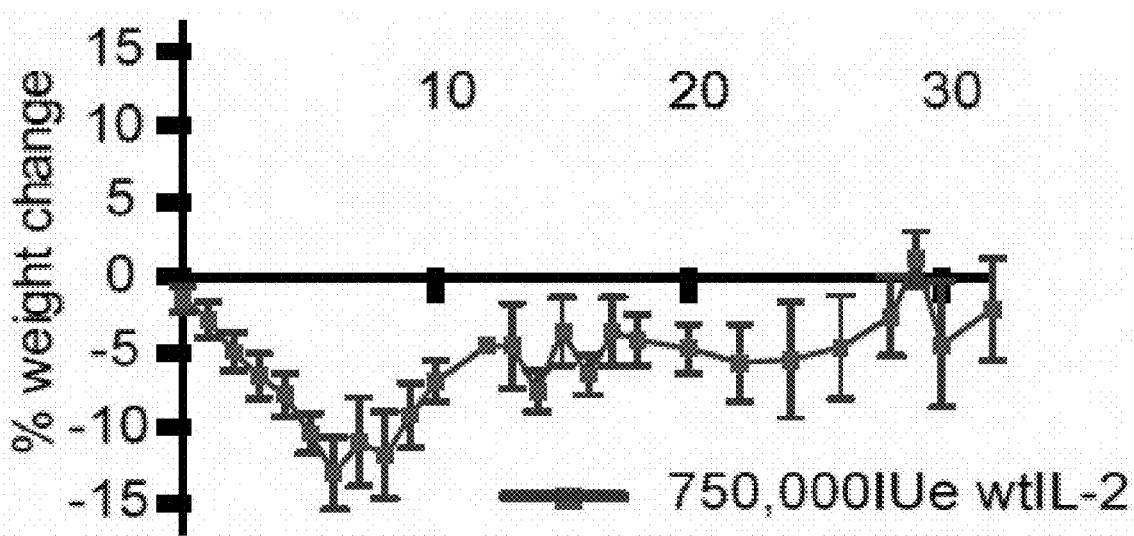
Figures 2C, 2D:
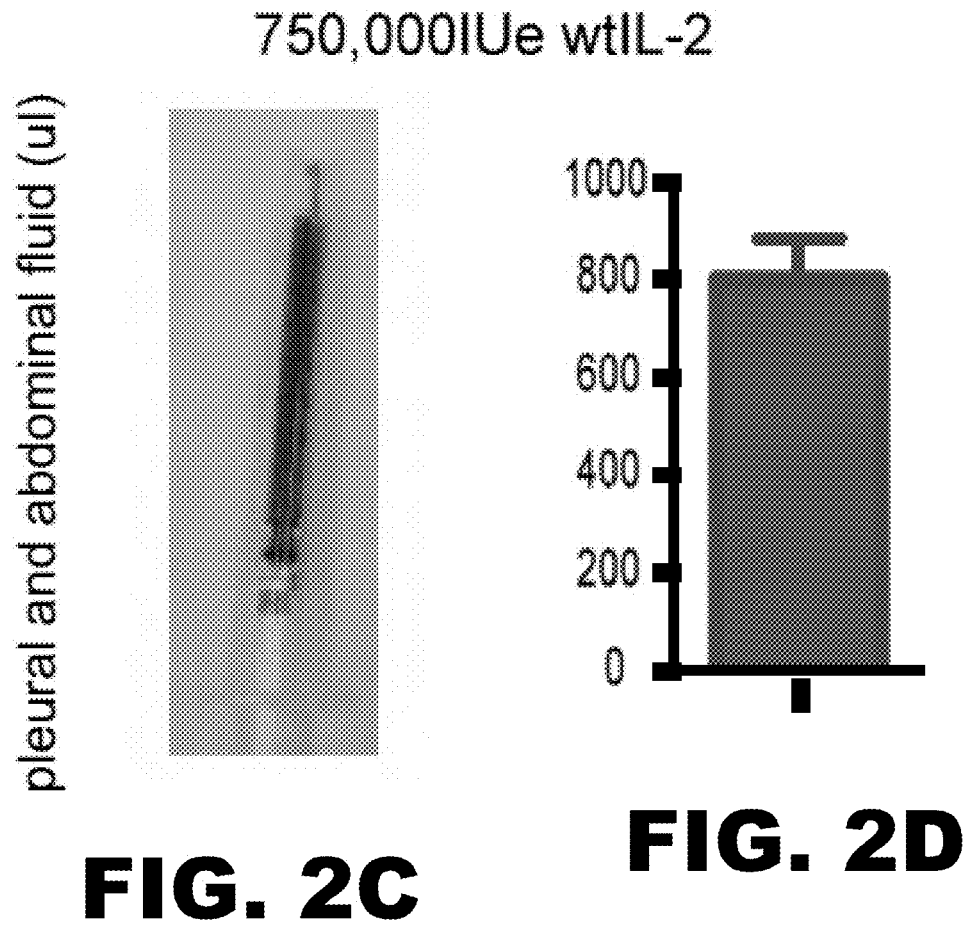
Figure 2F:
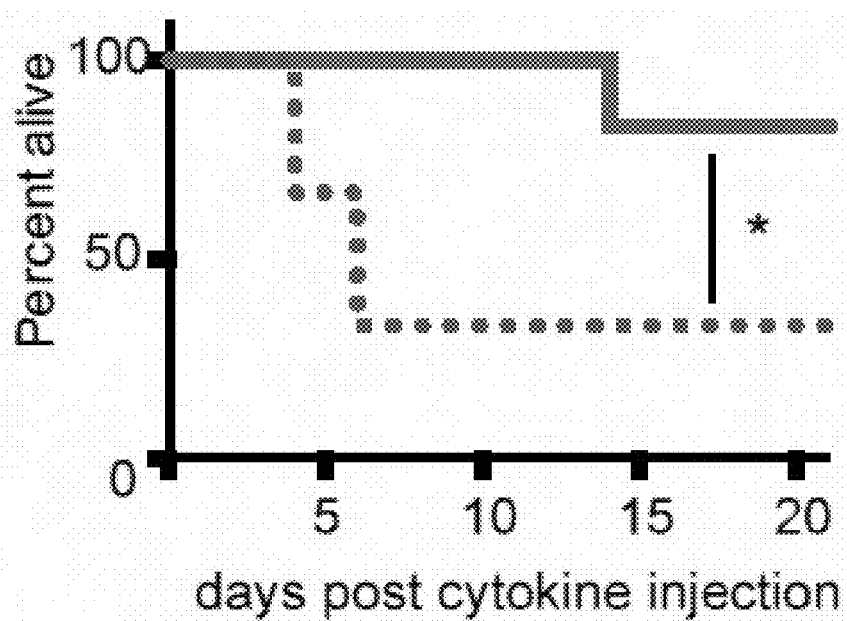
Figure 2G:
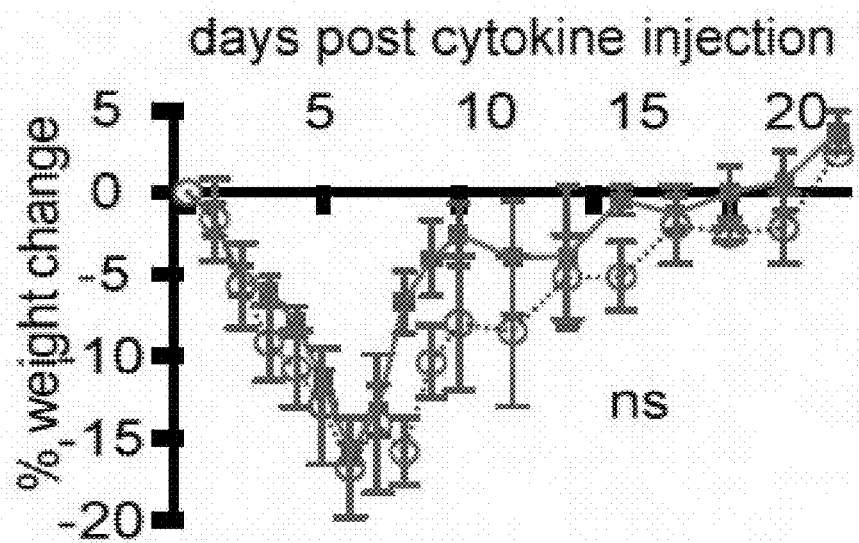
Figure 2H:
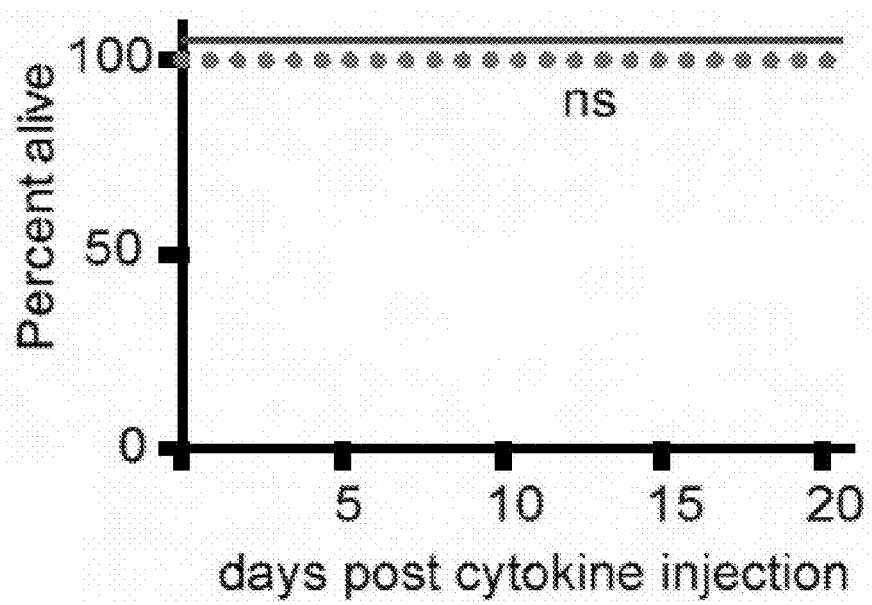
Figure 2I:
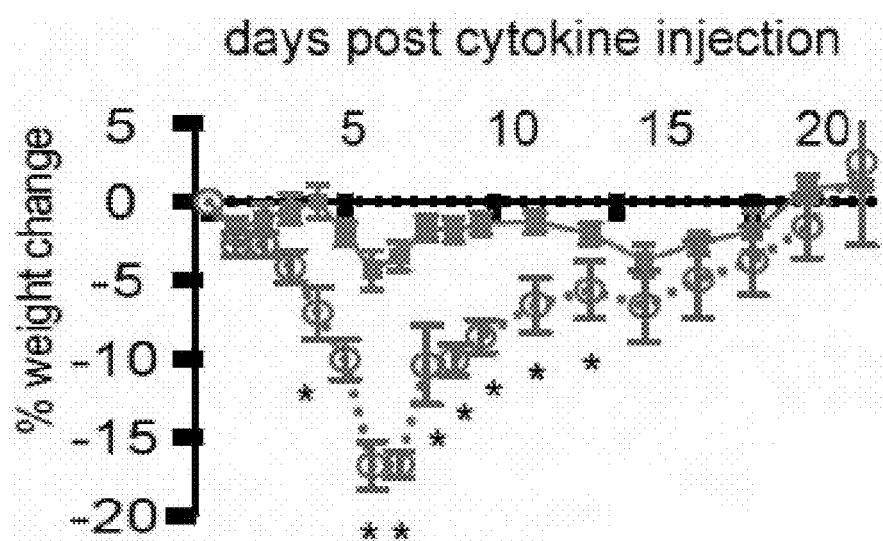
Figure 2J:
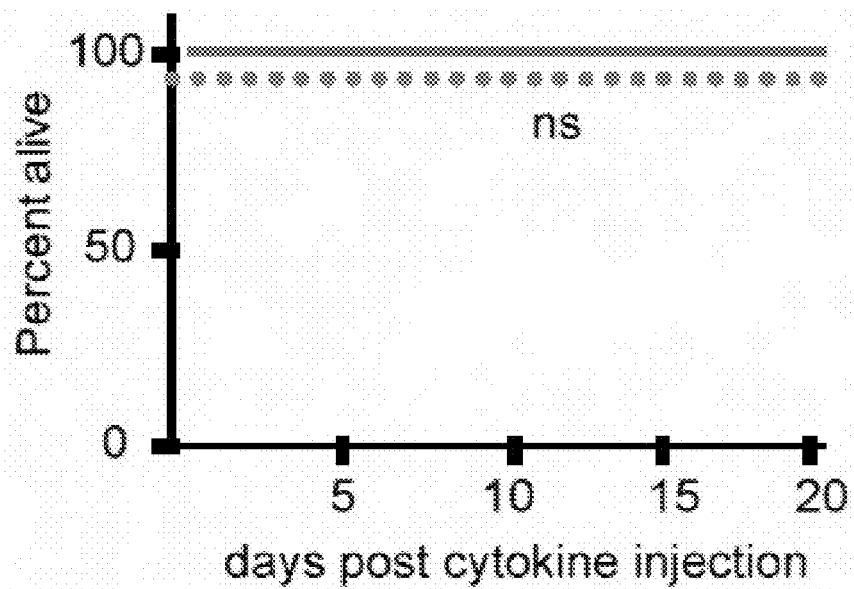
Figure 2K:
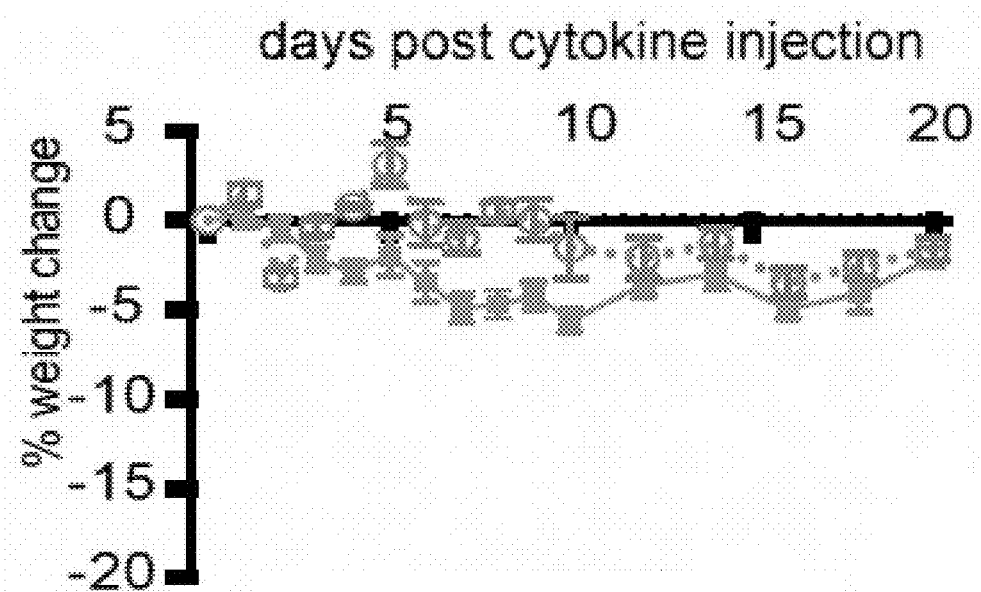
Figure 2L:
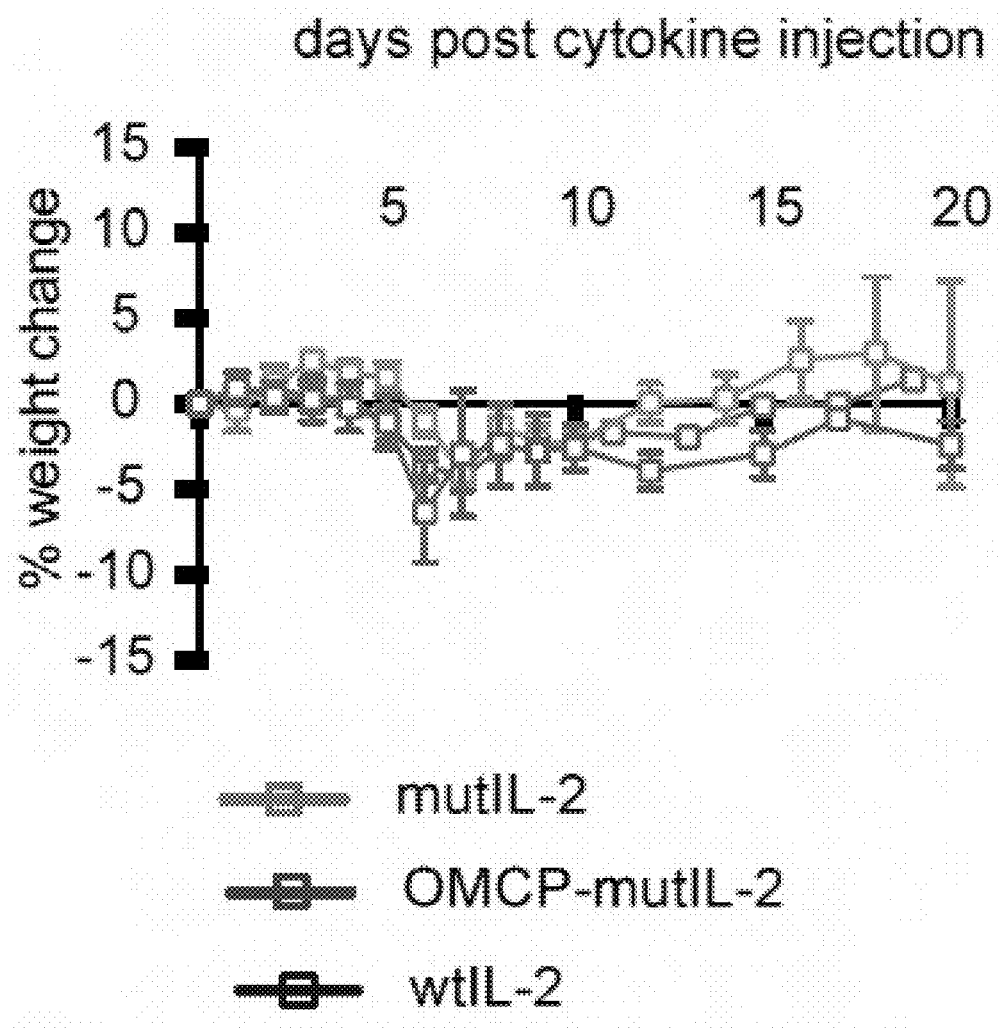
Figure 2M:
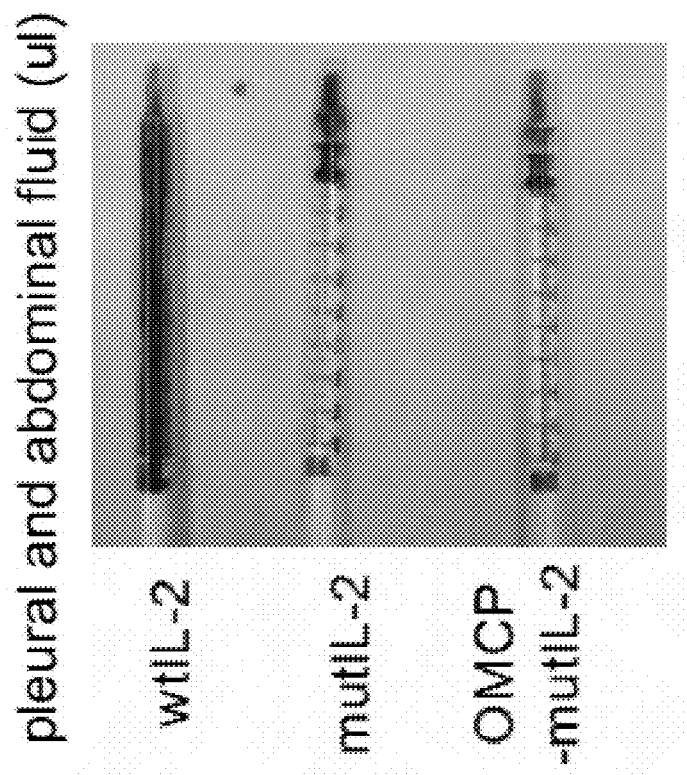
Figure 2N:
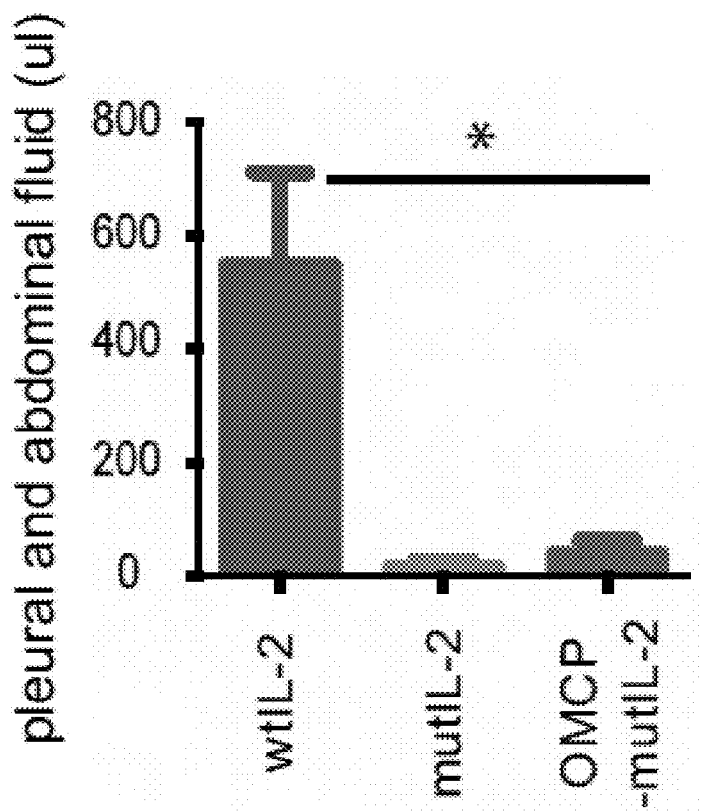
Figure 2O:
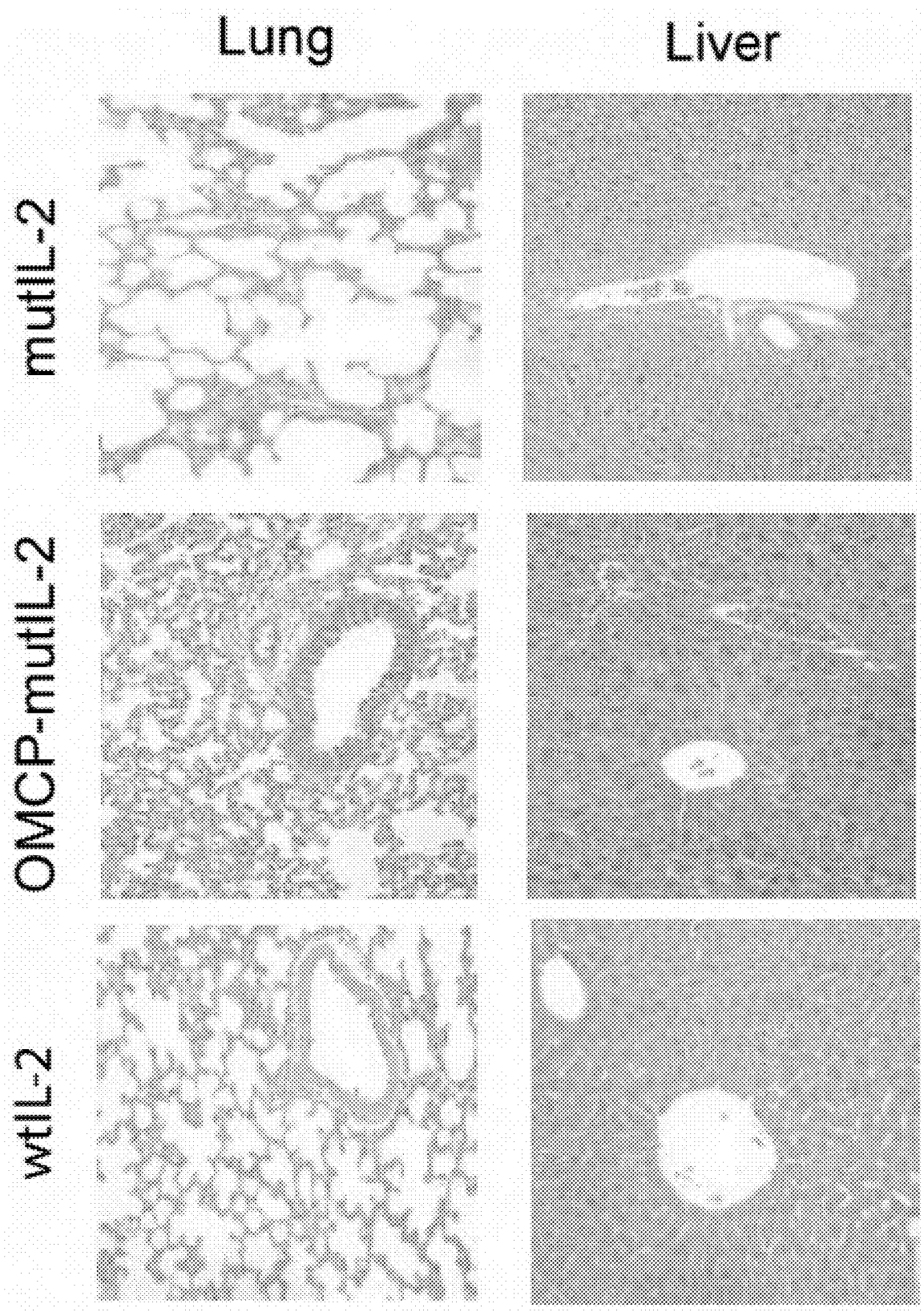

IL-2 signaling results in the internalization of IL-2/IL-2R, with subsequent degradation of IL-2 and IL-2Rβγ. The binding of OMCP-mutIL-2 to both the IL-2 receptor and NKG2D could thus lead to altered internalization and enhanced NK cell activation by prolonging IL-2 signaling. To test this we stimulated freshly isolated NK cells for 15 minutes, replaced the culture media with cytokine free media, and monitored STAT5 phosphorylation for four hours. Identical decay of phospho-STAT5 was evident for both wtIL-2 and OMCP-mutIL-2 (FIG. 5F-G). Thus altering duration of IL-2 signaling is not responsible for superior NK activation by OMCP-mutIL-2.

We next considered the possibility that superior NK activation by OMCP-mutIL-2 may be the result of altered cytokine interaction with competing stromal cells (FIG. 5H). Indeed, in the presence of other splenocytes OMCP-mutIL-2 demonstrated a dose-dependent enhancement in NK STAT5 phosphorylation over wtIL-2 (FIG. 5I). We next explored the interplay between IL-2Ra expression by stromal cells and NKG2D expression by NK cells on IL-2 signal transduction. To accomplish this we isolated splenic NK cells from either wild-type or NKG2D$^{-/-}$ B6 mice and combined them with wild-type splenocytes depleted of NK cells. Cultures were recombined in a 1:20 NK:splenocyte ratio, resembling the proportion normally present in resting wild-type B6 mice. For some cultures NK cell depleted splenocytes were treated with saturating concentrations of IL-2Ra-blocking antibody (clone 3C7) prior to recombining with wild-type NK cells. The cultures were then stimulated with 1000 IUe of either wtIL-2 or OMCP-mutIL-2 for 15 minutes. STAT5 phosphorylation was identical in NKG2D$^{-/-}$ or wild type NK cells in the presence of wtIL-2 (FIG. 5J, left two columns). Wild-type NK cells cultured with OMCP-mutIL-2 demonstrated superior STAT5 phosphorylation to cultures with wtIL-2. Little STAT5 phosphorylation was evident in NKG2D$^{-/-}$ NK cells cultured with OMCP-mutIL-2 (FIG. 5J, right two columns). In the presence of IL-2Ra-blockade of competing splenocyte stromal cells, NK cell STAT5 phosphorylation by wtIL-2 increased to levels comparable to OMCP-mutIL-2 (FIG. 5K). Taken together these data demonstrate that IL-2-Rα expression by "competing" stromal cells limits NK cell activation by wtIL-2 and this competition can be eliminated by the NKG2D-targeted, IL-2Rα-binding impaired OMCP-mutIL-2 construct.

Discussion for Examples 1-6

While IL-2 therapy initially showed great promise, it has been limited by activation of $T_{regs}$ and toxic side effects associated with activation of vascular endothelium. Several strategies have been proposed to preferentially activate cytotoxic lymphocytes. One strategy has been to create mutants with increased affinity for IL-2R3 to remove the preference for IL-2Rα[26,27]. Importantly, these IL-2 mutants retain wild type binding for IL-2Rα, and would therefore still be recognized by $T_{reg}$ cells and vascular endothelium. Our results also suggest that competition with IL2-Rα$^{+}$-expressing cells limits bioavailability of wtIL-2 to cytotoxic lymphocytes.

Another promising therapy involves anti-IL2 antibodies that sterically inhibit wtIL-2 binding to IL-2Rα[1,28,29]. Such treatment can extend serum half-life[24] due to the Fc region of the antibody and potentially due to reduced competition for wtIL-2 from IL-2Rα-expressing cells. Antibody-IL-2 fusion proteins have also been designed to target IL-2 to specific tumor antigens[30,31]. While offering the potential for personalized therapy such antibody-mediated delivery of IL-2 to the tumor depends on the expression of a known tumor associated antigen, a situation that often does not exist. This approach could potentially be further limited by tumor-mediated alteration of the targeted antigen.

Finally, IL-2 mutants with reduced affinity for IL-2Ra have been tested extensively. Compared to wtIL-2 these mutants can be administered in supratherapeutic doses without IL-2Rα-mediated capillary leak or systemic toxicity[32]. While these mutants have excellent safety profiles, they activate cytotoxic lymphocytes poorly (FIG. 5C-E)[33]. Our approach combines several of the concepts above to target a safe form of IL-2 directly to cytotoxic lymphocytes, instead of tumors. This is accomplished by replacing the normal targeting of IL-2 to IL-2Rα with NKG2D. The combination of an IL-2Rα-deficient IL-2 fused to a high affinity NKG2D-ligand improves upon previous strategies by specifically expanding NK cells without any apparent activation of $T_{regs}$ or capillary leak. These findings offer the promise of a potentially safe and highly efficacious form of IL-2.

One limitation in translating results from inbred lab animals to humans is the natural diversity in cytokine reactivity and environmentally dependent threshold for lymphocyte activation. Previous studies have demonstrated a correlation between ex vivo killing of tumor cells and enhanced long-term cancer immunity[34]. Therefore, any potential therapy needs to account for a population that has differential levels of cytotoxic lymphocyte activity. We have thus attempted to model this natural variation by using two strains of mice known to be highly resistant (B6) or susceptible (A/J) to carcinogenesis. For example, NK cells from B6 mice, are activated by wtIL-2 and extreme doses of mutIL-2. In contrast, IL-2/anti-IL-2 antibody complexes resulted in expansion of NK cells in A/J but not in B6 mice. Such variations highlight the limitations of translating results derived from a single strain of mice to immunologically diverse humans. Importantly, the OMCP-mutIL-2 construct was able to expand NK cells in both strains of mice, indicating that this therapy could be efficacious in populations with diverse NK function and cytokine reactivity.

Since OMCP has been described as an evolutionary antagonist of NKG2D[35] blockade of this immunoreceptor at the time of tumor therapy may be construed as counterproductive. Nevertheless, natural cytotoxicity and tumor clearance was augmented in OMCP-mutIL-2-treated mice even in the presence of established tumors. This suggests minimal or transient NKG2D receptor occupancy and preservation of function. Alternatively recent reports have demonstrated that shed NKG2D ligands may actually promote tumor immunity through reversal of NK desensitization imposed by chronic agonistic engagement[36]. While we did not detect NK activation or expansion by monomeric or even pentameric OMCP, it is possible that within the tumor bed such competitive antagonism plays a paradoxical role in NK activation. In addition, IL-2 may upregulate receptors necessary for NK migration and tumor infiltration. It is thus possible that anti-tumor immunity mediated by OMCP-mutIL-2 may depend on NK cells located outside the tumor bed and not subject to local tumor-specific tolerance or anergy. Furthermore, OMCP maybe the ideal "targeting vector" due to its high affinity and long half-life of binding to human NKG2D.

While NK cells from two separate strains of mice were activated by OMCP-mutIL-2 we did not detect global expansion of activation of $CD8^{+}$ T cells by our construct. This is most likely due to the fact that NKG2D is expressed only on select subsets of CD8+ T cells, namely memory or activated cytotoxic lymphocytes. Based on the paucity of this cell population in mice raised in specific pathogen-free environment, OMCP-mutIL-2-mediated activation was limited in our system to NK cells. To this end we focused on immunotherapy for lung cancer and lymphoma, whose growth is regulated primarily by NK cells[16,17,22,37]. Nevertheless OMCP-mutIL-2 was able to expand CD8+ T cells when administered in high concentrations in vitro (FIG. 1E-F). Thus, it may be possible that NKG2D-targeted delivery of immunostimulatory cytokines may lead to the expansion and/or activation of antigen-specific CD8+ memory cells for long-term tumor immunity under normal immunologic conditions.

Methods for Examples 1-6

Cytokine and Construct Generation: The sequences encoding human IL-2 (1-133; C125S) and mutant IL2 (1-133; R38A, F42K, C125S) were cloned into the pFM1.2R[38] with an N-terminal FLAG/hexahistidine tag. The chimeric OMCP-mutIL-2 molecule comprises the full-length OMCP (1-152) coding sequence cloned in frame with a C-terminal FLAG/hexahistidine tag-mutant IL-2 (1-133; R38A, F42k, C125S) cloned into the pFM1.2R vector. Proteins were expressed by transient transfection into HEK293F (Life_Technologies). Supernatant was recovered at 72 h and 144 h post-transfection. Supernatants were supplemented with 5 mM imidazole and 0.02% sodium azide and purified by nickel-nitrilotriacetic acid (Ni-NTA) chromatography (Qiagen). Purified proteins were buffer exchanged into saline and flash frozen in liquid nitrogen. Equivalent in vitro and in vivo activity was documented for wild-type IL-2 generated in house and Teceleukin (Tecin™) available from the NCI repository (Frederick National Laboratory for Cancer Research). Thus for some experiments these two preparations of IL-2 were used interchangeably.

Wild-type IL-2 has a specific activity of $15 \times 10^6$ IU/mg[39]. Thus, based on the molecular weight of 15.5 kDa a 4.4 µM solution is equivalent to 1000 IU/µl. Based on this calculation all cytokines and construct were administered on a molar basis with 1 µl of 4.4 µM solution defined as 1000 IU equivalents (IUe from here on). Such a system allows for equimolar comparison between IL-2, mutIL-2 and OMCP-mutIL-2 despite difference in molecular weight.

Animals: A/J (8-12 weeks) and C57BL/6J (6-9 weeks) strains of mice were purchased from the Jackson Laboratory (Bar Harbor, Me.). NKG2D$^{-/-}$ mice on the B6 background were kindly provided by Wayne Yokoyama and bred in house (Howard Hughes Institute of Medicine at Washington University in St. Louis). Animals were housed in a barrier facility in air-filtered cages and allowed free access to food and water. For some experiments A/J mice were treated with depleting concentrations of anti-Asialo-GM1 (50 µl day −2; 25 µl day −1) or control rabbit IgG (Wako Chemical Company). Animal procedures were approved by the animal studies committee of Washington University School of Medicine, St. Louis, Mo.

Tissue harvest and in vitro cultures: Single cell suspension of splenocytes were obtained by crushing whole spleens through 70 µm cell strainers prior to RBC lysis by ACK buffer (Lonza, Walkersville, Md.) and re-filtration through a 40 µm filter. Lungs were digested for 90 minutes at 37° C. in 1 mg/ml collagenase II (Fisher Scientific), and 5 U/ml DNase I (Sigma-Aldridge) prior to processing in an identical fashion to spleens.

For in vitro cultures splenocytes from either A/J, B6, or NKG2D$^{-/-}$ mice were extracted in a sterile fashion and seeded in 12-well plates in complete media (RPMI 1640 supplemented with 10% FBS, 100 U/ml Penicillin and Streptomycin, 2 mM L-glutamine and 50 µM 2-Mercaptoethanol) at 5 million cells per ml per well. The cells were treated with increasing doses of human recombinant IL-2, mutIL-2, OMCP-mutIL-2, or OMCP for 36 hours as described in the manuscript. For some experiments bulk splenocytes were labeled with CFSE and cultured in 1000 IUe/ml of cytokine for 5 days prior to flow cytometric analysis. For NK isolation experiments bulk splenocytes were processed using either the NK cell isolation kit II or CD49b (DX5) positive magnetic bead selection (both from Miltenyi Biotech). For STAT5 phosphorylation experiments, isolated NK cells were stimulated in increasing concentrations of IL-2 or construct at 100,000 cells/500 µl for 15 minutes. For experiments evaluating the interaction of NK cells with splenic stroma, DX5 positively selected NK cells were labeled with CFSE (for identification after fixation and permeabilization) and recombined with NK depleted stromal cells. As described in the manuscript, for some studies NKG2D$^{-/-}$ NK cells were combined with wild-type splenocyte stromal cells. For other experiments, NK-depleted splenocytes from wild-type B6 mice were treated with saturating concentrations of anti-IL-2α blocking antibody (clone 3C7) or isotype control (both from Biolegend) prior to recombining with NK cells. For such competitive STAT5 phosphorylation experiments 100,000 cells were resuspended into 2 µl complete media containing 1,000 IU/ml of either wtIL2, mutIL-2 or OMCP-mut-IL-2 (freshly prepared and pre-warmed). The cells were then incubated at 37° C. for 15 minutes Flow Cytometry: All flow cytometric analysis was performed using saturating concentrations of fluorochrome-conjugated antibodies at 4° C. in FACS buffer consisting of PBS with 2% FBS and 0.4% EDTA. All antibodies were anti-mouse and purchased from BD Bioscience or eBioscience and consisted of anti-CD4 (clones GK1.5 or RM4-5), anti-CD8 (clone 53-6.7), anti-CD278 (ICOS) (clone: 7E.17G9), anti-CD25 (clone PC61), anti-KLRG1 (clone 2F1), CD49b (Integrin alpha 2) (clone DX5), anti-CD3e (clone 1452C11), anti-CD45 (clone 30-F11), anti-CD69 PE (clone H1.2F3), anti-GITR (clone DTA-1), anti-Foxp3 (clone: FJK-16s) and Anti-Stat5 (clone 47/Stat5; pY694). Antibodies were conjugated to either FITC, PE, PerCP-CyTM5.5, PE-Cyanine7, APC, APC-eFluor®780, eFluor® 450, or Alexa Fluor® 647.

Phospho-STAT5 evaluation was performed by paraformaldehyde fixation, methanol permeabilization and staining with AlexaFluor488-conjugated Anti-Stat5 (pY694) (BD Pharmingen; clone 612599). To accomplish this isolated NK cells or NK cells combined with NK-depleted splenocyte stromal cells were fixed in 2% paraformaldehyde (PFA) at 37° C. for 10 minutes after IL-2 stimulation for 15 minutes. The cells were then washed once with ice-cold PBS and permeabilized by adding 0.5 ml/tube of 90% Methanol on ice for 1 hour. The cells were washed once with ice-cold PBS (to remove methanol), and stained for 1 hour with anti-Stat5 (pY694) antibody at room temperature followed by one wash in PBS/0.5% fetal calf serum.

In Vitro Cytotoxicity: $^{51}$Chromium release was conducted by incubating the target cells with 100 mCi sodium$^{51}$chromate (PerkinElmer) for 1 hour. Bulk splenocytes were used as effector cells and incubated with targets at defined effector:target ratios for 4 hours at 37° C. in round bottom 96 well plates. Specific lysis was expressed as (experimental release-spontaneous release)/(maximum release-spontaneous release)×100% with 0% specific lysis as lowest expressed value.

In vivo cytokine injections: For select experiment, the mice received intraperitoneal injections of cytokines in 200 µl volume given as ten equal doses given twice a day over a period of five days. As described above all cytokines were normalized to IUe on a molar basis. For select experiments, the mice were then sacrificed on day 6 and organs were fixed in 10% buffered formalin for histological analyses. For other experiments splenocyte and lung lymphocyte populations were analyzed flow cytometrically. For all the in vivo cytokine treatment experiments, animals were weighed (daily or every other day) and expressed as % change from start of cytokine therapy.

For evaluation of serum concentration wtIL-2, mutIL-2 or OMCP-mutIL-2 were labeled with Alexa Fluor® 647 (LifeTechnologies Inc.) according to manufacturer instructions. Serum was collected at times specified and concentration of cytokine determined fluoroscopically according to a standard curve.

In vivo tumor studies: Lewis lung carcinoma (LLC) cells were subcutaneously injected into B6 or B6 NKG2D$^{-/-}$ mice at $1\times10^5$ cells per mouse in 100 µl of sterile saline. Once visible tumors were evident, day 5 post-injection, a five day course of cytokine treatment was started as described above. Measurement of cross sectional tumor diameter was performed using calipers and tumor volume estimated as $4/3\pi r^3$. The mice were sacrificed on day 24 post injection or once they reached a maximal tumor diameter of 20 mm. For NK cell depletion, mice were treated with anti-NK1.1 antibody (clone PK136) or mouse IgG isotype control (both from BioXcell) at 500 µg day −2, 250 µg day −1 and 250 µg weekly for the duration of the experiment. For lymphoma clearance experiments A/J mice were treated with ten doses of cytokine over a period of five days as described above and on day #6 injected intravenously with YAC-1 cells that were labeled with CFSE at $5\times10^6$ cells/mouse. Mice were sacrificed 4 hours later, lungs were digested and viability of YAC-1 determined by forward and side scatter analysis of CFSE$^+$ cells.

Statistics Comparison of splenic and lung-resident lymphocytes between various cytokine treatment conditions was performed by unpaired T-test with Welch's correction to account for unequal variance or unequal sample size. Tumor growth between different cytokine conditions was compared by multiple unpaired-T tests performed between various conditions at various time points using the Sidak-Bonferroni correction. Fold change in STAT5 phosphorylation was evaluated by unpaired T-test with Welch's correction in a similar fashion.

Introduction to Examples 7-10

Intracellular surveillance mediated by MHC class I (MHCI) is a critical host immune function and as such MHCI molecules are frequently targeted for destruction or intracellular retention by viruses [1]. Many herpesviruses encode at least one protein that prevents the cell surface expression of MHCI [1,2]. However, this immune evasion strategy renders the infected cell susceptible to NK cell-mediated lysis due to loss of inhibitory signals [3]. Viral infection also leads to cell surface display of NKG2D ligands (NKG2DLs) recognized by the activating receptor NKG2D, further predisposing the infected cell towards NK cell-mediated lysis. Therefore, viruses that target MHCI expression often also sabotage NKG2D-mediated cell responses by targeting NKG2DLs on the infected cell [4-7].

NKG2DLs are not normally expressed on the cell surface but can be induced by cellular stress [8]. The specific trigger for NKG2DL expression is not known but NKG2DLs are upregulated in response to several viral infections [9-12]. NKG2DLs comprise a large group of proteins all recognized by NKG2D, despite having low sequence identity. NKG2DLs include the MIC (A and B) and ULBP (1-6) families in humans as well as MULT1 and the RAE-1 (α-ε) and H60 (a-c) families in mice [13]. The redundancy in NKG2DLs is likely due to a combination of tissue specific expression patterns of the ligands and the need to counter viral NKG2D evasion strategies [14]. Many viruses have evolved mechanisms to inhibit the cell surface expression of NKG2DLs as a means of interfering with NKG2D surveillance of viral infection. This strategy is most apparent among β- and γ-herpesviruses, in which four murine cytomegalovirus proteins (m138, m145, m152, m155) [15-18], two human cytomegalovirus proteins (UL16, UL142) [19, 20] and one Kaposi's sarcoma-associated herpesvirus protein (K5) [21] have been demonstrated to block NKG2DL surface expression. This evasion strategy is also found in RNA viruses, as hepatitis C virus NS3/4a and human immunodeficiency virus Nef proteins also block the expression of a subset of NKG2DLs [22,23]. Additionally, human cytomegalovirus, herpes simplex virus type 1 and Epstein-Barr virus each also encode at least one miRNA that prevents translation of MICB [24,25]. Similarly, JCV and BKV polyoma viruses target ULBP3 with miRNAs [26]. However, blocking NKG2DL expression on the infected cell is an imperfect evasion strategy, since no single viral protein or miRNA has been shown to block the expression of all NKG2DLs.

Like several herpesviruses, cowpoxvirus (CPXV) also sabotages MHCI expression. CPXV expresses CPXV012 and CPXV203, two proteins that prevent TAP-mediated peptide transport and MHCI trafficking to the cell surface, respectively [27-34]. Ectromelia virus, a related orthopoxvirus, induces NKG2DL expression and NKG2D is critical for the control of ectromelia virus pathogensis [35]. Infection with another orthopoxvirus, monkeypox virus, leads to dramatic expansion of NK cells but impaired NK cell function [36]. Together this suggests that CPXV infected cells would be sensitive to NK cell-mediated lysis.

Unlike herpesviruses, CPXV does not target NKG2DLs. Instead this virus targets NKG2D directly by encoding a competitive inhibitor of NKG2DLs, orthopoxvirus MHC class I-like protein (OMCP) [37,38]. OMCP is a 152 residue protein that is secreted from infected cells and antagonizes the NKG2D-mediated killing of NKG2DL-expressing target cells [37]. OMCP also plays an important role in vivo, with OMCP-null CPXV attenuated in mouse models of infection (M. Sun et al, personal communication). OMCP binds to murine NKG2D with an affinity equal or greater than all tested murine NKG2DLs, and to human NKG2D with an affinity ~5,000-fold higher than human NKG2DLs [37-40].

Despite their divergence in sequence identity, all known host NKG2DLs share common structural features [41,42]. NKG2DLs contain an MHCI-like platform domain composed of an eight-stranded beta sheet with two helices [43-47]. The platform domain is subdivided into α1 and α2 domains, with each domain containing four beta strands and an alpha helix. Unlike MHCI, the groove between the helices of the NKG2DL platform domain is closed and therefore NKG2DLs do not bind peptides.

Like host NKG2DLs, OMCP also adopts an MHCI-like platform domain [38]. However, the platform domain of OMCP has been trimmed to have only a six-stranded beta sheet with shorter flanking helices. We termed the helix of the α1 domain H1 and the discontinuous helix of the α2 domain is termed H2a and H2b. The H2a and H2b helices of OMCP are also rearranged to be flatter against the beta sheet and to be splayed apart from each other. These differences in the OMCP structure were hypothesized to be important for the high affinity binding of OMCP to NKG2D. However, OMCP was still expected to bind to NKG2D in the same orientation as host NKG2DLs, i.e. with the alpha helices oriented diagonally within the symmetric NKG2D binding groove.

Here we report the 2.0 Å-resolution structure of human NKG2D bound to OMCP of the Brighton Red strain of cowpoxvirus. The structure reveals a significant reorientation of OMCP in the NKG2D binding groove relative to host NKG2DLs. The interface of OMCP with NKG2D is highly complementary, buries a significantly larger surface area than host NKG2DLs, and remains continuous across the entire NKG2D binding groove. This novel binding adaptation and high affinity allows OMCP to compete with the high local concentration of membrane-associated host NKG2DLs. We further show that the mechanism of NKG2D antagonism requires OMCP to be secreted, lest it lead to NKG2D signaling.

Example 7. Structure Determination of OMCP-NKG2D

We had previously solved the structure of OMCP alone and shown that, similar to host NKG2DLs, OMCP adopts an MHCI-like platform domain [38]. Despite the overall similarity of the domain structure of OMCP to host NKG2DLs, OMCP had several notable deviations in the putative NKG2D-binding site that were hypothesized to be important for the high affinity binding of OMCP to NKG2D. To further understand the unusually high affinity of OMCP for NKG2D, we crystallized and solved the structure of OMCP bound to human NKG2D.

Figure 24A:
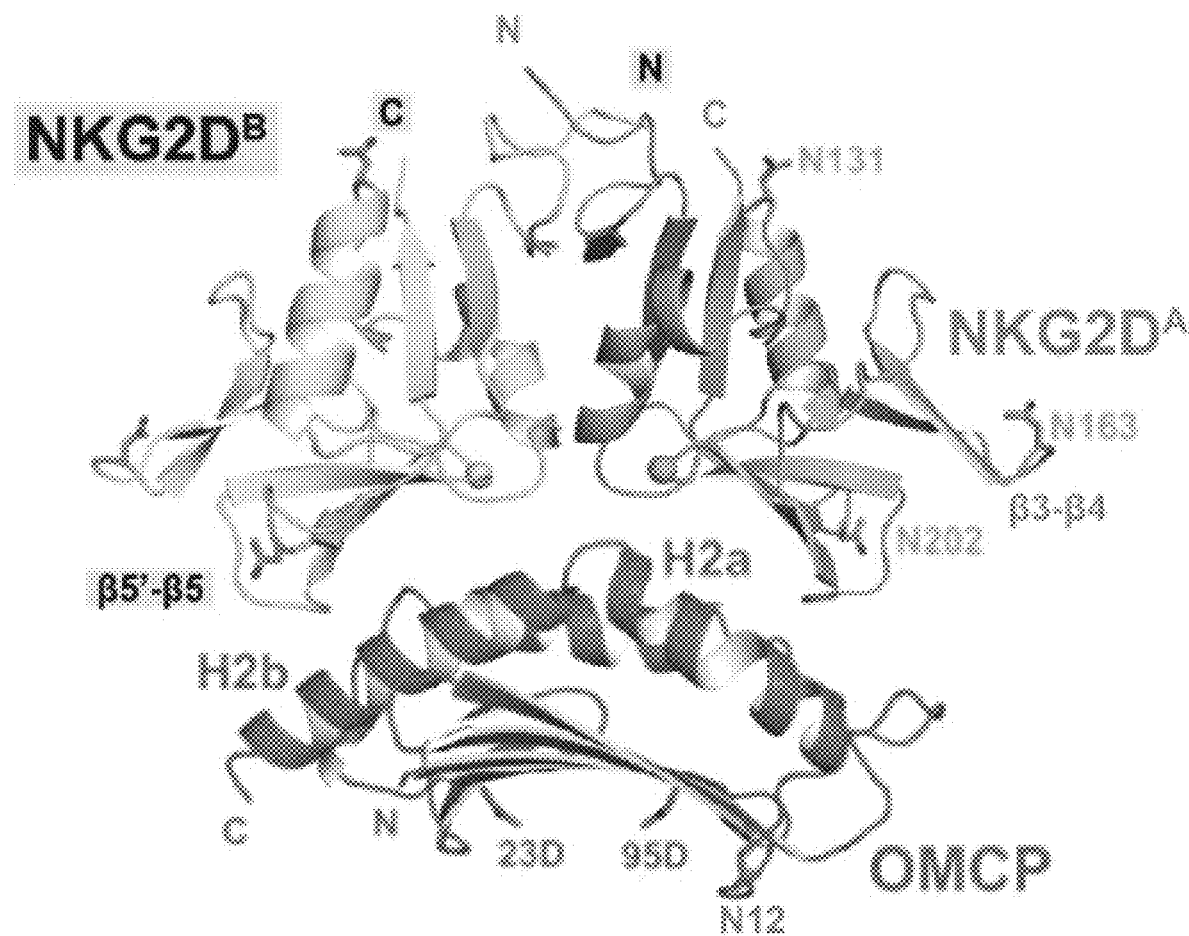
FIG. 24A and FIG. 24B depict the structure of OMCP in complex with NKG2D.

Initial crystallization trials with OMCP and NKG2D yielded ~30 different crystallization conditions. Subsequent data collection and molecular replacement of multiple low-resolution crystal forms all yielded similar partial solutions, with alternating sheets of OMCP-NKG2D complexes separated by undefined density. In the original structure of OMCP alone, the beta sheets packed to form a trimer with the alpha helices oriented away from the center [38]. An identical OMCP trimer formed in the OMCP-NKG2D partial solutions, with NKG2D now bound to the outward facing helices (data not shown). In an attempt to change the lattice packing, we introduced mutations into the beta sheet of OMCP that were designed to break the trimeric interface. These mutations were on the opposite face of OMCP from the NKG2D binding site to avoid disrupting OMCP-NKG2D binding. A mutant form of OMCP (Y23D, F95D) crystallized with NKG2D in a new space group and the crystals diffracted to 2.0 Å (Table 1)(FIG. 24A).

Figure 29A:
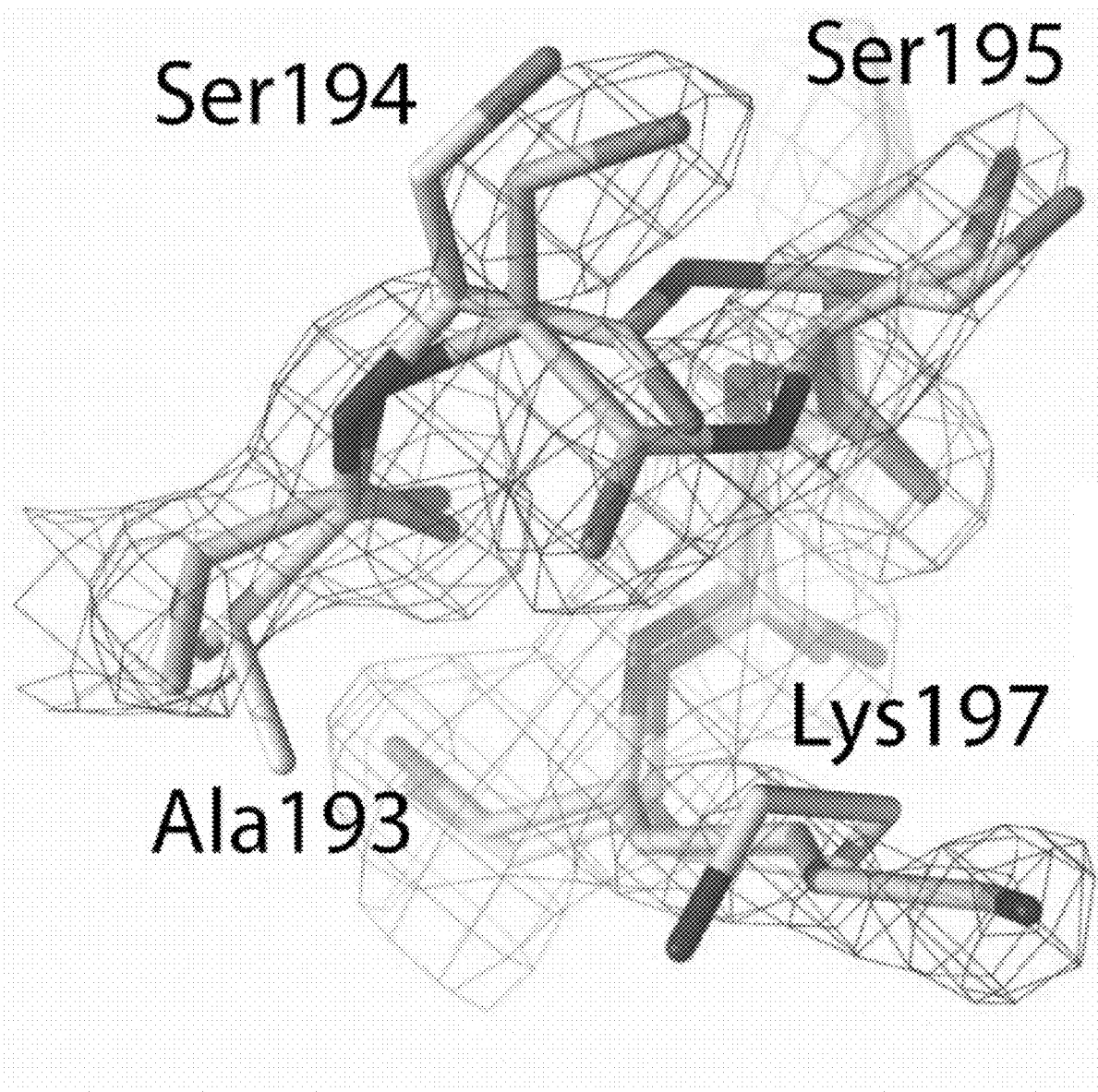
Figure 29B:
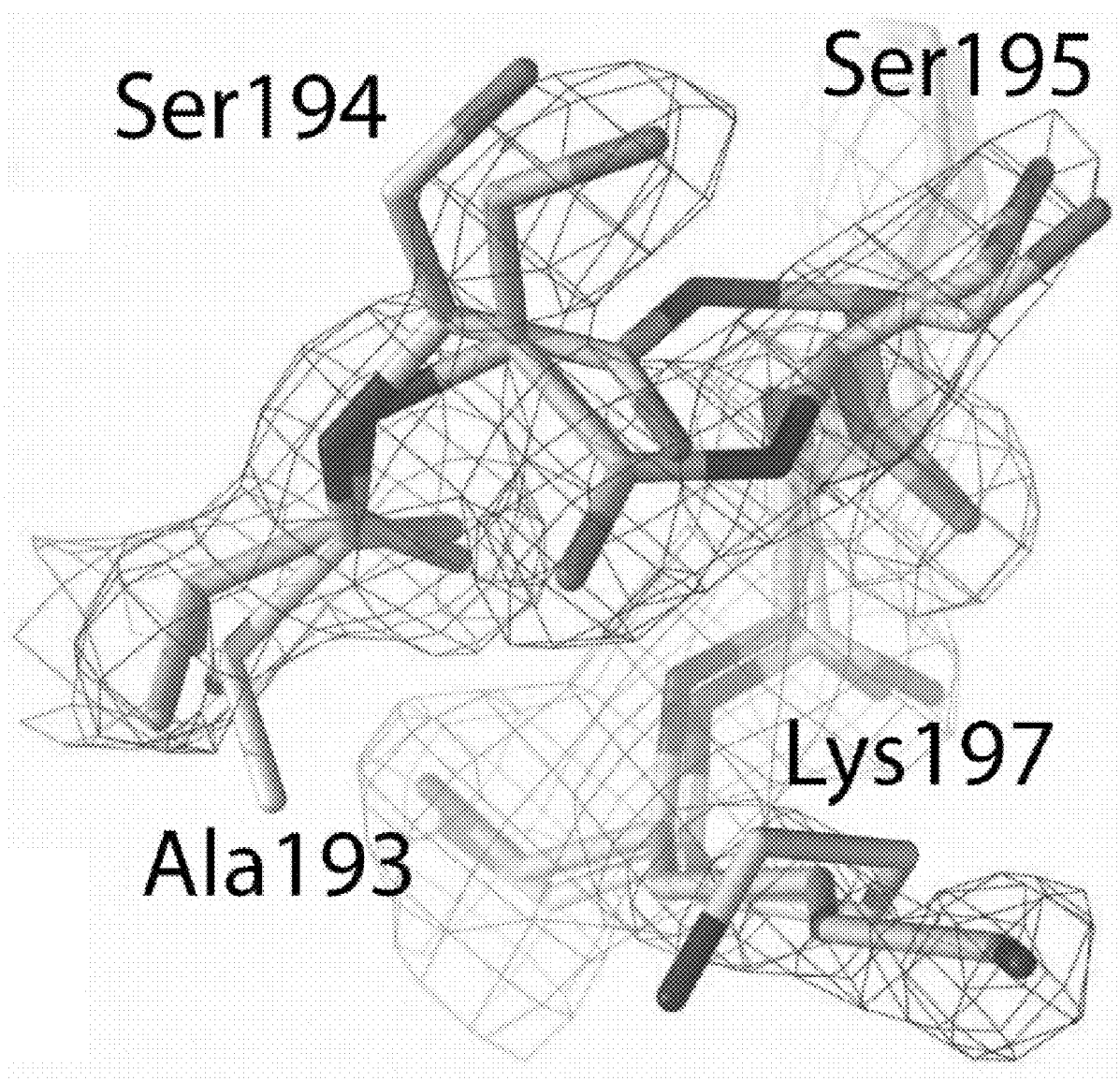

The electron density map was continuous and unambiguous throughout all chains of the structure, with the exception of Q108 in OMCP. This residue was situated in the center of the largest loop of OMCP and unambiguous density for this residue was also absent from the structure of OMCP alone [38]. The structure of OMCP bound to NKG2D showed no major differences from our previous structure of OMCP alone, with an RMSD for all atoms of 0.8 Å. Likewise, NKG2D was also similar to previous NKG2D structures with RMSDs ranging from 0.5-0.9 Å. The 33-34 loop of NKG2D is the only region of either OMCP or NKG2D that displayed above-average B factors. This loop is thought to be flexible and has had above average B factors in all previous NKG2D structures [48]. Interestingly, the peptide bond between S193-S194 in our NKG2D structure had a cis conformation not described in other NKG2D structures (FIG. 29).

Example 8. The Interface Between OMCP and NKG2D

Figure 24B:
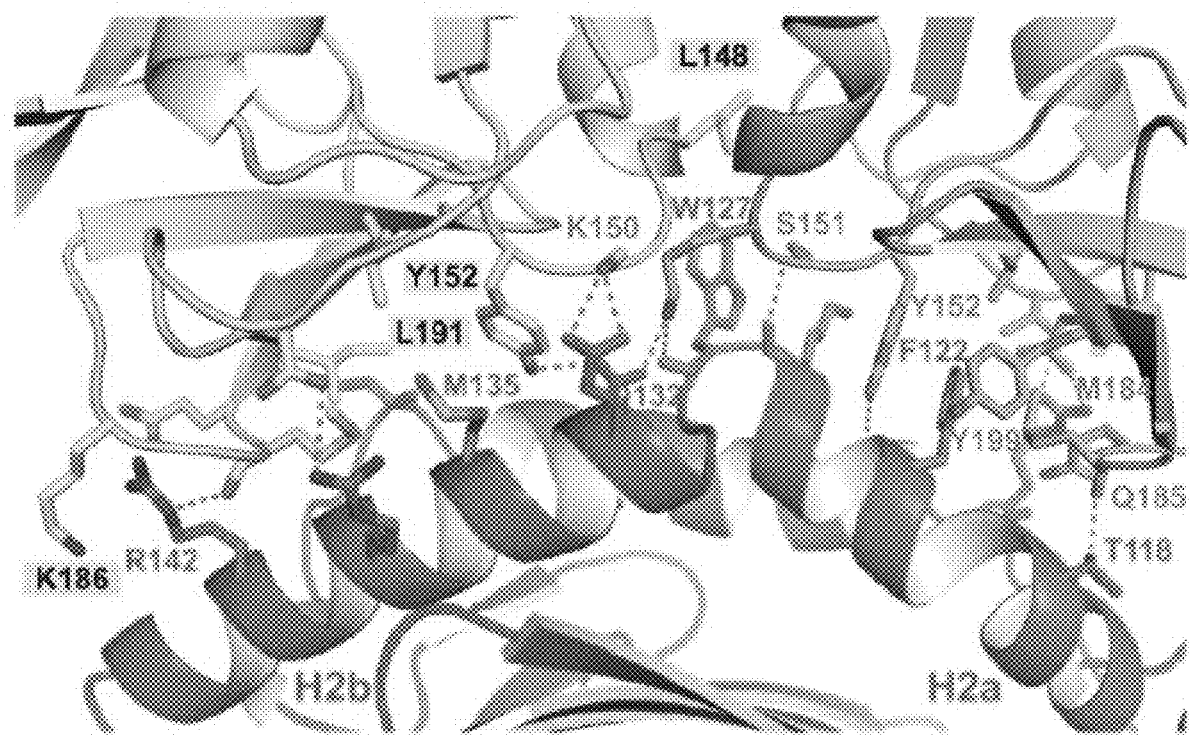

OMCP was hypothesized to bind to the same surface of NKG2D used by host NKG2DLs because (i) OMCP competed with host NKG2DLs for NKG2D and (ii) mutations within the NKG2DL-binding pocket of NKG2D altered OMCP binding affinity [38]. OMCP does bind NKG2D using the same concave binding pocket as host NKG2DLs (FIG. 24A). OMCP binds primarily using the discontinuous helices of its α2 domain, H2a and H2b. The position of the H2a and H2b helices is such that every surface exposed side chain of both helices within the binding site directly contacts NKG2D (FIG. 24B). Only two contacts are found outside of H2a and H2b, Ile49 and Arg66. Both of these residues are within the α1 domain but lie outside of the H1 helix.

Figure 25A:
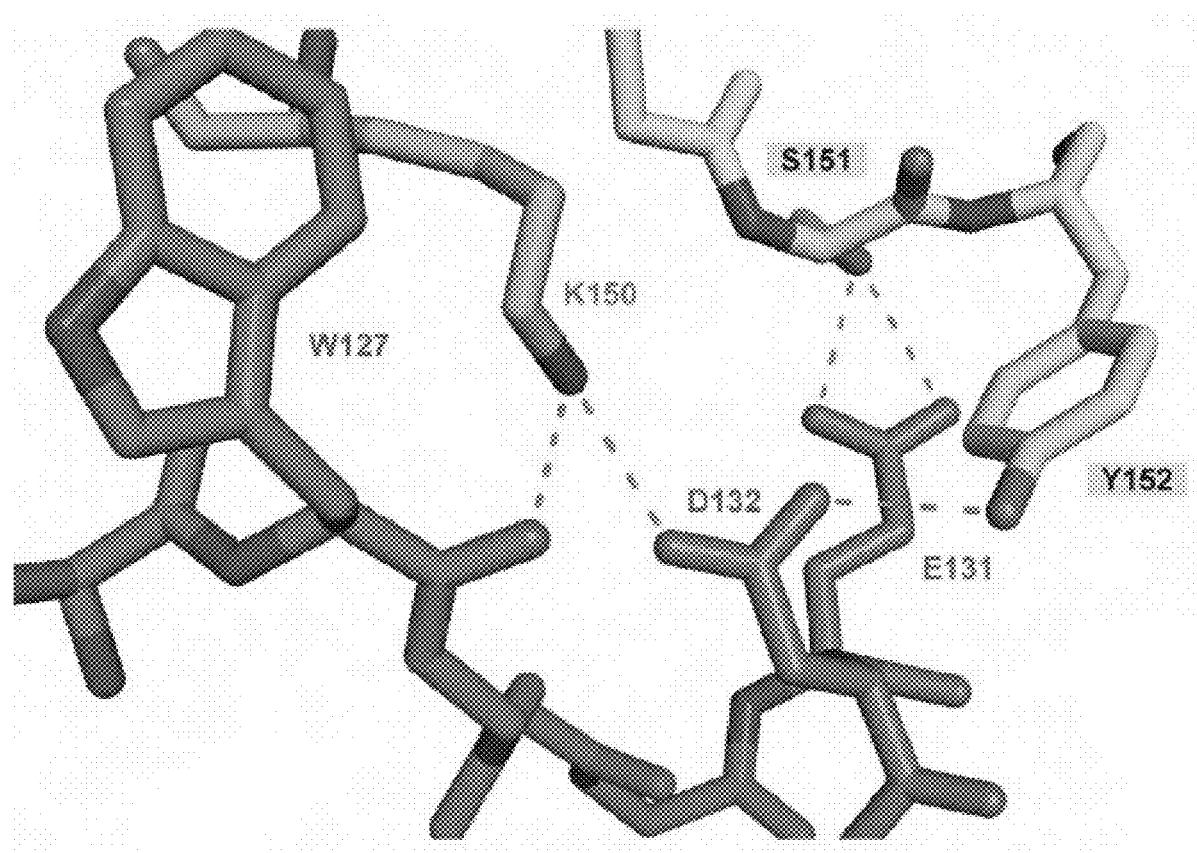
FIG. 25A, FIG. 25B and FIG. 25C depicts the interface of OMCP and NKG2D.

Twelve OMCP residues contact eighteen NKG2D residues to form a mixture of bond types (Table 2). Three residues in each NKG2D half-site are known as core binding residues because they make contacts with all known host NKG2DLs. The core residues of NKG2D subunit A ($NKG2D^A$) (Tyr152, Tyr199, Met184) form two hydrogen bonds and make extensive hydrophobic contacts with OMCP residues. The core residues of $NKG2D^A$ contact four OMCP residues and the most critical of these residues is Phe122. Phe122 makes multiple hydrophobic contacts with all three $NKG2D^A$ core residues, including pi-stacking with Tyr152. Phe122 also forms a backbone-to-sidechain hydrogen bond with Tyr152. Interestingly, OMCP is the first NKG2D ligand not to utilize all six NKG2D core-binding residues, with only Met184 and Tyr152 of NKG2D subunit B ($NKG2D^B$) contacting OMCP. $NKG2D^B$ Met184 and Tyr152 each make a single hydrogen bond and hydrophobic contacts with OMCP residues. Two OMCP residues, Trp127 and Asp132, make contacts with both NKG2D protomers. OMCP Trp127 forms a hydrogen bond to Lys150 of $NKG2D^A$ and makes several hydrophobic contacts with Leu148 of $NKG2D^B$, Lys150 and Ser151 of $NKG2D^A$. OMCP Asp132 forms a hydrogen bond with Tyr152 of $NKG2D^B$ and a salt bridge with Lys150 of $NKG2D^A$ (FIG. 25A).

Figure 25B:
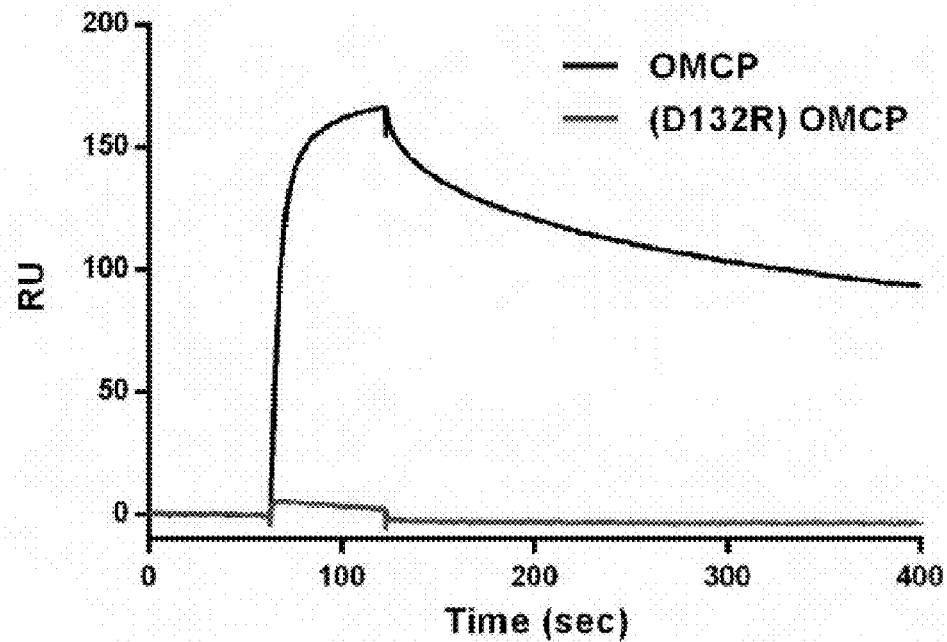
Figure 25C:
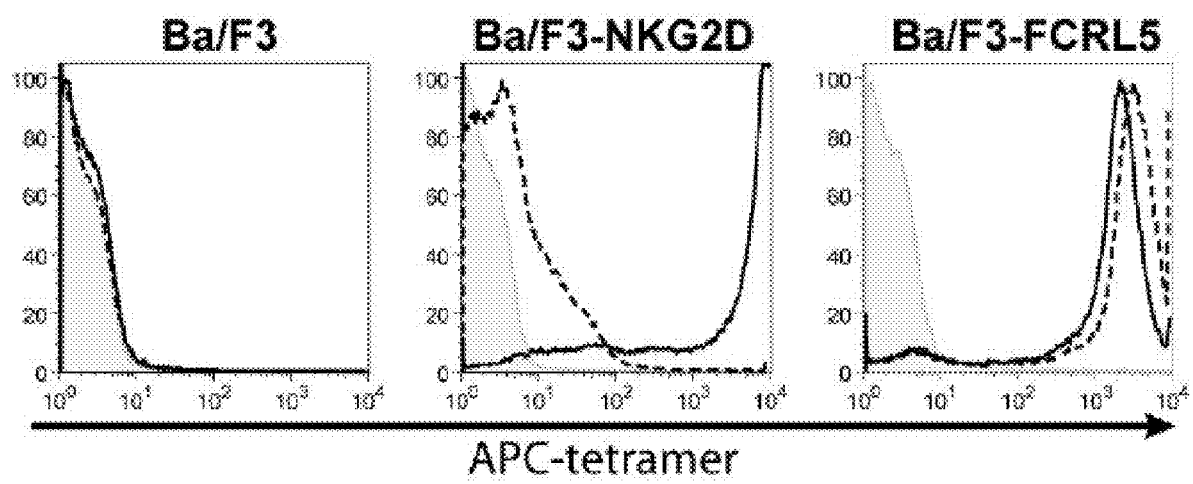

Due to the high affinity of the OMCP-NKG2D interaction we harnessed a high throughput in vitro selection approach to find NKG2D-binding null mutants (Table 3). The results of the screen identified D132 as an important residue for disrupting NKG2D binding. We then generated the mutation D132R in attempt to completely ablate NKG2D binding. Surprisingly, the D132R mutant alone was unable to bind to NKG2D at concentrations 35-fold above the $K_D$ (FIG. 25B), but did not affect binding of OMCP to FcRL5-expressing cells (FIG. 25C). This mutation is likely to cause significant steric clashes, as well as disrupting both interactions made by Asp132 to $NKG2D^A$ Lys150 and $NKG2D^B$ Tyr152 (FIG. 25A).

Previously, the 14-fold higher affinity of OMCP for human vs murine NKG2D was mapped to three amino acid substitutions in the β5'-β5 loop of NKG2D, abbreviated L2

Figure 26A:
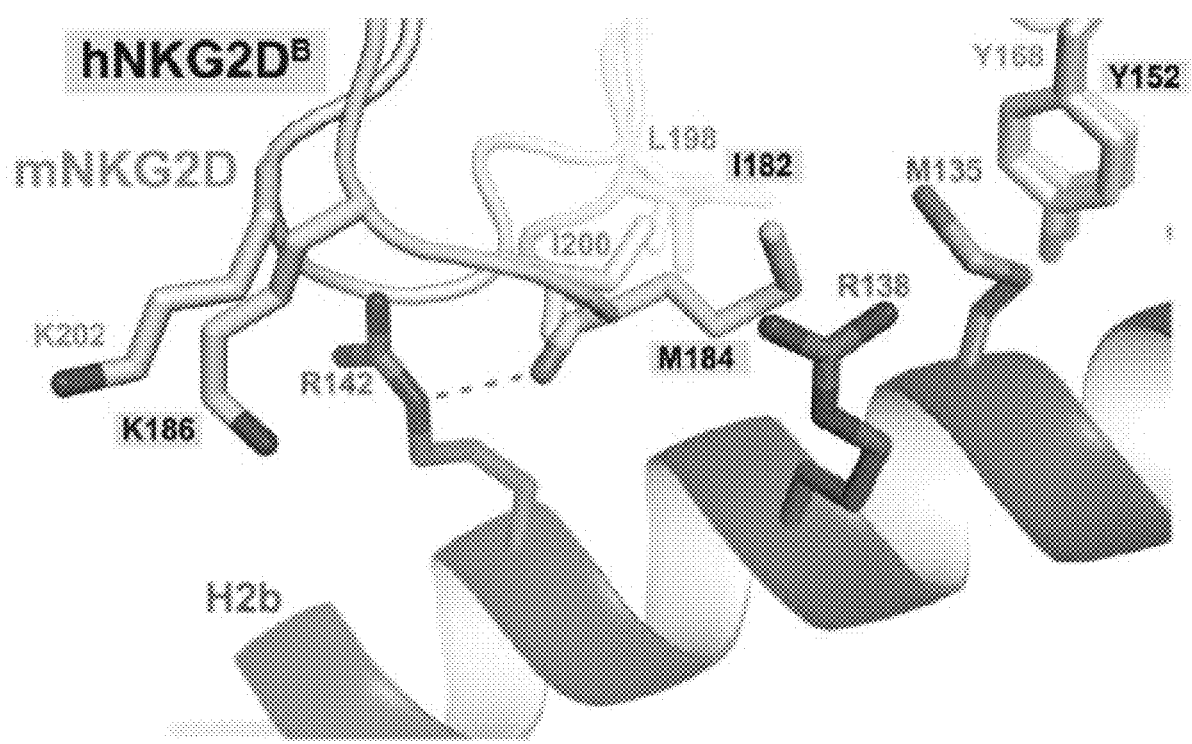
FIG. 26A, FIG. 26B, FIG. 26C and FIG. 26D depict the differences in the β5'-β5 loop (L2) of human and murine NKG2D.
Figure 26B:
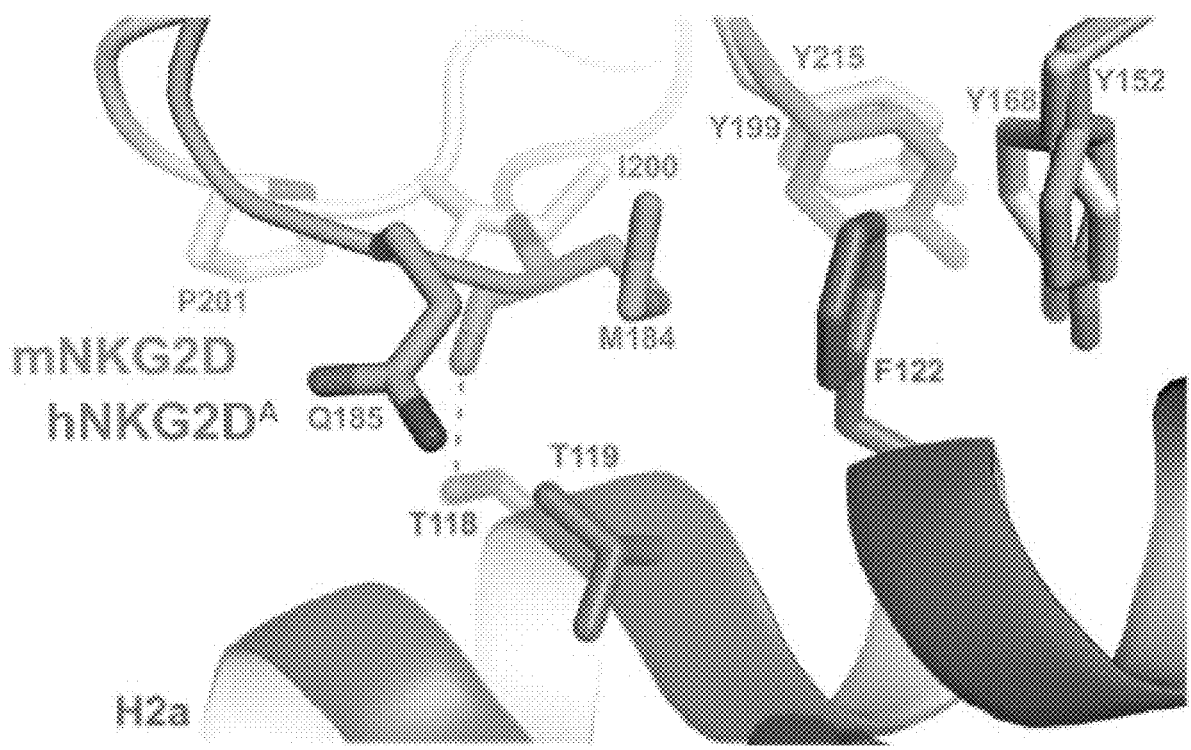
Figure 26C:
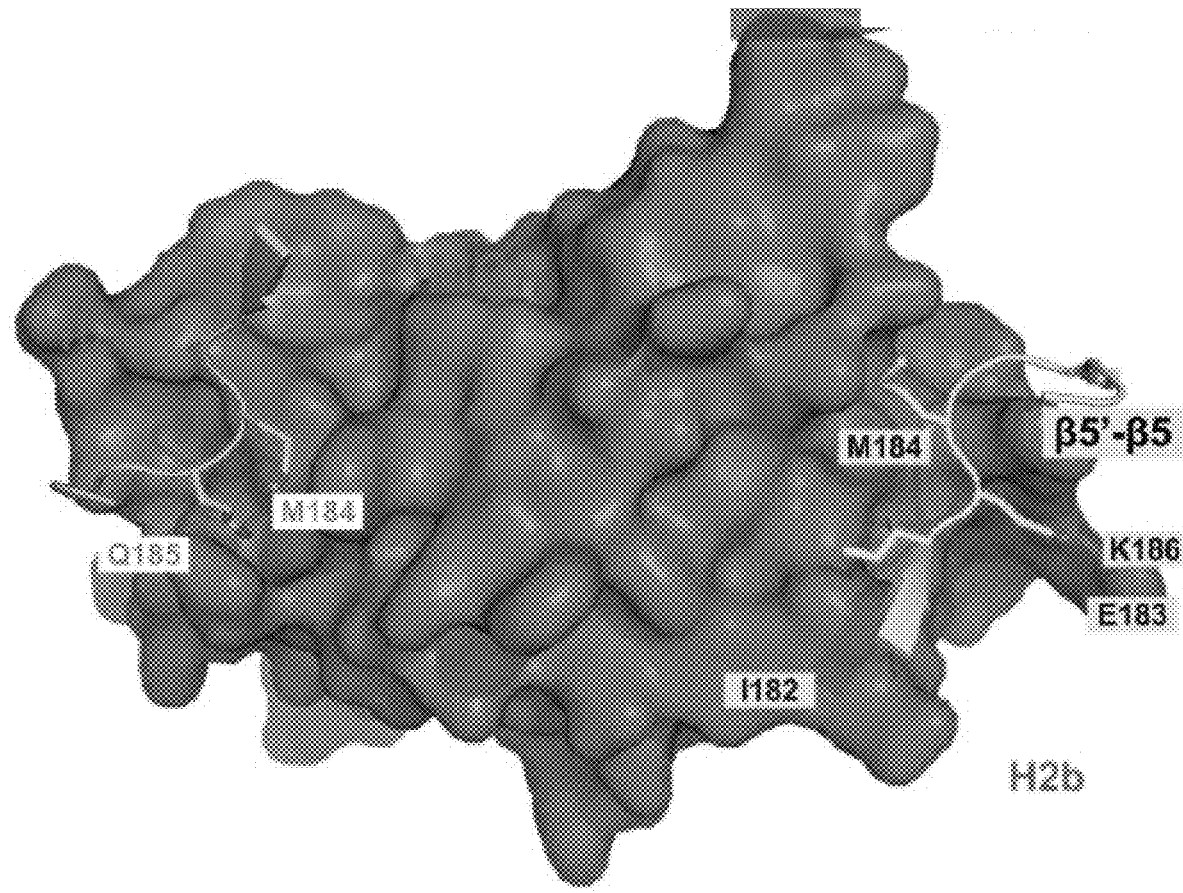
Figure 26D:
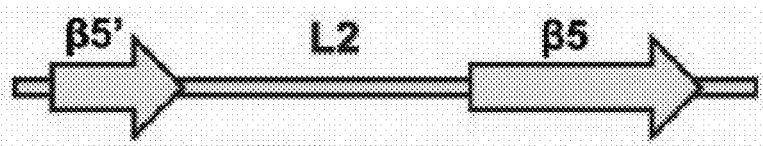
Figure 27A:
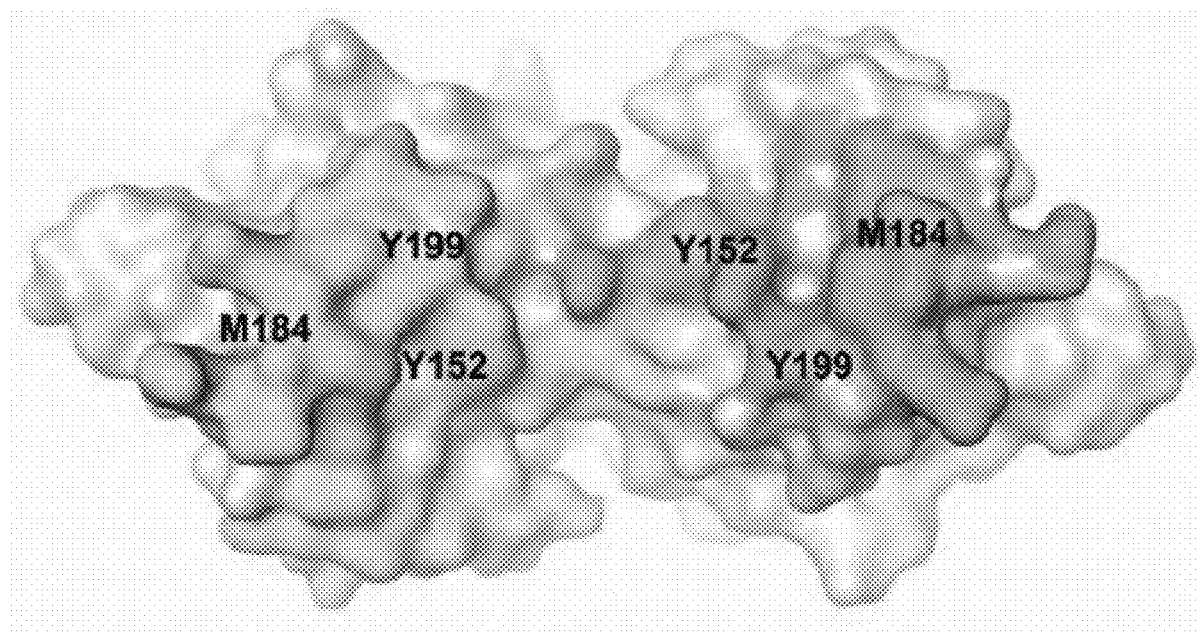
FIG. 27A, FIG. 27B, FIG. 27C, FIG. 27D, FIG. 27E, FIG. 27F, FIG. 27G, FIG. 27H and FIG. 27I depict a novel NKG2D binding adaptation. Surface representation of NKG2D and surface and cartoon representations of OMCP, MICA and ULBP3. Buried surface areas for NKG2D$^A$ and NKG2D$^B$ are indicated in cyan and yellow, respectively. Buried surface area by NKG2D is indicated for OMCP (magenta), MICA (green), and ULBP3 (orange). The core binding residues of NKG2D and NKG2D-binding elements of NKG2DLs are indicated. NKG2D (FIG. 27A) and OMCP (FIG. 27B, FIG. 27C) binding interactions. NKG2D (FIG. 27D) and MICA (FIG. 27E, FIG. 27F) binding interactions. NKG2D (FIG. 27G) and ULBP3 (FIG. 27H, FIG. 27I) binding interactions.
Figure 27B:
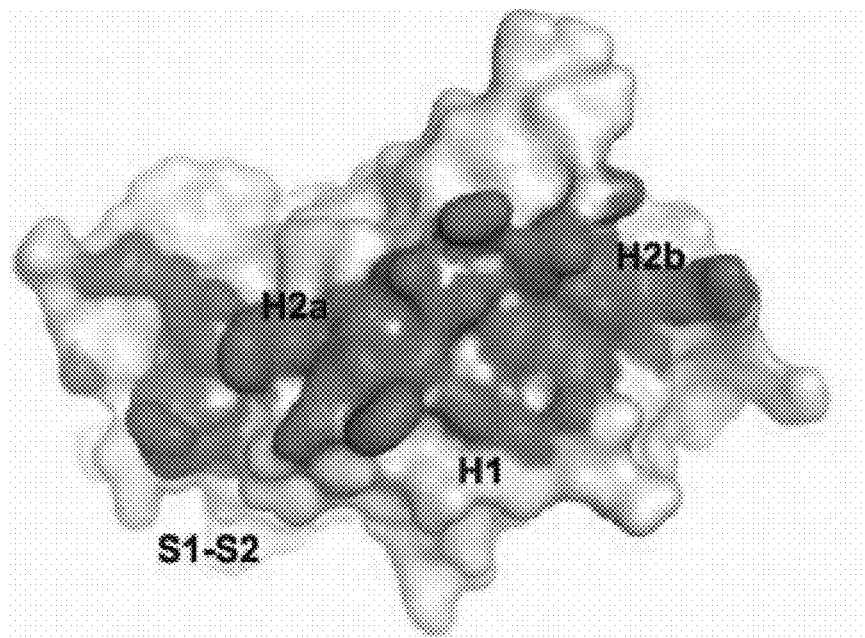
Figure 27C:
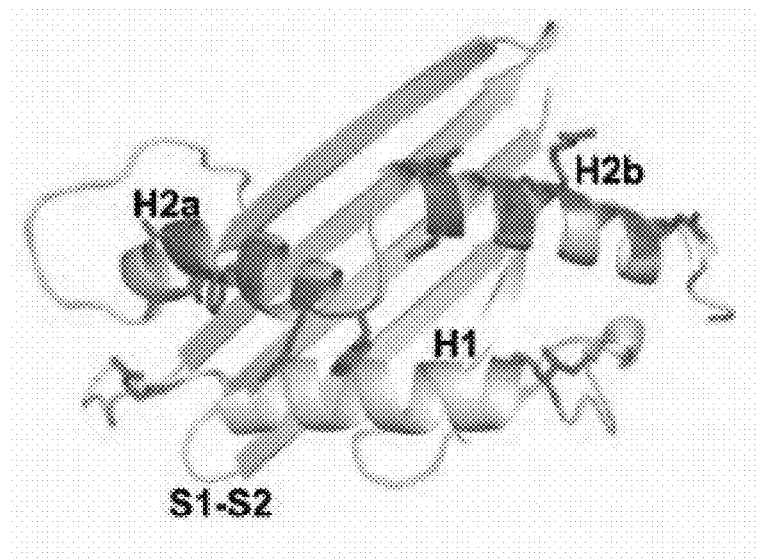
Figure 27D:
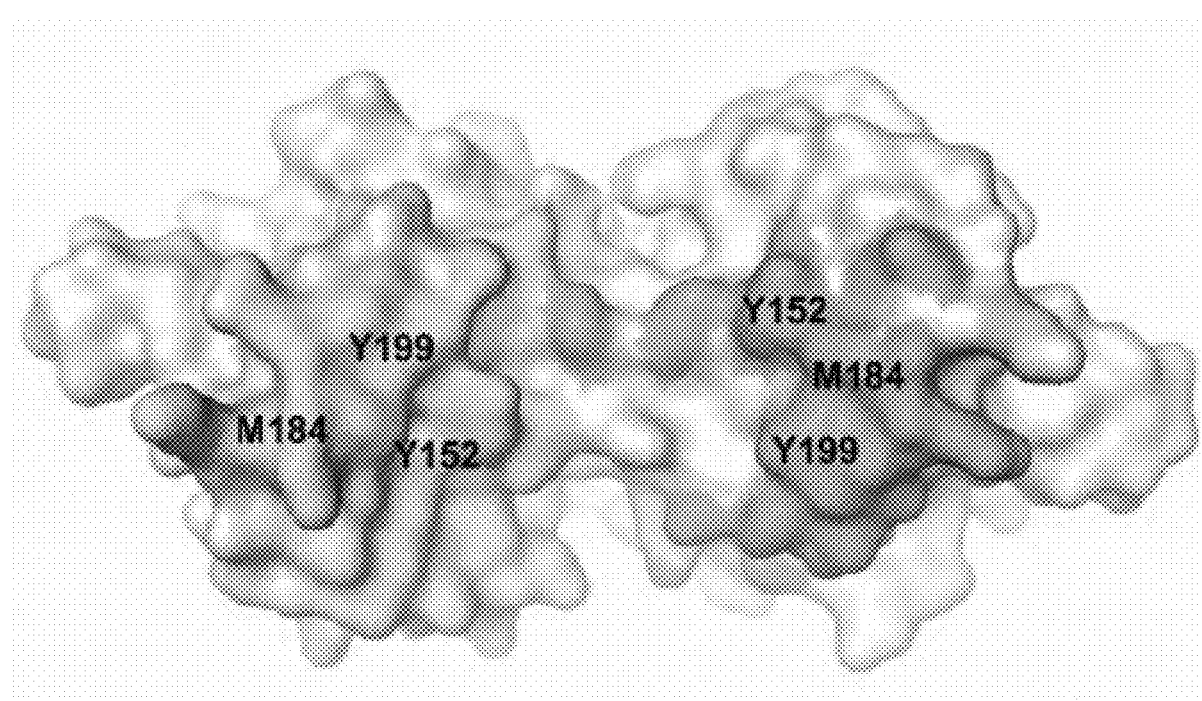
Figure 27E:
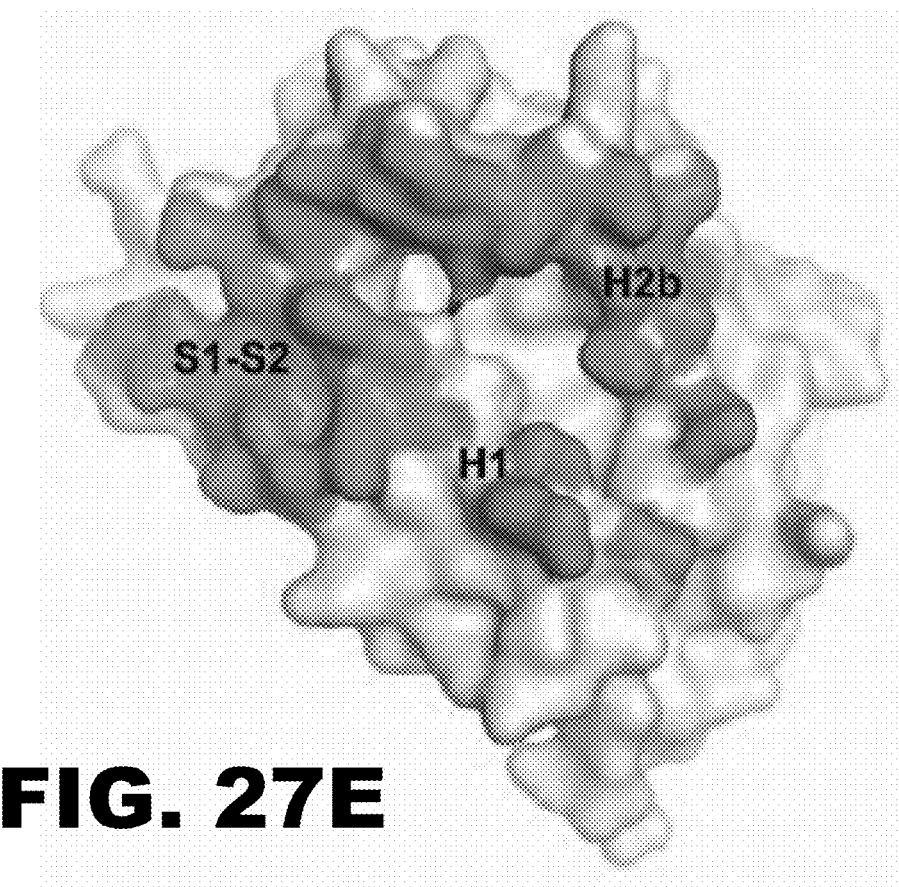
Figure 27F:
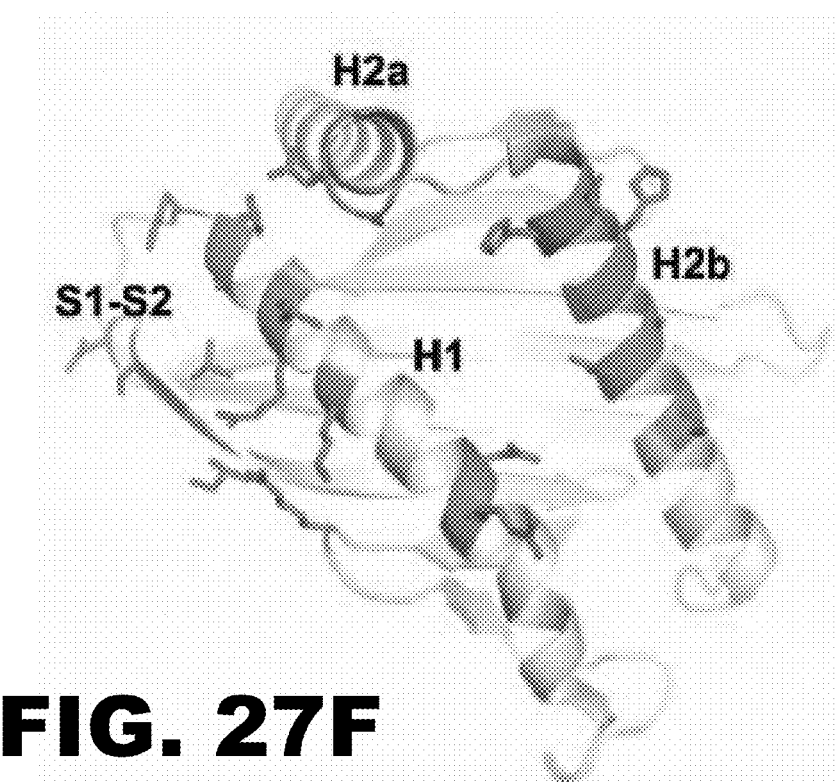
Figure 27G:
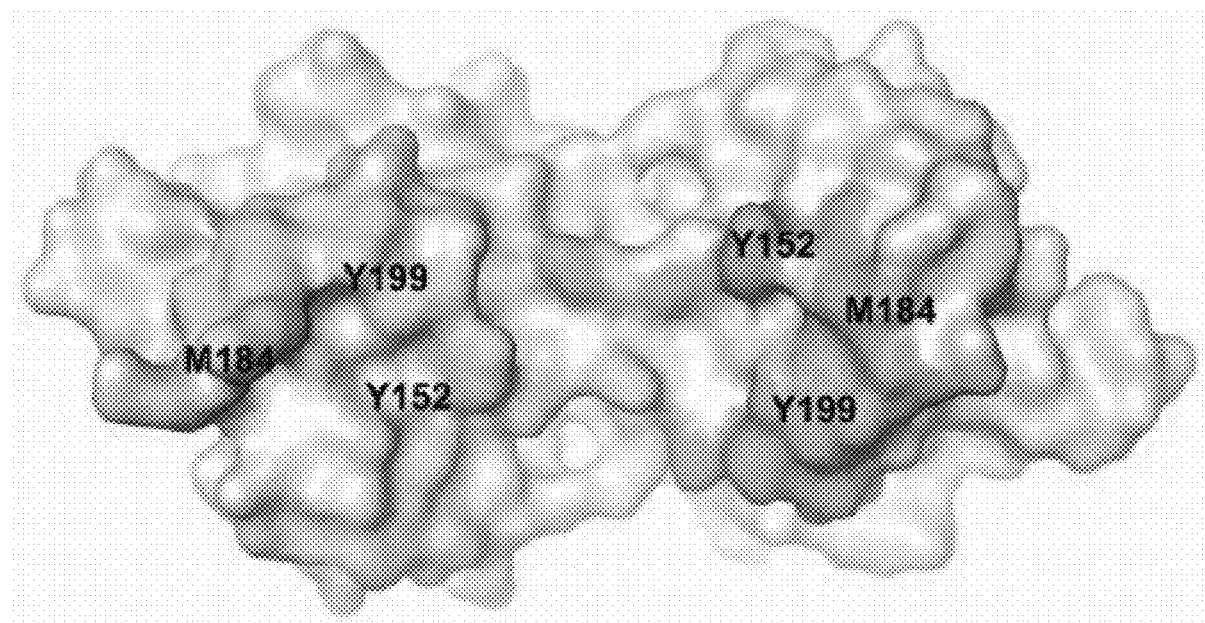
Figure 27H:
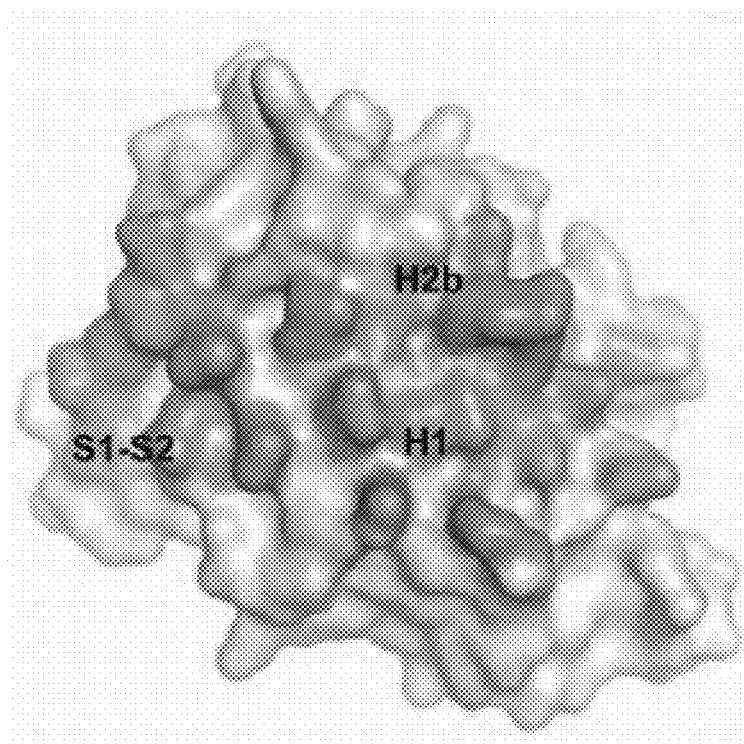
Figure 27I:
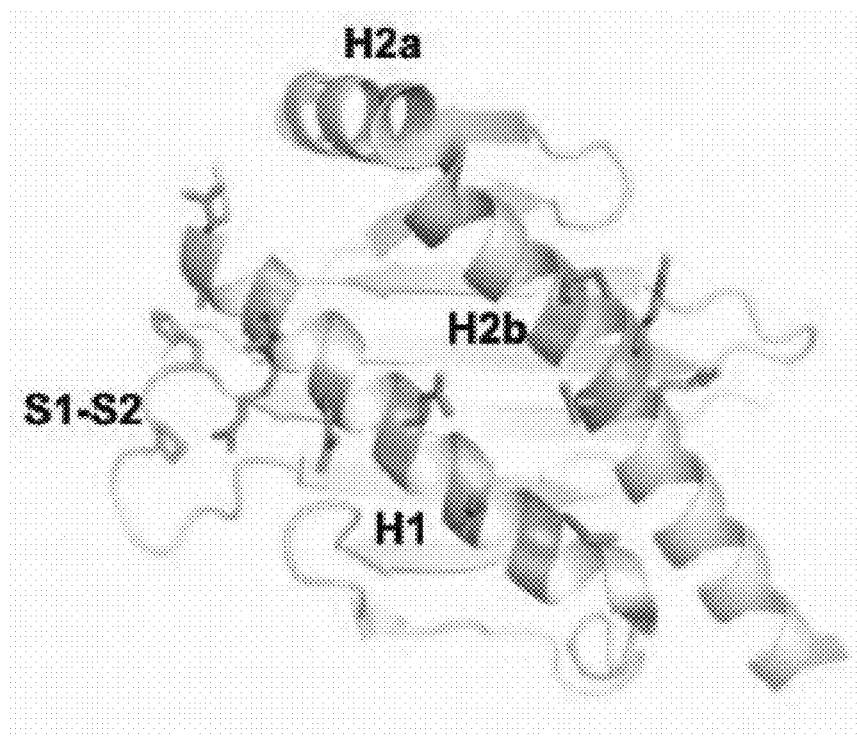
Figure 27J:
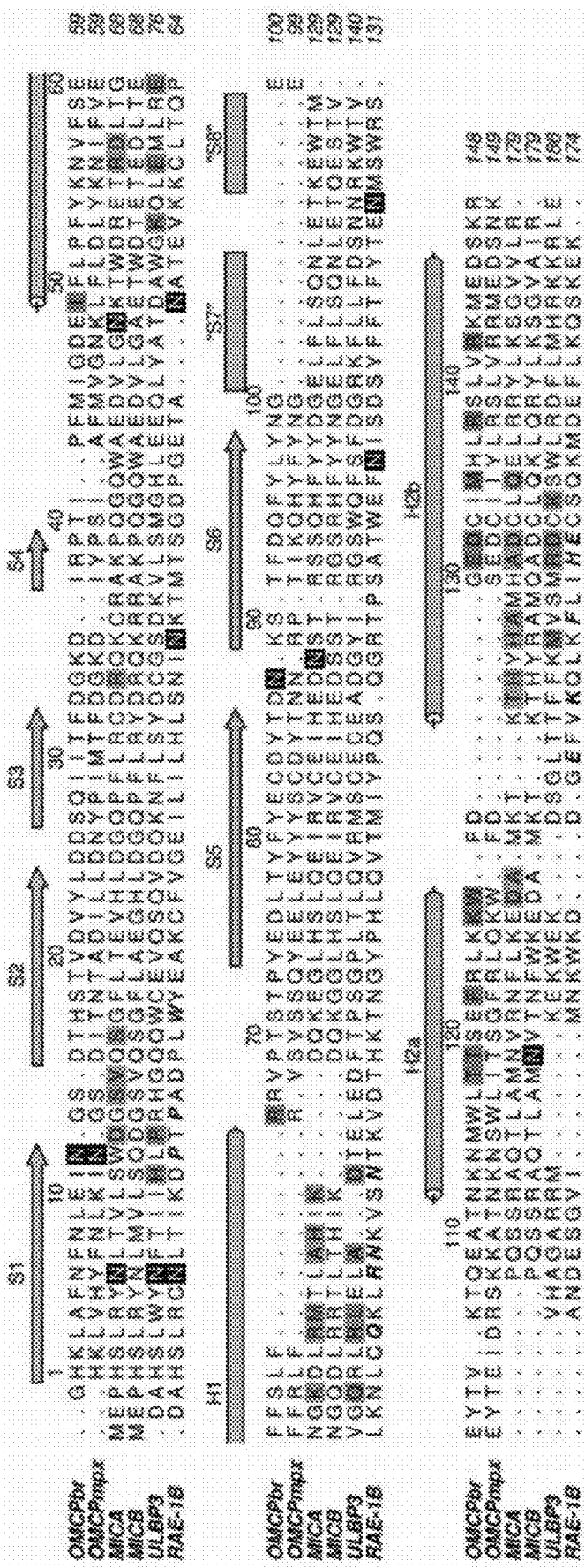
(FIG. 27J) Alignment by secondary structure of NKG2DLs (PDB ID: OMCP (4FFE), MICA (1HYR), MICB (1JE6), ULBP3 (1KCG) and RAE-1β (1JSK)). Contact residues are indicated for OMCP (magenta), MICA (green), ULBP3 (orange) and RAE-1β (bold and italics). Secondary structure elements are noted above the sequence (arrow for beta sheets, cylinders for alpha helices). Predicted glycan sites are highlighted in black. OMCPbr=SEQ ID NO:13; OMCPmpx=SEQ ID NO:14; MICA=SEQ ID NO:15; MICB=SEQ ID NO:16; ULBP3=SEQ ID NO:17; and RAE-1B=SEQ ID NO:18

[38]. In addition to the substitutions themselves (I182V, M184I and Q185P), the position of the loop between NKG2D orthologs differs. L2 in human NKG2D is bent towards the center of the concave binding cavity compared to L2 of murine NKG2D. Superimposition of murine NKG2D onto the human NKG2D-OMCP structure reveals that the contacts between OMCP and Met184 (mNKG2D residue 1200) in NKG2D$^B$ and between Met184 (1200) and Glu185 (P201) in NKG2D$^A$ would be altered due to the different position of the murine β5'-β5 loop (FIG. 26A-B). This alteration would disrupt contacts with three residues in OMCP H2a, three residues in H2b and Arg66 within the α1 domain. Of the contact residues of L2, Met184 makes the most significant contacts in both NKG2Ds (Table 2)(FIG. 26C). Critically, of the 58 NKG2D sequences available in GenBank, 54 conserve the Met184 and Glu185 found in the high affinity human NKG2D (FIG. 26D).

Eighteen OMCP variants have been described between different CPXV and MPXV strains [51]. In this study we have crystallized OMCP from the Brighton Red strain of CPXV which has >60% sequence identity with the highly conserved sequence of the other 17 OMCP variants, collectively termed OMCP$_{mpx}$. Of the 12 OMCP contact residues observed, 9 are identical to OMCP$_{mpx}$. Of the remaining contacts, all three are conservative hydrophobic substitutions (I49L, T118I and M135I) (FIG. 27). OMCP$_{mpx}$ binds to NKG2D and the substitutions in the NKG2D contact residues are unlikely to grossly affect the affinity of OMCP$_{mpx}$ for NKG2D [37].

Example 9. A Novel NKG2D-Binding Adaptation

Host NKG2DLs have low sequence identity but overall similar structures, with MHCI-like platform domains binding diagonally across the symmetric binding groove created by the NKG2D homodimer [13,41,52]. Host ligands contact one NKG2D half site with H1 and the S1-S2 loop, and contact the second NKG2D half site with H2b. Despite the similar MHCI-like fold, OMCP binds the NKG2D binding groove in a novel orientation, rotating 45° relative to host NKG2DLs (FIG. 27). Instead of using H1 and S1-S2 loop like host ligands, OMCP has replaced these contacts with H2a. This rotation leads to the helices of OMCP being perpendicular to the NKG2D binding groove, instead of lying diagonally across it.

Two unique rearrangements of H2a and H2b make the OMCP orientation possible. The α2 helices of OMCP and host NKG2DLs are discontinuous, with the two shorter helices hinged relative to each other. For host ligands, the angle between H2a and H2b is ~90°, positioning H2a away from the NKG2D interface. In contrast, OMCP has increased the hinge angle between the helices by ~20°, leading to a α2 helix that is flatter relative to the beta sheet of OMCP. The flattening of the α2 helix allows H2a and H2b to closely complement the concave binding groove of the NKG2D homodimer (FIG. 24B). The tight fit of the α2 helix for NKG2D is reflected in the high shape complementarity (0.77) and buried surface area (2,612 Å$^2$). In contrast, host NKG2DLs have shape complementarity ranging from 0.63-0.72 and buried surface areas ranging from 1,700-2,180 Å$^2$ [43,44,46].

The second unique feature of the α2 helix is the separation of H2a and H2b relative to each other. This region also contains a translation that completely separates H2a and H2b into two distinct helices. This translation is critical for NKG2D binding because it allows each helix to be directly centered on the core binding sites of each NKG2D monomer (FIG. 27). This creates a symmetric binding site on OMCP that recognizes the symmetric binding groove created by the NKG2D dimer. The symmetry between OMCP and NKG2D binding is in stark contrast to the canonical binding of an asymmetric host ligand to the symmetric NKG2D binding groove [52]. However, one element of asymmetry remains in the OMCP-NKG2D interaction because each NKG2D half-site recognizes an OMCP helix in a different N- to C-terminal orientation, demonstrating again the flexibility of NKG2Ds rigid adaptation recognition [41,53].

The contact sites between NKG2D and host NKG2DLs are made up of two patches centered on the core binding sites of NKG2D and H1/S1-S2 loop and H2b of NKG2DLs [41]. As a result, the interface of NKG2D with NKG2DLs is discontinuous, particularly in the center of the NKG2D binding groove (FIG. 27). Due to the unique orientation of OMCP, H2a and H2b make continuous contacts along the entire NKG2D binding groove (FIG. 27). The sidechains of OMCP Lys126, Trp127, Glu131 and Asp132 make contacts with residues in the center of the NKG2D binding groove and bridge the core binding sites on each NKG2D monomer (FIG. 24B). In particular, OMCP Trp127 is directed towards the center of the NKG2D dimer and makes hydrophobic contacts with residues on both NKG2D monomers, effectively closing any gaps in the binding interface.

Example 10. Signaling of NKG2D Upon Ligand Engagement

Figure 28A:
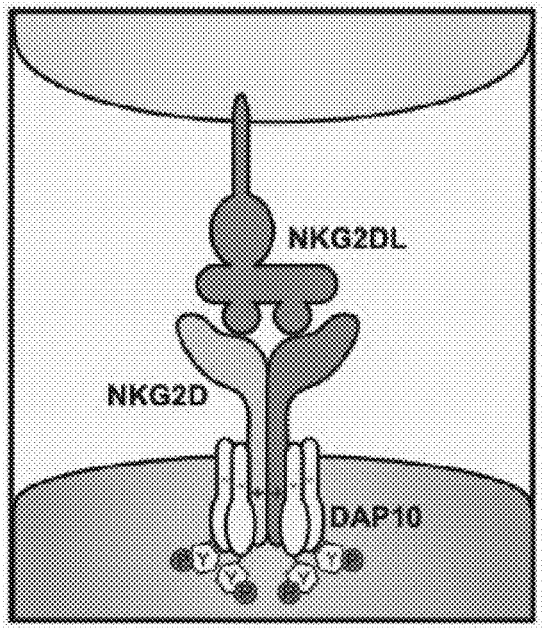
FIG. 28A, FIG. 28B, FIG. 28C, FIG. 28D and FIG. 28E depict activation of NK cells by cell-associated OMCP. Model depicting NKG2D interaction with (FIG. 28A) host, (FIG. 28B) cancer-induced, (FIG. 28C) viral, or (FIG. 28D) chimeric ligands. Binding interactions that lead to NKG2D-mediated signaling are indicated by DAP10 tyrosine phosphorylation (red filled circles).
Figure 28B:
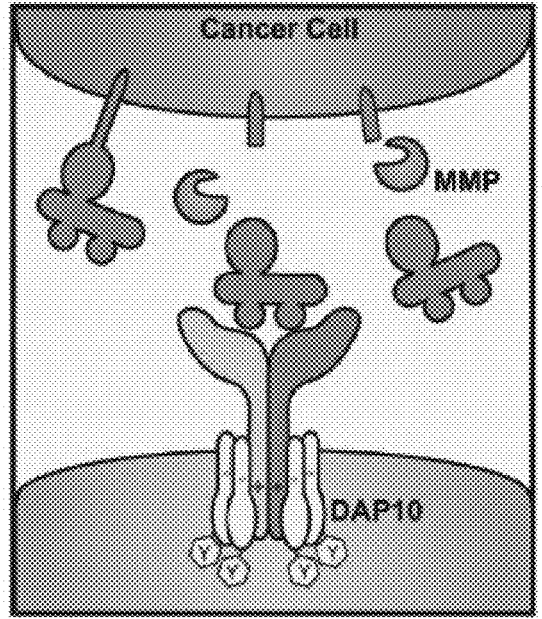
Figure 28C:
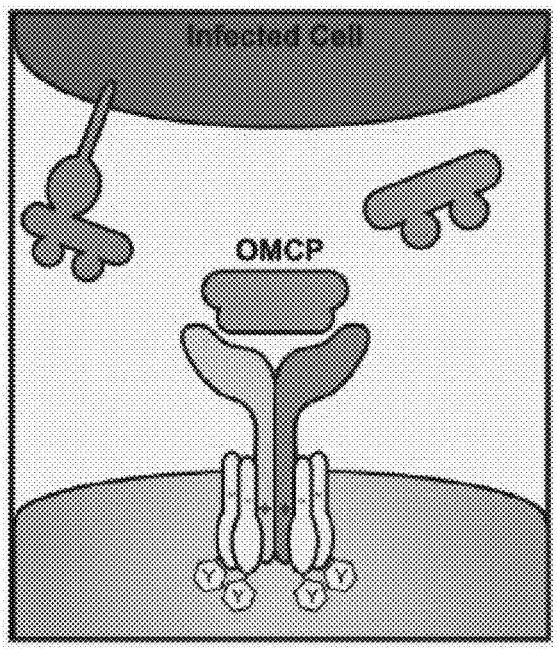
Figure 28D:
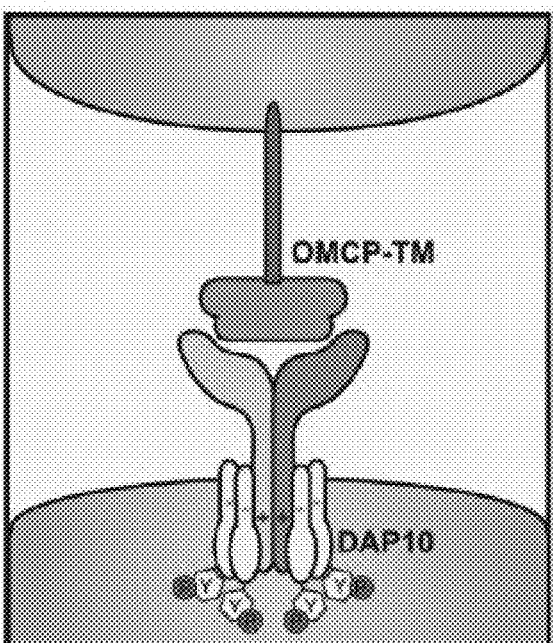
Figure 28E:
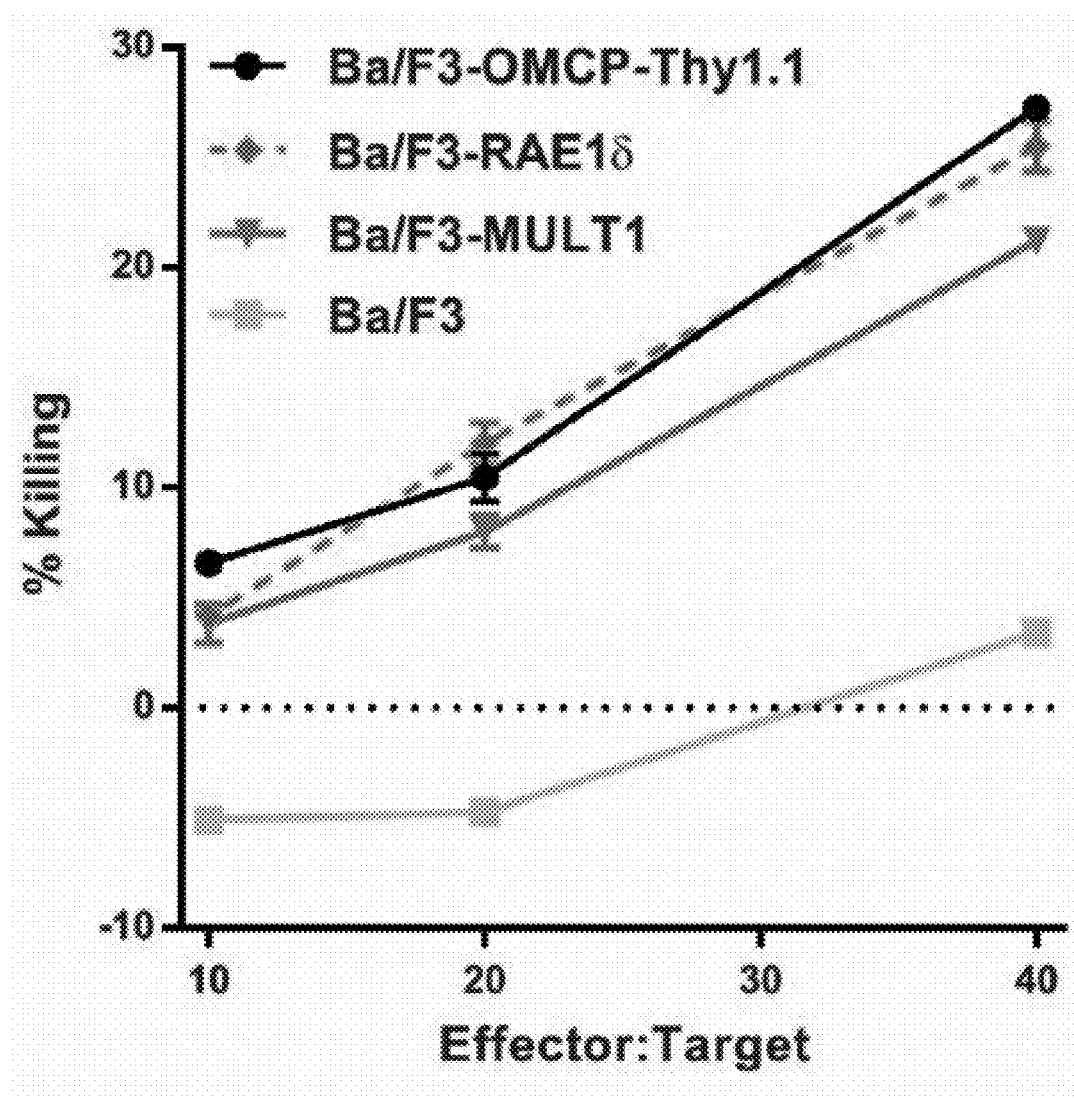

CPXV and MPXV-infected cells secrete OMCP, which can act as an NKG2D-antagonist [37]. This immune evasion strategy is reminiscent of cancer induced-NKG2DL shedding. Some cancer cells proteolytically cleave NKG2DLs from the cell surface using matrix metalloproteinases (MMPs), simultaneously preventing NKG2D-bearing lymphocytes from targeting the cancer cell, as well as creating soluble NKG2DLs to inhibit NKG2D in trans. Cell-associated NKG2DLs trigger NKG2D effector functions (FIG. 28A), while cancer-induced, soluble NKG2DLs block NKG2D function (FIG. 28B). Like shed NKG2DLs, OMCP is soluble and blocks NKG2D function in trans [37] (FIG. 28C). Unlike host NKG2DLs, OMCP binds NKG2D with a novel orientation. We therefore asked whether OMCP could serve as a NKG2D agonist in the context of the cell membrane, analogously to host NKG2D ligands. Since OMCP is a secreted protein, an artificially cell-associated OMCP was constructed by using a heterologous transmembrane domain from Thy1.1 [37] (FIG. 28D). To measure NKG2D-mediated cell killing, we stably transduced Ba/F3 cells with retroviral vectors expressing either the OMCP-Thy1.1 construct or host NKG2DLs. OMCP-Thy1.1-expressing target cells were killed equivalently to host NKG2DL-transduced target cells, indicating that despite its altered binding orientation, cell-associated OMCP was able to activate NKG2D signaling (FIG. 28E). Thus, OMCP must be secreted lest it active NKG2D-effector functions itself, despite potential loss of efficacy due to diffusion.

Discussion for Examples 7-10

While many viruses have adopted a general mechanism of NKG2D-sabotage by trying to retain multiple host-encoded NKG2D ligands within the infected cell, CPXV and MPXV take the very different approach of targeting NKG2D directly. Since NKG2D is monomorphic, this mechanism has the significant advantage of requiring a single protein to prevent NKG2D recognition of the infected cell. The large number of sequence-divergent host NKG2DLs and their associated polymorphisms are thought to be driven by selection from pathogen-encoded NKG2DL antagonists [14]. Likewise, viral NKG2L antagonists are under selective pressure from the diverse host NKG2DLs in a continual cycle of adaptation. Due to the need to recognize multiple NKG2DLs, NKG2D has a limited mutational space to adapt. The limited ability of NKG2D to mutate is yet another advantage of OMCP directly targeting NKG2D, instead of NKG2DLs.

Similarly to OMCP, some cancer cells shed host NKG2DLs to create their own soluble NKG2D antagonists. However, this strategy has the additional benefit of removing host NKG2DL from the surface of cancer cells. In contrast, CPXV and MPXV lack a known mechanism of blocking host NKG2DL surface expression. Secreted OMCP must then be able to compete efficiently against the high local concentration of multiple host NKG2DLs on the infected cell, as well as against diffusion away from the infected cell. One possible way to increase OMCP's ability to compete with host ligands would be to increase the avidity of OMCP by having multiple NKG2D-binding domains. However, a multimeric OMCP could crosslink NKG2D and potentially trigger NKG2D-mediated killing. Therefore, secreted OMCP must be monomeric to prevent aberrant NKG2D signaling. Thus to compensate for these deficiencies, OMCP must have the highest affinity possible to effectively compete against cell-associated host NKG2DLs [37,38]. The half-life of ligand-receptor interactions correlate well with physiological competitiveness [55]. OMCP binds human and murine NKG2D with half-lives of 348 and 54 seconds, respectively, compared to half-lives of 1.5-18 seconds for most NKG2DLs [38,44,56]. Indeed, the increased half-life for NKG2D allows OMCP to effectively antagonize NKG2D-mediated immunity in a murine infection model (M. Sun et al, personal communication).

To understand the molecular basis for the long half-life of OMCP for NKG2D, we previously determined the structure of OMCP alone, and here, we report the structure of OMCP bound to NKG2D. The structure of OMCP alone was grossly similar to that of host NKG2D ligands, containing an atypical MHCI-like platform domain. Host NKG2D ligands bind with the helices of their platform domains oriented diagonally within the symmetric binding groove of NKG2D. Thus it was expected that OMCP was a viral mimic of host NKG2D ligands and would interact with NKG2D analogously.

The structure of OMCP-NKG2D instead revealed a novel orientation for an NKG2D ligand in the NKG2D binding groove. Alterations within the α2 domain helix allow OMCP to arrange its helices perpendicularly within the binding groove. This reorientation places the H2a and H2b helices directly in contact with the core binding sites of NKG2D and also forms the largest and most continuous binding interface with NKG2D. Because the forces (hydrogen bonds, van der Waals, hydrophobic interactions) that mediate protein-protein interactions are individually weak, a large, continuous interface with high shape complementary allows for a cumulatively strong interaction between proteins. This change in the binding orientation of OMCP reveals how the MHCI-like platform used by host ligands can be adapted by a pathogen to enhance NKG2D binding.

Since host NKG2DLs and OMCP have a similar MHCI-like platform, it is reasonable to wonder why no host ligand has evolved an analogous high-affinity interaction with NKG2D. One likely reason is that the host immune response must be carefully calibrated to balance the need for protection against the threat of autoimmunity. Since the expression of NKG2DLs on the cell surface signals for effector functions, even a small amount of high affinity host ligand on the cell surface could trigger an immune response, and the resulting tissue damage could be deleterious for the host. Indeed, NKG2D-expressing cells and/or aberrant expression of host NKG2DLs have been implicated in diabetes, celiac disease and rheumatoid arthritis [57-60]. Viruses are not constrained by autoimmune selective pressures. Therefore, CPXV and MPXV were free to evolve a viral NKG2DL with the highest possible affinity to maximize immune evasion potential.

Interestingly, OMCP triggers NKG2D signaling when attached to a target cell membrane, despite the novel orientation of OMCP relative to host NKG2DLs. The interaction of host NKG2DLs with the dimeric NKG2D bears broad structural similarity to the interaction between MHC molecules with their cognate T cell receptors (TCRs). In both cases, the NKG2DL/MHC lies diagonally across the surface created by the dimeric NKG2D/TCR. However, there are several examples of MHC-TCR complexes that, like OMCP-NKG2D, interact with unconventional orientations [61-65]. Several of these complexes involved autoimmune MHC-TCR complexes that were tilted or rotated outside of the normal range for MHC-TCR complexes [61,65]. While these receptors could induce TCR signaling at high MHC concentrations, they failed to assemble characteristic immunological synapses [66]. A striking example of unconventional binding was found when an in vitro peptide library-MHC-TCR (H2-$L^d$-42F3) screen produced a p3A1-H2-$L^d$-42F3 complex with an interface rotated 40° relative to other H2-$L^d$-42F3 complexes. This rotation places the TCR nearly parallel with the MHC peptide-binding groove and shifted the interface center almost entirely on one of the MHC α helices—an orientation strikingly similar to the interface of OMCP-NKG2D [65]. Interestingly, the p3A1-H2-$L^d$-42F3 complex failed to induce TCR signaling [65]. Thus, unlike OMCP/NKG2D, the orientation of MHC relative to TCR is an important factor for signaling.

OMCP-NKG2D and p3A1-H2-$L^d$-42F3 have opposite signaling outcomes, despite having very similar orientations. TCR signaling requires co-receptor binding to either the α2/β2 or α3 domains of MHCII or MHCI, respectively. The failure of p3A1-H2-$L^d$-42F3 to signal, and of other unconventional MHC-TCR complexes to form true immunological synapses, is potentially due to the inability of co-receptors to form correct quaternary structures for signaling [64,65,67]. Signaling by NKG2D is not known to require co-receptor stimulation and the majority of NKG2DLs lack the co-receptor binding α2/β2 or α3 domains of true MHC molecules. This difference in co-receptor dependency likely explains why OMCP (when attached via transmembrane) is still competent to stimulate NKG2D-signaling compared to MHC-TCR complexes with unconventional binding orientations. Further, it suggests that clustering of NKG2D on the cell surface is the major determinant of NKG2D-mediated activation.

Methods for Examples 7-10

Identification of NKG2D-binding null mutant D132R. A high throughput in vitro selection approach based on combinatorial cell surface display was utilized to identify NKG2D-binding null mutants. The sequence of OMCP was globally mutagenized using error-prone PCR, and the mutated amplicons were spliced to a signal-less Thy1.1 cDNA via overlap extension PCR. This library of mutated OMCPs fused to unmutated Thy1.1 was cloned into the pMXs-IRES-EGFP retroviral transfer vector (kind gift of Toshio Kitamura, University of Tokyo) to generate a molecular library for transduction into Ba/F3 cells. The transductants were then sorted for green fluorescence and anti-Thy1.1 expression to yield a cellular library whose members all had surface expression of OMCP, filtering out mutations giving frameshifts, premature stop codons, and folding-incompetent OMCP. This OMCP library was sorted for NKG2D binding using NKG2D-tetramers. Sorted cells were cloned by limiting dilution and analyzed. The retroviral cassettes of cells lacking or having reduced NKG2D-binding activity were amplified and sequenced. Utilizing this approach, we identified Asp132 as a critical residue for NKG2D binding.

Protein expression and purification. $OMCP_{BR}$ and human NKG2D expression constructs were previously described [38]. The (D132R) $OMCP_{BR}$ protein was prepared identically to WT $OMCP_{BR}$. (23D/95D) OMCP-NKG2D complex was reconstituted by oxidative co-refolding from purified inclusion bodies, as described previously [38]. Refolded protein was slowly diluted 10-fold with water and captured on a 5 ml HiTrap Q HP column (GE Healthcare) using a Profinia instrument (Bio-Rad). The captured protein was washed with 50 mM Tris, pH 8.5, 20 mM NaCl and bulk eluted with 50 mM Tris, pH 8.5, 250 mM NaCl. The eluted protein was then concentrated and further purified by gel filtration chromatography on a Superdex S75 column (16/60; Amersham Biosciences). Fractions containing mono-dispersed OMCP-NKG2D complex (~50 KDa) were pooled and buffer exchanged into 25 mM Ammonium acetate pH 7.4.

Crystallization, data collection and processing. Native protein crystals were grown by hanging drop vapor diffusion at 20° C. by streak seeding into a well solution containing 15% PEG 3350, 0.2M $MgCl_2$, 0.1M Bis-Tris pH 6.75. Crystals were cryoprotected with well solution containing 15% glycerol before flash freezing directly in a liquid nitrogen bath. Diffraction data were collected at the Advanced Light Source synchrotron (beamline 4.2.2). Native (23D/95D) OMCP-hNKG2D crystal diffraction data were collected at 100 K and at a wavelength of 1.00004 Å. Additional diffraction data statistics are summarized in Table 1. Data processing with HKL2000 [68] showed the crystals belonged to the primitive monoclinic space group $P2_1$ (space group #4). The asymmetric unit of the crystal contained two copies of the (23D/95D) OMCP-hNKG2D complex.

Model building and refinement. The structures of human NKG2D (1MPU) [48] and OMCP (4FFE) [38] were used as search models for molecular replacement through Phenix [69]. Reiterative refinement and manual rebuilding were performed using Phenix and Coot [70], respectively. Both 2Fo-Fc and Fo-Fc maps were used for manual building and to place solvent molecules. The final model yielded an $R_{work}$ of 16.6% and $R_{free}$ of 21.4%, with 4% of all reflections set aside for free R factor cross-validation. Progress in refinement was also measured using the MOLPROBITY webserver [71]. The final Ramachandran statistics for the model were 98% favored and 0% outliers. Additional refinement statistics are summarized in Table 1. Images of structures were produced using the program PyMol [72].

Structure analysis. Analysis of the contact residues, buried surface area and shape complementarity of the OMCP-NKG2D interface were carried out using the programs Ligplot+ [73], PISA [74] and SC [75]. Structural programs as compiled by the SBGrid consortium [76]. Analysis of NKG2D conservation was performed using the ConSurf server [77-80]. GenBank numbers for species used in Consurf analysis are: Humans (30749494), Borean orangutan (21902299), Chimpanzee (57113989), Gibbon (332232684), Macaque (355785888), Green Monkey (635063485), Common marmoset (380848799), Mouse (148667521), Brown rat (149049263), Guinea Pig (348569092), Ground squirrel (532114387), Deer mouse (589967905), Naked mole rat (512868733), Prairie vole (532053033), European Shrew (505834608), Star-nosed mole (507978716), Chinese hamster (537136230), and Cat (410963826).

Atomic coordinates. The atomic coordinates (accession code 4PDC) have been deposited in the Protein Data Bank, Research Collaboratory for Structural Bioinformatics (Rutgers University, New Brunswick, N.J.)

In vitro NK cell killing assays. Splenocytes from C57B16 mice were preactivated with 200 U/ml IL-2 for 24 hours and used as cytotoxic effectors against stably transduced Ba/F3 cell lines in standard killing assays. Target cells were carboxyfluorescein succinimidyl ester (CFSE) labeled and co-incubated with activated splenocytes at 37° C., 5% CO2 for 4 hours at effector:target ratios of 10:1, 20:1, and 40:1. Killing percentage was determined by incorporation of the dead cell exclusion dye 7-amino-actinomycin D (7AAD) in the CFSE+ target population as assessed by flow cytometry. Percent specific lysis was calculated using the formula [(experimental dead %–background dead %)/(maximum release dead %-background dead %)]×100. C57BL/6 mice were obtained from the National Cancer Institute (Charles River, Mass.). Mice were maintained under specific pathogen-free conditions and used between 8 and 12 weeks of age. Single cell suspensions of splenocytes used in killing assays were generated using standard protocols [81].

TABLE 1

Data collection and refinement statistics

| | $OMCP_{BR}$-hNKG2D |
|---|---|
| Data collection | |
| Space group | $P2_1$ |
| Cell dimensions | |
| a, b, c (Å) | 43.3, 101.1, 91.4 |
| α, β, γ (°) | 90.0, 91.6, 90.0 |
| Resolution (Å) | 50-2.0 (2.07-2.00) |
| $R_{sym}$ | 11.8 (48.5) |
| I / σ | 14.5 (3.8) |
| Completeness (%) | 93.5 (91.5) |
| Redundancy | 6.2 (5.3) |
| Refinement | |
| Resolution (Å) | 44-2.0 |
| Total reflections | 309693 |
| Unique reflection | 50139 |
| $R_{work}$ | 16.6% (21.0%) |
| $R_{free}$ | 21.4% (29.5%) |
| Wilson B-factor | 21.62 |
| Protein residues | 791 |
| Water molecules | 524 |
| R.M.S. deviations | |
| Bond lengths (Å) | 0.003 |
| Bond angles (°) | 0.79 |

<sup>a</sup>As defined by PHENIX [69]

TABLE 2

Interface contacts between NKG2D and OMCP

| NKG2D-A | OMCP | Bond type |
|---|---|---|
| Lys150 | Asp132 | Salt bridge |
| Lys150 | Trp127 | H bond |
| Lys150 | Trp127 | Φ (3) |
| Ser151 | Lys126 | H bond |
| Ser151 | Trp127 | Φ (1) |
| Tyr152 | Phe122 | H bond |
| Tyr152 | Phe122 | Φ (9) |
| Tyr152 | Lys126 | Φ (5) |
| Met184 | Thr118 | H bond |
| Met184 | Thr119 | Φ (1) |
| Met184 | Phe122 | Φ (5) |
| Gln185 | Arg66 | Φ (1) |
| Leu191 | Phe122 | Φ (1) |
| Tyr199 | Phe122 | Φ (4) |
| Glu201 | Arg66 | Salt bridge |
| Thr205 | Arg66 | H bond |

| NKG2D-B | OMCP | Bond type |
|---|---|---|
| Leu148 | Trp127 | Φ (1) |
| Ser151 | Glu131 | H bond |
| Tyr152 | Asp132 | H bond |
| Tyr152 | Glu131 | Φ (3) |
| Tyr152 | Met135 | Φ (5) |
| Ile182 | Ile49 | Φ (2) |
| Glu183 | Arg142 | Salt bridge |
| Met184 | Met135 | Φ (1) |
| Met184 | Arg138 | Φ (2) |
| Met184 | Arg142 | H bond |
| Lys186 | Arg142 | Φ (1) |
| Leu191 | Met135 | Φ (1) |
| Glu201 | Arg138 | Salt bridge |

Hydrogen bonds (H bonds), salt bridges and carbon-to-carbon hydrophobic interactions (Φ) are shown for each contact residue. The number of hydrophobic interactions between contact residues is designated in parenthesis.

TABLE 3

NKG2D binding mutations identified through global

| Amino Acid | Frequency of Mutation | Associated Mutations | Solvent Accessible |
|---|---|---|---|
| D132 | 4 | D132N | ++ |
| | | D132N, T31S, V68A | |
| | | D132G, K126N, D76V | |
| | | D132G, K126N, D76V | |
| K126 | 4 | K126N | ++ |
| | | K126N, S71G | |
| | | K126N, D132G, D76V | |
| | | K126N, D132G, D76V | |
| K125 | 2 | K125E, F65C | − |
| | | K125E, F92V | |
| S120 | 2 | S120Y | − |
| | | S120Y, E10A, N56K | |
| D76 | 2 | D76V, D132G, K126N | ++ |
| | | D76V, D132G, K126N | |
| W116 | 2 | W116R | − |
| | | W116R, K113Q | |
| R123 | 2 | R123G, D26G, F50L | − |
| | | R123G, D21V, F128L | |
| E75 | 1 | E75D | − |
| S71 | 1 | S71G, K126N | ++ |
| F92 | 1 | F92V, K125E | + |
| F65 | 1 | F65C, K125E | − |
| K113 | 1 | K113Q, W116R | + |
| E10 | 1 | E10A, N56K, S120Y | ++ |
| N56 | 1 | E10A, N56K, S120Y | ++ |
| D21 | 1 | D21V, R123G, F128L | ++ |
| F128 | 1 | D21V, R123G, F128L | − |
| D26 | 1 | D26G, F50L, R123G | ++ |
| F50 | 1 | D26G, F50L, R123G | − |
| T31 | 1 | T31S, V68A, D132N | ++ |

TABLE 3-continued

NKG2D binding mutations identified through global

| Amino Acid | Frequency of Mutation | Associated Mutations | Solvent Accessible |
|---|---|---|---|
| V68 | 1 | T31S, V68A, D132N | + |
| I30 | 1 | I30L, L51F, L64P, M135T | − |
| L51 | 1 | I30L, L51F, L64P, M135T | − |
| L64 | 1 | I30L, L51F, L64P, M135T | ++ |
| M135 | 1 | I30L, L51F, L64P, M135T | ++ |
| R67 | 1 | R67S, L117P, T119N, F122L | + |
| L117 | 1 | R67S, L117P, T119N, F122L | − |
| T119 | 1 | R67S, L117P, T119N, F122L | ++ |
| F122 | 1 | R67S, L117P, T119N, F122L | ++ |

Mutations were sequenced from 17 clones expressing mutagenized OMCP-Thy1.1. Clones were selected for reduced binding to NKG2D tetramers. The selected clones showed variable deficits in NKG2D binding. Each clone had 1-4 mutations in the amino acid sequence of OMCP (5 clones with 1 mutation; 4 clones with 2 mutations; 6 clones with 3 mutations; 2 clones with 4 mutations). Silent mutations are not indicated. Mutations are listed in the order of frequency sequenced from the selected clones, and mutations that occurred together within individual clones are listed where applicable. Clones underlined have at least one mutation in a solvent inaccessible residue that may alter the overall stability of OMCP.

Example 11. Individuals with Poorly Functioning Natural Killer Cells are More Susceptible to Malignancies FIG. 14A shows that AJ and 129 are lung cancer susceptible strain of mice and B6 and C3H are lung cancer resistant strains of mice based on the larger tumor burden found in AJ and 129 mice. FIG. 14B shows that when NK cells from the various mouse strains were incubated with LM2 lung carcinoma cells at varying ratios, the NK cells freshly isolated from B6 and C3H mice (lung cancer resistant strains) resulted in significantly more lysis of LM2 lung carcinoma cells than the NK cells freshly isolated from AJ and 129 mice (lung cancer susceptible strains). Taken together these data show that strains of mice that are resistant to lung cancer have NK cells that more effectively lyse lung carcinoma cells. Further, susceptible strains have poorly functioning NK cells.

That data also correlates with human data. FIG. 15 shows that a greater percentage of NK cells appear to produce TNFα in "resistant" patients versus "susceptible" patients. Further, it has been shown that tumors downregulate the lytic capacity of NK cells, even if they were highly functional before.[53] Thus, even individuals with highly functioning NK cells may benefit from therapy to enhance NK cell function.

Notably, ex vivo cytokine activation can reverse natural killer cell dysfuction. FIG. 16 shows that IL-2 activated NK cells from both resistant (B6 and C3H) and susceptible (AJ and 129) mouse strains can lyse LM2 lung cancer cells. Accordingly, mouse NK Cells that did not show significant lysis of cancer cells (NK cells from 129 & AJ strains) were much more effective at lysis when treated with IL-2. NK cells from cancer-resistant strains also showed increase % of specific lysis.

Example 12. OMCP-mutIL2 Mediated Immunotherapy In Vivo

Immunoregulation of malignancies involves an intricate interplay of multiple cellular components. $CD4^+Foxp3^+$ $T_{regs}$ have been shown in multiple models to contribute to tumor-specific tolerance and facilitate tumor growth[4,16,17]. NK cells and $CD8^+$ CTLs contribute to immunoregulation of multiple tumors, such as melanoma[12,18]. Other tumors, such as lung cancer, are controlled almost exclusively by NK cells with little contribution by the adaptive immune system[19,20] (and unpublished data AS. Krupnick). In order to test OMCP-mutIL2 mediated immunotherapy we will rely on B16 melanoma expressing the model tumor antigen ovalbumin (MOS tumor cell line)[21]. Multiple studies have demonstrated a role for both NK cells and CD8+ CTLs in controlling melanoma growth[22-24]. Thus the melanoma model offers an experimental advantage in studying OMCP-mutIL2, which can activate both types of cells (FIG. 1E-F). Reagents specific to this tumor, such as tetramers for the MHC Class I-restricted CD8+ T cell receptor specific for the melanoma tumor associated antigen tyrosinase-related protein 2 peptide SVYDFFVWL (SEQ ID NO:3), can be readily purchased commercially (Proimmune, Sarasota, Fla.). The use of an ovalbumin-expressing cell line also offers the advantage of studying the immune response to a the highly immunogenic peptide SIINFEKL (SEQ ID NO:4) in addition to naturally occurring tumor associated antigens such as tyrosinase-related protein 2 which generally expands T cells with low avidity[25,26].

Figure 12:
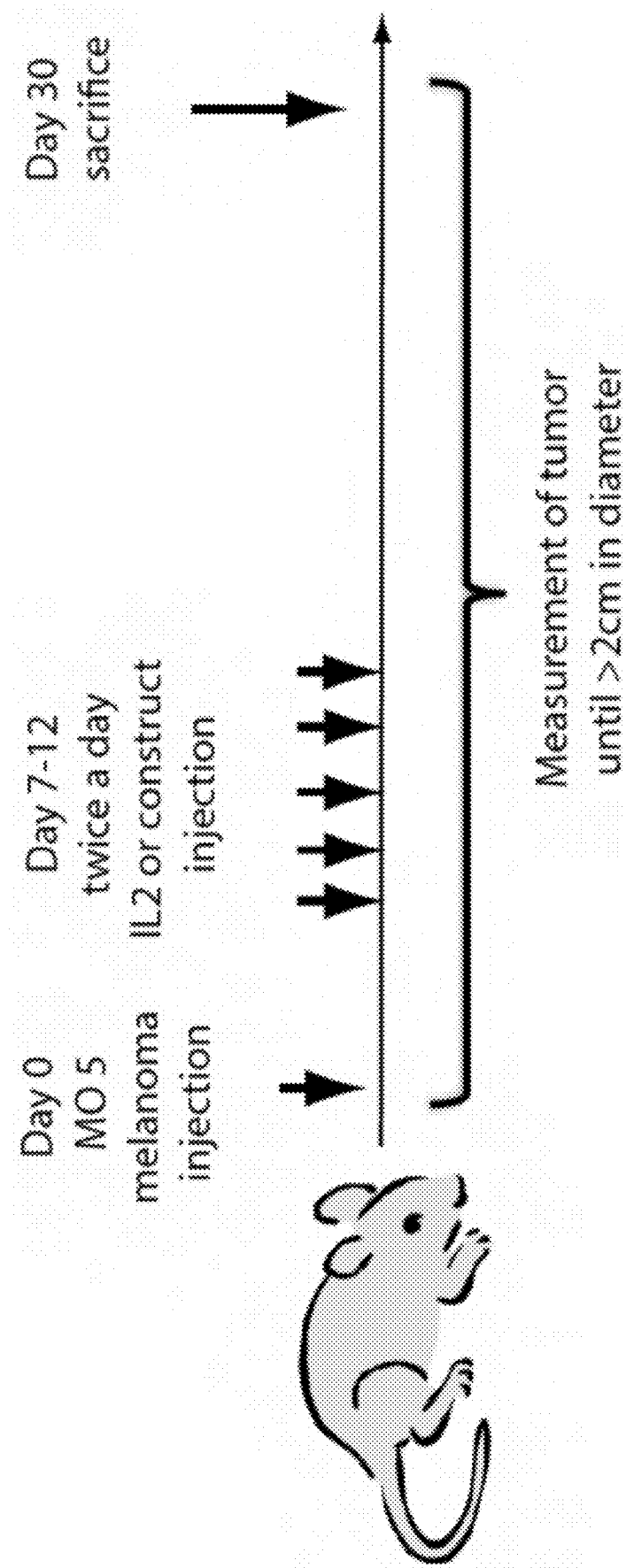
FIG. 12 depicts a schematic of the experimental design of immunotherapy experiments.

In order to perform the studies B6 mice will be injected subcutaneously with 1×10$^6$ MO5 melanoma cells. One week after tumor injection mice will be divided into 4 groups (10 mice per group) and treated with ten twice a day injections of either: wild type IL2 (group #1); mutIL2 (group #2); OMCP-mutIL2 (group #3) or; saline (group #4) (FIG. 12). Tumor growth will be followed by daily measurements of diameter for 4 weeks, or until one of the groups develops tumors >2 cm in diameter. At that point mice in all groups will be sacrificed for analysis. In addition to tumor growth, lymphocyte infiltration of both the tumor and draining inguinal lymph node will be evaluated by flow cytometry. We will quantitate the total number and activation status of CD4+Foxp3+ Tregs (evaluated by ICOS and GITR upregulation). We will also evaluate NK cell number and activation as measured by IFN-γ production and CD69 upregulation. Antigen-specific CTL generation will be evaluated by quantitating both CD8+ T cells and CD8+CD44$^{hi}$CD62L$^{low}$ effector cells (ECs) that are primarily responsible for tumor clearance[22,27,28]. Antigen specificity will be determined by identifying CD8+ CTLs with T cell receptor specific for either the ovalbumin peptide SIINFEKL (SEQ ID NO:4) or melanoma specific tyrosinase-related protein 2 peptide SVYDFFVWL (SEQ ID NO:3) (both tetramers from Proimmune, Sarasota, Fla.). Tumor apoptosis will be quantitated by TUNEL staining.

Based on our in vitro tumor data and in vivo phenotypic analysis we suspect that the OMCP-mutIL2 group will demonstrate attenuation in tumor growth with high number of NK cells, antigen-specific CTLs, specifically CD8+ ECs, and fewer CD4+Foxp3+ T$_{regs}$. If this turns out to be the case we would determine the relative role for CD8+ or NK CTLs by depletion experiments. Even if CTLs increase it is possible that MOS growth will not be altered. If that turns out to be the case we would look in closer detail at the CD4+Foxp3+T$_{regs}$ or in the presence and activation of myeloid-derived suppressor cells in OMCP-mutIL2 treated mice. Based on melanoma data additional tumors will be tested using similar methods.

Example 13. CD8+ Memory T Cell Generation after Treatment with OMCP-mutIL2 Fusion Construct Once activation through their T cell receptor, naive CD8+ T cells primarily differentiate into short-lived CD44$^{hi}$CD62L$^{Low}$ effector cells (ECs) with cytolytic potential. A portion of activated cells, however, differentiate to long-lived CD44$^{hi}$CD62L$^{hi}$ central memory T cells (CD8+ CMs)[29-31]. CD8+ CMs act as an antigen specific reservoir for cellular protection and upon restimulation differentiate into CD8+ ECs with cytolytic function. The durability of CD8+ CMs makes them an ideal target for ex vivo generation and adoptive transfer for long-term protection[31]. The possibility of generating this cell population in vivo offers multiple advantages over an ex vivo system, including establishing a polyclonal population reactive to multiple tumor associated antigens and avoidance of costs associated with donor pheresis and ex vivo expansion. In vivo expansion of tumor antigen specific CD8+ CMs could also eliminate the need for frequent pheresis and cell readministration.

High dose IL2 therapy results in activation of both CD4+Foxp3+T$_{regs}$ and CD8+ T cells but its effect on tumor associated antigen specific CD8+ CM generation is unknown. Some have demonstrated, using antibody depletion, that CD4+Foxp3+T$_{regs}$ interfere with tumor specific CD8+ CM generation[17,32] while others, using different models, have demonstrated that CD4+Foxp3+T$_{reg}$ depletion impairs CD8+ memory formation[33,34]. OMCP-mutIL2 creates a unique immunologic environment where CD4+Foxp3+T$_{regs}$ are maintained but not actively expanded (FIG. 3). While NKG2D is not expressed on resting CD8+ T cells, it is induced on this population upon activation[35]. Thus, unlike mutIL2, OMCP-mutIL2 results in CD8+ T cell proliferation at levels comparable to wild-type IL2 in NKG2D-sufficient mice (FIG. 1E-F). The effect of OMCP-mutIl2 on CD8+ T cell memory formation, however, is unknown but is critical to decipher based on the long-term tumor specific immunity that this cell population can confer.

Figure 13:
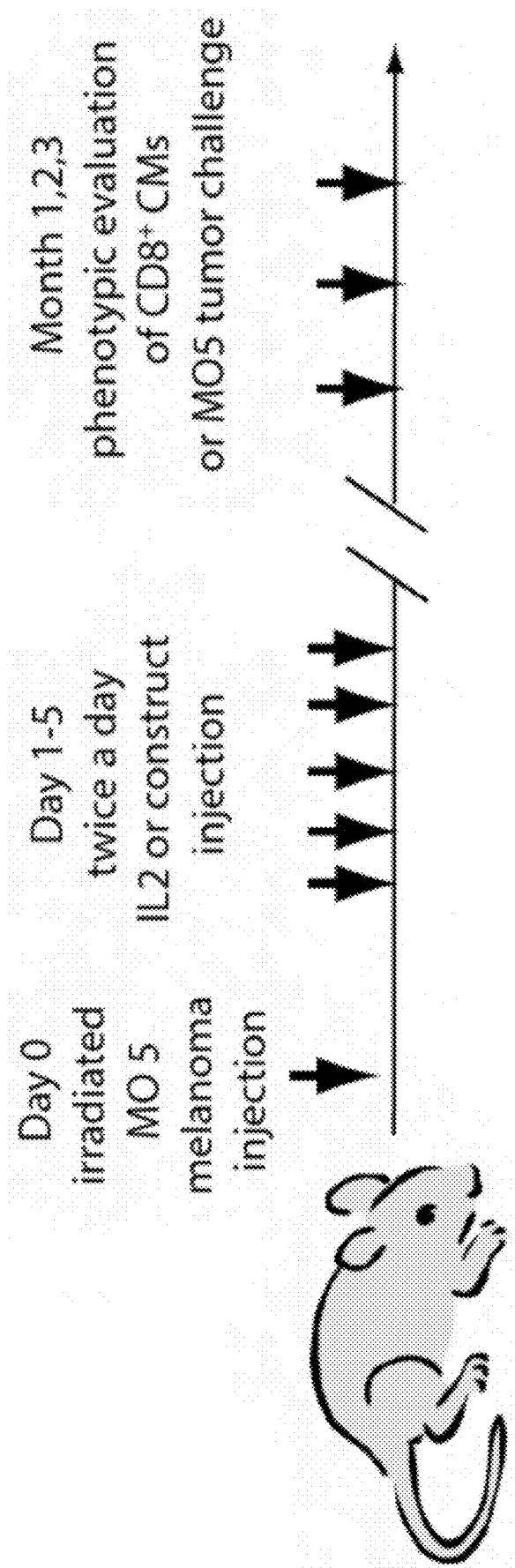
FIG. 13 depicts a schematic of the experimental design of vaccination experiments.
Figure 14A:
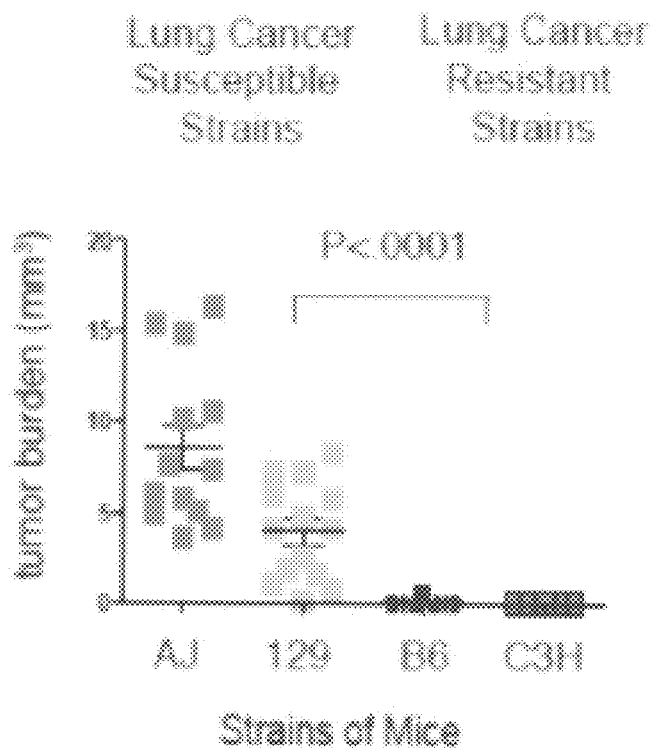
FIG. 14A and FIG. 14B depict graphs showing lung cancer susceptible and resistant strains of mice.
Figure 14B:
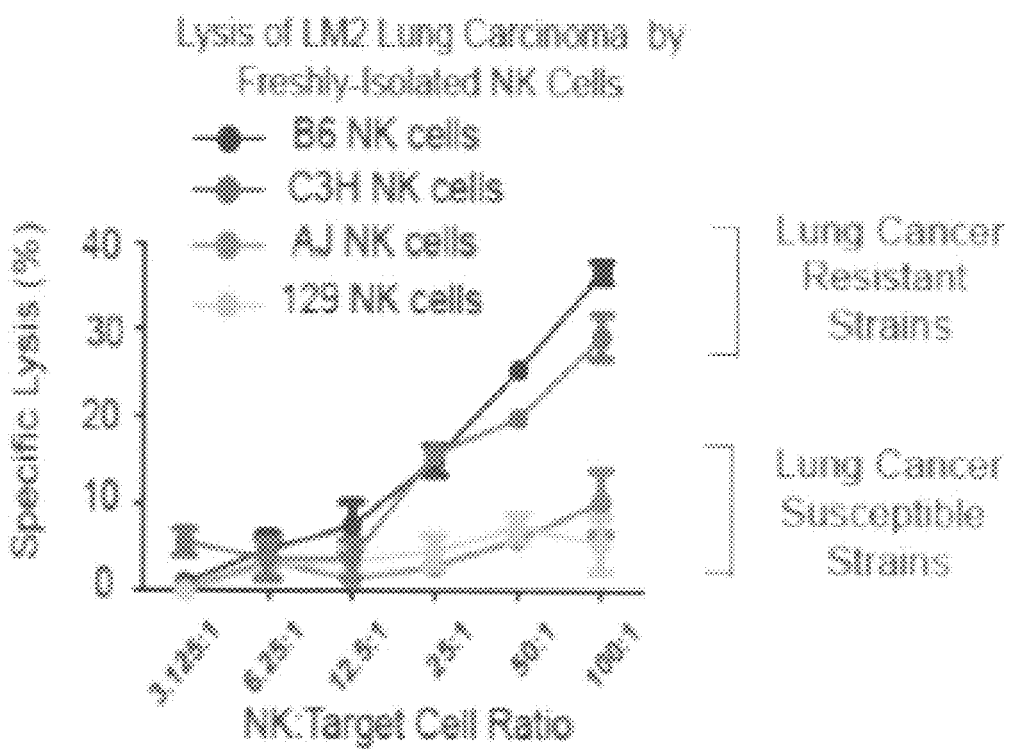
Figure 15:
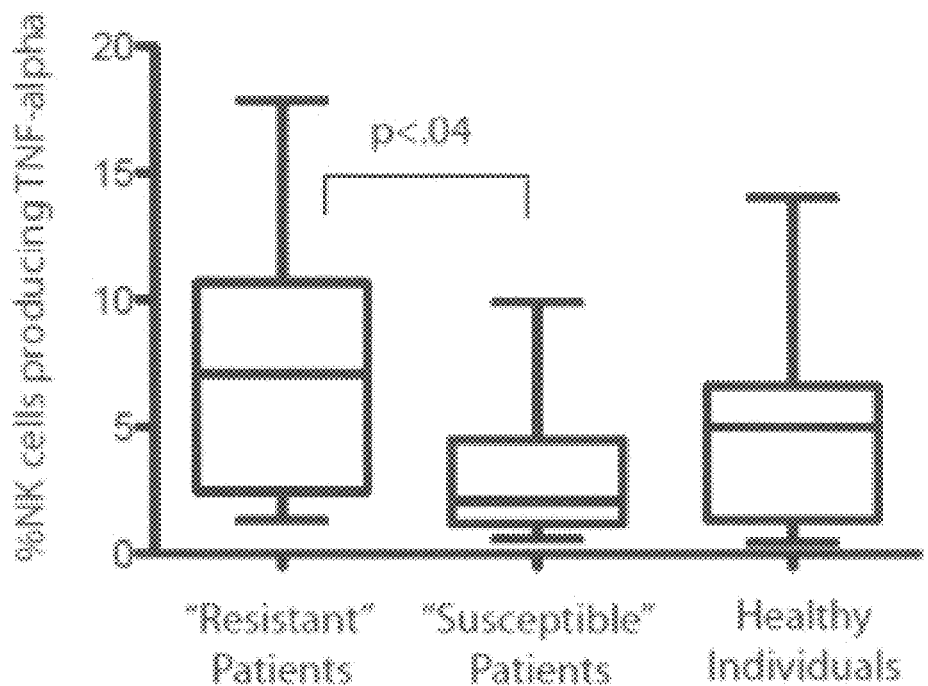
FIG. 15 depicts a graph showing that in human men, a greater percentage of NK cells appear to produce TNFα in "resistant" patients versus "susceptible" patients.
Figure 16:
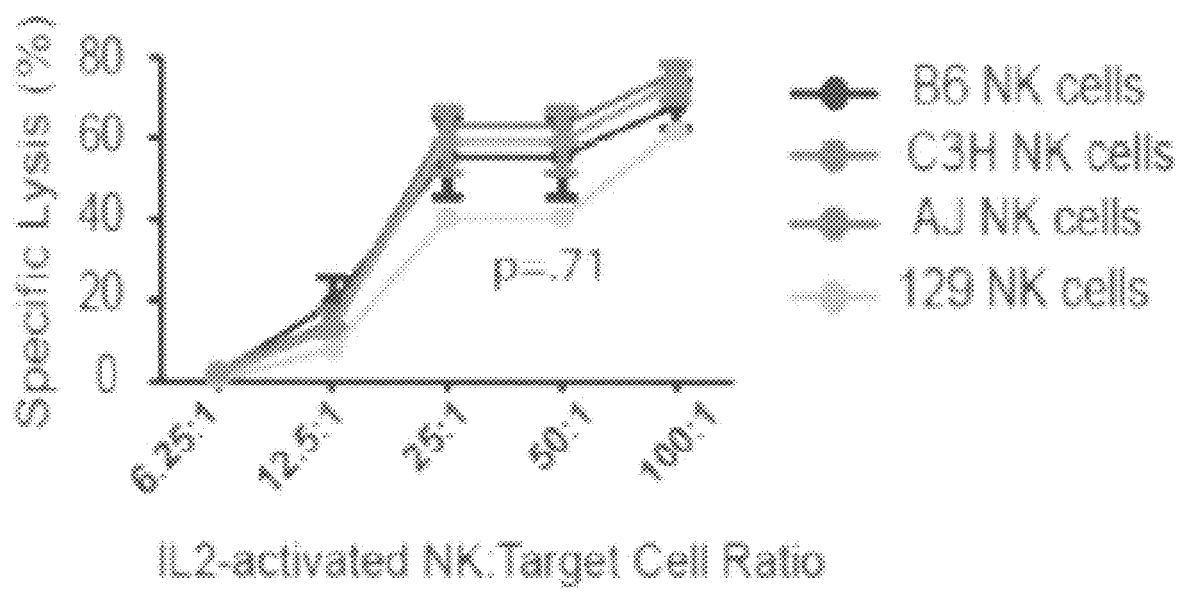
FIG. 16 depicts a graph showing that ex vivo cytokine activation can reverse natural killer cell dysfunction. Mouse NK Cells that did not show significant lysis of cancer cells (NK cells from 129 & AJ strains) were much more effective at lysis when treated with IL-2. NK cells from cancer-resistant strains also showed increase % of specific lysis.
Figure 17A:
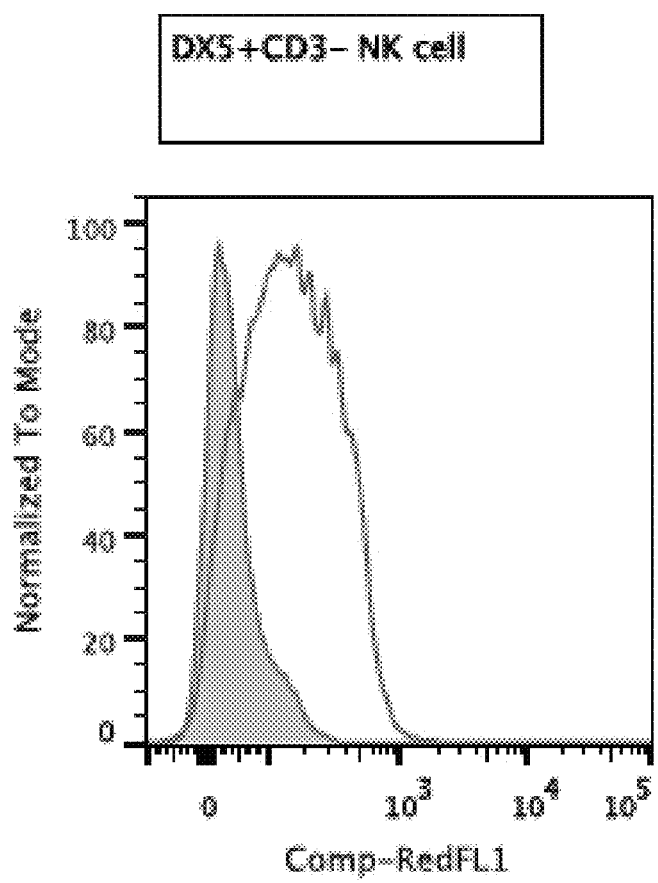
FIG. 17A, FIG. 17B, FIG. 17C, FIG. 17D, FIG. 17E and FIG. 17F depict graphs showing binding of fluorescently labeled construct tested in vitro at 37 degrees in bulk splenocytes. The construct appears to only bind to NK cells (express NKG2D). Red line is OMCP-IL2 construct.
Figure 17B:
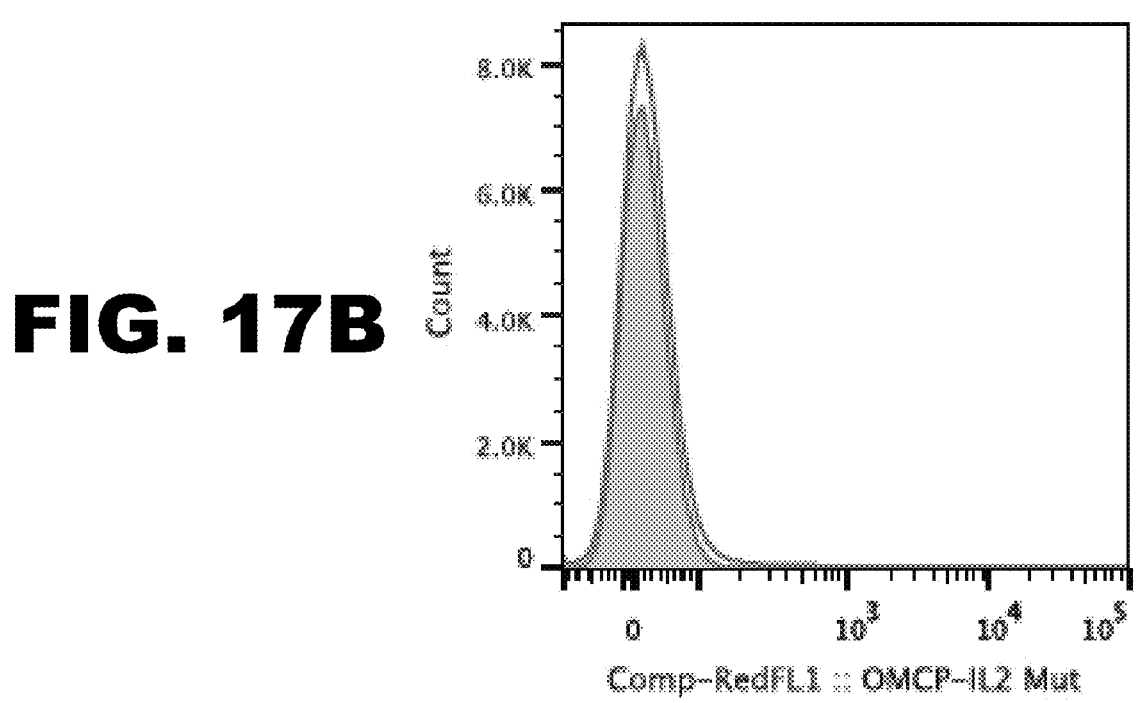
Figure 17C:
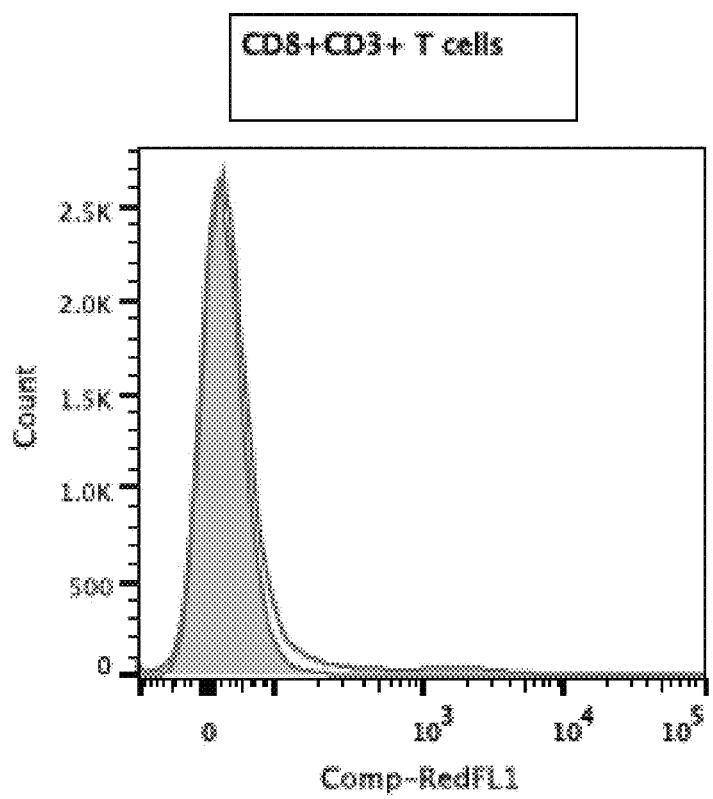
Figure 17D:
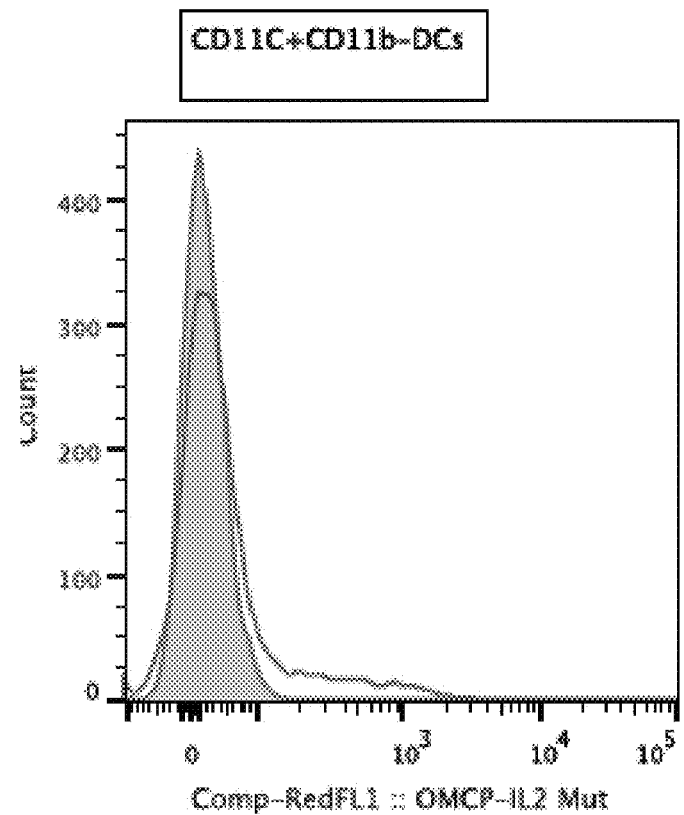
Figure 17E:
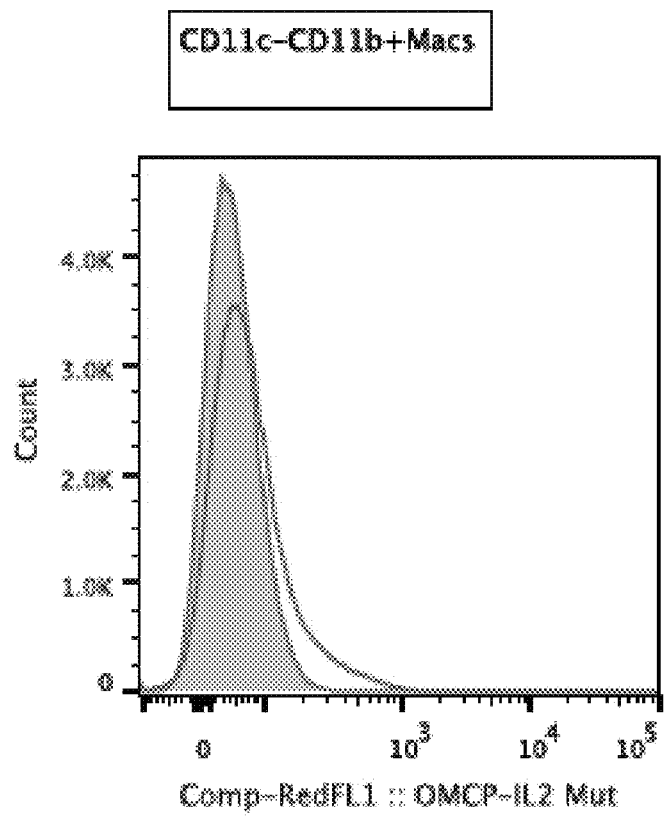
Figure 17F:
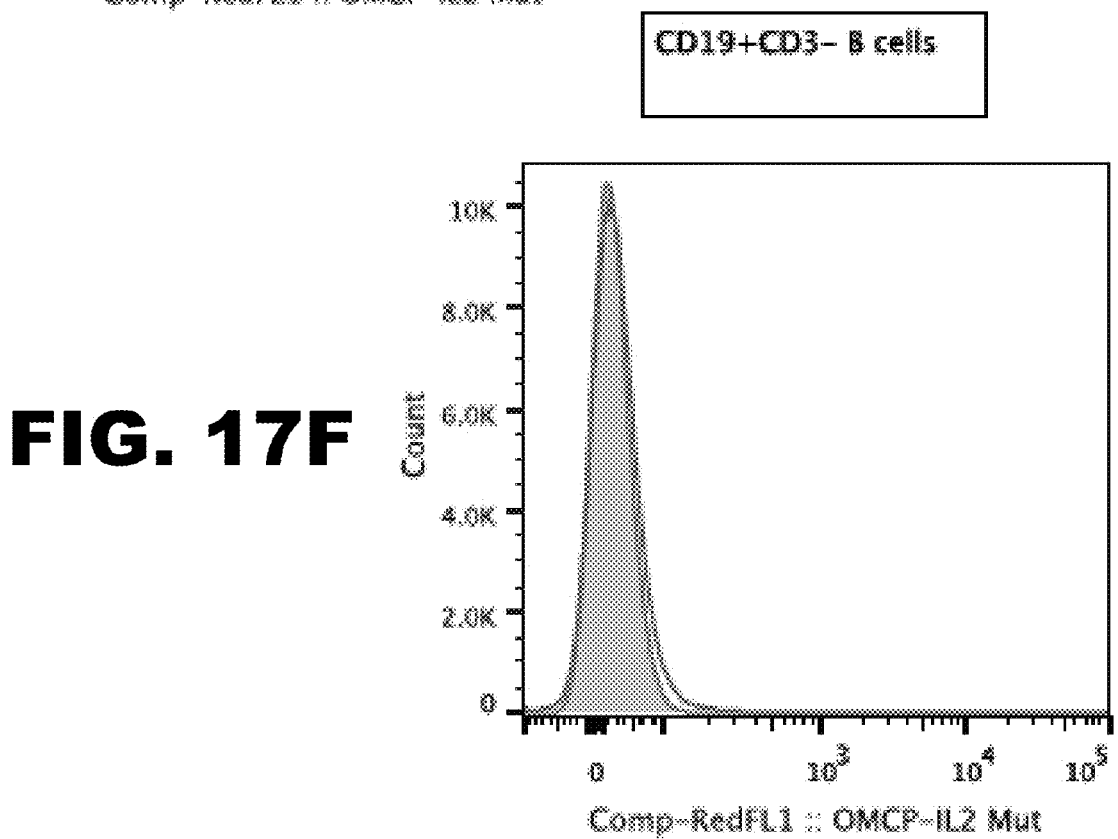

In order to test long-term memory formation after cytokine stimulation in vivo we will utilize a model of irradiated tumor cell vaccination and cytokine treatment. In order to accomplish this we will subcutaneously inject 1×10$^7$ lethally irradiated (10Gy) MOS melanoma cells into C57Bl/6 mice. The recipient mice will then be treated either regular IL2 (group #1), mutIL2 (group #2), OMCP-mutIL2 (group #3) or saline (group #4) in twice daily doses over a course of 5 days (FIG. 13). The mice will be sacrificed at various time points ranging from one to three months post infection (FIG. 13). Antigen-specific CD8+ CM formation will be assessed by phenotypic analysis of splenic, peripheral lymph node, lung, and liver-resident CD8+CD44$^{hi}$CD62L$^{hi}$ CMs. Antigen specificity will be determined by MHC Class I staining for either the ovalbumin peptide, SIINFEKL (SEQ ID NO:4), or melanoma specific tyrosinase-related protein 2 peptide SVYDFFVWL (SEQ ID NO:3) (both from Proimmune, Sarasota, Fla.).

In order to test the functional protection of such vaccination protocols in a separate set of experiments mice from the four groups described above will not be sacrificed for phenotypic analysis and will be reinjected with live MOS melanoma (1×10$^6$ cells/mouse subcutaneously). Melanoma growth will be assessed by serial measurement of tumor diameter. Contribution of CD8+ T cells to any immunologic protection will be assessed by CD8-specific antibody depletion in a portion of mice (clone YTS 169.4, BioXcell Inc., West Lebanon, N.H.).

Example 14. Mechanism of CTL Activation by OMCP-mutIL2 Fusion Construct

A mechanistic understanding of the enhanced activation of effector cell function by the OMCP-mutIL2 chimera will be critical for optimizing this therapeutic agent. The interaction of the fusion protein with IL2R and NKG2D are likely to be dependent on several factors including the length of the linker peptide (FIG. 1E-F). Therefore, it is critical to understand the mechanism of OMCP-mutIL2 chimera mediated CTL activation in order to allow for optimization of the construct and design of future immunotherapy protocols. The two-domain chimeric protein could potentially increase the activation of NKG2D-expressing cells by three non-mutually exclusive mechanisms. First and foremost the OMCP-mutIL2 construct could increase the avidity of mutIL2 binding to targeted cells. This could lead to an increase in the number of receptors occupied and increased signaling intensity compared to mutIL2. Additionally dual binding to both NKG2D and IL2R could decrease the rate of receptor internalization and increase the duration of signaling by IL2. It is also possible that the OMCP-mutIL2 construct alters the signaling profile by the target cell by activating both the IL2 and NKG2D stimulatory pathways. These three non-mutually exclusive effects could explain the increase in activation of our construct of CTLs in an NKG2D-mediated fashion.

There are several methods for determining the avidity of a protein for a cell, either directly (radiolabeled, fluorescent) or indirectly (antigen exclusion)[39]. We plan to determine the avidity of wild-type IL2, mutIL2, or OMCP-mutIL2 for CD4$^+$Foxp3$^+$ T$_{regs}$, NK cells, and CD8$^+$ T lymphocytes using KinExA[40]. To accomplish this we will isolate cells from splenocytes of either wild-type C57Bl/6 or NKG2D$^{-/-}$ mice on a C57Bl/6 background using a magnetic bead isolation kit (Miltenyi Biotech, San Diego, Calif.). Target cells will be serially diluted by a factor of 2 in 11 falcon tubes in media containing 0.05% NaN$_3$. The 12th tube will contain just the media. OMCP-mutIL2 or mutIL2 alone will then be added to each tube of either wild-type or NKG2D$^{-/-}$ cells and the cells with cytokine will be rotated at 4° C. for 36 h. At the end of 36 h, the cells were centrifuged at 2400 rpm for 4 min and the free construct present in the supernatant will be measured by an anti-IL2 ELISA. The equilibrium dissociation constant (K$_d$) will then be calculated. This approach has the advantage of measuring the avidity of cell surface molecules at physiologic densities and obviates the need for labeling, which can artificially lower the affinity of antibodies for their antigens[42,43].

The two-domain structure of the fusion protein is likely to significantly increase the half-life of the protein on the surface of NKG2D$^+$ and IL2R$^+$ cells. Any increase in surface half-life likely affects both the internalization of the bound receptors and signaling intensity and duration. To address the internalization of receptors, we will incubate each construct with the above mentioned cell types over a range of times and monitor the change in cell surface expression of IL2Rβγ and NKG2D using flow cytometry as previously described[44]. Of key interest will be the signaling profile of each construct. IL2-IL2R engagement signals through JAK-STAT pathways, while NKG2D signals through DAP10/12 pathways. While monomeric, soluble OMCP does not induce NKG2D signaling, OMCP can signal when concentrated locally on the cell surface[45]. Therefore, it is critical to determine whether the chimera is capable of inducing dual signaling through IL2R and NKG2D. IL2-mediated signaling will be assessed by Western blot for phosphorylated JAK1 and JAK3 in freshly isolated CD4+Foxp3+ T$_{regs}$, NK cells or CD8$^+$ T cells incubated in vitro with the construct[46,47]. NKG2D-mediated signaling will be assessed by immunoprecipitation of DAP10 or DAP12 followed by Western blotting for phosphotyrosine as previously described[48,49].

Both IL2 and OMCP interact with their cognate receptors with high affinity; the fusion of the two proteins is anticipated to greatly enhance the avidity of the chimeric construct for cells expressing both IL2R and NKG2D. As a consequence, the tethering of the construct to two cell surface receptors may lead to reduced internalization and increased duration of signaling. Combined these two phenomena represent the most likely mechanism for increased proliferation of NK cells in vivo. The signaling via NKG2D relies upon receptor clustering[45]. Since the construct is soluble it is possible, though unlikely, that the chimera will cluster NKG2D and induce DAP10/12 signaling. However, should DAP10/12 signaling be detected, we will then investigate the importance of this signaling in the expansion of NK cells using cells derived from Vav1 knockout mice. Vav1 is a signal mediator downstream of DAP10[50]. Using a Vav1 knockout has the advantage of leaving NKG2D expression intact, in contrast to DAP knockouts[50]. This will remove the NKG2D signaling component while leaving the NKG2D-dependent targeting intact. A clearer understanding of the mechanism of action for OMCP-IL2 chimera dependent expansion will be crucial for further refinements of the therapeutic agent. Understanding these parameters will allow for testing of different construct designs, primarily in the length of the linker between OMCP and IL2, to calibrate the effects of the chimera.

Example 15. In Vivo Immunotherapy with IL-2, R38 Å/F42K IL2 or OMCP Targeted IL2 Constructs In order to determine if our construct plays a role in immunoregulation of malignancies as well as viral infections we will rely on in vivo models of B16 melanoma and mouse cytomegalovirus (MCMV). In one set of experiments B6 mice will be injected subcutaneously with 1×10$^6$ cells of the poorly immunogenic B16 melanoma cell line. One week after tumor injection mice will be divided into 13 groups (5 mice per group) and treated with five daily injections of IL2, R38 Å/F42K IL2, OMCP fusion constructs or saline as described in FIG. 18 and Table 4. Tumor growth will be followed by daily measurements of diameter for 4 weeks or until one of the groups develops tumors >2 cm in diameter. At that point mice in all groups will be sacrificed for analysis. In addition to tumor growth lymphocyte infiltration of both the tumor and draining inguinal lymph node will be evaluated by flow cytometry. We will quantitate the total number and activation status of CD4$^+$Foxp3$^+$ Tregs (expressed as % of tumor infiltrating lymphocytes and % ICOS$^+$). We will also evaluate NK cell number and activation as measured by IFN-γ production and CD69 upregulation. Tumor apoptosis will be evaluated by TUNEL staining.

TABLE 4

Experimental Design for Dosing for IL2, R38A/F42K IL2, OMCP-R38A/F42K IL2 or OMCP linked IL2 constructs

| Dose Cytokine | LOW DOSE | INTERMEDIATE DOSE | HIGH DOSE |
|---|---|---|---|
| IL2 | Group 1 | Group 2 | Group 3 |
| R38A/F42K IL2 | Group 4 | Group 5 | Group 6 |
| OMCP-wild-type IL2 | Group 7 | Group 8 | Group 9 |
| OMCP-R38A/ F42K IL2 | Group 10 | Group 11 | Group 12 |
| Saline | | Group 13 | |

In order to evaluate the therapeutic potential of IL2 in an infectious disease model, B6 mice will be infected with a sublethal dose of MCMV ($5\times10^4$) particle forming units (PFUs) as previously described[29]. Day 1 post infection the mice will be divided into 13 groups (5 mice per group) and treated with five daily injections of IL2, R38 Å/F42K IL2, OMCP fusion constructs or saline as described in FIG. 18 and Table 4. On post-infection day #6 the mice will be sacrificed and splenic and pulmonary viral load determined by standard plaque assay.

We expect that treatment with pure IL2 will have little effect on tumor growth or viral load as we expect to see preferential activation of $T_{regs}$ over CTLs. We suspect that administration of the mutant R38 Å/F42K form of IL2 will result a lower tumor and viral burden compared to wild-type IL2 due to less activation of $CD4^+Foxp3^+$ $T_{regs}$. Nevertheless it is possible that despite lower levels of $T_{reg}$ activation the tumor burden will be identical between IL2 and R38 Å/F42K IL2 due to decreased NK activation by the mutant form of IL2 as well. We expect OMCP IL2 construct-treated mice to have lower tumor burden compared to pure cytokine and predict that OMCP-R38 Å/F42K IL2 will demonstrate the best efficacy for immunotherapy with the most favorable side effect profile.

If we do not see an effect of OMCP expressing IL2 constructs we will closely evaluate our data for confounding factors such as excessive CTL death due to extreme stimulation as well as possible sequestration of CTLs in systemic organs such as the liver and lungs. If our hypothesis is supported and NK cells are activated and tumor growth ameliorated after OMCP-construct treatment we would repeat these experiments after NK depletion (using anti-NK1.1 clone PK136, mouse anti-mouse depleting antibody) and CD8 depletion (clone YTS169, rat anti-mouse $CD8^+$ T cell-depleting antibody) (both from BioXcell, West Lebanon, N.H.). Based on these results future work will focus on immunotherapy in primary carcinogenesis models.

Example 16. The Effects of IL-2, R38 Å/F42K IL2 or OMCP Targeted IL2 Constructs on Immunosuppression after Radiation Exposure Sublethal radiation exposure is a constant risk to those involved in combat duty. In addition to the direct carcinogenic effects of radiation-induced DNA damage, sublethal irradiation results in immunologic damage due to selective death of lymphocyte subsets. $CD8^+$ T cells and $CD44^{10}$ naïve T cells are specifically sensitive to radiation-induced death while NK cell function significantly declines after irradiation. $CD4^+25^+$ T cells as well as CD44 memory-like T cells, however, have a survival advantage after radiation. Both $CD4^+25^+$ T cells and $CD8^+CD44^{hi}$ T cells can down-regulate immune responses, explaining why even limited exposure to radiation can result in significant immunosuppression. Pharmacologic interventions to restore the immune system can alleviate morbidity and mortality of radiation poisoning. Surprisingly the role of IL2 in alleviating radiation-induced changes has never been studied. The low affinity IL2 receptor is expressed on bone marrow-resident hematopoietic stem cells and committed NK progenitors. NK cells, in turn, can secrete granulocyte-macrophage colony-stimulating factor (GM-CSF) upon stimulation, a cytokine that can assist with hematopoietic recovery. Based on these data in this aim we plan to test the hypothesis that IL2 or OMCP-IL2 constructs can assist with hematopoietic recovery after sublethal and lethal irradiation.

Figure 18:
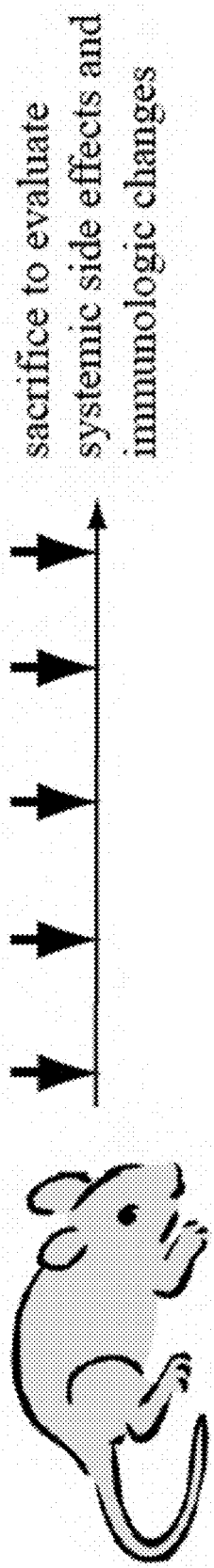
FIG. 18 depicts a schematic dosing regimen for IL2 or IL2 constructs.

Based on previously described models of radiation-induced hematopoietic damage and recovery we will irradiate B6 mice with either sublethal 4.5 or lethal 7.5Gy from a cesium source. Within one hour of exposure mice in both radiation doses will be randomly divided into 13 groups as described in Table 4 and treated for five days with low, intermediate or high dose IL2, R38 Å/F42K IL2 or OMCP expressing IL2 constructs (FIG. 18). A portion of the mice will be injected with saline after irradiation (group 13) (Table 4) and unirradiated untreated B6 mice will be included as a control as well (group 14). On day 6 hematopoietic recovery will be monitored by flow cytometric analysis of peripheral blood obtained by superficial mandibular vein sampling. The sample will be analyzed for total number of NK cells, T cells, B cells, granulocytes, as well as monocytes and macrophages per ml of blood. Since 90% of untreated mice die 15-25 days after exposure to 7.5Gy, mice will be followed daily and survival curves in each treatment group will be compared by Kaplan-Meier analysis. Moribund mice in the 7.5Gy group will be carefully analyzed for cause of death evaluating the bone marrow, spleen and peripheral organs for both infection as well as hematopoietic failure by flow cytometry and tissue culture. Since mice in the sublethal 4.5Gy group are expected to survive long term, they will be sacrificed one month after exposure and peripheral lymphoid organs as well as bone marrow evaluated for hematopoietic recovery by flow cytometric analysis.

Figure 19:
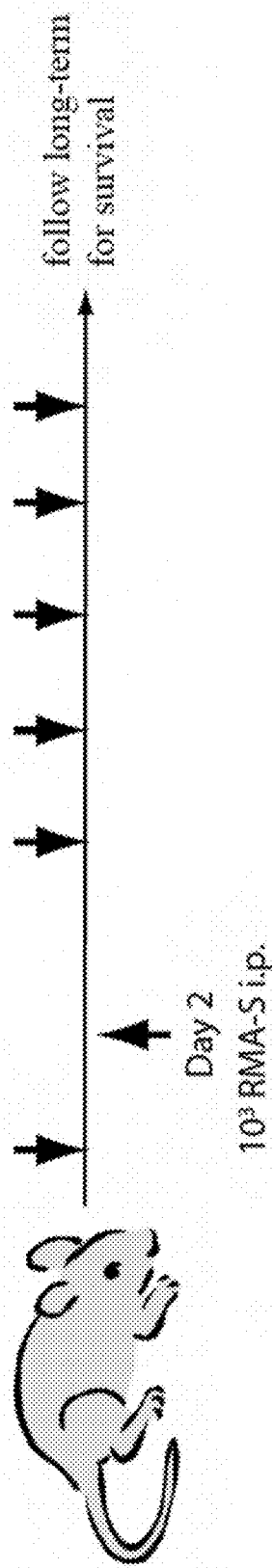
FIG. 19 depicts a schematic dosing regimen for IL2 or IL2 constructs after irradiation.

Radiation related DNA damage results in malignant transformation. Hematopoietic malignancies are especially prominent after radiation exposure. In order to evaluate the ability of IL2 or OMCP linked IL2 constructs to facilitate in clearing hematopoietic malignancies after radiation exposure we will treat B6 mice with sublethal exposure to 4.5Gy from a cesium source. Two days after irradiation the mice will be injected with 103 RMA-S lymphoma cells i.p. and three days later treated for a five day course with low, intermediate or high dose IL2, R38 Å/F42K IL2 or OMCP expressing IL2 constructs (Table 4, FIG. 19). Unirradiated B6 mice will be included as a control (group 14) as well. The mice will be followed for survival.

We anticipate that wild-type IL2 alone will have a negligible effect on immunorestoration since it will most likely result in preferential expansion of $CD4^+Foxp3^+$ $T_{regs}$, which are already preserved after irradiation. We suspect, however, that R38 Å/F42K IL2 as well as OMCP expressing IL2 constructs will expand the NK fraction in the peripheral blood and will contribute to broad hematopoietic recovery, albeit indirectly through secretion of homeostatic cytokines such as GM-CSF. If we detect no differences in hematopoietic recovery between IL2 and saline-treated groups, we will examine other confounding factors, such as homeostatic proliferation induced alteration of the immune system and the effect of IL2 or OMCP expressing IL2 constructs on such proliferation. While 200,000 IU of IL2 administered daily to B6 mice is not lethal, we realize that in the face of irradiation the mice might be weaker. It is thus possible that dosing might need to be adjusted. For the "functional" part of this experiment we plan to specifically utilize the well-established model of RMA-S lymphoma challenge due to the role of NK cells in controlling hematologic malignancies. This established assay will allow us to gain rapid experimental data to advance this aim. Based on this data we would extend this aim in the future utilizing a primary carcinogenesis model as well.

Example 17. OMCP-Targeted Delivery of IL15 Enhances CD25 Upregulation

Interleukin 15 (IL15) is a cytokine with structural similarity to IL2. Like IL2, IL15 binds to and signals through a complex composed of L2/IL15 receptor beta chain (CD122) and the common gamma chain (gamma-C, CD132). IL15 is secreted by mononuclear phagocytes (and some other cells) following infection by viruses. IL15 regulates T and natural killer (NK) cell activation and proliferation. Survival signals that maintain memory T cells in the absence of antigen are provided by IL15. This cytokine is also implicated in NK cell development. IL-15 belongs to the four α-helix bundle family of cytokine.

Figure 21:
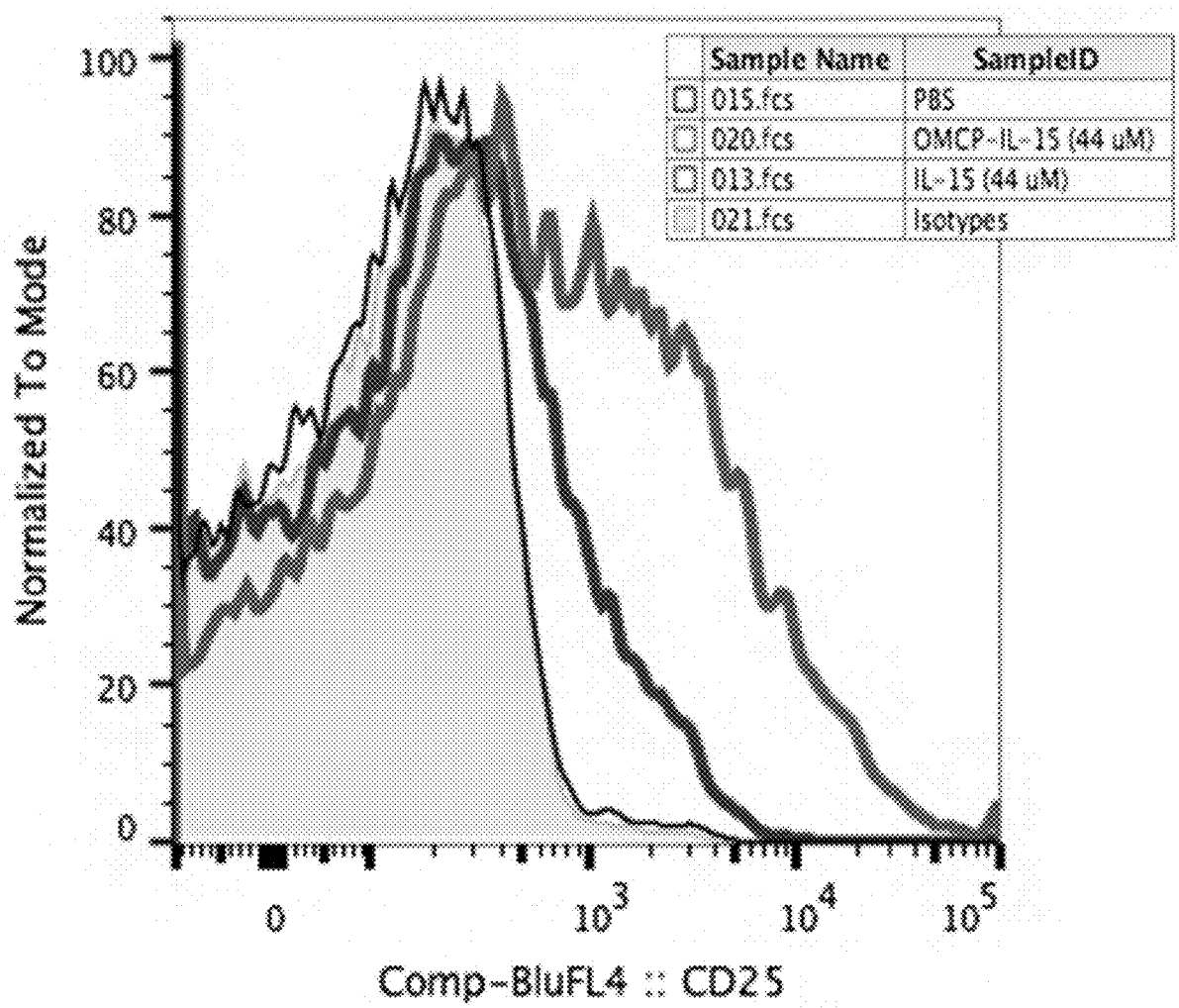
FIG. 21 depicts a graph showing OMCP-targeted delivery of IL15. Higher levels of CD25 are evident when IL15 is delivered by OMCP vs naked cytokine alone in equimolar doses.

OMCP was linked to the cytokine IL15 and its ability to active NK cells compared to IL15 alone was examined. NK cell activation was measured by CD25 upregulation. As demonstrated in FIG. 21, higher levels of CD25 are evident when IL15 is delivered by OMCP vs naked cytokine alone in equimolar doses.

Example 18. OMCP-Targeted Delivery of IL18 Enhances NK Cell Activation

Figure 32:
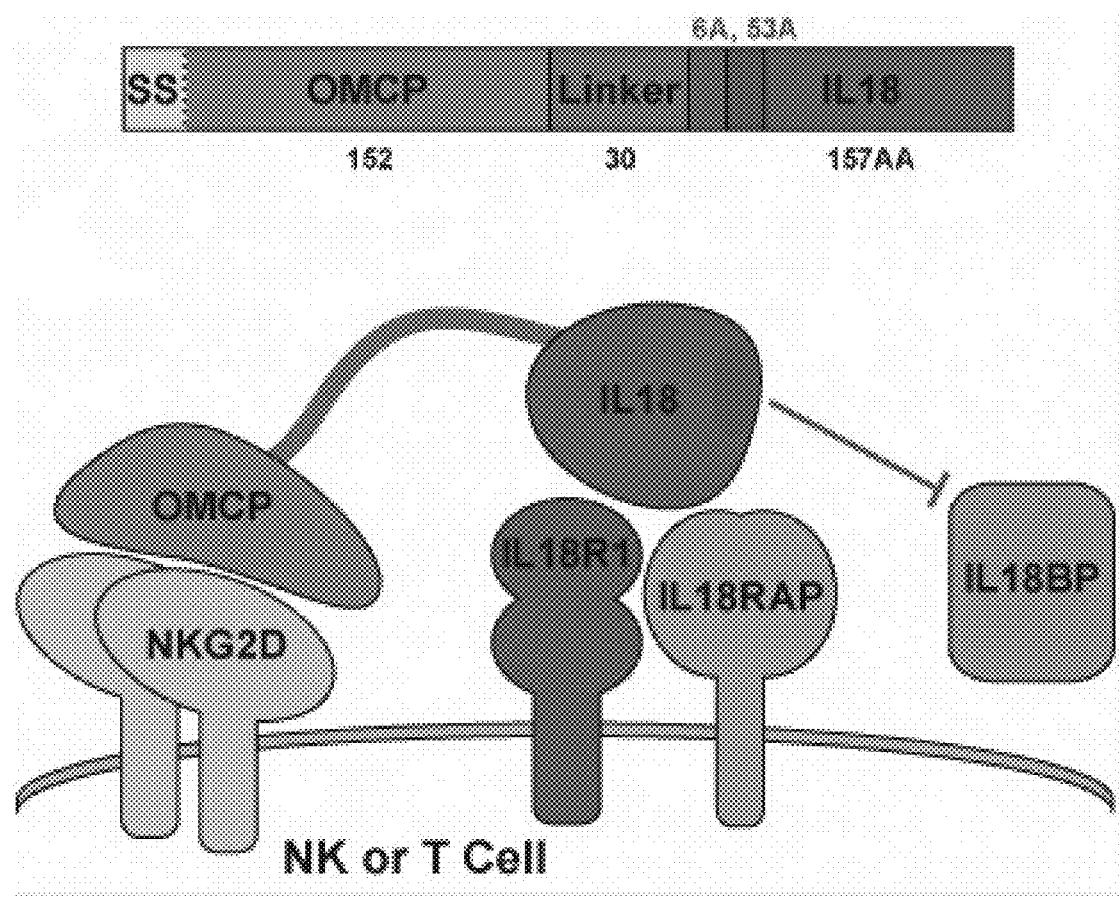
FIG. 32 depicts a schematic of the various IL18-OMCP constructs. Three versions were made, each having OMCP attached to either WT human IL-18, WT murine IL-18, or mutant human IL-18 (which inhibits its interaction with IL-18BP).
Figure 33:
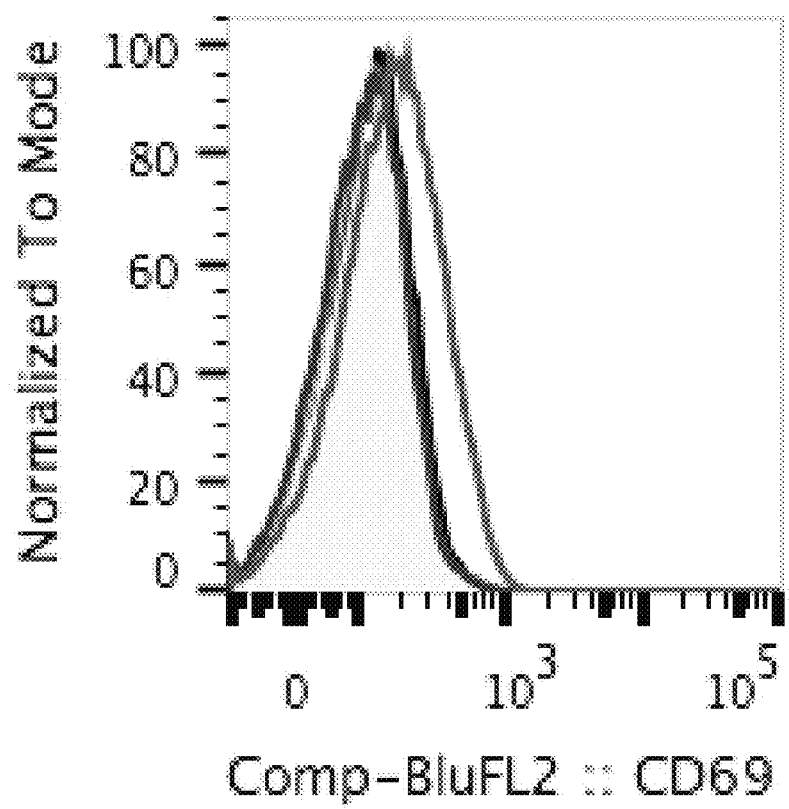
FIG. 33 depicts a flow cytometry plot showing that IL18-OMCP activates NK cells. Peripheral blood lymphocytes were cultured for 48 hours in 4.4 µM of either wild-type IL18 (blue), OMCP-IL18 (red) or saline (black). Activation of CD56+CD3-Natural killer cells, as measured by surface CD69 expression, was superior by OMCP-IL18 compared to wild-type IL18.

OMCP was linked to WT human IL18, WT murine IL18 or mutant human IL18 (which inhibits its interaction with IL18BP) and its ability to active NK cells was examined (FIG. 32). Peripheral blood lymphocytes were cultured for 48 hours in 4.4 µM of either wild-type IL18 (blue), OMCP-IL18 (red) or saline (black). Activation of CD56+CD3– natural killer cells, as measured by surface CD69 expression, was superior by OMCP-IL18 compared to wild-type IL18 (FIG. 33). This data demonstrates that linking OMCP to IL18 also enhances NK cell activation relative to IL18 without OMCP.

Figure 22:
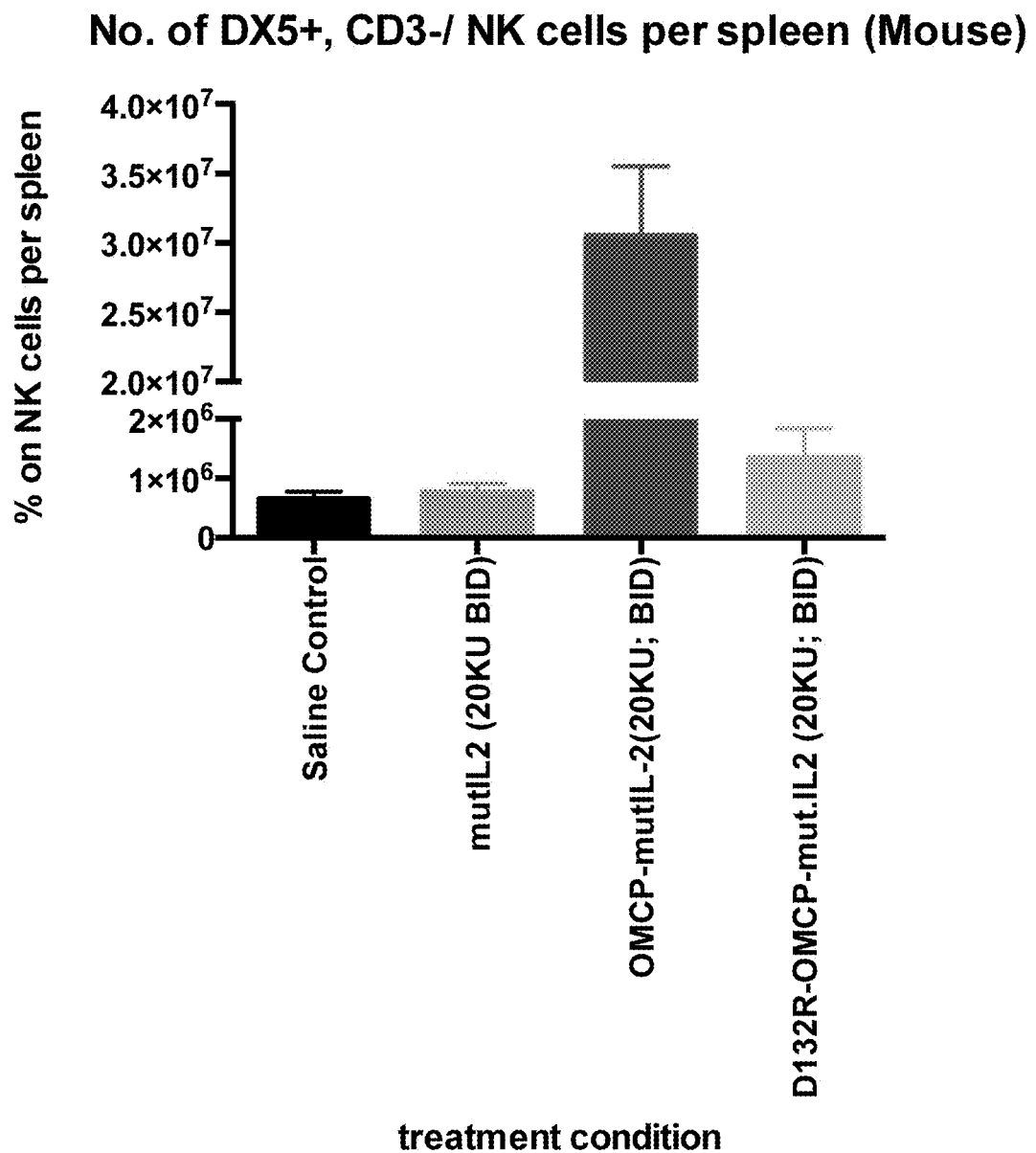
FIG. 22 depicts a graph showing that the D132R mutation in OMCP significantly decreases its NKG2D binding. NK expansion and activation in the presence of mutIL2, OMCP-mutIL2, and D132ROMCP-mutIL2 was tested. The D132R mutation ameliorated the superiority of natural killer cell activation over cytokine alone.

Example 19. The D132R Mutation in OMCP Significantly Decreases its NKG2D Binding To further test the necessity of NKG2D binding in targeted delivery of IL2, we tested NK expansion and activation in the presence of mutIL2, OMCP-mutIL2, and (D132R) OMCP-mutIL2. The D132R mutation ameliorated the superiority of natural killer cell activation over cytokine alone (FIG. 22). Thus high affinity NKG2D binding is critical for targeted delivery and lymphocyte activation by IL2.

Example 20. OMCP-IL2 Effectively Treats Infection Caused by West Nile Virus (WNV)

Figure 30A:
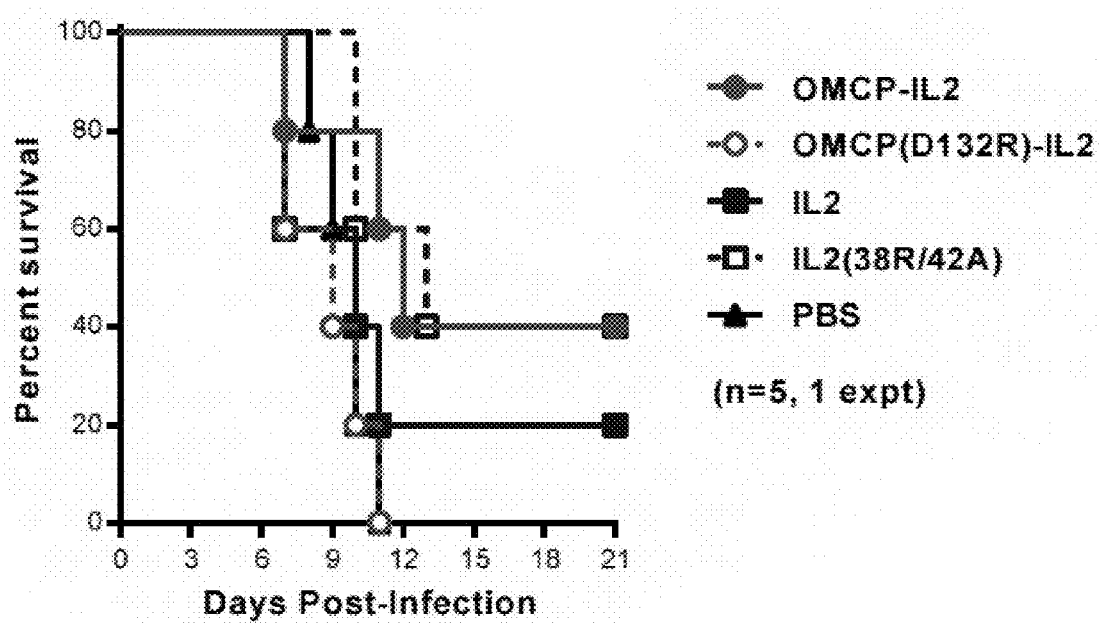
FIG. 30A and FIG. 30B depicts graphs showing survival curves of C57Bl/6J mice following infection with West Nile Virus (WNV). Mice were treated with OMCP-IL2, OMCP (D132R)-IL2, IL2, IL(38R/42A) or PBS after infection with WNV. Infection with OMCP-IL2 and IL2(38R/42A) resulted in survival beyond 21 days in 40% of mice compared to 0 mice following treatment with PBS or OMCP (D132R)-IL2.
Figure 30B:
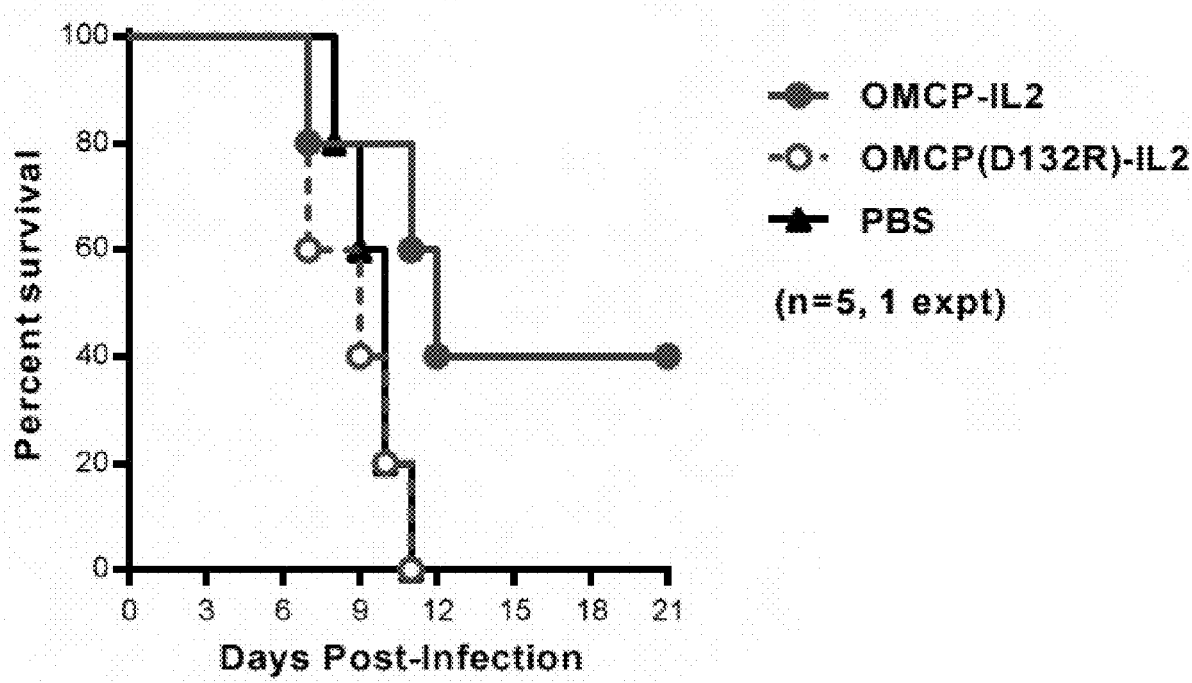

The ability of various constructs of the invention to treat infection caused by West Nile Virus (WNV) was evaluated. Mice were given OMCP-IL2, the binding null mutant of OMCP, OMCP(D132R)-IL2, IL2 alone, IL2(38R/42A) alone and PBS. Upon treatment with OMCP(D132R)-IL2 and PBS all mice succumbed to infection by about day 11. Following treatment with IL2 alone, approximately 20% of mice survived until day 21. However, treatment with IL2 (38R/42A) and OMCP-IL2 resulted in about 40% of mice surviving beyond 21 days (FIG. 30A). These results were consistently repeatable as demonstrated in FIG. 30B.

Lengthy table referenced here

US11713342-20230801-T00001

Please refer to the end of the specification for access instructions.

REFERENCES FOR EXAMPLES 1-6

1. Spangler, J. B. et al. Antibodies to Interleukin-2 Elicit Selective T Cell Subset Potentiation through Distinct Conformational Mechanisms. *Immunity* 42, 815-825 (2015).
2. French, A. R. et al. DAP12 signaling directly augments proproliferative cytokine stimulation of NK cells during viral infections. *J Immunol* 177, 49814990 (2006).
3. Rosenberg, S. A. et al. Experience with the use of high-dose interleukin-2 in the treatment of 652 cancer patients. *Annals of surgery* 210, 474-484; discussion 484-475 (1989).
4. Rosenberg, S. A. IL-2: the first effective immunotherapy for human cancer. *J Immunol* 192, 5451-5458 (2014).
5. Atkins, M. B. et al. High-dose recombinant interleukin 2 therapy for patients with metastatic melanoma: analysis of 270 patients treated between 1985 and 1993. *J Clin Oncol* 17, 2105-2116 (1999).
6. Sim, G. C. et al. IL-2 therapy promotes suppressive ICOS+ Treg expansion in melanoma patients. *J Clin Invest* 124, 99-110 (2014).
7. Kolitz, J. E. et al. Recombinant interleukin-2 in patients aged younger than 60 years with acute myeloid leukemia in first complete remission: results from Cancer and Leukemia Group B 19808. *Cancer* 120, 1010-1017 (2014).
8. Krieg, C., Letourneau, S., Pantaleo, G. & Boyman, O. Improved IL-2 immunotherapy by selective stimulation of IL-2 receptors on lymphocytes and endothelial cells. *Proc Natl Acad Sci USA* 107, 11906-11911 (2010).
9. Heaton, K. M., Ju, G. & Grimm, E. A. Human interleukin 2 analogues that preferentially bind the intermediate-affinity interleukin 2 receptor lead to reduced secondary cytokine secretion: implications for the use of these interleukin 2 analogues in cancer immunotherapy. *Cancer Res* 53, 2597-2602 (1993).
10. Ullrich, E., Koch, J., Cerwenka, A. & Steinle, A. New prospects on the NKG2D/NKG2DL system for oncology. *Oncoimmunology* 2, e26097 (2013).
11. Raulet, D. H. Roles of the NKG2D immunoreceptor and its ligands. *Nat Rev Immunol* 3, 781-790 (2003).
12. Raulet, D. H., Gasser, S., Gowen, B. G., Deng, W. & Jung, H. Regulation of ligands for the NKG2D activating receptor. *Annu Rev Immunol* 31, 413-441 (2013).
13. Giuliani, E., Vassena, L., Cerboni, C. & Doria, M. Release of Soluble Ligands for the Activating NKG2D Receptor: One More Immune Evasion Strategy Evolved by HIV-1 ? *Current drug targets* (2015).
14. Campbell, J. A., Trossman, D. S., Yokoyama, W. M. & Carayannopoulos, L. N. Zoonotic orthopoxviruses encode a high-affinity antagonist of NKG2D. *J Exp Med* 204, 1311-1317 (2007).
15. Lazear, E., Peterson, L. W., Nelson, C. A. & Fremont, D. H. Crystal structure of the cowpox virus-encoded NKG2D ligand OMCP. *J Virol* 87, 840-850 (2013).
16. Kreisel, D. et al. Strain-specific variation in murine natural killer gene complex contributes to differences in immunosurveillance for urethane-induced lung cancer. *Cancer Res* 72, 4311-4317 (2012).
17. Frese-Schaper, M. et al. Influence of natural killer cells and perforinmediated cytolysis on the development of chemically induced lung cancer in A/J mice. *Cancer Immunol Immunother* 63, 571-580 (2014).
18. Dandamudi, U. B. et al. A phase II study of bevacizumab and high-dose interleukin-2 in patients with metastatic renal cell carcinoma: a Cytokine Working Group (CWG) study. *J Immunother* 36, 490-495 (2013).
19. Boyman, O., Kovar, M., Rubinstein, M. P., Surh, C. D. & Sprent, J. Selective stimulation of T cell subsets with antibody-cytokine immune complexes. *Science* 311, 1924-1927 (2006).
20. Smyth, M. J. et al. CD4+CD25+T regulatory cells suppress NK cell-mediated immunotherapy of cancer. *J Immunol* 176, 1582-1587 (2006).
21. Chang, S. et al. Unique pulmonary antigen presentation may call for an alternative approach toward lung cancer immunotherapy. *Oncoimmunology* 2, e23563 (2013).
22. Plonquet, A. et al. Peripheral blood natural killer cell count is associated with clinical outcome in patients with aaIPI 2-3 diffuse large B-cell lymphoma. *Annals of oncology: official journal of the European Society for Medical Oncology/ESMO* 18, 1209-1215 (2007).
23. Tzeng, A., Kwan, B. H., Opel, C. F., Navaratna, T. & Wittrup, K. D. Antigen specificity can be irrelevant to immunocytokine efficacy and biodistribution. *Proc Natl Acad Sci USA* 112, 3320-3325 (2015).
24. Letourneau, S. et al. IL-2/anti-IL-2 antibody complexes show strong biological activity by avoiding interaction with IL-2 receptor alpha subunit CD25. *Proc Natl Acad Sci USA* 107, 2171-2176 (2010).
25. Ho, E. L. et al. Costimulation of multiple NK cell activation receptors by NKG2D. *J Immunol* 169, 3667-3675 (2002).
26. Levin, A. M. et al. Exploiting a natural conformational switch to engineer an interleukin-2 'superkine'. *Nature* 484, 529-533 (2012).
27. Mitra, S. et al. Interleukin-2 activity can be fine tuned with engineered receptor signaling clamps. *Immunity* 42, 826-838 (2015).
28. Boyman, O. et al. Selectively expanding subsets of T cells in mice by injection of interleukin-2/antibody complexes: implications for transplantation tolerance. *Transplantation proceedings* 44, 1032-1034 (2012).
29. Tomala, J. et al. Chimera of IL-2 linked to light chain of anti-IL-2 mAb mimics IL-2/anti-IL-2 mAb complexes both structurally and functionally. *ACS chemical biology* 8, 871-876 (2013).
30. Gutbrodt, K. L., Casi, G. & Neri, D. Antibody-based delivery of IL2 and cytotoxics eradicates tumors in immunocompetent mice. *Molecular cancer therapeutics* 13, 1772-1776 (2014).
32. Yamane, B. H., Hank, J. A., Albertini, M. R. & Sondel, P. M. The development of antibody-IL-2 based immunotherapy with hu14.18-IL2 (EMD-273063) in melanoma and neuroblastoma. *Expert opinion on investigational drugs* 18, 991-1000 (2009).
33. Carmenate, T. et al. Human IL-2 mutein with higher antitumor efficacy than wild type IL-2. *J Immunol* 190, 6230-6238 (2013).
34. Heaton, K. M. et al. Characterization of lymphokine-activated killing by human peripheral blood mononuclear cells stimulated with interleukin 2 (IL-2) analogs specific for the intermediate affinity IL-2 receptor. *Cellular immunology* 147, 167-179 (1993).
35. Imai, K., Matsuyama, S., Miyake, S., Suga, K. & Nakachi, K. Natural cytotoxic activity of peripheral-blood lymphocytes and cancer incidence: an 11-year follow-up study of a general population. *Lancet* 356, 1795-1799 (2000).
36. Lazear, E. et al. Cowpox virus OMCP antagonizes NKG2D via an unexpected binding orientation. *PLos Pathogen In revision* (2014).
37. Deng, W. et al. Antitumor immunity. A shed NKG2D ligand that promotes natural killer cell activation and tumor rejection. *Science* 348, 136-139 (2015).
38. Gorelik, E. & Herberman, R. B. Susceptibility of various strains of mice to urethan-induced lung tumors and depressed natural killer cell activity. *J Natl Cancer Inst* 67, 1317-1322 (1981).
39. Mancia, F. et al. Optimization of protein production in mammalian cells with a coexpressed fluorescent marker. *Structure* 12, 1355-1360 (2004).
40. Hank, J. A. et al. Distinct clinical and laboratory activity of two recombinant interleukin-2 preparations. *Clin Cancer Res* 5, 281-289 (1999).

REFERENCES FOR EXAMPLES 7-10

1. Hansen T H, Bouvier M (2009) MHC class I antigen presentation: learning from viral evasion strategies. Nat Rev Immunol 9: 503-513.
2. Griffin B D, Verweij M C, Wiertz E J (2010) Herpesviruses and immunity: the art of evasion. Vet Microbiol 143: 89-100.
3. Karre K, Ljunggren H G, Piontek G, Kiessling R (1986) Selective rejection of H-2-deficient lymphoma variants suggests alternative immune defence strategy. Nature 319: 675-678.
4. Orange J S, Fassett M S, Koopman L A, Boyson J E, Strominger J L (2002) Viral evasion of natural killer cells. Nat Immunol 3: 1006-1012.
5. Lisnic V J, Krmpotic A, Jonjic S (2010) Modulation of natural killer cell activity by viruses. Curr Opin Microbiol 13: 530-539.
6. Finton K A, Strong R K (2012) Structural insights into activation of antiviral NK cell responses. Immunol Rev 250: 239-257.
7. Li Y, Mariuzza R A (2014) Structural Basis for Recognition of Cellular and Viral Ligands by NK Cell Receptors. Front Immunol 5: 123.
8. Raulet D H (2003) Roles of the NKG2D immunoreceptor and its ligands. Nat Rev Immunol 3: 781-790.
9. Draghi M, Pashine A, Sanjanwala B, Gendzekhadze K, Cantoni C, et al. (2007) NKp46 and NKG2D recognition of infected dendritic cells is necessary for NK cell activation in the human response to influenza infection. J Immunol 178: 2688-2698.
10. Pappworth I Y, Wang E C, Rowe M (2007) The switch from latent to productive infection in epstein-barr virus-infected B cells is associated with sensitization to NK cell killing. J Virol 81: 474-482.
11. Welte S A, Sinzger C, Lutz S Z, Singh-Jasuja H, Sampaio K L, et al. (2003) Selective intracellular retention of virally induced NKG2D ligands by the human cytomegalovirus UL16 glycoprotein. Eur J Immunol 33: 194-203.
12. Ward J, Bonaparte M, Sacks J, Guterman J, Fogli M, et al. (2007) HIV modulates the expression of ligands important in triggering natural killer cell cytotoxic responses on infected primary T-cell blasts. Blood 110: 1207-1214.

13. Obeidy P, Sharland A F (2009) NKG2D and its ligands. Int J Biochem Cell Biol 41: 2364-2367.
14. Eagle R A, Trowsdale J (2007) Promiscuity and the single receptor: NKG2D. Nat Rev Immunol 7: 737-744.
15. Lodoen M, Ogasawara K, Hamerman J A, Arase H, Houchins J P, et al. (2003) NKG2D-mediated natural killer cell protection against cytomegalovirus is impaired by viral gp40 modulation of retinoic acid early inducible 1 gene molecules. J Exp Med 197: 1245-1253.
16. Lodoen M B, Abenes G, Umamoto S, Houchins J P, Liu F, et al. (2004) The cytomegalovirus m155 gene product subverts natural killer cell antiviral protection by disruption of H60-NKG2D interactions. J Exp Med 200: 1075-1081.
17. Krmpotic A, Hasan M, Loewendorf A, Saulig T, Halenius A, et al. (2005) NK cell activation through the NKG2D ligand MULT-1 is selectively prevented by the glycoprotein encoded by mouse cytomegalovirus gene m145. J Exp Med 201: 211-220.
18. Lenac T, Budt M, Arapovic J, Hasan M, Zimmermann A, et al. (2006) The herpesviral Fc receptor fcr-1 down-regulates the NKG2D ligands MULT-1 and H60. J Exp Med 203: 1843-1850.
19. Cosman D, Mullberg J, Sutherland C L, Chin W, Armitage R, et al. (2001) ULBPs, novel MHC class I-related molecules, bind to CMV glycoprotein UL16 and stimulate NK cytotoxicity through the NKG2D receptor. Immunity 14: 123-133.
20. Chalupny N J, Rein-Weston A, Dosch S, Cosman D (2006) Down-regulation of the NKG2D ligand MICA by the human cytomegalovirus glycoprotein UL142. Biochem Biophys Res Commun 346: 175-181.
21. Thomas M, Boname J M, Field S, Nejentsev S, Salio M, et al. (2008) Down-regulation of NKG2D and NKp80 ligands by Kaposi's sarcoma-associated herpesvirus K5 protects against NK cell cytotoxicity. Proc Natl Acad Sci USA 105: 1656-1661.
22. Cerboni C, Neri F, Casartelli N, Zingoni A, Cosman D, et al. (2007) Human immunodeficiency virus 1 Nef protein downmodulates the ligands of the activating receptor NKG2D and inhibits natural killer cell-mediated cytotoxicity. J Gen Virol 88: 242-250.
23. Wen C, He X, Ma H, Hou N, Wei C, et al. (2008) Hepatitis C virus infection downregulates the ligands of the activating receptor NKG2D. Cell Mol Immunol 5: 475-478.
24. Stern-Ginossar N, Elefant N, Zimmermann A, Wolf D G, Saleh N, et al. (2007) Host immune system gene targeting by a viral miRNA. Science 317: 376-381.
25. Nachmani D, Stern-Ginossar N, Sarid R, Mandelboim O (2009) Diverse herpesvirus microRNAs target the stress-induced immune ligand MICB to escape recognition by natural killer cells. Cell Host Microbe 5: 376-385.
26. Bauman Y, Nachmani D, Vitenshtein A, Tsukerman P, Drayman N, et al. (2011) An identical miRNA of the human JC and BK polyoma viruses targets the stress-induced ligand ULBP3 to escape immune elimination. Cell Host Microbe 9: 93-102.
27. Gainey M D, Rivenbark J G, Cho H, Yang L, Yokoyama W M (2012) Viral MHC class I inhibition evades CD8+ T-cell effector responses in vivo but not CD8+ T-cell priming. Proc Natl Acad Sci USA 109: E3260-3267.
28. Byun M, Verweij M C, Pickup D J, Wiertz E J, Hansen T H, et al. (2009) Two mechanistically distinct immune evasion proteins of cowpox virus combine to avoid antiviral CD8 T cells. Cell Host Microbe 6: 422-432.
29. Byun M, Wang X, Pak M, Hansen T H, Yokoyama W M (2007) Cowpox virus exploits the endoplasmic reticulum retention pathway to inhibit MHC class I transport to the cell surface. Cell Host Microbe 2: 306-315.
30. McCoy W H t, Wang X, Yokoyama W M, Hansen T H, Fremont D H (2013) Cowpox virus employs a two-pronged strategy to outflank MHCI antigen presentation. Mol Immunol.
31. McCoy W H t, Wang X, Yokoyama W M, Hansen T H, Fremont D H (2012) Structural mechanism of ER retrieval of MHC class I by cowpox. PLoS Biol 10: e1001432.
32. Alzhanova D, Edwards D M, Hammarlund E, Scholz I G, Horst D, et al. (2009) Cowpox virus inhibits the transporter associated with antigen processing to evade T cell recognition. Cell Host Microbe 6: 433-445.
33. Dasgupta A, Hammarlund E, Slifka M K, Fruh K (2007) Cowpox virus evades CTL recognition and inhibits the intracellular transport of MHC class I molecules. J Immunol 178: 1654-1661.
34. Luteijn R D, Hoelen H, Kruse E, van Leeuwen W F, Grootens J, et al. (2014) Cowpox Virus Protein CPXV012 Eludes CTLs by Blocking ATP Binding to TAP. J Immunol 193: 1578-1589.
35. Fang M, Lanier L L, Sigal L J (2008) A role for NKG2D in NK cell-mediated resistance to poxvirus disease. PLoS Pathog 4: e30.
36. Song H, Josleyn N, Janosko K, Skinner J, Reeves R K, et al. (2013) Monkeypox virus infection of rhesus macaques induces massive expansion of natural killer cells but suppresses natural killer cell functions. PLoS One 8: e77804.
37. Campbell J A, Trossman D S, Yokoyama W M, Carayannopoulos L N (2007) Zoonotic orthopoxviruses encode a high-affinity antagonist of NKG2D. J Exp Med 204: 1311-1317.
38. Lazear E, Peterson L W, Nelson C A, Fremont D H (2013) Crystal structure of the cowpox virus-encoded NKG2D ligand OMCP. J Virol 87: 840-850.
39. Carayannopoulos L N, Naidenko O V, Kinder J, Ho E L, Fremont D H, et al. (2002) Ligands for murine NKG2D display heterogeneous binding behavior. Eur J Immunol 32: 597-605.
40. Mistry A R, O'Callaghan C A (2007) Regulation of ligands for the activating receptor NKG2D. Immunology 121: 439-447.
41. Strong R K, McFarland B J (2004) NKG2D and Related Immunoreceptors. Adv Protein Chem 68: 281-312.
42. Deng L, Mariuzza R A (2006) Structural basis for recognition of MHC and MHC-like ligands by natural killer cell receptors. Semin Immunol 18: 159-166.
43. Li P, McDermott G, Strong R K (2002) Crystal structures of RAE-1beta and its complex with the activating immunoreceptor NKG2D. Immunity 16: 77-86.
44. Li P, Morris D L, Willcox B E, Steinle A, Spies T, et al. (2001) Complex structure of the activating immunoreceptor NKG2D and its MHC class I-like ligand MICA. Nat Immunol 2: 443-451.
45. Li P, Willie S T, Bauer S, Morris D L, Spies T, et al. (1999) Crystal structure of the MHC class I homolog MIC-A, a gammadelta T cell ligand. Immunity 10: 577-584.
46. Radaev S, Rostro B, Brooks A G, Colonna M, Sun P D (2001) Conformational plasticity revealed by the cocrystal structure of NKG2D and its class I MHC-like ligand ULBP3. Immunity 15: 1039-1049.

47. Adams E J, Luoma A M (2013) The adaptable major histocompatibility complex (MHC) fold: structure and function of nonclassical and MHC class I-like molecules. Annu Rev Immunol 31: 529-561.
48. McFarland B J, Kortemme T, Yu S F, Baker D, Strong R K (2003) Symmetry recognizing asymmetry: analysis of the interactions between the C-type lectin-like immunoreceptor NKG2D and MHC class I-like ligands. Structure 11: 411-422.
49. Stewart D E, Sarkar A, Wampler J E (1990) Occurrence and role of cis peptide bonds in protein structures. J Mol Biol 214: 253-260.
50. Craveur P, Joseph A P, Poulain P, de Brevern A G, Rebehmed J (2013) Cis-trans isomerization of omega dihedrals in proteins. Amino Acids 45: 279-289.
51. Lefkowitz E J, Upton C, Changayil S S, Buck C, Traktman P, et al. (2005) Poxvirus Bioinformatics Resource Center: a comprehensive Poxviridae informational and analytical resource. Nucleic Acids Res 33: D311-316.
52. Strong R K (2002) Asymmetric ligand recognition by the activating natural killer cell receptor NKG2D, a symmetric homodimer. Mol Immunol 38: 1029-1037.
53. Radaev S, Sun P D (2003) Structure and function of natural killer cell surface receptors. Annu Rev Biophys Biomol Struct 32: 93-114.
54. Campbell J A, Davis R S, Lilly L M, Fremont D H, French A R, et al. (2010) Cutting edge: FcR-like 5 on innate B cells is targeted by a poxvirus MHC class I-like immunoevasin. J Immunol 185: 28-32.
55. Copeland R A, Pompliano D L, Meek T D (2006) Drug-target residence time and its implications for lead optimization. Nat Rev Drug Discov 5: 730-739.
56. O'Callaghan C A, Cerwenka A, Willcox B E, Lanier L L, Bjorkman P J (2001) Molecular competition for NKG2D: H60 and RAE1 compete unequally for NKG2D with dominance of H60. Immunity 15: 201-211.
57. Groh V, Bruhl A, El-Gabalawy H, Nelson J L, Spies T (2003) Stimulation of T cell autoreactivity by anomalous expression of NKG2D and its MIC ligands in rheumatoid arthritis. Proc Natl Acad Sci USA 100: 9452-9457.
58. Hue S, Mention J J, Monteiro R C, Zhang S, Cellier C, et al. (2004) A direct role for NKG2D/MICA interaction in villous atrophy during celiac disease. Immunity 21: 367-377.
59. Meresse B, Chen Z, Ciszewski C, Tretiakova M, Bhagat G, et al. (2004) Coordinated induction by IL15 of a TCR-independent NKG2D signaling pathway converts CTL into lymphokine-activated killer cells in celiac disease. Immunity 21: 357-366.
60. Ogasawara K, Hamerman J A, Hsin H, Chikuma S, Bour-Jordan H, et al. (2003) Impairment of NK cell function by NKG2D modulation in NOD mice. Immunity 18: 41-51.
61. Hahn M, Nicholson M J, Pyrdol J, Wucherpfennig K W (2005) Unconventional topology of self peptide-major histocompatibility complex binding by a human autoimmune T cell receptor. Nat Immunol 6: 490-496.
62. Sethi D K, Schubert D A, Anders A K, Heroux A, Bonsor D A, et al. (2011) A highly tilted binding mode by a self-reactive T cell receptor results in altered engagement of peptide and MHC. J Exp Med 208: 91-102.
63. Wucherpfennig K W, Call M J, Deng L, Mariuzza R (2009) Structural alterations in peptide-MHC recognition by self-reactive T cell receptors. Curr Opin Immunol 21: 590-595.
64. Yin Y, Li Y, Mariuzza R A (2012) Structural basis for self-recognition by autoimmune T-cell receptors. Immunol Rev 250: 32-48.
65. Adams J J, Narayanan S, Liu B, Birnbaum M E, Kruse A C, et al. (2011) T cell receptor signaling is limited by docking geometry to peptide-major histocompatibility complex. Immunity 35: 681-693.
66. Schubert D A, Gordo S, Sabatino J J, Jr., Vardhana S, Gagnon E, et al. (2012) Self-reactive human CD4 T cell clones form unusual immunological synapses. J Exp Med 209: 335-352.
67. Li Y, Yin Y, Mariuzza R A (2013) Structural and biophysical insights into the role of CD4 and CD8 in T cell activation. Front Immunol 4: 206.
68. Otwinowski Z, Minor W (1997) Processing of X-ray diffraction data collected in oscillation mode. Macromolecular Crystallography, Pt A 276: 307-326.
69. Adams P D, Grosse-Kunstleve R W, Hung L W, Ioerger T R, McCoy A J, et al. (2002) PHENIX: building new software for automated crystallographic structure determination. Acta Crystallogr D Biol Crystallogr 58: 1948-1954.
70. Emsley P, Cowtan K (2004) Coot: model-building tools for molecular graphics. Acta Crystallogr D Biol Crystallogr 60: 2126-2132.
71. Chen V B, Arendall W B, 3rd, Headd J J, Keedy D A, Immormino R M, et al. (2010) MolProbity: all-atom structure validation for macromolecular crystallography. Acta Crystallogr D Biol Crystallogr 66: 12-21.
72. Schrodinger, LLC (2010) The PyMOL Molecular Graphics System, Version 1.3r1.
73. Laskowski R A, Swindells M B (2011) LigPlot+: multiple ligand-protein interaction diagrams for drug discovery. J Chem Inf Model 51: 2778-2786.
74. Krissinel E, Henrick K (2007) Inference of macromolecular assemblies from crystalline state. J Mol Biol 372: 774-797.
75. Lawrence M C, Colman P M (1993) Shape complementarity at protein/protein interfaces. J Mol Biol 234: 946-950.
76. Morin A, Eisenbraun B, Key J, Sanschagrin P C, Timony M A, et al. (2013) Collaboration gets the most out of software. Elife 2: e01456.
77. Ashkenazy H, Erez E, Martz E, Pupko T, Ben-Tal N (2010) ConSurf 2010: calculating evolutionary conservation in sequence and structure of proteins and nucleic acids. Nucleic Acids Res 38: W529-533.
78. Landau M, Mayrose I, Rosenberg Y, Glaser F, Martz E, et al. (2005) ConSurf 2005: the projection of evolutionary conservation scores of residues on protein structures. Nucleic Acids Res 33: W299-302.
79. Glaser F, Pupko T, Paz I, Bell R E, Bechor-Shental D, et al. (2003) ConSurf: identification of functional regions in proteins by surface-mapping of phylogenetic information. Bioinformatics 19: 163-164.
80. Celniker G, Nimrod G, Ashkenazy H, Glaser F, Martz E, et al. (2013) ConSurf: Using Evolutionary Data to Raise Testable Hypotheses about Protein Function. Israel Journal of Chemistry 53: 199-206.
81. Dokun A O, Kim S, Smith H R, Kang H S, Chu D T, et al. (2001) Specific and nonspecific NK cell activation during virus infection. Nat Immunol 2: 951-956.

REFERENCES FOR EXAMPLE 11-20

1. Rosenberg, S. A. IL-2: the first effective immunotherapy for human cancer. J Immunol 192, 5451-5458 (2014).

2. Atkins, M. B., et al. High-dose recombinant interleukin 2 therapy for patients with metastatic melanoma: analysis of 270 patients treated between 1985 and 1993. J Clin Oncol 17, 2105-2116 (1999).
3. Krieg, C., Letourneau, S., Pantaleo, G. & Boyman, O. Improved IL-2 immunotherapy by selective stimulation of IL-2 receptors on lymphocytes and endothelial cells. Proc Natl Acad Sci USA 107, 11906-11911 (2010).
4. Ghiringhelli, F., Menard, C., Martin, F. & Zitvogel, L. The role of regulatory T cells in the control of natural killer cells: relevance during tumor progression. Immunol Rev 214, 229-238 (2006).
5. French, A. R., et al. DAP12 signaling directly augments proproliferative cytokine stimulation of NK cells during viral infections. J Immunol 177, 4981-4990 (2006).
6. Heaton, K. M., Ju, G. & Grimm, E. A. Human interleukin 2 analogues that preferentially bind the intermediate-affinity interleukin 2 receptor lead to reduced secondary cytokine secretion: implications for the use of these interleukin 2 analogues in cancer immunotherapy. Cancer Res 53, 2597-2602 (1993).
7. Heaton, K. M., et al. Characterization of lymphokine-activated killing by human peripheral blood mononuclear cells stimulated with interleukin 2 (IL-2) analogs specific for the intermediate affinity IL-2 receptor. Cellular immunology 147, 167-179 (1993).
8. Levin, A. M., et al. Exploiting a natural conformational switch to engineer an interleukin-2 'superkine'. Nature 484, 529-533 (2012).
9. Campbell, J. A., Trossman, D. S., Yokoyama, W. M. & Carayannopoulos, L. N. Zoonotic orthopoxviruses encode a high-affinity antagonist of NKG2D. J Exp Med 204, 1311-1317 (2007).
10. Rosenberg, S. A., et al. Experience with the use of high-dose interleukin-2 in the treatment of 652 cancer patients. Annals of surgery 210, 474-484; discussion 484-475 (1989).
11. Gately, M. K., Anderson, T. D. & Hayes, T. J. Role of asialo-GM1-positive lymphoid cells in mediating the toxic effects of recombinant IL-2 in mice. J Immunol 141, 189-200 (1988).
12. Sim, G. C., et al. IL-2 therapy promotes suppressive ICOS+ Treg expansion in melanoma patients. J Clin Invest 124, 99-110 (2014).
13. Raulet, D. H. Roles of the NKG2D immunoreceptor and its ligands. Nat Rev Immunol 3, 781-790 (2003).
14. Ullrich, E., Koch, J., Cerwenka, A. & Steinle, A. New prospects on the NKG2D/NKG2DL system for oncology. Oncoimmunology 2, e26097 (2013).
15. Lazear, E., Peterson, L. W., Nelson, C. A. & Fremont, D. H. Crystal structure of the cowpox virus-encoded NKG2D ligand OMCP. J Virol 87, 840-850 (2013).
16. Bui, J. D., Uppaluri, R., Hsieh, C. S. & Schreiber, R. D. Comparative analysis of regulatory and effector T cells in progressively growing versus rejecting tumors of similar origins. Cancer Res 66, 7301-7309 (2006).
17. Wang, Y., Sparwasser, T., Figlin, R. & Kim, H. L. Foxp3+ T cells inhibit antitumor immune memory modulated by mTOR inhibition. Cancer Res 74, 2217-2228 (2014).
18. Poschke, I., et al. A phase I clinical trial combining dendritic cell vaccination with adoptive T cell transfer in patients with stage IV melanoma. Cancer immunology, immunotherapy: CII 63, 1061-1071 (2014).
19. Kreisel, D., et al. Strain-specific variation in murine natural killer gene complex contributes to differences in immunosurveillance for urethane-induced lung cancer. Cancer Res 72, 4311-4317 (2012).
20. Frese-Schaper, M., et al. Influence of natural killer cells and perforinmediated cytolysis on the development of chemically induced lung cancer in NJ mice. Cancer immunology, immunotherapy: CII 63, 571-580 (2014).
21. Ryu, M. S., et al. Accumulation of cytolytic CD8(+) T cells in B16-melanoma and proliferation of mature T cells in TIS21-knockout mice after T cell receptor stimulation. Experimental cell research 327, 209¬221 (2014).
22. Anichini, A., et al. Tumor-reactive CD8+ early effector T cells identified at tumor site in primary and metastatic melanoma. Cancer Res 70, 8378-8387 (2010).
23. Glasner, A., et al. Recognition and prevention of tumor metastasis by the NK receptor NKp46/NCR1. J Immunol 188, 2509-2515 (2012).
24. Hersey, P., Edwards, A., Honeyman, M. & McCarthy, W. H. Low natural-killer-cell activity in familial melanoma patients and their relatives. Br J Cancer 40, 113-122 (1979).
25. Ji, Q., Gondek, D. & Hurwitz, A. A. Provision of granulocyte-macrophage colony-stimulating factor converts an autoimmune response to a self-antigen into an antitumor response. J Immunol 175, 14561463 (2005).
26. Zhu, Z., et al. High-avidity T cells are preferentially tolerized in the tumor microenvironment. Cancer Res 73, 595-604 (2013).
27. Klein, O., et al. Melan-A-specific cytotoxic T cells are associated with tumor regression and autoimmunity following treatment with anti-CTLA-4. Clinical cancer research: an official journal of the American Association for Cancer Research 15, 2507-2513 (2009).
28. Meiraz, A., Garber, O. G., Harari, S., Hassin, D. & Berke, G. Switch from perforin-expressing to perforin-deficient CD8(+) T cells accounts for two distinct types of effector cytotoxic T lymphocytes in vivo. Immunology 128, 69-82 (2009).
29. Stemberger, C., et al. A single naive CD8+ T cell precursor can develop into diverse effector and memory subsets. Immunity 27, 985-997 (2007).
30. Sallusto, F., Lenig, D., Forster, R., Lipp, M. & Lanzavecchia, A. Two subsets of memory T lymphocytes with distinct homing potentials and effector functions. Nature 401, 708-712 (1999).
31. Araki, K., et al. mTOR regulates memory CD8 T-cell differentiation. Nature 460, 108-112 (2009).
32. Kim, H. L. Antibody-based depletion of Foxp3+ T cells potentiates antitumor immune memory stimulated by mTOR inhibition. Oncoimmunology 3, e29081 (2014).
33. Graham, J. B., Da Costa, A. & Lund, J. M. Regulatory T cells shape the resident memory T cell response to virus infection in the tissues. J Immunol 192, 683-690 (2014).
34. de Goer de Nerve, M. G., Jaafoura, S., Vallee, M. & Taoufik, Y. FoxP3(+) regulatory CD4 T cells control the generation of functional CD8 memory. Nature communications 3, 986 (2012).
35. Gilfillan, S., Ho, E. L., Cella, M., Yokoyama, W. M. & Colonna, M. NKG2D recruits two distinct adapters to trigger NK cell activation and costimulation. Nature immunology 3, 1150-1155 (2002).
36. Shane, H. L. & Klonowski, K. D. Every breath you take: the impact of environment on resident memory CD8 T cells in the lung. Frontiers in immunology 5, 320 (2014).
37. Marcus, A. & Raulet, D. H. Evidence for natural killer cell memory. Current biology: CB 23, R817-820 (2013).
38. Tam, S. H., Sassoli, P. M., Jordan, R. E. & Nakada, M. T. Abciximab (ReoPro, chimeric 7E3 Fab) demonstrates 39. Trikha, M., et al. CNTO 95, a fully human monoclonal antibody that inhibits alphav integrins, has antitumor and antiangiogenic activity in vivo. International journal of cancer. Journal international du cancer 110, 326-335 (2004).
40. Rathanaswami, P., Babcook, J. & Gallo, M. High-affinity binding measurements of antibodies to cell-surface-expressed antigens. Anal Biochem 373, 52-60 (2008).
41. Drake, A. W., Myszka, D. G. & Klakamp, S. L. Characterizing high-affinity antigen/antibody complexes by kinetic- and equilibrium-based methods. Anal Biochem 328, 35-43 (2004).
42. Siiman, O. & Burshteyn, A. Cell surface receptor-antibody association constants and enumeration of receptor sites for monoclonal antibodies. Cytometry 40, 316-326 (2000).
43. Debbia, M. & Lambin, P. Measurement of anti-D intrinsic affinity with unlabeled antibodies. Transfusion 44, 399-406 (2004).
44. Tsao, P. I. & von Zastrow, M. Type-specific sorting of G protein-coupled receptors after endocytosis. The Journal of biological chemistry 275, 11130-11140 (2000).
45. Lazear, E., et al. Cowpox virus OMCP antagonizes NKG2D via an unexpected binding orientation. PLos Pathogen Under review (2014).
46. Liu, K. D., Gaffen, S. L., Goldsmith, M. A. & Greene, W. C. Janus kinases in interleukin-2-mediated signaling: JAK1 and JAK3 are differentially regulated by tyrosine phosphorylation. Current biology: C B 7, 817-826 (1997).
47. Zhou, Y. J., et al. Distinct tyrosine phosphorylation sites in JAK3 kinase domain positively and negatively regulate its enzymatic activity. Proc Natl Acad Sci USA 94, 13850-13855 (1997).
48. Horng, T., Bezbradica, J. S. & Medzhitov, R. NKG2D signaling is coupled to the interleukin 15 receptor signaling pathway. Nature immunology 8, 1345-1352 (2007).
49. Zou, W., Reeve, J. L., Liu, Y., Teitelbaum, S. L. & Ross, F. P. DAP12 couples c-Fms activation to the osteoclast cytoskeleton by recruitment of Syk. Molecular cell 31, 422-431 (2008).
50. Graham, D. B., et al. Vav1 controls DAP10-mediated natural cytotoxicity by regulating actin and microtubule dynamics. J Immunol 177, 2349-2355 (2006).
51. Yamane, B. H., Hank, J. A., Albertini, M. R. & Sondel, P. M. The development of antibody-IL-2 based immunotherapy with hu14.18-IL2 (EMD-273063) in melanoma and neuroblastoma. Expert opinion on investigational drugs 18, 991-1000 (2009).
52. Becker, J. C., Pancook, J. D., Gillies, S. D., Furukawa, K. & Reisfeld, R. A. T cell-mediated eradication of murine metastatic melanoma induced by targeted interleukin 2 therapy. J Exp Med 183, 2361-2366 (1996).
53. Lundholm et al., Prostate tumor-derived exosomes down-regulate NKG2D expression on natural killer cells and CD8+ T cells: mechanism of immune evasion. PLoS One 2014; 9(9):e108925.

LENGTHY TABLES

The patent contains a lengthy table section. A copy of the table is available in electronic form from the USPTO web site (https://seqdata.uspto.gov/?pageRequest=docDetail&DocID=US11713342B2). An electronic copy of the table will also be available from the USPTO upon request and payment of the fee set forth in 37 CFR 1.19(b)(3).

What is claimed is:

1. A chimeric peptide comprising a first peptide linked to a second peptide, wherein the first peptide comprises an amino acid sequence of at least 60.8% homology to SEQ ID NO:7 and specifically binds to NKG2D receptor; and the second peptide comprises an amino acid sequence of at least 97% homology to SEQ ID NO:5 and binds to the IL2βγ receptor subunit.

2. The chimeric peptide of claim 1, wherein the first peptide has a binding affinity to the NKG2D receptor of from 0.1 nM to 100 nM.

3. The chimeric peptide of claim 1, wherein the second peptide comprises one or more mutations selected from the group consisting of R38A, F42K and/or C125S relative to SEQ ID NO: 5.

4. The chimeric peptide of claim 1, wherein the second peptide comprises SEQ ID NO: 6.

5. The chimeric peptide of claim 1, wherein the first peptide is linked to the second peptide via a linker.

6. The chimeric peptide of claim 5, wherein the linker comprises the sequence set forth in SEQ ID NO: 8.

7. The chimeric peptide of claim 1, wherein the first peptide comprises an amino acid sequence of at least 98.7% homology to SEQ ID NO: 7.

* * * * *